US009109234B2

(12) United States Patent
Charneau et al.

(10) Patent No.: US 9,109,234 B2
(45) Date of Patent: Aug. 18, 2015

(54) LENTIVIRAL VECTOR BASED IMMUNOLOGICAL COMPOUNDS AGAINST MALARIA

(76) Inventors: Pierre Charneau, Paris (FR); Frederic Philippe Coutant, Rodez (FR)

( * ) Notice: Subject to any disclaimer, the term of this patent is extended or adjusted under 35 U.S.C. 154(b) by 0 days.

(21) Appl. No.: 13/695,683

(22) PCT Filed: Apr. 29, 2011

(86) PCT No.: PCT/EP2011/056887

§ 371 (c)(1), (2), (4) Date: Mar. 8, 2013

(87) PCT Pub. No.: WO2011/138251

PCT Pub. Date: Nov. 10, 2011

(65) Prior Publication Data

US 2013/0171195 A1 Jul. 4, 2013

(30) Foreign Application Priority Data

May 3, 2010 (EP) .................................... 10290238

(51) Int. Cl.

| | |
|---|---|
| ***C12N 15/867*** | (2006.01) |
| ***A61K 39/015*** | (2006.01) |
| ***C12N 7/00*** | (2006.01) |
| ***C12N 15/86*** | (2006.01) |
| *A61K 39/00* | (2006.01) |

(52) U.S. Cl.

CPC ............ *C12N 15/867* (2013.01); *A61K 39/015* (2013.01); *C12N 7/00* (2013.01); *C12N 15/86* (2013.01); *A61K 2039/525* (2013.01); *A61K 2039/5256* (2013.01); *A61K 2039/5258* (2013.01); *C12N 2740/16023* (2013.01); *C12N 2740/16043* (2013.01); *C12N 2810/6081* (2013.01)

(58) Field of Classification Search

None

See application file for complete search history.

(56) References Cited

U.S. PATENT DOCUMENTS 7,521,229 B2 4/2009 Pau

FOREIGN PATENT DOCUMENTS

| | | | |
|---|---|---|---|
| WO | 9428930 | | 12/1994 |
| WO | 2004043488 | A1 | 5/2004 |
| WO | 2007027860 | A2 | 3/2007 |
| WO | 2007052165 | A2 | 5/2007 |
| WO | 2007095201 | A2 | 8/2007 |
| WO | 2009019612 | A2 | 2/2009 |

OTHER PUBLICATIONS

Bowie et al. (Science, 1990, 247:1306-1310).*
Greenspan et al. (Nature Biotechnology 7: 936-937, 1999).*
Genbank Locus AAA48370.1, Oct. 21, 2002.
Audran, Regine, et al., PLoS ONE, vol. 4, Issue 10, e7304 (Oct. 2009).
GenBank Locus AY135360.1, Oct. 11, 2005.
GenBank Locus AY674050.1, Aug. 1, 2005.
Beignon, Anne-Sophie, et al., Journal of Virology, vol. 83, No. 21, pp. 10963-10974 (2009).
Beignon, A., et al., Retrovirology, vol. 6, Suppl. 3, p. 302 (2009).
Bruna-Romero, Oscar, et al., PNAS, vol. 98, No. 20, pp. 11491-11496 (2001).
Bruna-Romero, Oscar, et al., Vaccine, vol. 22, pp. 3575-3584 (2004).
Cockrell, Adam S., et al., Molecular Therapy, vol. 14, No. 2, pp. 276-284 (2006).
Cockrell, Adam S., et al., Mol. Biotechnol. vol. 36, pp. 184-204 (2007).
Coutant, Frederic, et al., PLoS ONE, vol. 3, Issue 12, e3973 (2008).
Cronin, James, et al., Curr. Gene Ther., vol. 5, No. 4, pp. 387-398 (2005).
Developing a Malaria Vaccine Fact Sheet, Jul. 2009.
Daneshvar, Cyrus, Clinical Infectious Disease, vol. 49, pp. 852-860 (2009).
Dobano, C., et al., Molecular Immunology, vol. 44, pp. 3037-3048 (2007).
Dobano, Carlota, et al., Experimental Parasitology, vol. 122, pp. 112-123 (2009).
GenBank Locus DQ350294.2, Sep. 25, 2009.
Firat, Huseyin, et al., The Journal of Gene Medicine, vol. 4, pp. 38-45 (2002).
Gonzalez-Aseguinolaza, Gloria, et al., Journal of Virology, vol. 77, No. 21, pp. 11859-11866 (2003).
Ikeda, Yasuhiro, et al., Nature Biotechnology, vol. 21, pp. 569-572 (2003).
GenBank Locus J02695.1, Mar. 14, 1994.
GenBank Locus J03992.1, Mar. 14, 1994.
Jones, Stephanie, et al., Human Gene Therapy, vol. 20, pp. 630-640 (2009).
Kafri, Tal, et al., Journal of Virology, vol. 73, No. 1, pp. 576-584 (1999).
Limbach, K. J., Parasite Immunology, vol. 31, pp. 501-519 (2009).
GenBank Locus M15505.1, Apr. 26, 1993.
Maeda, Ken, et al., Viral Immunology, vol. 18, No. 4, pp. 657-667 (2005).
Miyahira, Y., et al., PNAS, vol. 95, pp. 3954-3959 (1998).
Nussenzweig, Victor, Am. J. Trop. Hyg., vol. 35, No. 4, pp. 678-688 (1986).
Ophorst, O. J. A. E., Infection and Immunity, vol. 74, No. 1, pp. 313-320 (2006).
Ophorst, Olga J. A. E., Vaccine, vol. 25, pp. 6501-6510 (2007).
Overstreet, M. G., Immunol. Rev., vol. 225, No. 1, pp. 272-283 (2008).
Rocha, C. D., International Microbiology, vol. 7, pp. 83-94 (2004).
Rodrigues, E. G., Journal of Immunology, vol. 158, pp. 1268-1274 (1997).

(Continued)

*Primary Examiner* — Brian J Gangle
(74) *Attorney, Agent, or Firm* — Law Office of Salvatore Arrigo and Scott Lee, LLP

(57) ABSTRACT

The invention relates to lentiviral vector particles pseudotyped with a determined heterologous viral envelope protein or viral envelope proteins originating from a RNA virus and which comprise in its genome at least one recombinant polynucleotide encoding at least one polypeptide(s) carrying epitope(s) of an antigen of a *Plasmodium* parasite capable of infecting a mammalian host. The lentiviral vector particles are used in order to elicit an immunological response against malaria parasites.

15 Claims, 15 Drawing Sheets

(56) References Cited

OTHER PUBLICATIONS

Figure 3:
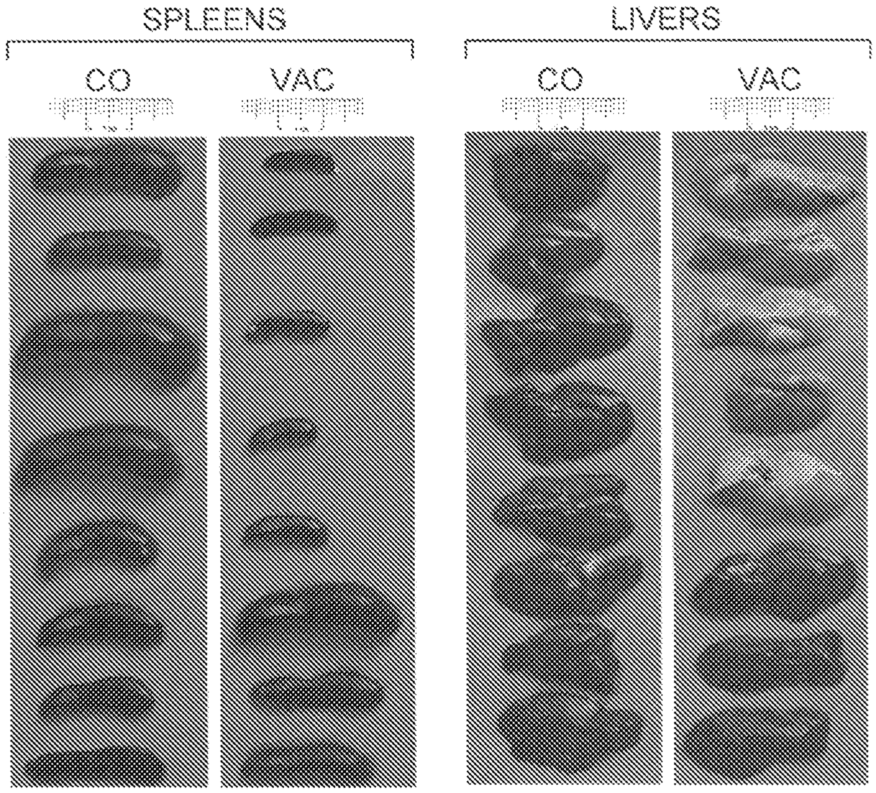

Speake, C., Parasite Immunology, vol. 31, pp. 539-546 (2009).
Tine, J. A., Infection and Immunity, vol. 64, No. 9, pp. 3833-3844 (1996).
GenBank Locus U65959.1, Nov. 7, 1996.
Vandendriessche, T., et al., Blood, vol. 100, No. 3, pp. 813-822 (2002).
Vaughan, K., et al., Parasite Immunology, vol. 31, pp. 78-97 (2009).
Xu, K., et al., Molecular Therapy, vol. 3, No. 1, pp. 97-104 (2001).
Zennou, V., et al., Cell, vol. 101, pp. 173-185 (2000).
Coutant, Frederic, et al., "A Nonintegrative Lentiviral Vector-Based Vaccine Provides Long-Term Sterile Protection Against Maleria," PLOS ONE, vol. 7, Issue 11, e48644, pp. 1-14 (2012).
Fenton, Brian, et al., "Structural and Antigenic Polymorphism of the 35- to 48-Kilodalton Merozoite Surface Antigen (MSA-2) of the Malaria Parasite *Plasmodium falciparum*," Moleculuar and Cellular Biology, vol. 11, No. 2, pp. 963-971 (1991).
Langhorn, Jean, et al., "Malaria," Encyclopedia of Immunology, pp. 1658-1663 (1998).
Marussig, M., et al., "Linear and multiple antigen peptides containing defined T and B epitopes of the *Plasmodium yoelii* circumsporozoite protein: antibody-mediated protection and boosting by sporozoite infection," International Immunology, vol. 9, No. 12, pp. 1817-1824 (1997).
Ramasamy, Ranjan, et al., "Antibodies and *Plasmodium falciparum* merozoites," Trends in Parasitology, vol. 17, No. 4, pp. 194-197 (2001).
Rzepczyk, Christine M., "Comparative Study of the T Cell Response to Two Alelic Forms of a Malarial Vaccine Candidate Protein," The Journal of Immunology, vol. 148, No. 4, pp. 1197-1204 (1992).
Sheehy, Susanne H., "Phase la Clinical Evaluation of the *Plasmodium falciparum* Blood-stage Antigen MSP1 in ChAd63 and MVA Vaccine Vectors," Molecular Therapy, pp. 1-8 (Aug. 23, 2011).
Tamminga, Cindy, et al., "Adenovirus-5-Vectored *P. falciparum* Faccine Expressing CSP and AMA1. Part B: Safety, Immunogenicity and Protective Efficacy of teh CSP Component," PLoS ONE, vol. 6, No. 10, e25868, pp. 1-20 (2011).
Tarun, Alice S., "Protracted Sterile Protection with *Plasmodium yoelii* Pre-erythrocytic Genetically Attenuated Parasite Malaria Vaccines Is Independent of Significant Liver-Stage Persistence and Is Mediated by CD8+ T Cells," The Journal of Infectious Diseases, vol. 196, pp. 608-616 (2007).
Mishra, Satish, et al., "Identification of non-CSP antigens bearing CD8 epitopes in mice immunized with irradiated sporozoites," Vaccine, vol. 29, pp. 7335-7342 (2011).
GenBank: M28887.1, Apr. 26, 1993.
GenBank: M60972.1, Apr. 26, 1993.

* cited by examiner

A
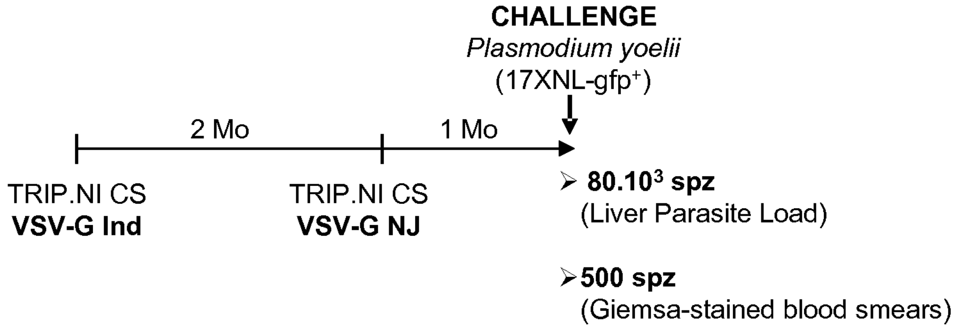
B
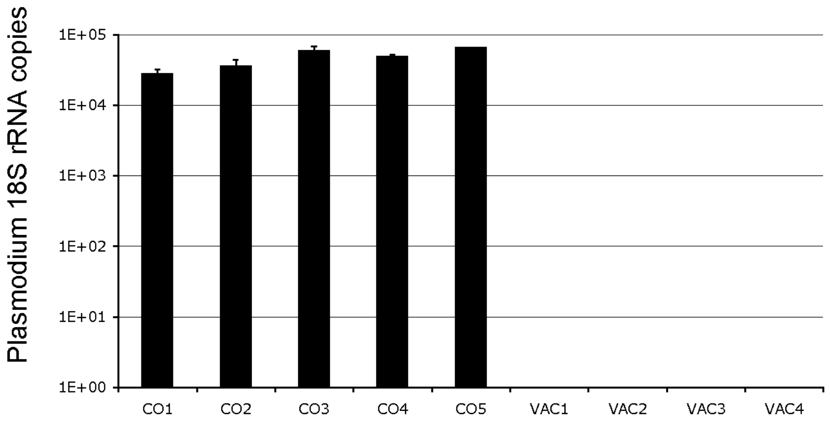
C
| | 3 | 4 | 5 | 6 | 7 | 8 | 9 | 10 | 11 | 12 | 13 | 14 |
|---|---|---|---|---|---|---|---|---|---|---|---|---|
| CO1 | 0 | 0 | 0 | 0 | + | + | + | + | + | + | + | + |
| CO2 | 0 | 0 | 0 | 0 | + | + | + | + | + | + | + | + |
| CO3 | 0 | 0 | 0 | 0 | + | + | + | + | + | + | + | + |
| CO4 | 0 | 0 | 0 | 0 | 0 | 0 | 0 | 0 | 0 | 0 | 0 | 0 |
| CO5 | 0 | 0 | 0 | 0 | + | + | + | + | + | + | + | + |
| VAC1 | 0 | 0 | 0 | 0 | + | + | + | + | + | + | + | + |
| VAC2 | 0 | 0 | 0 | 0 | + | + | + | + | + | + | + | + |
| VAC3 | 0 | 0 | 0 | 0 | 0 | 0 | 0 | 0 | 0 | 0 | 0 | 0 |
| VAC4 | 0 | 0 | 0 | 0 | 0 | 0 | 0 | 0 | 0 | 0 | 0 | 0 |
| VAC5 | 0 | 0 | 0 | 0 | 0 | 0 | 0 | 0 | 0 | 0 | 0 | 0 |
FIGURE 1

A
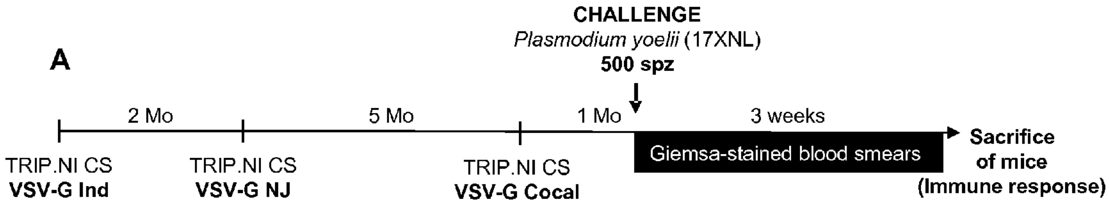
B
| | Protected/ Challenged | % sterile immunity |
|---|---|---|
| **CO** | 0/8 | 0 |
| **VAC** | *5/8* | *62,5* |
C D
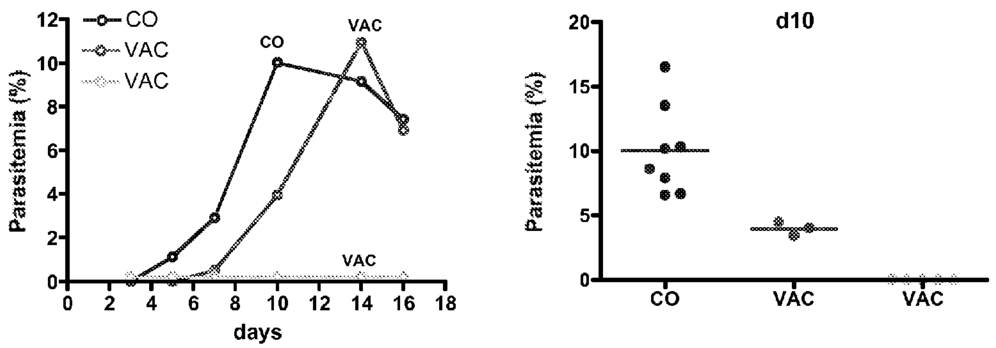
FIGURE 2

A. Hep17-specific CD4+ T cell responses
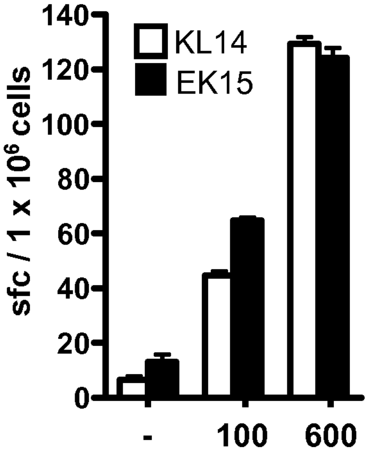
B. Hep17-specific CD8+ T cell responses
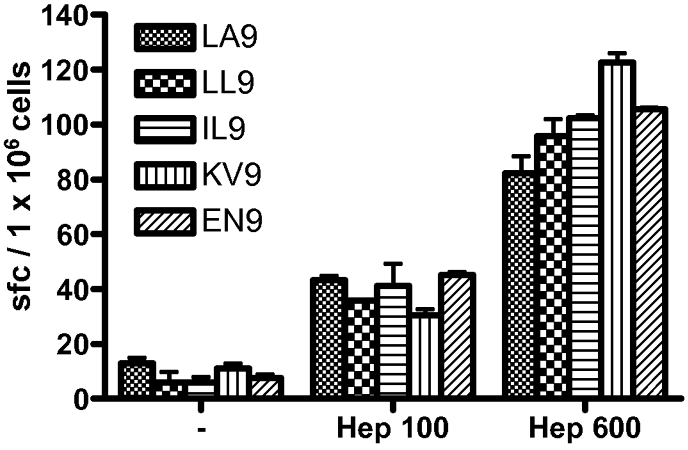
FIGURE 6

A. Hep17-specific CD4+ T cell responses
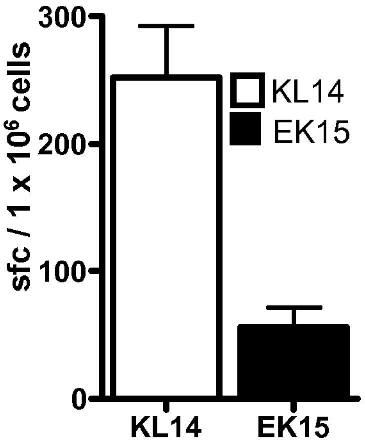
B. Hep17-specific CD8+ T cell responses
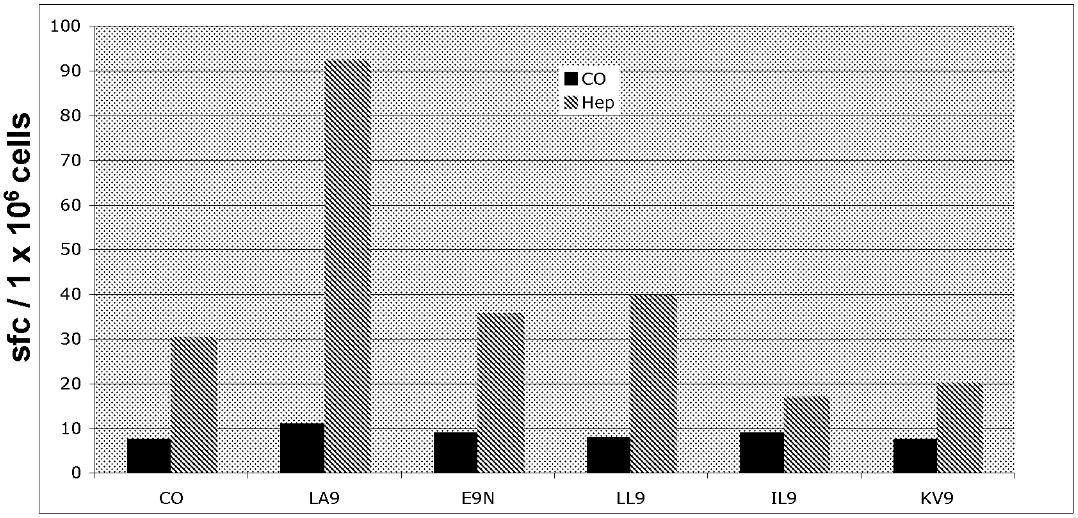
FIGURE 7

ALIGNEMENTS

```
                                   1                                                50
CSP Plasmodium falciparum    (1)   --------------------------------MMRKLAILSVSSFL
CSP Plasmodium yoleii        (1)   --------------------------------MKKCTILVVASLL
CSP Plasmodium berghei       (1)   --------------------------------MKKCTILVVASLL
CSP Plasmodium malariae      (1)   MKKLSVLAISSFLIVDFLFPGYHHNSNSTKSRNLSELCYNNVDTKLFNEL
CSP Plasmodium coatneyi      (1)   ----------------------------------MKNFILLAVSSIL
CSP Plasmodium knowlesi      (1)   ----------------------------------MRNFILLAVSSIL
CSP Plasmodium reichenowi    (1)   --------------------------------MMRKLAILSVSSFL
CSP Plasmodium gallinaceum   (1)   --------------------------------MKKLAILSASSFL
                Consensus    (1)                                   MKK   ILSVSSIL

                                   51                                               100
CSP Plasmodium falciparum    (15)  FVEALFQEYQCYGSSSNTRVLNELN--YDNAGTNLYNELEMNYYGKQENW
CSP Plasmodium yoleii        (14)  LVDSLLPGYGQNKSVQAQRNLNELCY------NEENDNKLYHVLNSKNG
CSP Plasmodium berghei       (14)  LVNSLLPGYGQNKIIQAQRNLNELCY------NEGNDNKLYHVLNSKNG
CSP Plasmodium malariae      (51)  EVRYSTNQDHFYNYNKTIRLLNENNNEKDGNVTNERKKKPTKAVENKLKQ
CSP Plasmodium coatneyi      (14)  LVDLFPTHFGHNVDLSRAINLNGVS----------FNNVDTSLLGAAQVR
CSP Plasmodium knowlesi      (14)  LVDLFPTHFEHNVDLSRAINVNGVS----------FNNVDTSSLGAAQVR
CSP Plasmodium reichenowi    (15)  FVEALFQEYQCYGSSSNTRVLNELNY--DNAGTNLYNELEMNYYGKQENW
CSP Plasmodium gallinaceum   (14)  FADPLFQEYQHNGNYKNFRLLNEVCY--NNMNIQLYNELEMENYMSNTYF
                Consensus    (51)  LVDAL Q Y N  LS RNLNEL Y       N YNELEM  HVG A N

                                   101                                              150
CSP Plasmodium falciparum    (63)  YSLKKNSRSLGENDDGNNEDNEKLRKP-----------KHKKLKQPADGN
CSP Plasmodium yoleii        (57)  KIYNRNIVNRLLGDALNGKPEEKKD--------------DPPKDGNKDD
CSP Plasmodium berghei       (57)  KIYNRNTVNRLLADAPEGKKNEKKN--------------EKIERNNKLK
CSP Plasmodium malariae     (101)  PPGDDDG---AGNDAGNDAGNDAGN-------------AAGNAAGNAAGN
CSP Plasmodium coatneyi      (54)  QSASRGRGLGEK--PKKKAEK---------------KEEEPKKPNENK
CSP Plasmodium knowlesi      (54)  QSASRGRGLGEK--RKEGADKEKKKE-----------KEEEPKKPNENK
CSP Plasmodium reichenowi    (63)  YSLKKNSRSLGENDDADNGDADNGDEGIDENRRHRNKEGKEKLKKPKHNK
CSP Plasmodium gallinaceum   (62)  YNNKKTIRLLGENDNEANVNRANNNVAND---------NRANGNRGNVNR
                Consensus   (101)     S  RN    G ND    AD EK               E   KKPN NK

                                   151                                              200
CSP Plasmodium falciparum   (102)  PDPNANPNVDPNANPNVDPNANPNVDPNANPNANPNANPNANPNANPNAN
CSP Plasmodium yoleii        (92)  LPKEEKKDDLPKEEKKDDPPKDPKKDDPPK-----EAQNKLNQPVVADEN
CSP Plasmodium berghei       (92)  QPP-------PPPNPNDPPPPNPNDPPPP-------------------N
CSP Plasmodium malariae     (135)  AAGNAAGNAAGNAAGNAAGNAAGNAAGNDAGNAAGNAAGNAAGNAAGNAA
CSP Plasmodium coatneyi      (85)  LKQPVDGARDGPA-PAADGARDGPAPAADGA-------RDGPAPAADGAR
CSP Plasmodium knowlesi      (90)  LKQPDQAAPGAGG-EQPAPGAGGEQPAPGAG--------GERPAPGAGGE-
CSP Plasmodium reichenowi   (113)  LKQPGNDNVDPNANPNVDPNANPNVDPNANP--------NVDPNANPNVD
CSP Plasmodium gallinaceum  (103)  ANDRNIPYFRENVVNLNQPVGGNGGVQPAGGNGGVQPAGGNGGVQPAGGN
                Consensus   (151)  L       PNA PN DP A PN   PAAG           A  A A AN

                                   201                                              250
CSP Plasmodium falciparum   (152)  PNANPNANPNANPNANPNANPNANPNANPNANPNANPNANPNANPNVDPN
CSP Plasmodium yoleii       (137)  VDQGPGAPQGPGAPQGPGAPQGPGAPQGPGAPQGPGAPQGPGAPQGPGAP
CSP Plasmodium berghei      (115)  PNDPP--PPNPNDPAPPNANDPAPPNANDPAPPNANDPAPPNANDPAPPN
CSP Plasmodium malariae     (185)  GNDAGNAAGNAAGNAAGNAAGNAAGNAAGNAAGNAAGNAAGNAAGNDAGN
CSP Plasmodium coatneyi     (127)  DGPAPAADGARDGPAPAADGARDGPAPAADGARDGPAPAADGARDGPAPP
CSP Plasmodium knowlesi     (131)  -QPAPGAGGE--QPAPGAGGERPAPGAGGEQPAPGAGGEQPAPGAGGEQP
CSP Plasmodium reichenowi   (155)  PNANPNVNPNANPNVDPNANPNVNPNANPNVNPNANPNVNPNANPNANPN
CSP Plasmodium gallinaceum  (153)  GGVQPAGGNGGVQPAGGNGGVQPAGGNGGVQPAGGNGGAQPVAAGGGAQP
                Consensus   (201)  N APAA  NA  PA PNAG N APNAGG AP  NANG ANPNA  GAAPP

                                   251                                              300
CSP Plasmodium falciparum   (202)  ANPNANPNANPNANPNANPNANPN--ANPNANPNANPNANPNANPNANPN
CSP Plasmodium yoleii       (187)  QGPGAPQGPGAPQGPGAPQGPGA----PQGPGAPQGPGAPQGPGAPQEPPQ
CSP Plasmodium berghei      (163)  ANDPAPPNANDPAPPNANDPP--------PPNPNDPAPPQGNNNPQ--PQ
CSP Plasmodium malariae     (235)  AAGNAAGNAAGNAAGNAAGNAAGN--AAGNAAGNAAGNAAGNAAGNAAGN
CSP Plasmodium coatneyi     (177)  ADGARDGPAPPAADGARDGPAP----PAADGARDGPAPPAGQGGN----
CSP Plasmodium knowlesi     (178)  APGAGGEQPAPGAGGERPAPGAGGERPAPGAGGEQPAPGAGGEQPA----
CSP Plasmodium reichenowi   (205)  ANPNANPNANPNANPNANPNAN------PNANPNANPNANPNANPNANPN
CSP Plasmodium gallinaceum  (203)  VVADGGVQPLRQEGDAEEDGGNGGAQPAGGNGGAQPAGGNGGAQPAGGNG
                Consensus   (251)  A G A   NA  PNAGPNA    A  G    PAG  AAPNAPA ANGNANPNA  PN
```

FIGURE 10(A)

```
CSP Plasmodium falciparum  (250) ANPNANPNANPNANPNANPNANPNKNNQGNGQGHNMPNDPNRNVDENANA
     CSP Plasmodium yoleii  (234) QPPQQPPQQPPQQPPQQPPQQPPQQ------------------PRPQPDG
    CSP Plasmodium berghei  (203) PRPQPQPQPQPQPQPQPQPQPRPQ-------------------PQPQPGG
   CSP Plasmodium malariae  (283) AAGNAAGNAAGNAAGNAAGNAAGNAAGNAAG------NEKAKNKDNKVDA
   CSP Plasmodium coatneyi  (219) ---AAGQAQGGGNAGNKKAGDAAGN-------------------------
   CSP Plasmodium knowlesi  (224) ---PAPRREQPAPGPGAGDGARGGN-------------------------
 CSP Plasmodium reichenowi  (249) ANPNANPNANPNANPNRNNEANGQGHN--------------KPNDQNRNV
CSP Plasmodium gallinaceum  (253) GAQPAGGNGGAQPAGGNDAAKPDGG-----------------NDDDKPE
                 Consensus  (301) A PNA PNANPN APN   NA GQ                    D N  A

                                  351                                            400
 CSP Plasmodium falciparum  (300) NSAVKNN---NNEE---PSDKHIKEYLNKIQNSLSTEWSPCSVTCGNGIQ
     CSP Plasmodium yoleii  (266) NNNNNNNNGNNNEDSYVPSAEQILEFVKQISSQLTEEWSQCSVTCGSGVR
    CSP Plasmodium berghei  (234) NNNNKNNN---NDDSYIPSAEKILEFVKQIRDSITEEWSQCNVTCGSGIR
   CSP Plasmodium malariae  (327) NTNKKDNQEENNDSSNGPSEEHIKNYLESIRNSITEEWSPCSVTCGSGIR
   CSP Plasmodium coatneyi  (241) -AGAAKGQGQNNEGANVPNEKVVNDYLQKIRSTVTTEWTPCSVTCGNGVR
   CSP Plasmodium knowlesi  (246) -AGAGKGQGQNNQGANVPNEKVVNDYLHKIRSSVTTEWTPCSVTCGNGVR
 CSP Plasmodium reichenowi  (285) NENANANNAGRNNNNEEPSDKHIEEFLKQIQNNLSTEWSPCSVTCGNGIQ
CSP Plasmodium gallinaceum  (285) GGDEKSEEEKEDEPIPDPTQEEIDKYLKSILGNVTSEWTNCNVTCGKGIQ
                 Consensus  (351) N N K NNG NNE S VPSEK I EYLK IR SLTTEWSPCSVTCGNGIR

                                  401                                            450
 CSP Plasmodium falciparum  (344) VRIKPGSANKPKDELDYANDIEKKICKMEKCS-SVFNVVNSSIGLIMVLS
     CSP Plasmodium yoleii  (316) VRKRKNVNKQ--PENLTLEDIDTEICKMDKCS-SIFNIVSNSLGFVILLV
    CSP Plasmodium berghei  (281) VRKRKGSNKK--AEDLTLEDIDTEICKMDKCS-SIFNIVSNSLGFVILLV
   CSP Plasmodium malariae  (377) ARRKVGAKNK-KPAELVLSDLETEICSLDKCS-SIFNVVSNSLGIVLVLV
   CSP Plasmodium coatneyi  (290) LRRKAHAEKK-KPEDLTMDDLDVEVCAMDKCA-GIFNFVSNSLGLVILLV
   CSP Plasmodium knowlesi  (295) IRRRQNAGNK-KAEDLTMDDLEVEACVMDKCA-GIFNVVSNSLGLVILLV
 CSP Plasmodium reichenowi  (335) VRIKPGSAGKPKDQLDYENDLEKKICKMEKCS-SVFNVVNSSIGLIMVLS
CSP Plasmodium gallinaceum  (335) AKIKSTSANK-KREEITPNDVEVKICELERCSFSIFNVISNSLGLAIILT
                 Consensus  (401) VRRK GSANK K EDLTLDDLE EICKMDKCS SIFNVVSNSLGLVILLV

                                  451
 CSP Plasmodium falciparum  (393) FLFLN
     CSP Plasmodium yoleii  (363) LVFFN
    CSP Plasmodium berghei  (328) LVFFN
   CSP Plasmodium malariae  (425) LILFH
   CSP Plasmodium coatneyi  (338) LAFN-
   CSP Plasmodium knowlesi  (343) LALFN
 CSP Plasmodium reichenowi  (384) FLFLN
CSP Plasmodium gallinaceum  (384) FLFFY
                 Consensus  (451) LLFFN
```

FIGURE 10(B)

pTRIP-DeltaU3-CMV-HEP17 CO-WPRE 4300 bp pTRIP-DeltaU3-CMV-Hep17 dSP CO WPRE 4261 bp pTRIP-DeltaU3-CMV-CSP dGPI CO WPRE 4858 bp

SEQUENCE LISTING

<160> NUMBER OF SEQ ID NOS: 90

<210> SEQ ID NO 1
<211> LENGTH: 33
<212> TYPE: DNA
<213> ORGANISM: artificial
<220> FEATURE:
<223> OTHER INFORMATION: oligonucleotide

<400> SEQUENCE: 1
ggtaccggat ccgccaccat gaagaaatgc acc 33

<210> SEQ ID NO 2
<211> LENGTH: 43
<212> TYPE: DNA
<213> ORGANISM: Artificial
<220> FEATURE:
<223> OTHER INFORMATION: oligonucleotide

<400> SEQUENCE: 2
agctcgagtc atcacaggct gttggacacg atgttgaaga tgc 43

<210> SEQ ID NO 3
<211> LENGTH: 17
<212> TYPE: PRT
<213> ORGANISM: artificial
<220> FEATURE:
<223> OTHER INFORMATION: sequence coding for the secretion signal of the calreticuline

<400> SEQUENCE: 3

```
Met Leu Leu Ser Val Pro Leu Leu Leu Gly Leu Leu Gly Leu Ala Val
1               5                   10                  15

Ala


<210> SEQ ID NO 4
<211> LENGTH: 25
<212> TYPE: DNA
<213> ORGANISM: artificial
<220> FEATURE:
<223> OTHER INFORMATION: primer

<400> SEQUENCE: 4

ggggattggt tttgacgttt ttgcg                                          25


<210> SEQ ID NO 5
<211> LENGTH: 30
<212> TYPE: DNA
<213> ORGANISM: Artificial
<220> FEATURE:
<223> OTHER INFORMATION: primer

<400> SEQUENCE: 5

aagcattaaa taaagcgaat acatccttat                                     30


<210> SEQ ID NO 6
<211> LENGTH: 9
<212> TYPE: PRT
<213> ORGANISM: Artificial
<220> FEATURE:
<223> OTHER INFORMATION: peptide from Plasmodium yoelii cs protein

<400> SEQUENCE: 6

Ser Tyr Val Pro Ser Ala Glu Gln Ile
1               5


<210> SEQ ID NO 7
<211> LENGTH: 10
<212> TYPE: PRT
<213> ORGANISM: Artificial
<220> FEATURE:
<223> OTHER INFORMATION: peptide from Plasmodium yoelii cs protein

<400> SEQUENCE: 7

Ile Tyr Asn Arg Asn Ile Val Asn Arg Leu
1               5                   10


<210> SEQ ID NO 8
<211> LENGTH: 16
<212> TYPE: PRT
<213> ORGANISM: Artificial
<220> FEATURE:
<223> OTHER INFORMATION: peptide from Plasmodium yoelii cs protein

<400> SEQUENCE: 8

Ser Tyr Val Pro Ser Ala Glu Gln Ile Leu Glu Phe Val Lys Gln Ile
1               5                   10                  15


<210> SEQ ID NO 9
<211> LENGTH: 14
<212> TYPE: PRT
<213> ORGANISM: Artificial
<220> FEATURE:
<223> OTHER INFORMATION: synthetic peptide from Plasmodium yoelii CSP

<400> SEQUENCE: 9
```

Lys Ile Tyr Asn Arg Asn Ile Val Asn Arg Leu Leu Gly Asp
1 5 10

<210> SEQ ID NO 10
<211> LENGTH: 21
<212> TYPE: PRT
<213> ORGANISM: Artificial
<220> FEATURE:
<223> OTHER INFORMATION: synthetic peptide from Plasmodium yoelii CSP

<400> SEQUENCE: 10

Tyr Asn Arg Asn Ile Val Asn Arg Leu Leu Gly Asp Ala Leu Asn Gly
1 5 10 15

Lys Pro Glu Glu Lys
20

<210> SEQ ID NO 11
<211> LENGTH: 9
<212> TYPE: PRT
<213> ORGANISM: Artificial
<220> FEATURE:
<223> OTHER INFORMATION: synthetic peptide from Plasmodium yoelii Hep17 protein

<400> SEQUENCE: 11

Leu Arg Lys Ile Asn Val Ala Leu Ala
1 5

<210> SEQ ID NO 12
<211> LENGTH: 9
<212> TYPE: PRT
<213> ORGANISM: Artificial
<220> FEATURE:
<223> OTHER INFORMATION: synthetic peptide from Plasmodium yoelii Hep17 protein

<400> SEQUENCE: 12

Glu Glu Ile Val Lys Leu Thr Lys Asn
1 5

<210> SEQ ID NO 13
<211> LENGTH: 9
<212> TYPE: PRT
<213> ORGANISM: Artificial
<220> FEATURE:
<223> OTHER INFORMATION: synthetic peptide from Plasmodium yoelii Hep17 protein

<400> SEQUENCE: 13

Lys Lys Ser Leu Arg Lys Ile Asn Val
1 5

<210> SEQ ID NO 14
<211> LENGTH: 9
<212> TYPE: PRT
<213> ORGANISM: Artificial
<220> FEATURE:
<223> OTHER INFORMATION: synthetic peptide from Plasmodium yoelii Hep17 protein

<400> SEQUENCE: 14

Ile Asn Val Ala Leu Ala Thr Ala Leu
1 5

<210> SEQ ID NO 15
<211> LENGTH: 9
<212> TYPE: PRT

<213> ORGANISM: Artificial
<220> FEATURE:
<223> OTHER INFORMATION: synthetic peptide from Plasmodium yoelii Hep17
protein

<400> SEQUENCE: 15

Leu Ser Val Val Ser Ala Ile Leu Leu
1 5

<210> SEQ ID NO 16
<211> LENGTH: 15
<212> TYPE: PRT
<213> ORGANISM: Artificial
<220> FEATURE:
<223> OTHER INFORMATION: synthetic peptide from Plasmodium yoelii Hep17
protein

<400> SEQUENCE: 16

Glu Glu Ile Val Lys Leu Thr Lys Asn Lys Lys Ser Leu Arg Lys
1 5 10 15

<210> SEQ ID NO 17
<211> LENGTH: 14
<212> TYPE: PRT
<213> ORGANISM: Artificial
<220> FEATURE:
<223> OTHER INFORMATION: synthetic peptide from Plasmodium yoelii Hep17
protein

<400> SEQUENCE: 17

Lys Ser Leu Arg Lys Ile Asn Val Ala Leu Ala Thr Ala Leu
1 5 10

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
cgtggatcca tggacggcat ggatctgctg 30

<210> SEQ ID NO 19
<211> LENGTH: 31
<212> TYPE: DNA
<213> ORGANISM: Artificial
<220> FEATURE:
<223> OTHER INFORMATION: primer

<400> SEQUENCE: 19
gatgaattcg gagctgctgc tgcagaacac g 31

<210> SEQ ID NO 20
<211> LENGTH: 367
<212> TYPE: PRT
<213> ORGANISM: Plasmodium yoelii
<220> FEATURE:
<221> NAME/KEY: MISC_FEATURE
<222> LOCATION: (1)..(367)
<223> OTHER INFORMATION: CSP protein

<400> SEQUENCE: 20

Met Lys Lys Cys Thr Ile Leu Val Val Ala Ser Leu Leu Leu Val Asp
1 5 10 15

Ser Leu Leu Pro Gly Tyr Gly Gln Asn Lys Ser Val Gln Ala Gln Arg
20 25 30

-continued

```
Asn Leu Asn Glu Leu Cys Tyr Asn Glu Glu Asn Asp Asn Lys Leu Tyr
        35                  40                  45

His Val Leu Asn Ser Lys Asn Gly Lys Ile Tyr Asn Arg Asn Ile Val
    50                  55                  60

Asn Arg Leu Leu Gly Asp Ala Leu Asn Gly Lys Pro Glu Glu Lys Lys
65                  70                  75                  80

Asp Asp Pro Pro Lys Asp Gly Asn Lys Asp Asp Leu Pro Lys Glu Glu
                85                  90                  95

Lys Lys Asp Asp Leu Pro Lys Glu Glu Lys Lys Asp Asp Pro Pro Lys
            100                 105                 110

Asp Pro Lys Lys Asp Asp Pro Pro Lys Glu Ala Gln Asn Lys Leu Asn
        115                 120                 125

Gln Pro Val Val Ala Asp Glu Asn Val Asp Gln Gly Pro Gly Ala Pro
    130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Gly Pro Gly Ala Pro Gln Gly Pro Gly Ala Pro Gln Gly
    210                 215                 220

Pro Gly Ala Pro Gln Glu Pro Pro Gln Gln Pro Pro Gln Gln Pro Pro
225                 230                 235                 240

Gln Gln Pro Pro Gln Gln Pro Pro Gln Gln Pro Pro Gln Gln Pro Pro
                245                 250                 255

Gln Gln Pro Arg Pro Gln Pro Asp Gly Asn Asn Asn Asn Asn Asn Asn
            260                 265                 270

Asn Gly Asn Asn Asn Glu Asp Ser Tyr Val Pro Ser Ala Glu Gln Ile
        275                 280                 285

Leu Glu Phe Val Lys Gln Ile Ser Ser Gln Leu Thr Glu Glu Trp Ser
    290                 295                 300

Gln Cys Ser Val Thr Cys Gly Ser Gly Val Arg Val Arg Lys Arg Lys
305                 310                 315                 320

Asn Val Asn Lys Gln Pro Glu Asn Leu Thr Leu Glu Asp Ile Asp Thr
                325                 330                 335

Glu Ile Cys Lys Met Asp Lys Cys Ser Ser Ile Phe Asn Ile Val Ser
            340                 345                 350

Asn Ser Leu Gly Phe Val Ile Leu Leu Val Leu Val Phe Phe Asn
        355                 360                 365


<210> SEQ ID NO 21
<211> LENGTH: 355
<212> TYPE: PRT
<213> ORGANISM: Plasmodium yoelii
<220> FEATURE:
<221> NAME/KEY: MISC_FEATURE
<222> LOCATION: (1)..(355)
<223> OTHER INFORMATION: CSP DGPI protein (deletion from residues
      GFVILLVLVFFN from CSP)

<400> SEQUENCE: 21

Met Lys Lys Cys Thr Ile Leu Val Val Ala Ser Leu Leu Leu Val Asp
1               5                   10                  15
```

-continued

```
Ser Leu Leu Pro Gly Tyr Gly Gln Asn Lys Ser Val Gln Ala Gln Arg
            20                  25                  30

Asn Leu Asn Glu Leu Cys Tyr Asn Glu Glu Asn Asp Asn Lys Leu Tyr
        35                  40                  45

His Val Leu Asn Ser Lys Asn Gly Lys Ile Tyr Asn Arg Asn Ile Val
    50                  55                  60

Asn Arg Leu Leu Gly Asp Ala Leu Asn Gly Lys Pro Glu Glu Lys Lys
65                  70                  75                  80

Asp Asp Pro Pro Lys Asp Gly Asn Lys Asp Asp Leu Pro Lys Glu Glu
                85                  90                  95

Lys Lys Asp Asp Leu Pro Lys Glu Glu Lys Lys Asp Asp Pro Pro Lys
            100                 105                 110

Asp Pro Lys Lys Asp Asp Pro Pro Lys Glu Ala Gln Asn Lys Leu Asn
        115                 120                 125

Gln Pro Val Val Ala Asp Glu Asn Val Asp Gln Gly Pro Gly Ala Pro
    130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Gly Pro Gly Ala Pro Gln Gly Pro Gly Ala Pro Gln Gly
    210                 215                 220

Pro Gly Ala Pro Gln Glu Pro Pro Gln Gln Pro Pro Gln Gln Pro Pro
225                 230                 235                 240

Gln Gln Pro Pro Gln Gln Pro Pro Gln Gln Pro Pro Gln Gln Pro Pro
                245                 250                 255

Gln Gln Pro Arg Pro Gln Pro Asp Gly Asn Asn Asn Asn Asn Asn Asn
            260                 265                 270

Asn Gly Asn Asn Asn Glu Asp Ser Tyr Val Pro Ser Ala Glu Gln Ile
        275                 280                 285

Leu Glu Phe Val Lys Gln Ile Ser Ser Gln Leu Thr Glu Glu Trp Ser
    290                 295                 300

Gln Cys Ser Val Thr Cys Gly Ser Gly Val Arg Val Arg Lys Arg Lys
305                 310                 315                 320

Asn Val Asn Lys Gln Pro Glu Asn Leu Thr Leu Glu Asp Ile Asp Thr
                325                 330                 335

Glu Ile Cys Lys Met Asp Lys Cys Ser Ser Ile Phe Asn Ile Val Ser
            340                 345                 350

Asn Ser Leu
        355
```

<210> SEQ ID NO 22
<211> LENGTH: 349
<212> TYPE: PRT
<213> ORGANISM: Plasmodium yoelii
<220> FEATURE:
<221> NAME/KEY: MISC_FEATURE
<222> LOCATION: (1)..(349)
<223> OTHER INFORMATION: CSP NTer protein (Deletion of residues 1-19
from CSP)

<400> SEQUENCE: 22

-continued

```
Met Pro Gly Tyr Gly Gln Asn Lys Ser Val Gln Ala Gln Arg Asn Leu
1               5                   10                  15

Asn Glu Leu Cys Tyr Asn Glu Glu Asn Asp Asn Lys Leu Tyr His Val
            20                  25                  30

Leu Asn Ser Lys Asn Gly Lys Ile Tyr Asn Arg Asn Ile Val Asn Arg
        35                  40                  45

Leu Leu Gly Asp Ala Leu Asn Gly Lys Pro Glu Glu Lys Lys Asp Asp
    50                  55                  60

Pro Pro Lys Asp Gly Asn Lys Asp Asp Leu Pro Lys Glu Glu Lys Lys
65                  70                  75                  80

Asp Asp Leu Pro Lys Glu Glu Lys Lys Asp Asp Pro Pro Lys Asp Pro
                85                  90                  95

Lys Lys Asp Asp Pro Pro Lys Glu Ala Gln Asn Lys Leu Asn Gln Pro
            100                 105                 110

Val Val Ala Asp Glu Asn Val Asp Gln Gly Pro Gly Ala Pro Gln Gly
        115                 120                 125

Pro Gly Ala Pro Gln Gly Pro Gly Ala Pro Gln Gly Pro Gly Ala Pro
    130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Glu Pro Pro Gln Gln Pro Pro Gln Gln Pro Pro Gln Gln
    210                 215                 220

Pro Pro Gln Gln Pro Pro Gln Gln Pro Pro Gln Gln Pro Pro Gln Gln
225                 230                 235                 240

Pro Arg Pro Gln Pro Asp Gly Asn Asn Asn Asn Asn Asn Asn Asn Gly
                245                 250                 255

Asn Asn Asn Glu Asp Ser Tyr Val Pro Ser Ala Glu Gln Ile Leu Glu
            260                 265                 270

Phe Val Lys Gln Ile Ser Ser Gln Leu Thr Glu Glu Trp Ser Gln Cys
        275                 280                 285

Ser Val Thr Cys Gly Ser Gly Val Arg Val Arg Lys Arg Lys Asn Val
    290                 295                 300

Asn Lys Gln Pro Glu Asn Leu Thr Leu Glu Asp Ile Asp Thr Glu Ile
305                 310                 315                 320

Cys Lys Met Asp Lys Cys Ser Ser Ile Phe Asn Ile Val Ser Asn Ser
                325                 330                 335

Leu Gly Phe Val Ile Leu Leu Val Leu Val Phe Phe Asn
            340                 345
```

<210> SEQ ID NO 23
<211> LENGTH: 397
<212> TYPE: PRT
<213> ORGANISM: Plasmodium falciparum
<220> FEATURE:
<221> NAME/KEY: MISC_FEATURE
<222> LOCATION: (1)..(397)
<223> OTHER INFORMATION: CSP protein

<400> SEQUENCE: 23

-continued

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Lys Asn Asn Gln Gly Asn Gly Gln Gly His Asn Met Pro Asn Asp
        275                 280                 285

Pro Asn Arg Asn Val Asp Glu Asn Ala Asn Ala Asn Ser Ala Val Lys
    290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
                325                 330                 335

Thr Cys Gly Asn Gly Ile Gln Val Arg Ile Lys Pro Gly Ser Ala Asn
            340                 345                 350

Lys Pro Lys Asp Glu Leu Asp Tyr Ala Asn Asp Ile Glu Lys Lys Ile
        355                 360                 365

Cys Lys Met Glu Lys Cys Ser Ser Val Phe Asn Val Val Asn Ser Ser
    370                 375                 380

Ile Gly Leu Ile Met Val Leu Ser Phe Leu Phe Leu Asn
385                 390                 395
```

<210> SEQ ID NO 24
<211> LENGTH: 368
<212> TYPE: PRT

<213> ORGANISM: Plasmodium falciparum
<220> FEATURE:
<221> NAME/KEY: MISC_FEATURE
<222> LOCATION: (1)..(368)
<223> OTHER INFORMATION: CSP DGPI protein

<400> SEQUENCE: 24

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Lys Asn Asn Gln Gly Asn Gly Gln Gly His Asn Met Pro Asn Asp
        275                 280                 285

Pro Asn Arg Asn Val Asp Glu Asn Ala Asn Ala Asn Ser Ala Val Lys
    290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
                325                 330                 335

Thr Cys Gly Asn Gly Ile Gln Val Arg Ile Lys Pro Gly Ser Ala Asn
            340                 345                 350

Lys Pro Lys Asp Glu Leu Asp Tyr Ala Asn Asp Ile Glu Lys Lys Ile
        355                 360                 365
```

<210> SEQ ID NO 25

-continued

<211> LENGTH: 378
<212> TYPE: PRT
<213> ORGANISM: Plasmodium falciparum
<220> FEATURE:
<221> NAME/KEY: MISC_FEATURE
<222> LOCATION: (1)..(378)
<223> OTHER INFORMATION: CSP NTer protein

<400> SEQUENCE: 25

```
Met Gln Glu Tyr Gln Cys Tyr Gly Ser Ser Ser Asn Thr Arg Val Leu
1               5                   10                  15

Asn Glu Leu Asn Tyr Asp Asn Ala Gly Thr Asn Leu Tyr Asn Glu Leu
            20                  25                  30

Glu Met Asn Tyr Tyr Gly Lys Gln Glu Asn Trp Tyr Ser Leu Lys Lys
        35                  40                  45

Asn Ser Arg Ser Leu Gly Glu Asn Asp Asp Gly Asn Asn Glu Asp Asn
    50                  55                  60

Glu Lys Leu Arg Lys Pro Lys His Lys Lys Leu Lys Gln Pro Ala Asp
65                  70                  75                  80

Gly Asn Pro Asp Pro Asn Ala Asn Pro Asn Val Asp Pro Asn Ala Asn
                85                  90                  95

Pro Asn Val Asp Pro Asn Ala Asn Pro Asn Val Asp Pro Asn Ala Asn
            100                 105                 110

Pro Asn Ala Asn Pro Asn Ala Asn Pro Asn Ala Asn Pro Asn Ala Asn
        115                 120                 125

Pro Asn Ala Asn Pro Asn Ala Asn Pro Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Val Asp Pro Asn Ala Asn Pro Asn Ala Asn Pro Asn Ala Asn
            180                 185                 190

Pro Asn Ala Asn Pro Asn Ala Asn Pro Asn Ala Asn Pro Asn Ala Asn
        195                 200                 205

Pro Asn Ala Asn Pro Asn Ala Asn Pro Asn Ala Asn Pro Asn Ala Asn
    210                 215                 220

Pro Asn Ala Asn Pro Asn Ala Asn Pro Asn Ala Asn Pro Asn Ala Asn
225                 230                 235                 240

Pro Asn Ala Asn Pro Asn Ala Asn Pro Asn Ala Asn Pro Asn Lys Asn
                245                 250                 255

Asn Gln Gly Asn Gly Gln Gly His Asn Met Pro Asn Asp Pro Asn Arg
            260                 265                 270

Asn Val Asp Glu Asn Ala Asn Ala Asn Ser Ala Val Lys Asn Asn Asn
        275                 280                 285

Asn Glu Glu Pro Ser Asp Lys His Ile Lys Glu Tyr Leu Asn Lys Ile
    290                 295                 300

Gln Asn Ser Leu Ser Thr Glu Trp Ser Pro Cys Ser Val Thr Cys Gly
305                 310                 315                 320

Asn Gly Ile Gln Val Arg Ile Lys Pro Gly Ser Ala Asn Lys Pro Lys
                325                 330                 335

Asp Glu Leu Asp Tyr Ala Asn Asp Ile Glu Lys Lys Ile Cys Lys Met
            340                 345                 350

Glu Lys Cys Ser Ser Val Phe Asn Val Val Asn Ser Ser Ile Gly Leu
        355                 360                 365
```

Ile Met Val Leu Ser Phe Leu Phe Leu Asn
370 375

<210> SEQ ID NO 26
<211> LENGTH: 329
<212> TYPE: PRT
<213> ORGANISM: Plasmodium berghei
<220> FEATURE:
<221> NAME/KEY: MISC_FEATURE
<222> LOCATION: (1)..(329)
<223> OTHER INFORMATION: CSP protein

<400> SEQUENCE: 26

Met Lys Lys Cys Thr Ile Leu Val Val Ala Ser Leu Leu Leu Val Asn
1 5 10 15

Ser Leu Leu Pro Gly Tyr Gly Gln Asn Lys Ile Ile Gln Ala Gln Arg
20 25 30

Asn Leu Asn Glu Leu Cys Tyr Asn Glu Gly Asn Asp Asn Lys Leu Tyr
35 40 45

His Val Leu Asn Ser Lys Asn Gly Lys Ile Tyr Asn Arg Asn Thr Val
50 55 60

Asn Arg Leu Leu Ala Asp Ala Pro Glu Gly Lys Lys Asn Glu Lys Lys
65 70 75 80

Asn Glu Lys Ile Glu Arg Asn Asn Lys Leu Lys Pro Pro Pro Asn Pro
85 90 95

Asn Asp Pro Pro Pro Pro Asn Pro Asn Asp Pro Pro Pro Pro Asn Pro
100 105 110

Asn Asp Pro Pro Pro Pro Asn Pro Asn Asp Pro Ala Pro Pro Asn Ala
115 120 125

Asn Asp Pro Ala Pro Pro Asn Ala Asn Asp Pro Ala Pro Pro Asn Ala
130 135 140

Asn Asp Pro Ala Pro Pro Asn Ala Asn Asp Pro Ala Pro Pro Asn Ala
145 150 155 160

Asn Asp Pro Ala Pro Pro Asn Ala Asn Asp Pro Ala Pro Pro Asn Ala
165 170 175

Asn Asp Pro Pro Pro Pro Asn Pro Asn Asp Pro Ala Pro Pro Gln Gly
180 185 190

Asn Asn Asn Pro Gln Pro Gln Pro Arg Pro Gln Pro Gln Pro Gln Pro
195 200 205

Gln Pro Gln Pro Gln Pro Gln Pro Gln Pro Gln Pro Arg Pro Gln Pro
210 215 220

Gln Pro Gln Pro Gly Gly Asn Asn Asn Asn Lys Asn Asn Asn Asn Asp
225 230 235 240

Asp Ser Tyr Ile Pro Ser Ala Glu Lys Ile Leu Glu Phe Val Lys Gln
245 250 255

Ile Arg Asp Ser Ile Thr Glu Glu Trp Ser Gln Cys Asn Val Thr Cys
260 265 270

Gly Ser Gly Ile Arg Val Arg Lys Arg Lys Gly Ser Asn Lys Lys Ala
275 280 285

Glu Asp Leu Thr Leu Glu Asp Ile Asp Thr Glu Ile Cys Lys Met Asp
290 295 300

Lys Cys Ser Ser Ile Phe Asn Ile Val Ser Asn Ser Leu Gly Phe Val
305 310 315 320

Ile Leu Leu Val Leu Val Phe Phe Asn
325

<210> SEQ ID NO 27
<211> LENGTH: 429
<212> TYPE: PRT
<213> ORGANISM: Plasmodium malariae
<220> FEATURE:
<221> NAME/KEY: MISC_FEATURE
<222> LOCATION: (1)..(429)
<223> OTHER INFORMATION: CSP protein

<400> SEQUENCE: 27

```
Met Lys Lys Leu Ser Val Leu Ala Ile Ser Ser Phe Leu Ile Val Asp
1               5                   10                  15

Phe Leu Phe Pro Gly Tyr His His Asn Ser Asn Ser Thr Lys Ser Arg
            20                  25                  30

Asn Leu Ser Glu Leu Cys Tyr Asn Asn Val Asp Thr Lys Leu Phe Asn
        35                  40                  45

Glu Leu Glu Val Arg Tyr Ser Thr Asn Gln Asp His Phe Tyr Asn Tyr
    50                  55                  60

Asn Lys Thr Ile Arg Leu Leu Asn Glu Asn Asn Asn Glu Lys Asp Gly
65                  70                  75                  80

Asn Val Thr Asn Glu Arg Lys Lys Lys Pro Thr Lys Ala Val Glu Asn
                85                  90                  95

Lys Leu Lys Gln Pro Pro Gly Asp Asp Asp Gly Ala Gly Asn Asp Ala
            100                 105                 110

Gly Asn Asp Ala Gly Asn Asp Ala Gly Asn Ala Ala Gly Asn Ala Ala
        115                 120                 125

Gly Asn Ala Ala Gly Asn Ala Ala Gly Asn Ala Ala Gly Asn Ala Ala
    130                 135                 140

Gly Asn Ala Ala Gly Asn Ala Ala Gly Asn Ala Ala Gly Asn Ala Ala
145                 150                 155                 160

Gly Asn Asp Ala Gly Asn Ala Ala Gly Asn Ala Ala Gly Asn Ala Ala
                165                 170                 175

Gly Asn Ala Ala Gly Asn Ala Ala Gly Asn Asp Ala Gly Asn Ala Ala
            180                 185                 190

Gly Asn Ala Ala Gly Asn Ala Ala Gly Asn Ala Ala Gly Asn Ala Ala
        195                 200                 205

Gly Asn Ala Ala Gly Asn Ala Ala Gly Asn Ala Ala Gly Asn Ala Ala
    210                 215                 220

Gly Asn Ala Ala Gly Asn Asp Ala Gly Asn Ala Ala Gly Asn Ala Ala
225                 230                 235                 240

Gly Asn Ala Ala Gly Asn Ala Ala Gly Asn Ala Ala Gly Asn Ala Ala
                245                 250                 255

Gly Asn Ala Ala Gly Asn Ala Ala Gly Asn Ala Ala Gly Asn Ala Ala
            260                 265                 270

Gly Asn Ala Ala Gly Asn Ala Ala Gly Asn Ala Ala Gly Asn Ala Ala
        275                 280                 285

Gly Asn Ala Ala Gly Asn Ala Ala Gly Asn Ala Ala Gly Asn Ala Ala
    290                 295                 300

Gly Asn Ala Ala Gly Asn Ala Ala Gly Asn Glu Lys Ala Lys Asn Lys
305                 310                 315                 320

Asp Asn Lys Val Asp Ala Asn Thr Asn Lys Lys Asp Asn Gln Glu Glu
                325                 330                 335

Asn Asn Asp Ser Ser Asn Gly Pro Ser Glu Glu His Ile Lys Asn Tyr
            340                 345                 350

Leu Glu Ser Ile Arg Asn Ser Ile Thr Glu Glu Trp Ser Pro Cys Ser
        355                 360                 365
```

```
Val Thr Cys Gly Ser Gly Ile Arg Ala Arg Arg Lys Val Gly Ala Lys
    370                 375                 380

Asn Lys Lys Pro Ala Glu Leu Val Leu Ser Asp Leu Glu Thr Glu Ile
385                 390                 395                 400

Cys Ser Leu Asp Lys Cys Ser Ser Ile Phe Asn Val Val Ser Asn Ser
                405                 410                 415

Leu Gly Ile Val Leu Val Leu Val Leu Ile Leu Phe His
            420                 425


<210> SEQ ID NO 28
<211> LENGTH: 344
<212> TYPE: PRT
<213> ORGANISM: Plasmodium coatneyi
<220> FEATURE:
<221> NAME/KEY: MISC_FEATURE
<222> LOCATION: (1)..(344)
<223> OTHER INFORMATION: CSP protein

<400> SEQUENCE: 28

Met Lys Asn Phe Ile Leu Leu Ala Val Ser Ser Ile Leu Leu Val Asp
1               5                   10                  15

Leu Phe Pro Thr His Phe Gly His Asn Val Asp Leu Ser Arg Ala Ile
            20                  25                  30

Asn Leu Asn Gly Val Ser Phe Asn Asn Val Asp Thr Ser Leu Leu Gly
        35                  40                  45

Ala Ala Gln Val Arg Gln Ser Ala Ser Arg Gly Arg Gly Leu Gly Glu
    50                  55                  60

Lys Pro Lys Lys Lys Ala Glu Lys Lys Glu Glu Glu Pro Lys Lys Pro
65                  70                  75                  80

Asn Glu Asn Lys Cys Ser Pro Leu Lys Gln Pro Val Asp Gly Ala Arg
                85                  90                  95

Asp Gly Pro Ala Pro Ala Ala Asp Gly Ala Arg Asp Gly Pro Ala Pro
            100                 105                 110

Ala Ala Asp Gly Ala Arg Asp Gly Pro Ala Pro Ala Ala Asp Gly Ala
        115                 120                 125

Arg Asp Gly Pro Ala Pro Ala Ala Asp Gly Ala Arg Asp Gly Pro Ala
    130                 135                 140

Pro Ala Ala Asp Gly Ala Arg Asp Gly Pro Ala Pro Ala Ala Asp Gly
145                 150                 155                 160

Ala Arg Asp Gly Pro Ala Pro Ala Ala Asp Gly Ala Arg Asp Gly Pro
                165                 170                 175

Ala Pro Pro Ala Asp Gly Ala Arg Asp Gly Pro Ala Pro Pro Ala Ala
            180                 185                 190

Asp Gly Ala Arg Asp Gly Pro Ala Pro Pro Ala Ala Asp Gly Ala Arg
        195                 200                 205

Asp Gly Pro Ala Pro Pro Ala Gly Gln Gly Gly Gly Asn Ala Ala Gly
    210                 215                 220

Gln Ala Gln Gly Gly Gly Asn Ala Gly Asn Lys Lys Ala Gly Asp Ala
225                 230                 235                 240

Ala Gly Asn Ala Gly Ala Ala Lys Gly Gln Gly Gln Asn Asn Glu Gly
                245                 250                 255

Ala Asn Val Pro Asn Glu Lys Val Val Asn Asp Tyr Leu Gln Lys Ile
            260                 265                 270

Arg Ser Thr Val Thr Thr Glu Trp Thr Pro Cys Ser Val Thr Cys Gly
        275                 280                 285
```

```
Asn Gly Val Arg Leu Arg Arg Lys Ala His Ala Glu Lys Lys Lys Pro
    290                 295                 300

Glu Asp Leu Thr Met Asp Asp Leu Asp Val Glu Val Cys Ala Met Asp
305                 310                 315                 320

Lys Cys Ala Gly Ile Phe Asn Phe Val Ser Asn Ser Leu Gly Leu Val
                325                 330                 335

Ile Leu Leu Val Leu Ala Phe Asn
            340


<210> SEQ ID NO 29
<211> LENGTH: 347
<212> TYPE: PRT
<213> ORGANISM: Plasmodium knowlesi
<220> FEATURE:
<221> NAME/KEY: MISC_FEATURE
<222> LOCATION: (1)..(347)
<223> OTHER INFORMATION: CSP protein

<400> SEQUENCE: 29

Met Arg Asn Phe Ile Leu Leu Ala Val Ser Ser Ile Leu Leu Val Asp
1               5                   10                  15

Leu Phe Pro Thr His Phe Glu His Asn Val Asp Leu Ser Arg Ala Ile
            20                  25                  30

Asn Val Asn Gly Val Ser Phe Asn Asn Val Asp Thr Ser Ser Leu Gly
        35                  40                  45

Ala Ala Gln Val Arg Gln Ser Ala Ser Arg Gly Arg Gly Leu Gly Glu
    50                  55                  60

Lys Arg Lys Glu Gly Ala Asp Lys Glu Lys Lys Lys Glu Lys Glu Glu
65                  70                  75                  80

Glu Pro Lys Lys Pro Asn Glu Asn Lys Leu Lys Gln Pro Asp Gln Ala
                85                  90                  95

Ala Pro Gly Ala Gly Gly Glu Gln Pro Ala Pro Gly Ala Gly Gly Glu
            100                 105                 110

Gln Pro Ala Pro Gly Ala Gly Gly Glu Arg Pro Ala Pro Gly Ala Gly
        115                 120                 125

Gly Glu Gln Pro Ala Pro Gly Ala Gly Gly Glu Gln Pro Ala Pro Gly
    130                 135                 140

Ala Gly Gly Glu Arg Pro Ala Pro Gly Ala Gly Gly Glu Gln Pro Ala
145                 150                 155                 160

Pro Gly Ala Gly Gly Glu Gln Pro Ala Pro Gly Ala Gly Gly Glu Gln
                165                 170                 175

Pro Ala Pro Gly Ala Gly Gly Glu Gln Pro Ala Pro Gly Ala Gly Gly
            180                 185                 190

Glu Arg Pro Ala Pro Gly Ala Gly Gly Glu Arg Pro Ala Pro Gly Ala
        195                 200                 205

Gly Gly Glu Gln Pro Ala Pro Gly Ala Gly Gly Glu Gln Pro Ala Pro
    210                 215                 220

Ala Pro Arg Arg Glu Gln Pro Ala Pro Gly Pro Gly Ala Gly Asp Gly
225                 230                 235                 240

Ala Arg Gly Gly Asn Ala Gly Ala Gly Lys Gly Gln Gly Gln Asn Asn
                245                 250                 255

Gln Gly Ala Asn Val Pro Asn Glu Lys Val Val Asn Asp Tyr Leu His
            260                 265                 270

Lys Ile Arg Ser Ser Val Thr Thr Glu Trp Thr Pro Cys Ser Val Thr
        275                 280                 285

Cys Gly Asn Gly Val Arg Ile Arg Arg Arg Gln Asn Ala Gly Asn Lys
```

```
    290                 295                 300

Lys Ala Glu Asp Leu Thr Met Asp Asp Leu Glu Val Glu Ala Cys Val
305                 310                 315                 320

Met Asp Lys Cys Ala Gly Ile Phe Asn Val Val Ser Asn Ser Leu Gly
                325                 330                 335

Leu Val Ile Leu Leu Val Leu Ala Leu Phe Asn
            340                 345


<210> SEQ ID NO 30
<211> LENGTH: 388
<212> TYPE: PRT
<213> ORGANISM: Plasmodium reichenowi

<400> SEQUENCE: 30

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Ala Asp Asn
65                  70                  75                  80

Gly Asp Ala Asp Asn Gly Asp Glu Gly Ile Asp Glu Asn Arg Arg His
                85                  90                  95

Arg Asn Lys Glu Gly Lys Glu Lys Leu Lys Lys Pro Lys His Asn Lys
            100                 105                 110

Leu Lys Gln Pro Gly Asn Asp Asn Val Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Val Asp Pro Asn Ala Asn Pro Asn
145                 150                 155                 160

Val Asn Pro Asn Ala Asn Pro Asn Val Asp Pro Asn Ala Asn Pro Asn
                165                 170                 175

Val Asn Pro Asn Ala Asn Pro Asn Val Asn Pro Asn Ala Asn Pro Asn
            180                 185                 190

Val Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Arg Asn Asn Glu Ala Asn Gly Gln
            260                 265                 270

Gly His Asn Lys Pro Asn Asp Gln Asn Arg Asn Val Asn Glu Asn Ala
        275                 280                 285

Asn Ala Asn Asn Ala Gly Arg Asn Asn Asn Asn Glu Glu Pro Ser Asp
    290                 295                 300

Lys His Ile Glu Glu Phe Leu Lys Gln Ile Gln Asn Asn Leu Ser Thr
305                 310                 315                 320
```

```
Glu Trp Ser Pro Cys Ser Val Thr Cys Gly Asn Gly Ile Gln Val Arg
                325                 330                 335

Ile Lys Pro Gly Ser Ala Gly Lys Pro Lys Asp Gln Leu Asp Tyr Glu
            340                 345                 350

Asn Asp Leu Glu Lys Lys Ile Cys Lys Met Glu Lys Cys Ser Ser Val
        355                 360                 365

Phe Asn Val Val Asn Ser Ser Ile Gly Leu Ile Met Val Leu Ser Phe
    370                 375                 380

Leu Phe Leu Asn
385


<210> SEQ ID NO 31
<211> LENGTH: 388
<212> TYPE: PRT
<213> ORGANISM: Plasmodium gallinaceum

<400> SEQUENCE: 31

Met Lys Lys Leu Ala Ile Leu Ser Ala Ser Ser Phe Leu Phe Ala Asp
1               5                   10                  15

Phe Leu Phe Gln Glu Tyr Gln His Asn Gly Asn Tyr Lys Asn Phe Arg
            20                  25                  30

Leu Leu Asn Glu Val Cys Tyr Asn Asn Met Asn Ile Gln Leu Tyr Asn
        35                  40                  45

Glu Leu Glu Met Glu Asn Tyr Met Ser Asn Thr Tyr Phe Tyr Asn Asn
    50                  55                  60

Lys Lys Thr Ile Arg Leu Leu Gly Glu Asn Asp Asn Glu Ala Asn Val
65                  70                  75                  80

Asn Arg Ala Asn Asn Asn Val Ala Asn Asp Asn Arg Ala Asn Gly Asn
                85                  90                  95

Arg Gly Asn Val Asn Arg Ala Asn Asp Arg Asn Ile Pro Tyr Phe Arg
            100                 105                 110

Glu Asn Val Val Asn Leu Asn Gln Pro Val Gly Gly Asn Gly Gly Val
        115                 120                 125

Gln Pro Ala Gly Gly Asn Gly Gly Val Gln Pro Ala Gly Gly Asn Gly
    130                 135                 140

Gly Val Gln Pro Ala Gly Gly Asn Gly Gly Val Gln Pro Ala Gly Gly
145                 150                 155                 160

Asn Gly Gly Val Gln Pro Ala Gly Gly Asn Gly Gly Val Gln Pro Ala
                165                 170                 175

Gly Gly Asn Gly Gly Val Gln Pro Ala Gly Gly Asn Gly Gly Ala Gln
            180                 185                 190

Pro Val Ala Ala Gly Gly Gly Ala Gln Pro Val Val Ala Asp Gly Gly
        195                 200                 205

Val Gln Pro Leu Arg Gln Glu Gly Asp Ala Glu Glu Asp Gly Gly Asn
    210                 215                 220

Gly Gly Ala Gln Pro Ala Gly Gly Asn Gly Gly Ala Gln Pro Ala Gly
225                 230                 235                 240

Gly Asn Gly Gly Ala Gln Pro Ala Gly Gly Asn Gly Gly Ala Gln Pro
                245                 250                 255

Ala Gly Gly Asn Gly Gly Ala Gln Pro Ala Gly Gly Asn Asp Ala Ala
            260                 265                 270

Lys Pro Asp Gly Gly Asn Asp Asp Asp Lys Pro Glu Gly Gly Asp Glu
        275                 280                 285

Lys Ser Glu Glu Glu Lys Glu Asp Glu Pro Ile Pro Asp Pro Thr Gln
    290                 295                 300
```

```
Glu Glu Ile Asp Lys Tyr Leu Lys Ser Ile Leu Gly Asn Val Thr Ser
305                 310                 315                 320

Glu Trp Thr Asn Cys Asn Val Thr Cys Gly Lys Gly Ile Gln Ala Lys
                325                 330                 335

Ile Lys Ser Thr Ser Ala Asn Lys Lys Arg Glu Glu Ile Thr Pro Asn
            340                 345                 350

Asp Val Glu Val Lys Ile Cys Glu Leu Glu Arg Cys Ser Phe Ser Ile
        355                 360                 365

Phe Asn Val Ile Ser Asn Ser Leu Gly Leu Ala Ile Ile Leu Thr Phe
    370                 375                 380

Leu Phe Phe Tyr
385


<210> SEQ ID NO 32
<211> LENGTH: 258
<212> TYPE: PRT
<213> ORGANISM: Consensus

<400> SEQUENCE: 32

Met Lys Lys Ile Leu Ser Val Ser Ser Ile Leu Leu Val Asp Ala Leu
1               5                   10                  15

Gln Tyr Asn Leu Ser Arg Asn Leu Asn Glu Leu Tyr Asn Tyr Asn Glu
            20                  25                  30

Leu Glu Met His Val Gly Ala Asn Ser Arg Asn Gly Asn Asp Ala Asp
        35                  40                  45

Glu Lys Glu Lys Lys Pro Asn Asn Lys Leu Pro Asn Ala Pro Asn Asp
    50                  55                  60

Pro Ala Pro Asn Pro Ala Ala Gly Ala Ala Ala Ala Asn Asn Ala Pro
65                  70                  75                  80

Ala Ala Asn Ala Pro Ala Pro Asn Ala Gly Asn Ala Pro Asn Ala Gly
                85                  90                  95

Gly Ala Pro Asn Ala Asn Gly Ala Asn Pro Asn Ala Gly Ala Ala Pro
            100                 105                 110

Pro Ala Gly Ala Asn Ala Pro Asn Ala Gly Pro Asn Ala Ala Gly Pro
        115                 120                 125

Ala Gly Ala Ala Pro Asn Ala Pro Ala Ala Asn Gly Asn Ala Asn Pro
    130                 135                 140

Asn Ala Pro Asn Ala Pro Asn Ala Pro Asn Ala Asn Pro Asn Ala Pro
145                 150                 155                 160

Asn Asn Ala Gly Gln Asp Asn Ala Asn Asn Lys Asn Asn Gly Asn Asn
                165                 170                 175

Glu Ser Val Pro Ser Glu Lys Ile Glu Tyr Leu Lys Ile Arg Ser Leu
            180                 185                 190

Thr Thr Glu Trp Ser Pro Cys Ser Val Thr Cys Gly Asn Gly Ile Arg
        195                 200                 205

Val Arg Arg Lys Gly Ser Ala Asn Lys Lys Glu Asp Leu Thr Leu Asp
    210                 215                 220

Asp Leu Glu Glu Ile Cys Lys Met Asp Lys Cys Ser Ser Ile Phe Asn
225                 230                 235                 240

Val Val Ser Asn Ser Leu Gly Leu Val Ile Leu Leu Val Leu Leu Phe
                245                 250                 255

Phe Asn


<210> SEQ ID NO 33
```

<211> LENGTH: 4024
<212> TYPE: DNA
<213> ORGANISM: Artificial
<220> FEATURE:
<223> OTHER INFORMATION: PLASMID pTRIP-DeltaU3-CMVeGFP

<400> SEQUENCE: 33
tggaagggct aattcactcc caacgaagac aagatatcct tgatctgtgg atctaccaca 60
cacaaggcta cttccctgat tagcagaact acacaccagg gccagggatc agatatccac 120
tgacctttgg atggtgctac aagctagtac cagttgagcc agagaagtta gaagaagcca 180
acaaaggaga gaacaccagc ttgttacaac ctgtgagcct gcatgggatg gatgacccgg 240
agagagaagt gttagagtgg aggtttgaca gccgcctagc atttcatcac ggtggcccga 300
gagctgcatc cggagtactt caagaactgc tgatatcgag cttgctacaa gggactttcc 360
gctgggggac tttccaggga ggcgtggcct gggcgggact ggggagtggc gagccctcag 420
atcctgcata taagcagctg ctttttgcct gtactgggtc tctctggtta gaccagatct 480
gagcctggga gctctctggc taactaggga acccactgct taagcctcaa taaagcttgc 540
cttgagtgct tcaagtagtg tgtgcccgtc tgttgtgtga ctctggtaac tagagatccc 600
tcagaccctt ttagtcagtg tggaaaatct ctagcagtgg cgcccgaaca gggacttgaa 660
agcgaaaggg aaaccagagg agctctctcg acgcaggact cggcttgctg aagcgcgcac 720
ggcaagaggc gaggggcggc gactggtgag tacgccaaaa attttgacta gcggaggcta 780
gaaggagaga gatgggtgcg agagcgtcag tattaagcgg gggagaatta gatcgcgatg 840
ggaaaaaatt cggttaaggc cagggggaaa gaaaaaatat aaattaaaac atatagtatg 900
ggcaagcagg gagctagaac gattcgcagt taatcctggc ctgttagaaa catcagaagg 960
ctgtagacaa atactgggac agctacaacc atcccttcag acaggatcag aagaacttag 1020
atcattatat aatacagtag caaccctcta ttgtgtgcat caaaggatag agataaaaga 1080
caccaaggaa gctttagaca agatagagga agagcaaaac aaaagtaaga ccaccgcaca 1140
gcaagcggcc gctgatcttc agacctggag gaggagatat gagggacaat tggagaagtg 1200
aattatataa atataaagta gtaaaaattg aaccattagg agtagcaccc accaaggcaa 1260
agagaagagt ggtgcagaga gaaaaaagag cagtgggaat aggagctttg ttccttgggt 1320
tcttgggagc agcaggaagc actatgggcg cagcgtcaat gacgctgacg gtacaggcca 1380
gacaattatt gtctggtata gtgcagcagc agaacaattt gctgagggct attgaggcgc 1440
aacagcatct gttgcaactc acagtctggg gcatcaagca gctccaggca agaatcctgg 1500
ctgtggaaag atacctaaag gatcaacagc tcctggggat ttggggttgc tctggaaaac 1560
tcatttgcac cactgctgtg ccttggaatg ctagttggag taataaatct ctggaacaga 1620
tttggaatca cacgacctgg atggagtggg acagagaaat taacaattac acaagcttaa 1680
tacactcctt aattgaagaa tcgcaaaacc agcaagaaaa gaatgaacaa gaattattgg 1740
aattagataa atgggcaagt ttgtggaatt ggtttaacat aacaaattgg ctgtggtata 1800
taaaattatt cataatgata gtaggaggct tggtaggttt aagaatagtt tttgctgtac 1860
tttctatagt gaatagagtt aggcagggat attcaccatt atcgtttcag acccacctcc 1920
caaccccgag gggacccgac aggcccgaag gaatagaaga agaaggtgga gagagagaca 1980
gagacagatc cattcgatta gtgaacggat ctcgacggta tcgccgaatt cacaaatggc 2040
agtattcatc cacaatttta aaagaaaagg ggggattggg gggtacagtg caggggaaag 2100
aatagtagac ataatagcaa cagacataca aactaaagaa ttacaaaaac aaattacaaa 2160

```
aattcaaaat tttcgggttt attacaggga cagcagagat ccactttggg gcgataagct   2220
tgggagttcc gcgttacata acttacggta aatggcccgc ctggctgacc gcccaacgac   2280
ccccgcccat tgacgtcaat aatgacgtat gttcccatag taacgccaat agggactttc   2340
cattgacgtc aatgggtgga gtatttacgg taaactgccc acttggcagt acatcaagtg   2400
tatcatatgc caagtacgcc ccctattgac gtcaatgacg gtaaatggcc cgcctggcat   2460
tatgcccagt acatgacctt atgggacttt cctacttggc agtacatcta cgtattagtc   2520
atcgctatta ccatggtgat gcggttttgg cagtacatca atgggcgtgg atagcggttt   2580
gactcacggg gatttccaag tctccacccc attgacgtca atgggagttt gttttggcac   2640
caaaatcaac gggactttcc aaaatgtcgt aacaactccg ccccattgac gcaaatgggc   2700
ggtaggcgtg tacggtggga ggtctatata agcagagctc gtttagtgaa ccgtcagatc   2760
gcctggagac gccatccacg ctgttttgac ctccatagaa gacaccgact ctagaggatc   2820
cccaccggtc gccaccatgg tgagcaaggg cgaggagctg ttcaccgggg tggtgcccat   2880
cctggtcgag ctggacggcg acgtaaacgg ccacaagttc agcgtgtccg gcgagggcga   2940
gggcgatgcc acctacggca agctgaccct gaagttcatc tgcaccaccg gcaagctgcc   3000
cgtgccctgg cccaccctcg tgaccaccct gacctacggc gtgcagtgct tcagccgcta   3060
ccccgaccac atgaagcagc acgacttctt caagtccgcc atgcccgaag gctacgtcca   3120
ggagcgcacc atcttcttca aggacgacgg caactacaag acccgcgccg aggtgaagtt   3180
cgagggcgac accctggtga accgcatcga gctgaagggc atcgacttca aggaggacgg   3240
caacatcctg gggcacaagc tggagtacaa ctacaacagc cacaacgtct atatcatggc   3300
cgacaagcag aagaacggca tcaaggtgaa cttcaagatc cgccacaaca tcgaggacgg   3360
cagcgtgcag ctcgccgacc actaccagca gaacaccccc atcggcgacg gccccgtgct   3420
gctgcccgac aaccactacc tgagcaccca gtccgccctg agcaaagacc ccaacgagaa   3480
gcgcgatcac atggtcctgc tggagttcgt gaccgccgcc gggatcactc tcggcatgga   3540
cgagctgtac aagtaaagcg gccggactct agctcgagac ctagaaaaac atggagcaat   3600
cacaagtagc aatacagcag ctaccaatgc tgattgtgcc tggctagaag cacaagagga   3660
ggaggaggtg ggttttccag tcacacctca ggtaccttta agaccaatga cttacaaggc   3720
agctgtagat cttagccact ttttaaaaga aaaggggga ctggaagggc taattcactc    3780
ccaacgaaga caagatcgtc gagagatgct gcatataagc agctgctttt tgcttgtact   3840
gggtctctct ggttagacca gatctgagcc tgggagctct ctggctaact agggaaccca   3900
ctgcttaagc ctcaataaag cttgccttga gtgcttcaag tagtgtgtgc ccgtctgttg   3960
tgtgactctg gtaactagag atccctcaga cccttttagt cagtgtggaa aatctctagc   4020
agtg                                                                4024
```

```
<210> SEQ ID NO 34
<211> LENGTH: 4927
<212> TYPE: DNA
<213> ORGANISM: Artificial
<220> FEATURE:
<223> OTHER INFORMATION: plasmid pTRIP-deltaU3-CMV-MSP142 CO-WPRE
<220> FEATURE:
<221> NAME/KEY: misc_feature
<222> LOCATION: (1)..(4927)
<223> OTHER INFORMATION: Complete nucleotide sequence of the provirus

<400> SEQUENCE: 34
```

-continued

```
tggaagggct aattcactcc caacgaagac aagatatcct tgatctgtgg atctaccaca     60
cacaaggcta cttccctgat tagcagaact acacaccagg gccagggatc agatatccac    120
tgacctttgg atggtgctac aagctagtac cagttgagcc agagaagtta gaagaagcca    180
acaaaggaga gaacaccagc ttgttacaac ctgtgagcct gcatgggatg gatgacccgg    240
agagagaagt gttagagtgg aggtttgaca gccgcctagc atttcatcac ggtggcccga    300
gagctgcatc cggagtactt caagaactgc tgatatcgag cttgctacaa gggactttcc    360
gctgggggac tttccaggga ggcgtggcct gggcgggact ggggagtggc gagccctcag    420
atcctgcata taagcagctg ctttttgcct gtactgggtc tctctggtta gaccagatct    480
gagcctggga gctctctggc taactaggga acccactgct taagcctcaa taaagcttgc    540
cttgagtgct tcaagtagtg tgtgcccgtc tgttgtgtga ctctggtaac tagagatccc    600
tcagaccctt ttagtcagtg tggaaaatct ctagcagtgg cgcccgaaca gggacttgaa    660
agcgaaaggg aaaccagagg agctctctcg acgcaggact cggcttgctg aagcgcgcac    720
ggcaagaggc gaggggcggc gactggtgag tacgccaaaa attttgacta gcggaggcta    780
gaaggagaga gatgggtgcg agagcgtcag tattaagcgg gggagaatta gatcgcgatg    840
ggaaaaaatt cggttaaggc cagggggaaa gaaaaaatat aaattaaaac atatagtatg    900
ggcaagcagg gagctagaac gattcgcagt taatcctggc ctgttagaaa catcagaagg    960
ctgtagacaa atactgggac agctacaacc atcccttcag acaggatcag aagaacttag   1020
atcattatat aatacagtag caaccctcta ttgtgtgcat caaaggatag agataaaaga   1080
caccaaggaa gctttagaca agatagagga agagcaaaac aaaagtaaga ccaccgcaca   1140
gcaagcggcc gctgatcttc agacctggag gaggagatat gagggacaat tggagaagtg   1200
aattatataa atataaagta gtaaaaattg aaccattagg agtagcaccc accaaggcaa   1260
agagaagagt ggtgcagaga gaaaaaagag cagtgggaat aggagctttg ttccttgggt   1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag atacctaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
ggagttccgc gttacataac ttacggtaaa tggcccgcct ggctgaccgc ccaacgaccc   2280
ccgcccattg acgtcaataa tgacgtatgt tcccatagta acgccaatag ggactttcca   2340
ttgacgtcaa tgggtggagt atttacggta aactgcccac ttggcagtac atcaagtgta   2400
```

```
tcatatgcca agtacgcccc ctattgacgt caatgacggt aaatggcccg cctggcatta   2460
tgcccagtac atgaccttat gggactttcc tacttggcag tacatctacg tattagtcat   2520
cgctattacc atggtgatgc ggttttggca gtacatcaat gggcgtggat agcggtttga   2580
ctcacgggga tttccaagtc tccaccccat tgacgtcaat gggagtttgt tttggcacca   2640
aaatcaacgg gactttccaa aatgtcgtaa caactccgcc ccattgacgc aaatgggcgg   2700
taggcgtgta cggtgggagg tctatataag cagagctcgt ttagtgaacc gtcagatcgc   2760
ctggagacgc catccacgct gttttgacct ccatagaaga caccgcgatc ggatccgcca   2820
ccatgctgct gtccgtgccc ctgctgctgg gcctgctggg actggccgtg gccgctcccg   2880
agaaggacat cctgagcgag ttcaccaacg agagcctgta cgtgtacaca aagagactgg   2940
gcagcaccta caagagcctg aagaaacaca tgctgcggga gttcagcacc atcaaagaag   3000
atatgaccaa cggcctgaac aacaagagcc agaagcggaa cgacttcctg gaggtgctgt   3060
cccacgagct ggacctgttc aaggacctga gcaccaataa gtacgtgatc cggaacccct   3120
accagctgct ggacaacgac aagaaggaca agcagatcgt caacctgaag tacgccacca   3180
agggcatcaa cgaggatatc gagacaacca ccgacggcat caagttcttc aacaagatgg   3240
tggagctgta caacacccag ctggccgccg tgaaggagca gatcgccacc atcgaggccg   3300
agacaaacga cacaaacaag gaggagaaga agaagtacat ccccatcctg gaggacctga   3360
agggcctgta cgagacagtg attggccagg ccgaggagta cagcgaggag ctgcagaaca   3420
gactggataa ctacaagaac gagaaggccg agttcgagat cctgaccaag aacctggaga   3480
agtacatcca gatcgacgag aagctggacg agttcgtgga gcacgccgag aacaacaagc   3540
atatcgcctc tatcgccctg aacaacctga ataagagcgg cctggtggga gagggcgaga   3600
gcaaaaagat cctggctaag atgctgaaca tggacggcat ggatctgctg ggcgtggacc   3660
ccaagcacgt gtgcgtggac accagagaca tccccaagaa cgccggctgc ttcagggacg   3720
acaacggcac cgaggagtgg agatgtctgc tgggctacaa gaagggcgag ggcaacacct   3780
gcgtggagaa caataacccc acctgcgaca tcaacaacgg cggctgcgac cccaccgcca   3840
gctgccagaa cgccgagagc accgagaact ccaagaagat catctgcacc tgcaaggagc   3900
ccacccccaa cgcctactac gagggcgtgt tctgcagcag cagctccttc atgggctgat   3960
gactcgagct caagcttcga attcccgata atcaacctct ggattacaaa atttgtgaaa   4020
gattgactgg tattcttaac tatgttgctc cttttacgct atgtggatac gctgctttaa   4080
tgcctttgta tcatgctatt gcttcccgta tggctttcat tttctcctcc ttgtataaat   4140
cctggttgct gtctctttat gaggagttgt ggcccgttgt caggcaacgt ggcgtggtgt   4200
gcactgtgtt tgctgacgca acccccactg gttggggcat tgccaccacc tgtcagctcc   4260
tttccgggac tttcgctttc cccctcccta ttgccacggc ggaactcatc gccgcctgcc   4320
ttgcccgctg ctggacaggg gctcggctgt tgggcactga caattccgtg gtgttgtcgg   4380
ggaagctgac gtcctttcca tggctgctcg cctgtgttgc cacctggatt ctgcgcggga   4440
cgtccttctg ctacgtccct tcggccctca atccagcgga ccttccttcc cgcggcctgc   4500
tgccggctct gcggcctctt ccgcgtcttc gccttcgccc tcagacgagt cggatctccc   4560
tttgggccgc ctccccgcgt cgacgcgtga attcggtacc tttaagacca atgacttaca   4620
aggcagctgt agatcttagc cactttttaa aagaaaaggg gggactggaa gggctaattc   4680
actcccaacg aagacaagat cgtcgagaga tgctgcatat aagcagctgc tttttgcttg   4740
```

```
tactgggtct ctctggttag accagatctg agcctgggag ctctctggct aactagggaa   4800

cccactgctt aagcctcaat aaagcttgcc ttgagtgctt caagtagtgt gtgcccgtct   4860

gttgtgtgac tctggtaact agagatccct cagacccttt tagtcagtgt ggaaaatctc   4920

tagcagt                                                             4927


<210> SEQ ID NO 35
<211> LENGTH: 1140
<212> TYPE: DNA
<213> ORGANISM: Artificial
<220> FEATURE:
<223> OTHER INFORMATION: Plasmid pTRIP-deltaU3-CMV-MSP142 CO-WPRE
<220> FEATURE:
<221> NAME/KEY: misc_feature
<222> LOCATION: (1)..(1140)
<223> OTHER INFORMATION: Sequence of transgene for MSP142-CO
<220> FEATURE:
<221> NAME/KEY: CDS
<222> LOCATION: (1)..(1140)

<400> SEQUENCE: 35

atg ctg ctg tcc gtg ccc ctg ctg ctg ggc ctg ctg gga ctg gcc gtg       48
Met Leu Leu Ser Val Pro Leu Leu Leu Gly Leu Leu Gly Leu Ala Val
1               5                   10                  15

gcc gct ccc gag aag gac atc ctg agc gag ttc acc aac gag agc ctg       96
Ala Ala Pro Glu Lys Asp Ile Leu Ser Glu Phe Thr Asn Glu Ser Leu
            20                  25                  30

tac gtg tac aca aag aga ctg ggc agc acc tac aag agc ctg aag aaa      144
Tyr Val Tyr Thr Lys Arg Leu Gly Ser Thr Tyr Lys Ser Leu Lys Lys
        35                  40                  45

cac atg ctg cgg gag ttc agc acc atc aaa gaa gat atg acc aac ggc      192
His Met Leu Arg Glu Phe Ser Thr Ile Lys Glu Asp Met Thr Asn Gly
    50                  55                  60

ctg aac aac aag agc cag aag cgg aac gac ttc ctg gag gtg ctg tcc      240
Leu Asn Asn Lys Ser Gln Lys Arg Asn Asp Phe Leu Glu Val Leu Ser
65                  70                  75                  80

cac gag ctg gac ctg ttc aag gac ctg agc acc aat aag tac gtg atc      288
His Glu Leu Asp Leu Phe Lys Asp Leu Ser Thr Asn Lys Tyr Val Ile
                85                  90                  95

cgg aac ccc tac cag ctg ctg gac aac gac aag aag gac aag cag atc      336
Arg Asn Pro Tyr Gln Leu Leu Asp Asn Asp Lys Lys Asp Lys Gln Ile
            100                 105                 110

gtc aac ctg aag tac gcc acc aag ggc atc aac gag gat atc gag aca      384
Val Asn Leu Lys Tyr Ala Thr Lys Gly Ile Asn Glu Asp Ile Glu Thr
        115                 120                 125

acc acc gac ggc atc aag ttc ttc aac aag atg gtg gag ctg tac aac      432
Thr Thr Asp Gly Ile Lys Phe Phe Asn Lys Met Val Glu Leu Tyr Asn
    130                 135                 140

acc cag ctg gcc gcc gtg aag gag cag atc gcc acc atc gag gcc gag      480
Thr Gln Leu Ala Ala Val Lys Glu Gln Ile Ala Thr Ile Glu Ala Glu
145                 150                 155                 160

aca aac gac aca aac aag gag gag aag aag aag tac atc ccc atc ctg      528
Thr Asn Asp Thr Asn Lys Glu Glu Lys Lys Lys Tyr Ile Pro Ile Leu
                165                 170                 175

gag gac ctg aag ggc ctg tac gag aca gtg att ggc cag gcc gag gag      576
Glu Asp Leu Lys Gly Leu Tyr Glu Thr Val Ile Gly Gln Ala Glu Glu
            180                 185                 190

tac agc gag gag ctg cag aac aga ctg gat aac tac aag aac gag aag      624
Tyr Ser Glu Glu Leu Gln Asn Arg Leu Asp Asn Tyr Lys Asn Glu Lys
        195                 200                 205

gcc gag ttc gag atc ctg acc aag aac ctg gag aag tac atc cag atc      672
Ala Glu Phe Glu Ile Leu Thr Lys Asn Leu Glu Lys Tyr Ile Gln Ile
```

```
    210                 215                 220

gac gag aag ctg gac gag ttc gtg gag cac gcc gag aac aac aag cat      720
Asp Glu Lys Leu Asp Glu Phe Val Glu His Ala Glu Asn Asn Lys His
225                 230                 235                 240

atc gcc tct atc gcc ctg aac aac ctg aat aag agc ggc ctg gtg gga      768
Ile Ala Ser Ile Ala Leu Asn Asn Leu Asn Lys Ser Gly Leu Val Gly
                245                 250                 255

gag ggc gag agc aaa aag atc ctg gct aag atg ctg aac atg gac ggc      816
Glu Gly Glu Ser Lys Lys Ile Leu Ala Lys Met Leu Asn Met Asp Gly
            260                 265                 270

atg gat ctg ctg ggc gtg gac ccc aag cac gtg tgc gtg gac acc aga      864
Met Asp Leu Leu Gly Val Asp Pro Lys His Val Cys Val Asp Thr Arg
        275                 280                 285

gac atc ccc aag aac gcc ggc tgc ttc agg gac gac aac ggc acc gag      912
Asp Ile Pro Lys Asn Ala Gly Cys Phe Arg Asp Asp Asn Gly Thr Glu
    290                 295                 300

gag tgg aga tgt ctg ctg ggc tac aag aag ggc gag ggc aac acc tgc      960
Glu Trp Arg Cys Leu Leu Gly Tyr Lys Lys Gly Glu Gly Asn Thr Cys
305                 310                 315                 320

gtg gag aac aat aac ccc acc tgc gac atc aac aac ggc ggc tgc gac     1008
Val Glu Asn Asn Asn Pro Thr Cys Asp Ile Asn Asn Gly Gly Cys Asp
                325                 330                 335

ccc acc gcc agc tgc cag aac gcc gag agc acc gag aac tcc aag aag     1056
Pro Thr Ala Ser Cys Gln Asn Ala Glu Ser Thr Glu Asn Ser Lys Lys
            340                 345                 350

atc atc tgc acc tgc aag gag ccc acc ccc aac gcc tac tac gag ggc     1104
Ile Ile Cys Thr Cys Lys Glu Pro Thr Pro Asn Ala Tyr Tyr Glu Gly
        355                 360                 365

gtg ttc tgc agc agc agc tcc ttc atg ggc tga tga                     1140
Val Phe Cys Ser Ser Ser Ser Phe Met Gly
    370                 375


<210> SEQ ID NO 36
<211> LENGTH: 378
<212> TYPE: PRT
<213> ORGANISM: Artificial
<220> FEATURE:
<223> OTHER INFORMATION: Synthetic Construct

<400> SEQUENCE: 36

Met Leu Leu Ser Val Pro Leu Leu Leu Gly Leu Leu Gly Leu Ala Val
1               5                   10                  15

Ala Ala Pro Glu Lys Asp Ile Leu Ser Glu Phe Thr Asn Glu Ser Leu
            20                  25                  30

Tyr Val Tyr Thr Lys Arg Leu Gly Ser Thr Tyr Lys Ser Leu Lys Lys
        35                  40                  45

His Met Leu Arg Glu Phe Ser Thr Ile Lys Glu Asp Met Thr Asn Gly
    50                  55                  60

Leu Asn Asn Lys Ser Gln Lys Arg Asn Asp Phe Leu Glu Val Leu Ser
65                  70                  75                  80

His Glu Leu Asp Leu Phe Lys Asp Leu Ser Thr Asn Lys Tyr Val Ile
                85                  90                  95

Arg Asn Pro Tyr Gln Leu Leu Asp Asn Asp Lys Lys Asp Lys Gln Ile
            100                 105                 110

Val Asn Leu Lys Tyr Ala Thr Lys Gly Ile Asn Glu Asp Ile Glu Thr
        115                 120                 125

Thr Thr Asp Gly Ile Lys Phe Phe Asn Lys Met Val Glu Leu Tyr Asn
    130                 135                 140
```

-continued

Thr Gln Leu Ala Ala Val Lys Glu Gln Ile Ala Thr Ile Glu Ala Glu
145 150 155 160

Thr Asn Asp Thr Asn Lys Glu Glu Lys Lys Lys Tyr Ile Pro Ile Leu
165 170 175

Glu Asp Leu Lys Gly Leu Tyr Glu Thr Val Ile Gly Gln Ala Glu Glu
180 185 190

Tyr Ser Glu Glu Leu Gln Asn Arg Leu Asp Asn Tyr Lys Asn Glu Lys
195 200 205

Ala Glu Phe Glu Ile Leu Thr Lys Asn Leu Glu Lys Tyr Ile Gln Ile
210 215 220

Asp Glu Lys Leu Asp Glu Phe Val Glu His Ala Glu Asn Asn Lys His
225 230 235 240

Ile Ala Ser Ile Ala Leu Asn Asn Leu Asn Lys Ser Gly Leu Val Gly
245 250 255

Glu Gly Glu Ser Lys Lys Ile Leu Ala Lys Met Leu Asn Met Asp Gly
260 265 270

Met Asp Leu Leu Gly Val Asp Pro Lys His Val Cys Val Asp Thr Arg
275 280 285

Asp Ile Pro Lys Asn Ala Gly Cys Phe Arg Asp Asp Asn Gly Thr Glu
290 295 300

Glu Trp Arg Cys Leu Leu Gly Tyr Lys Lys Gly Glu Gly Asn Thr Cys
305 310 315 320

Val Glu Asn Asn Asn Pro Thr Cys Asp Ile Asn Asn Gly Gly Cys Asp
325 330 335

Pro Thr Ala Ser Cys Gln Asn Ala Glu Ser Thr Glu Asn Ser Lys Lys
340 345 350

Ile Ile Cys Thr Cys Lys Glu Pro Thr Pro Asn Ala Tyr Tyr Glu Gly
355 360 365

Val Phe Cys Ser Ser Ser Ser Phe Met Gly
370 375

<210> SEQ ID NO 37
<211> LENGTH: 4300
<212> TYPE: DNA
<213> ORGANISM: Artificial
<220> FEATURE:
<223> OTHER INFORMATION: plasmid pTRIP-deltaU3-CMV-Hep17 CO-WPRE
<220> FEATURE:
<221> NAME/KEY: misc_feature
<222> LOCATION: (1)..(4300)
<223> OTHER INFORMATION: Complete nucleotide sequence of the provirus

<400> SEQUENCE: 37
tggaagggct aattcactcc caacgaagac aagatatcct tgatctgtgg atctaccaca 60
cacaaggcta cttccctgat tagcagaact acacaccagg gccagggatc agatatccac 120
tgacctttgg atggtgctac aagctagtac cagttgagcc agagaagtta gaagaagcca 180
acaaaggaga gaacaccagc ttgttacaac ctgtgagcct gcatgggatg gatgacccgg 240
agagagaagt gttagagtgg aggtttgaca gccgcctagc atttcatcac ggtggcccga 300
gagctgcatc cggagtactt caagaactgc tgatatcgag cttgctacaa gggactttcc 360
gctgggggac tttccaggga ggcgtggcct gggcgggact ggggagtggc gagccctcag 420
atcctgcata taagcagctg ctttttgcct gtactgggtc tctctggtta gaccagatct 480
gagcctggga gctctctggc taactaggga acccactgct taagcctcaa taaagcttgc 540
cttgagtgct tcaagtagtg tgtgcccgtc tgttgtgtga ctctggtaac tagagatccc 600

-continued

```
tcagaccctt ttagtcagtg tggaaaatct ctagcagtgg cgcccgaaca gggacttgaa    660
agcgaaaggg aaaccagagg agctctctcg acgcaggact cggcttgctg aagcgcgcac    720
ggcaagaggc gaggggcggc gactggtgag tacgccaaaa attttgacta gcggaggcta    780
gaaggagaga gatgggtgcg agagcgtcag tattaagcgg gggagaatta gatcgcgatg    840
ggaaaaaatt cggttaaggc cagggggaaa gaaaaaatat aaattaaaac atatagtatg    900
ggcaagcagg gagctagaac gattcgcagt taatcctggc ctgttagaaa catcagaagg    960
ctgtagacaa atactgggac agctacaacc atcccttcag acaggatcag aagaacttag   1020
atcattatat aatacagtag caaccctcta ttgtgtgcat caaaggatag agataaaaga   1080
caccaaggaa gctttagaca agatagagga agagcaaaac aaaagtaaga ccaccgcaca   1140
gcaagcggcc gctgatcttc agacctggag gaggagatat gagggacaat tggagaagtg   1200
aattatataa atataaagta gtaaaaattg aaccattagg agtagcaccc accaaggcaa   1260
agagaagagt ggtgcagaga gaaaaaagag cagtgggaat aggagctttg ttccttgggt   1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag atacctaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
ggagttccgc gttacataac ttacggtaaa tggcccgcct ggctgaccgc ccaacgaccc   2280
ccgcccattg acgtcaataa tgacgtatgt tcccatagta acgccaatag ggactttcca   2340
ttgacgtcaa tgggtggagt atttacggta aactgcccac ttggcagtac atcaagtgta   2400
tcatatgcca agtacgcccc ctattgacgt caatgacggt aaatggcccg cctggcatta   2460
tgcccagtac atgaccttat gggactttcc tacttggcag tacatctacg tattagtcat   2520
cgctattacc atggtgatgc ggttttggca gtacatcaat gggcgtggat agcggtttga   2580
ctcacgggga tttccaagtc tccaccccat tgacgtcaat gggagtttgt tttggcacca   2640
aaatcaacgg gactttccaa aatgtcgtaa caactccgcc ccattgacgc aaatgggcgg   2700
taggcgtgta cggtgggagg tctatataag cagagctcgt ttagtgaacc gtcagatcgc   2760
ctggagacgc catccacgct gttttgacct ccatagaaga caccgcgatc ggatccgcca   2820
ccatgaagat caatatcgcc agcatcatct ttatcatctt cagcctgtgc ctggtcaacg   2880
acgcctacgg caagaacaag tacgggaaga acggcaagta cggcagccag aacgtgatca   2940
agaaacacgg cgagcccgtg atcaacgtgc aggacctgat cagcgacatg gtccggaaag   3000
```

```
aggaagagat cgtcaagctg accaagaaca agaagagcct gaggaagatc aacgtggccc   3060

tggccaccgc cctgagcgtg gtgtccgcca tcctgctggg cggagccggc ctggtcatgt   3120

acaacaccga gaagggcaga aggcccttcc agatcggcaa gagcaagaaa ggcggcagcg   3180

ccatggccag ggacagcagc ttccccatga acgaggaaag ccccctgggc ttcagccccg   3240

aggaaatgga agccgtggcc agcaagttcc gggagagcat gctgaaggac ggcgtgcctg   3300

cccccagcaa cacccccaac gtgcagaact gatgactcga gctcaagctt cgaattcccg   3360

ataatcaacc tctggattac aaaatttgtg aaagattgac tggtattctt aactatgttg   3420

ctccttttac gctatgtgga tacgctgctt taatgccttt gtatcatgct attgcttccc   3480

gtatggcttt cattttctcc tccttgtata aatcctggtt gctgtctctt tatgaggagt   3540

tgtggcccgt tgtcaggcaa cgtggcgtgg tgtgcactgt gtttgctgac gcaaccccca   3600

ctggttgggg cattgccacc acctgtcagc tcctttccgg gactttcgct ttccccctcc   3660

ctattgccac ggcggaactc atcgccgcct gccttgcccg ctgctggaca ggggctcggc   3720

tgttgggcac tgacaattcc gtggtgttgt cggggaagct gacgtccttt ccatggctgc   3780

tcgcctgtgt tgccacctgg attctgcgcg ggacgtcctt ctgctacgtc ccttcggccc   3840

tcaatccagc ggaccttcct tcccgcggcc tgctgccggc tctgcggcct cttccgcgtc   3900

ttcgccttcg ccctcagacg agtcggatct ccctttgggc cgcctccccg cgtcgacgcg   3960

tgaattcggt acctttaaga ccaatgactt acaaggcagc tgtagatctt agccactttt   4020

taaaagaaaa ggggggactg gaagggctaa ttcactccca acgaagacaa gatcgtcgag   4080

agatgctgca tataagcagc tgctttttgc ttgtactggg tctctctggt tagaccagat   4140

ctgagcctgg gagctctctg gctaactagg gaacccactg cttaagcctc aataaagctt   4200

gccttgagtg cttcaagtag tgtgtgcccg tctgttgtgt gactctggta actagagatc   4260

cctcagaccc ttttagtcag tgtggaaaat ctctagcagt                         4300
```

<210> SEQ ID NO 38
<211> LENGTH: 513
<212> TYPE: DNA
<213> ORGANISM: Artificial
<220> FEATURE:
<223> OTHER INFORMATION: Sequence for transgene for Hep17-CO
<220> FEATURE:
<221> NAME/KEY: CDS
<222> LOCATION: (1)..(513)

<400> SEQUENCE: 38

```
atg aag atc aat atc gcc agc atc atc ttt atc atc ttc agc ctg tgc       48
Met Lys Ile Asn Ile Ala Ser Ile Ile Phe Ile Ile Phe Ser Leu Cys
1               5                   10                  15

ctg gtc aac gac gcc tac ggc aag aac aag tac ggg aag aac ggc aag       96
Leu Val Asn Asp Ala Tyr Gly Lys Asn Lys Tyr Gly Lys Asn Gly Lys
            20                  25                  30

tac ggc agc cag aac gtg atc aag aaa cac ggc gag ccc gtg atc aac      144
Tyr Gly Ser Gln Asn Val Ile Lys Lys His Gly Glu Pro Val Ile Asn
        35                  40                  45

gtg cag gac ctg atc agc gac atg gtc cgg aaa gag gaa gag atc gtc      192
Val Gln Asp Leu Ile Ser Asp Met Val Arg Lys Glu Glu Glu Ile Val
    50                  55                  60

aag ctg acc aag aac aag aag agc ctg agg aag atc aac gtg gcc ctg      240
Lys Leu Thr Lys Asn Lys Lys Ser Leu Arg Lys Ile Asn Val Ala Leu
65                  70                  75                  80

gcc acc gcc ctg agc gtg gtg tcc gcc atc ctg ctg ggc gga gcc ggc      288
```

```
Ala Thr Ala Leu Ser Val Val Ser Ala Ile Leu Leu Gly Gly Ala Gly
                85                  90                  95

ctg gtc atg tac aac acc gag aag ggc aga agg ccc ttc cag atc ggc      336
Leu Val Met Tyr Asn Thr Glu Lys Gly Arg Arg Pro Phe Gln Ile Gly
            100                 105                 110

aag agc aag aaa ggc ggc agc gcc atg gcc agg gac agc agc ttc ccc      384
Lys Ser Lys Lys Gly Gly Ser Ala Met Ala Arg Asp Ser Ser Phe Pro
        115                 120                 125

atg aac gag gaa agc ccc ctg ggc ttc agc ccc gag gaa atg gaa gcc      432
Met Asn Glu Glu Ser Pro Leu Gly Phe Ser Pro Glu Glu Met Glu Ala
    130                 135                 140

gtg gcc agc aag ttc cgg gag agc atg ctg aag gac ggc gtg cct gcc      480
Val Ala Ser Lys Phe Arg Glu Ser Met Leu Lys Asp Gly Val Pro Ala
145                 150                 155                 160

ccc agc aac acc ccc aac gtg cag aac tga tga                          513
Pro Ser Asn Thr Pro Asn Val Gln Asn
                165


<210> SEQ ID NO 39
<211> LENGTH: 169
<212> TYPE: PRT
<213> ORGANISM: Artificial
<220> FEATURE:
<223> OTHER INFORMATION: Synthetic Construct

<400> SEQUENCE: 39

Met Lys Ile Asn Ile Ala Ser Ile Ile Phe Ile Ile Phe Ser Leu Cys
1               5                   10                  15

Leu Val Asn Asp Ala Tyr Gly Lys Asn Lys Tyr Gly Lys Asn Gly Lys
            20                  25                  30

Tyr Gly Ser Gln Asn Val Ile Lys Lys His Gly Glu Pro Val Ile Asn
        35                  40                  45

Val Gln Asp Leu Ile Ser Asp Met Val Arg Lys Glu Glu Glu Ile Val
    50                  55                  60

Lys Leu Thr Lys Asn Lys Lys Ser Leu Arg Lys Ile Asn Val Ala Leu
65                  70                  75                  80

Ala Thr Ala Leu Ser Val Val Ser Ala Ile Leu Leu Gly Gly Ala Gly
                85                  90                  95

Leu Val Met Tyr Asn Thr Glu Lys Gly Arg Arg Pro Phe Gln Ile Gly
            100                 105                 110

Lys Ser Lys Lys Gly Gly Ser Ala Met Ala Arg Asp Ser Ser Phe Pro
        115                 120                 125

Met Asn Glu Glu Ser Pro Leu Gly Phe Ser Pro Glu Glu Met Glu Ala
    130                 135                 140

Val Ala Ser Lys Phe Arg Glu Ser Met Leu Lys Asp Gly Val Pro Ala
145                 150                 155                 160

Pro Ser Asn Thr Pro Asn Val Gln Asn
                165


<210> SEQ ID NO 40
<211> LENGTH: 4261
<212> TYPE: DNA
<213> ORGANISM: Artificial
<220> FEATURE:
<223> OTHER INFORMATION: plasmid pTRIP-deltaU3-CMV-Hep17 deltaSP CO-WPRE
<220> FEATURE:
<221> NAME/KEY: misc_feature
<222> LOCATION: (1)..(4261)
<223> OTHER INFORMATION: Complete sequence of the plasmid
<220> FEATURE:
<221> NAME/KEY: misc_feature
```

<222> LOCATION: (1)..(4261)
<223> OTHER INFORMATION: Complete nucleotide sequence of the plasmid

<400> SEQUENCE: 40

```
tggaagggct aattcactcc caacgaagac aagatatcct tgatctgtgg atctaccaca     60
cacaaggcta cttccctgat tagcagaact acacaccagg gccagggatc agatatccac    120
tgacctttgg atggtgctac aagctagtac cagttgagcc agagaagtta gaagaagcca    180
acaaaggaga gaacaccagc ttgttacaac ctgtgagcct gcatgggatg gatgacccgg    240
agagagaagt gttagagtgg aggtttgaca gccgcctagc atttcatcac ggtggcccga    300
gagctgcatc cggagtactt caagaactgc tgatatcgag cttgctacaa gggactttcc    360
gctggggac tttccaggga ggcgtggcct gggcgggact ggggagtggc gagccctcag    420
atcctgcata taagcagctg ctttttgcct gtactgggtc tctctggtta gaccagatct    480
gagcctggga gctctctggc taactaggga acccactgct taagcctcaa taaagcttgc    540
cttgagtgct tcaagtagtg tgtgcccgtc tgttgtgtga ctctggtaac tagagatccc    600
tcagaccctt ttagtcagtg tggaaaatct ctagcagtgg cgcccgaaca gggacttgaa    660
agcgaaaggg aaaccagagg agctctctcg acgcaggact cggcttgctg aagcgcgcac    720
ggcaagaggc gaggggcggc gactggtgag tacgccaaaa attttgacta gcggaggcta    780
gaaggagaga gatgggtgcg agagcgtcag tattaagcgg gggagaatta gatcgcgatg    840
ggaaaaaatt cggttaaggc cagggggaaa gaaaaaatat aaattaaaac atatagtatg    900
ggcaagcagg gagctagaac gattcgcagt taatcctggc ctgttagaaa catcagaagg    960
ctgtagacaa atactgggac agctacaacc atcccttcag acaggatcag aagaacttag   1020
atcattatat aatacagtag caaccctcta ttgtgtgcat caaaggatag agataaaaga   1080
caccaaggaa gctttagaca agatagagga agagcaaaac aaaagtaaga ccaccgcaca   1140
gcaagcggcc gctgatcttc agacctggag gaggagatat gagggacaat tggagaagtg   1200
aattatataa atataaagta gtaaaaattg aaccattagg agtagcaccc accaaggcaa   1260
agagaagagt ggtgcagaga gaaaaaagag cagtgggaat aggagctttg ttccttgggt   1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag atacctaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
```

```
ggagttccgc gttacataac ttacggtaaa tggcccgcct ggctgaccgc ccaacgaccc   2280

ccgcccattg acgtcaataa tgacgtatgt tcccatagta acgccaatag ggactttcca   2340

ttgacgtcaa tgggtggagt atttacggta aactgcccac ttggcagtac atcaagtgta   2400

tcatatgcca agtacgcccc ctattgacgt caatgacggt aaatggcccg cctggcatta   2460

tgcccagtac atgaccttat gggactttcc tacttggcag tacatctacg tattagtcat   2520

cgctattacc atggtgatgc ggttttggca gtacatcaat gggcgtggat agcggtttga   2580

ctcacgggga tttccaagtc tccaccccat tgacgtcaat gggagtttgt tttggcacca   2640

aaatcaacgg gactttccaa aatgtcgtaa caactccgcc ccattgacgc aaatgggcgg   2700

taggcgtgta cggtgggagg tctatataag cagagctcgt ttagtgaacc gtcagatcgc   2760

ctggagacgc catccacgct gttttgacct ccatagaaga caccgcgatc ggatccgcca   2820

ccatgctgtg cctggtcaac gacgcctacg gcaagaacaa gtacgggaag aacggcaagt   2880

acggcagcca gaacgtgatc aagaaacacg gcgagcccgt gatcaacgtg caggacctga   2940

tcagcgacat ggtccggaaa gaggaagaga tcgtcaagct gaccaagaac aagaagagcc   3000

tgaggaagat caacgtggcc ctggccaccg ccctgagcgt ggtgtccgcc atcctgctgg   3060

gcggagccgg cctggtcatg tacaacaccg agaagggcag aaggcccttc cagatcggca   3120

agagcaagaa aggcggcagc gccatggcca gggacagcag cttccccatg aacgaggaaa   3180

gcccccctggg cttcagcccc gaggaaatgg aagccgtggc cagcaagttc cgggagagca   3240

tgctgaagga cggcgtgcct gcccccagca acacccccaa cgtgcagaac tgatgactcg   3300

agctcaagct tcgaattccc gataatcaac ctctggatta caaaatttgt gaaagattga   3360

ctggtattct taactatgtt gctcctttta cgctatgtgg atacgctgct ttaatgcctt   3420

tgtatcatgc tattgcttcc cgtatggctt tcattttctc ctccttgtat aaatcctggt   3480

tgctgtctct ttatgaggag ttgtggcccg ttgtcaggca acgtggcgtg gtgtgcactg   3540

tgtttgctga cgcaaccccc actggttggg gcattgccac cacctgtcag ctcctttccg   3600

ggactttcgc tttccccctc cctattgcca cggcggaact catcgccgcc tgccttgccc   3660

gctgctggac aggggctcgg ctgttgggca ctgacaattc cgtggtgttg tcggggaagc   3720

tgacgtcctt tccatggctg ctcgcctgtg ttgccacctg gattctgcgc gggacgtcct   3780

tctgctacgt cccttcggcc ctcaatccag cggaccttcc ttcccgcggc ctgctgccgg   3840

ctctgcggcc tcttccgcgt cttcgccttc gccctcagac gagtcggatc tccctttggg   3900

ccgcctcccc gcgtcgacgc gtgaattcgg taccttttaag accaatgact tacaaggcag   3960

ctgtagatct tagccacttt ttaaaagaaa aggggggact ggaagggcta attcactccc   4020

aacgaagaca agatcgtcga gagatgctgc atataagcag ctgctttttg cttgtactgg   4080

gtctctctgg ttagaccaga tctgagcctg ggagctctct ggctaactag ggaacccact   4140

gcttaagcct caataaagct tgccttgagt gcttcaagta gtgtgtgccc gtctgttgtg   4200

tgactctggt aactagagat ccctcagacc cttttagtca gtgtggaaaa tctctagcag   4260

t                                                                   4261
```

<210> SEQ ID NO 41
<211> LENGTH: 474
<212> TYPE: DNA
<213> ORGANISM: Artificial
<220> FEATURE:
<223> OTHER INFORMATION: Sequence of transgene from Hep17deltaSP CO
<220> FEATURE:
<221> NAME/KEY: CDS

```
<222> LOCATION: (1)..(474)

<400> SEQUENCE: 41

atg ctg tgc ctg gtc aac gac gcc tac ggc aag aac aag tac ggg aag       48
Met Leu Cys Leu Val Asn Asp Ala Tyr Gly Lys Asn Lys Tyr Gly Lys
1               5                   10                  15

aac ggc aag tac ggc agc cag aac gtg atc aag aaa cac ggc gag ccc       96
Asn Gly Lys Tyr Gly Ser Gln Asn Val Ile Lys Lys His Gly Glu Pro
            20                  25                  30

gtg atc aac gtg cag gac ctg atc agc gac atg gtc cgg aaa gag gaa      144
Val Ile Asn Val Gln Asp Leu Ile Ser Asp Met Val Arg Lys Glu Glu
        35                  40                  45

gag atc gtc aag ctg acc aag aac aag aag agc ctg agg aag atc aac      192
Glu Ile Val Lys Leu Thr Lys Asn Lys Lys Ser Leu Arg Lys Ile Asn
    50                  55                  60

gtg gcc ctg gcc acc gcc ctg agc gtg gtg tcc gcc atc ctg ctg ggc      240
Val Ala Leu Ala Thr Ala Leu Ser Val Val Ser Ala Ile Leu Leu Gly
65                  70                  75                  80

gga gcc ggc ctg gtc atg tac aac acc gag aag ggc aga agg ccc ttc      288
Gly Ala Gly Leu Val Met Tyr Asn Thr Glu Lys Gly Arg Arg Pro Phe
                85                  90                  95

cag atc ggc aag agc aag aaa ggc ggc agc gcc atg gcc agg gac agc      336
Gln Ile Gly Lys Ser Lys Lys Gly Gly Ser Ala Met Ala Arg Asp Ser
            100                 105                 110

agc ttc ccc atg aac gag gaa agc ccc ctg ggc ttc agc ccc gag gaa      384
Ser Phe Pro Met Asn Glu Glu Ser Pro Leu Gly Phe Ser Pro Glu Glu
        115                 120                 125

atg gaa gcc gtg gcc agc aag ttc cgg gag agc atg ctg aag gac ggc      432
Met Glu Ala Val Ala Ser Lys Phe Arg Glu Ser Met Leu Lys Asp Gly
    130                 135                 140

gtg cct gcc ccc agc aac acc ccc aac gtg cag aac tga tga              474
Val Pro Ala Pro Ser Asn Thr Pro Asn Val Gln Asn
145                 150                 155


<210> SEQ ID NO 42
<211> LENGTH: 156
<212> TYPE: PRT
<213> ORGANISM: Artificial
<220> FEATURE:
<223> OTHER INFORMATION: Synthetic Construct

<400> SEQUENCE: 42

Met Leu Cys Leu Val Asn Asp Ala Tyr Gly Lys Asn Lys Tyr Gly Lys
1               5                   10                  15

Asn Gly Lys Tyr Gly Ser Gln Asn Val Ile Lys Lys His Gly Glu Pro
            20                  25                  30

Val Ile Asn Val Gln Asp Leu Ile Ser Asp Met Val Arg Lys Glu Glu
        35                  40                  45

Glu Ile Val Lys Leu Thr Lys Asn Lys Lys Ser Leu Arg Lys Ile Asn
    50                  55                  60

Val Ala Leu Ala Thr Ala Leu Ser Val Val Ser Ala Ile Leu Leu Gly
65                  70                  75                  80

Gly Ala Gly Leu Val Met Tyr Asn Thr Glu Lys Gly Arg Arg Pro Phe
                85                  90                  95

Gln Ile Gly Lys Ser Lys Lys Gly Gly Ser Ala Met Ala Arg Asp Ser
            100                 105                 110

Ser Phe Pro Met Asn Glu Glu Ser Pro Leu Gly Phe Ser Pro Glu Glu
        115                 120                 125

Met Glu Ala Val Ala Ser Lys Phe Arg Glu Ser Met Leu Lys Asp Gly
```

```
    130                 135                 140

Val Pro Ala Pro Ser Asn Thr Pro Asn Val Gln Asn
145                 150                 155


<210> SEQ ID NO 43
<211> LENGTH: 4897
<212> TYPE: DNA
<213> ORGANISM: Artificial
<220> FEATURE:
<223> OTHER INFORMATION: Plasmid pTRIP-DeltaU3-CMV-CSP CO WPRE

<400> SEQUENCE: 43

tggaagggct aattcactcc caacgaagac aagatatcct tgatctgtgg atctaccaca     60

cacaaggcta cttccctgat tagcagaact acacaccagg gccagggatc agatatccac    120

tgacctttgg atggtgctac aagctagtac cagttgagcc agagaagtta gaagaagcca    180

acaaaggaga gaacaccagc ttgttacaac ctgtgagcct gcatgggatg gatgacccgg    240

agagagaagt gttagagtgg aggtttgaca gccgcctagc atttcatcac ggtggcccga    300

gagctgcatc cggagtactt caagaactgc tgatatcgag cttgctacaa gggactttcc    360

gctggggac tttccaggga ggcgtggcct gggcgggact ggggagtggc gagccctcag     420

atcctgcata taagcagctg ctttttgcct gtactgggtc tctctggtta gaccagatct    480

gagcctggga gctctctggc taactaggga acccactgct taagcctcaa taaagcttgc    540

cttgagtgct tcaagtagtg tgtgcccgtc tgttgtgtga ctctggtaac tagagatccc    600

tcagaccctt ttagtcagtg tggaaaatct ctagcagtgg cgcccgaaca gggacttgaa    660

agcgaaaggg aaaccagagg agctctctcg acgcaggact cggcttgctg aagcgcgcac    720

ggcaagaggc gaggggcggc gactggtgag tacgccaaaa attttgacta gcggaggcta    780

gaaggagaga gatgggtgcg agagcgtcag tattaagcgg gggagaatta gatcgcgatg    840

ggaaaaaatt cggttaaggc cagggggaaa gaaaaaatat aaattaaaac atatagtatg    900

ggcaagcagg gagctagaac gattcgcagt taatcctggc ctgttagaaa catcagaagg    960

ctgtagacaa atactgggac agctacaacc atcccttcag acaggatcag aagaacttag   1020

atcattatat aatacagtag caaccctcta ttgtgtgcat caaaggatag agataaaaga   1080

caccaaggaa gctttagaca agatagagga agagcaaaac aaaagtaaga ccaccgcaca   1140

gcaagcggcc gctgatcttc agacctggag gaggagatat gagggacaat tggagaagtg   1200

aattatataa atataaagta gtaaaaattg aaccattagg agtagcaccc accaaggcaa   1260

agagaagagt ggtgcagaga gaaaaaagag cagtgggaat aggagctttg ttccttgggt   1320

tcttgggagc agcaggaagc actatgggcg cagcgtcaat gacgctgacg gtacaggcca   1380

gacaattatt gtctggtata gtgcagcagc agaacaattt gctgagggct attgaggcgc   1440

aacagcatct gttgcaactc acagtctggg gcatcaagca gctccaggca agaatcctgg   1500

ctgtggaaag atacctaaag gatcaacagc tcctggggat ttggggttgc tctggaaaac   1560

tcatttgcac cactgctgtg ccttggaatg ctagttggag taataaatct ctggaacaga   1620

tttggaatca cacgacctgg atggagtggg acagagaaat taacaattac acaagcttaa   1680

tacactcctt aattgaagaa tcgcaaaacc agcaagaaaa gaatgaacaa gaattattgg   1740

aattagataa atgggcaagt ttgtggaatt ggtttaacat aacaaattgg ctgtggtata   1800

taaaattatt cataatgata gtaggaggct tggtaggttt aagaatagtt tttgctgtac   1860

tttctatagt gaatagagtt aggcagggat attcaccatt atcgtttcag acccacctcc   1920
```

-continued

```
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
ggagttccgc gttacataac ttacggtaaa tggcccgcct ggctgaccgc ccaacgaccc   2280
ccgcccattg acgtcaataa tgacgtatgt tcccatagta acgccaatag ggactttcca   2340
ttgacgtcaa tgggtggagt atttacggta aactgcccac ttggcagtac atcaagtgta   2400
tcatatgcca agtacgcccc ctattgacgt caatgacggt aaatggcccg cctggcatta   2460
tgcccagtac atgaccttat gggactttcc tacttggcag tacatctacg tattagtcat   2520
cgctattacc atggtgatgc ggttttggca gtacatcaat gggcgtggat agcggtttga   2580
ctcacgggga tttccaagtc tccaccccat tgacgtcaat gggagtttgt tttggcacca   2640
aaatcaacgg gactttccaa aatgtcgtaa caactccgcc ccattgacgc aaatgggcgg   2700
taggcgtgta cggtgggagg tctatataag cagagctcgt ttagtgaacc gtcagatcgc   2760
ctggagacgc catccacgct gttttgacct ccatagaaga caccgcgatc ggatccgcca   2820
ccatgaagaa atgcaccatc ctggtggtgg ccagcctgct gctggtcgat agcctgctgc   2880
ccggctacgg ccagaataag agcgtgcagg cccagcggaa cctgaacgag ctgtgctaca   2940
acgaggaaaa cgacaacaag ctgtaccacg tgctgaacag caagaacggc aagatctaca   3000
accggaacat cgtgaacagg ctgctgggcg acgctctgaa cggcaagccc gaggaaaaga   3060
aggacgaccc ccccaaggac ggcaacaagg acgacctgcc caaagaagag aagaaagacg   3120
atctgcctaa agaggaaaaa aaagacgatc ctcctaagga ccccaagaag gatgaccctc   3180
ctaaagaggc ccagaacaag ctgaaccagc ccgtggtggc cgacgagaac gtggatcagg   3240
gacctggcgc ccctcagggc ccaggcgctc cacagggacc cggggcaccc caggggcctg   3300
gggccccaca gggaccaggg gctcctcagg gccctggcgc acctcagggg ccaggggccc   3360
ctcaggggcc tggcgctccc cagggacctg gcgcaccaca gggccctggg gctccccagg   3420
gcccaggcgc ccctcaggga ccaggcgcac cccagggacc cggcgctcct cagggacctg   3480
gggctccaca ggggccaggc gcaccacagg aacctcccca gcagcctcct cagcagccac   3540
cccagcagcc ccctcagcag cctcctcagc agccccccaca gcagcctcca cagcagccta   3600
gaccccagcc cgacggcaat aacaacaaca ataataacaa cggcaacaac aacgaggaca   3660
gctacgtgcc cagcgccgag cagatcctgg aattcgtgaa gcagatcagc agccagctga   3720
ccgaagagtg gagccagtgc agcgtgacat gcggctctgg cgtgagagtg cggaagcgga   3780
agaacgtgaa caagcagccc gagaacctga ccctggaaga tatcgacacc gagatctgca   3840
agatggacaa gtgcagcagc atcttcaaca tcgtgtccaa cagcctgggc ttcgtgatcc   3900
tgctggtgct ggtgttcttc aactgatgac tcgagctcaa gcttcgaatt cccgataatc   3960
aacctctgga ttacaaaatt tgtgaaagat tgactggtat tcttaactat gttgctcctt   4020
ttacgctatg tggatacgct gctttaatgc ctttgtatca tgctattgct tcccgtatgg   4080
ctttcatttt ctcctccttg tataaatcct ggttgctgtc tctttatgag gagttgtggc   4140
ccgttgtcag gcaacgtggc gtggtgtgca ctgtgtttgc tgacgcaacc cccactggtt   4200
ggggcattgc caccacctgt cagctccttt ccgggacttt cgctttcccc ctccctattg   4260
ccacggcgga actcatcgcc gcctgccttg cccgctgctg gacaggggct cggctgttgg   4320
```

-continued gcactgacaa ttccgtggtg ttgtcgggga agctgacgtc ctttccatgg ctgctcgcct 4380
gtgttgccac ctggattctg cgcgggacgt ccttctgcta cgtcccttcg gccctcaatc 4440
cagcggacct tccttcccgc ggcctgctgc cggctctgcg gcctcttccg cgtcttcgcc 4500
ttcgccctca gacgagtcgg atctcccttt gggccgcctc cccgcgtcga cgcgtgaatt 4560
cggtaccttt aagaccaatg acttacaagg cagctgagat cttagccact ttttaaaaga 4620
aaagggggga ctggaagggc taattcactc ccaacgaaga caagatcgtc gagagatgct 4680
gcatataagc agctgctttt tgcttgtact gggtctctct ggttagacca gatctgagcc 4740
tgggagctct ctggctaact agggaaccca ctgcttaagc ctcaataaag cttgccttga 4800
gtgcttcaag tagtgtgtgc ccgtctgttg tgtgactctg gtaactagag atccctcaga 4860
cccttttagt cagtgtggaa aatctctagc agtattt 4897

<210> SEQ ID NO 44
<211> LENGTH: 1107
<212> TYPE: DNA
<213> ORGANISM: Artificial
<220> FEATURE:
<223> OTHER INFORMATION: Sequence of transgene for CSP-CO

<400> SEQUENCE: 44
atgaagaaat gcaccatcct ggtggtggcc agcctgctgc tggtcgatag cctgctgccc 60
ggctacggcc agaataagag cgtgcaggcc cagcggaacc tgaacgagct gtgctacaac 120
gaggaaaacg acaacaagct gtaccacgtg ctgaacagca agaacggcaa gatctacaac 180
cggaacatcg tgaacaggct gctgggcgac gctctgaacg gcaagcccga ggaaaagaag 240
gacgaccccc ccaaggacgg caacaaggac gacctgccca aagaagagaa gaaagacgat 300
ctgcctaaag aggaaaaaaa agacgatcct cctaaggacc ccaagaagga tgaccctcct 360
aaagaggccc agaacaagct gaaccagccc gtggtggccg acgagaacgt ggatcaggga 420
cctggcgccc ctcagggccc aggcgctcca cagggacccg gggcacccca ggggcctggg 480
gccccacagg gaccaggggc tcctcagggc cctggcgcac ctcaggggcc aggggcccct 540
caggggcctg gcgctcccca gggacctggc gcaccacagg gccctggggc tccccagggc 600
ccaggcgccc ctcagggacc aggcgcaccc cagggacccg gcgctcctca gggacctggg 660
gctccacagg ggccaggcgc accacaggaa cctccccagc agcctcctca gcagccaccc 720
cagcagcccc ctcagcagcc tcctcagcag cccccacagc agcctccaca gcagcctaga 780
ccccagcccg acggcaataa caacaacaat aataacaacg gcaacaacaa cgaggacagc 840
tacgtgccca gcgccgagca gatcctggaa ttcgtgaagc agatcagcag ccagctgacc 900
gaagagtgga gccagtgcag cgtgacatgc ggctctggcg tgagagtgcg gaagcggaag 960
aacgtgaaca agcagcccga gaacctgacc ctggaagata tcgacaccga gatctgcaag 1020
atggacaagt gcagcagcat cttcaacatc gtgtccaaca gcctgggctt cgtgatcctg 1080
ctggtgctgg tgttcttcaa ctgatga 1107

<210> SEQ ID NO 45
<211> LENGTH: 4840
<212> TYPE: DNA
<213> ORGANISM: Artificial
<220> FEATURE:
<223> OTHER INFORMATION: plasmid pTRIP-deltaU3-CMV-CSP deltaSP CO-WPRE

<400> SEQUENCE: 45

-continued

```
tggaagggct aattcactcc caacgaagac aagatatcct tgatctgtgg atctaccaca     60
cacaaggcta cttccctgat tagcagaact acacaccagg gccagggatc agatatccac    120
tgacctttgg atggtgctac aagctagtac cagttgagcc agagaagtta gaagaagcca    180
acaaaggaga gaacaccagc ttgttacaac ctgtgagcct gcatgggatg gatgacccgg    240
agagagaagt gttagagtgg aggtttgaca gccgcctagc atttcatcac ggtggcccga    300
gagctgcatc cggagtactt caagaactgc tgatatcgag cttgctacaa gggactttcc    360
gctgggggac tttccaggga ggcgtggcct gggcgggact ggggagtggc gagccctcag    420
atcctgcata taagcagctg ctttttgcct gtactgggtc tctctggtta gaccagatct    480
gagcctggga gctctctggc taactaggga acccactgct taagcctcaa taaagcttgc    540
cttgagtgct tcaagtagtg tgtgcccgtc tgttgtgtga ctctggtaac tagagatccc    600
tcagaccctt ttagtcagtg tggaaaatct ctagcagtgg cgcccgaaca gggacttgaa    660
agcgaaaggg aaaccagagg agctctctcg acgcaggact cggcttgctg aagcgcgcac    720
ggcaagaggc gaggggcggc gactggtgag tacgccaaaa attttgacta gcggaggcta    780
gaaggagaga gatgggtgcg agagcgtcag tattaagcgg gggagaatta gatcgcgatg    840
ggaaaaaatt cggttaaggc cagggggaaa gaaaaaatat aaattaaaac atatagtatg    900
ggcaagcagg gagctagaac gattcgcagt taatcctggc ctgttagaaa catcagaagg    960
ctgtagacaa atactgggac agctacaacc atcccttcag acaggatcag aagaacttag   1020
atcattatat aatacagtag caaccctcta ttgtgtgcat caaaggatag agataaaaga   1080
caccaaggaa gctttagaca agatagagga agagcaaaac aaaagtaaga ccaccgcaca   1140
gcaagcggcc gctgatcttc agacctggag gaggagatat gagggacaat tggagaagtg   1200
aattatataa atataaagta gtaaaaattg aaccattagg agtagcaccc accaaggcaa   1260
agagaagagt ggtgcagaga gaaaaaagag cagtgggaat aggagctttg ttccttgggt   1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag atacctaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
ggagttccgc gttacataac ttacggtaaa tggcccgcct ggctgaccgc ccaacgaccc   2280
ccgcccattg acgtcaataa tgacgtatgt tcccatagta acgccaatag ggactttcca   2340
ttgacgtcaa tgggtggagt atttacggta aactgcccac ttggcagtac atcaagtgta   2400
```

```
tcatatgcca agtacgcccc ctattgacgt caatgacggt aaatggcccg cctggcatta   2460
tgcccagtac atgaccttat gggactttcc tacttggcag tacatctacg tattagtcat   2520
cgctattacc atggtgatgc ggttttggca gtacatcaat gggcgtggat agcggtttga   2580
ctcacgggga tttccaagtc tccaccccat tgacgtcaat gggagtttgt tttggcacca   2640
aaatcaacgg gactttccaa aatgtcgtaa caactccgcc ccattgacgc aaatgggcgg   2700
taggcgtgta cggtgggagg tctatataag cagagctcgt ttagtgaacc gtcagatcgc   2760
ctggagacgc catccacgct gttttgacct ccatagaaga caccgcgatc ggatccgcca   2820
ccatgcccgg ctacggccag aataagagcg tgcaggccca gcggaacctg aacgagctgt   2880
gctacaacga ggaaaacgac aacaagctgt accacgtgct gaacagcaag aacggcaaga   2940
tctacaaccg gaacatcgtg aacaggctgc tgggcgacgc tctgaacggc aagcccgagg   3000
aaaagaagga cgaccccccc aaggacggca acaaggacga cctgcccaaa gaagagaaga   3060
aagacgatct gcctaaagag gaaaaaaaag acgatcctcc taaggacccc aagaaggatg   3120
accctcctaa agaggcccag aacaagctga accagcccgt ggtggccgac gagaacgtgg   3180
atcagggacc tggcgcccct cagggcccag gcgctccaca gggacccggg gcaccccagg   3240
ggcctggggc cccacaggga ccaggggctc ctcagggccc tggcgcacct caggggccag   3300
gggcccctca ggggcctggc gctccccagg gacctggcgc accacagggc cctggggctc   3360
cccagggccc aggcgcccct cagggaccag gcgcacccca gggacccggc gctcctcagg   3420
gacctggggc tccacagggg ccaggcgcac cacaggaacc tccccagcag cctcctcagc   3480
agccacccca gcagcccccct cagcagcctc ctcagcagcc cccacagcag cctccacagc   3540
agcctagacc ccagcccgac ggcaataaca acaacaataa taacaacggc aacaacaacg   3600
aggacagcta cgtgcccagc gccgagcaga tcctggaatt cgtgaagcag atcagcagcc   3660
agctgaccga agagtggagc cagtgcagcg tgacatgcgg ctctggcgtg agagtgcgga   3720
agcggaagaa cgtgaacaag cagcccgaga acctgaccct ggaagatatc gacaccgaga   3780
tctgcaagat ggacaagtgc agcagcatct tcaacatcgt gtccaacagc ctgggcttcg   3840
tgatcctgct ggtgctggtg ttcttcaact gatgactcga gctcaagctt cgaattcccg   3900
ataatcaacc tctggattac aaaatttgtg aaagattgac tggtattctt aactatgttg   3960
ctccttttac gctatgtgga tacgctgctt taatgccttt gtatcatgct attgcttccc   4020
gtatggcttt cattttctcc tccttgtata aatcctggtt gctgtctctt tatgaggagt   4080
tgtggcccgt tgtcaggcaa cgtggcgtgg tgtgcactgt gtttgctgac gcaaccccca   4140
ctggttgggg cattgccacc acctgtcagc tcctttccgg gactttcgct ttccccctcc   4200
ctattgccac ggcggaactc atcgccgcct gccttgcccg ctgctggaca ggggctcggc   4260
tgttgggcac tgacaattcc gtggtgttgt cggggaagct gacgtccttt ccatggctgc   4320
tcgcctgtgt tgccacctgg attctgcgcg ggacgtcctt ctgctacgtc ccttcggccc   4380
tcaatccagc ggaccttcct tcccgcggcc tgctgccggc tctgcggcct cttccgcgtc   4440
ttcgccttcg ccctcagacg agtcggatct ccctttgggc cgcctccccg cgtcgacgcg   4500
tgaattcggt acctttaaga ccaatgactt acaaggcagc tgtagatctt agccactttt   4560
taaaagaaaa ggggggactg gaagggctaa ttcactccca acgaagacaa gatcgtcgag   4620
agatgctgca tataagcagc tgctttttgc ttgtactggg tctctctggt tagaccagat   4680
ctgagcctgg gagctctctg gctaactagg gaacccactg cttaagcctc aataaagctt   4740
```

gccttgagtg cttcaagtag tgtgtgcccg tctgttgtgt gactctggta actagagatc 4800
cctcagaccc ttttagtcag tgtggaaaat ctctagcagt 4840

<210> SEQ ID NO 46
<211> LENGTH: 1053
<212> TYPE: DNA
<213> ORGANISM: Artificial
<220> FEATURE:
<223> OTHER INFORMATION: Sequence of transgene for CSP-deltaSP
<220> FEATURE:
<221> NAME/KEY: misc_feature
<222> LOCATION: (1)..(1053)
<223> OTHER INFORMATION: Sequence of transgene for CSP-deltaSP

<400> SEQUENCE: 46
atgcccggct acggccagaa taagagcgtg caggcccagc ggaacctgaa cgagctgtgc 60
tacaacgagg aaaacgacaa caagctgtac cacgtgctga acagcaagaa cggcaagatc 120
tacaaccgga acatcgtgaa caggctgctg ggcgacgctc tgaacggcaa gcccgaggaa 180
aagaaggacg accccccccaa ggacggcaac aaggacgacc tgcccaaaga agagaagaaa 240
gacgatctgc ctaaagagga aaaaaaagac gatcctccta aggaccccaa gaaggatgac 300
cctcctaaag aggcccagaa caagctgaac cagcccgtgg tggccgacga gaacgtggat 360
cagggacctg gcgcccctca gggcccaggc gctccacagg gacccggggc accccagggg 420
cctggggccc cacagggacc aggggctcct cagggccctg gcgcacctca ggggccaggg 480
gcccctcagg ggcctggcgc tccccaggga cctggcgcac cacagggccc tggggctccc 540
cagggcccag gcgcccctca gggaccaggc gcaccccagg gacccggcgc tcctcaggga 600
cctggggctc cacaggggcc aggcgcacca caggaacctc cccagcagcc tcctcagcag 660
ccaccccagc agcccctca gcagcctcct cagcagcccc cacagcagcc tccacagcag 720
cctagacccc agcccgacgg caataacaac aacaataata acaacggcaa caacaacgag 780
gacagctacg tgcccagcgc cgagcagatc ctggaattcg tgaagcagat cagcagccag 840
ctgaccgaag agtggagcca gtgcagcgtg acatgcggct ctggcgtgag agtgcggaag 900
cggaagaacg tgaacaagca gcccgagaac ctgaccctgg aagatatcga caccgagatc 960
tgcaagatgg acaagtgcag cagcatcttc aacatcgtgt ccaacagcct gggcttcgtg 1020
atcctgctgg tgctggtgtt cttcaactga tga 1053

<210> SEQ ID NO 47
<211> LENGTH: 4858
<212> TYPE: DNA
<213> ORGANISM: Artificial
<220> FEATURE:
<223> OTHER INFORMATION: Plasmid pTRIP-deltaU3-CMV-CSP deltaGPI CO-WPRE
<220> FEATURE:
<221> NAME/KEY: misc_feature
<222> LOCATION: (1)..(4858)
<223> OTHER INFORMATION: Complete nucleotide sequence of the provirus

<400> SEQUENCE: 47
tggaagggct aattcactcc caacgaagac aagatatcct tgatctgtgg atctaccaca 60
cacaaggcta cttccctgat tagcagaact acacaccagg gccagggatc agatatccac 120
tgacctttgg atggtgctac aagctagtac cagttgagcc agagaagtta gaagaagcca 180
acaaaggaga gaacaccagc ttgttacaac ctgtgagcct gcatgggatg gatgacccgg 240
agagagaagt gttagagtgg aggtttgaca gccgcctagc atttcatcac ggtggcccga 300
gagctgcatc cggagtactt caagaactgc tgatatcgag cttgctacaa gggactttcc 360
gctgggggac tttccaggga ggcgtggcct gggcgggact ggggagtggc gagccctcag 420
atcctgcata taagcagctg ctttttgcct gtactgggtc tctctggtta gaccagatct 480
gagcctggga gctctctggc taactaggga acccactgct taagcctcaa taaagcttgc 540
cttgagtgct tcaagtagtg tgtgcccgtc tgttgtgtga ctctggtaac tagagatccc 600
tcagaccctt ttagtcagtg tggaaaatct ctagcagtgg cgcccgaaca gggacttgaa 660
agcgaaaggg aaaccagagg agctctctcg acgcaggact cggcttgctg aagcgcgcac 720
ggcaagaggc gaggggcggc gactggtgag tacgccaaaa attttgacta gcggaggcta 780
gaaggagaga gatgggtgcg agagcgtcag tattaagcgg gggagaatta gatcgcgatg 840
ggaaaaaatt cggttaaggc cagggggaaa gaaaaaatat aaattaaaac atatagtatg 900
ggcaagcagg gagctagaac gattcgcagt taatcctggc ctgttagaaa catcagaagg 960
ctgtagacaa atactgggac agctacaacc atcccttcag acaggatcag aagaacttag 1020
atcattatat aatacagtag caaccctcta ttgtgtgcat caaaggatag agataaaaga 1080
caccaaggaa gctttagaca agatagagga agagcaaaac aaaagtaaga ccaccgcaca 1140
gcaagcggcc gctgatcttc agacctggag gaggagatat gagggacaat tggagaagtg 1200
aattatataa atataaagta gtaaaaattg aaccattagg agtagcaccc accaaggcaa 1260
agagaagagt ggtgcagaga gaaaaaagag cagtgggaat aggagctttg ttccttgggt 1320
tcttgggagc agcaggaagc actatgggcg cagcgtcaat gacgctgacg gtacaggcca 1380
gacaattatt gtctggtata gtgcagcagc agaacaattt gctgagggct attgaggcgc 1440
aacagcatct gttgcaactc acagtctggg gcatcaagca gctccaggca agaatcctgg 1500
ctgtggaaag atacctaaag gatcaacagc tcctggggat ttggggttgc tctggaaaac 1560
tcatttgcac cactgctgtg ccttggaatg ctagttggag taataaatct ctggaacaga 1620
tttggaatca cacgacctgg atggagtggg acagagaaat taacaattac acaagcttaa 1680
tacactcctt aattgaagaa tcgcaaaacc agcaagaaaa gaatgaacaa gaattattgg 1740
aattagataa atgggcaagt ttgtggaatt ggtttaacat aacaaattgg ctgtggtata 1800
taaaattatt cataatgata gtaggaggct tggtaggttt aagaatagtt tttgctgtac 1860
tttctatagt gaatagagtt aggcagggat attcaccatt atcgtttcag acccacctcc 1920
caaccccgag gggacccgac aggcccgaag gaatagaaga agaaggtgga gagagagaca 1980
gagacagatc cattcgatta gtgaacggat ctcgacggta tcgccgaatt cacaaatggc 2040
agtattcatc cacaatttta aaagaaaagg ggggattggg gggtacagtg caggggaaag 2100
aatagtagac ataatagcaa cagacataca aactaaagaa ttacaaaaac aaattacaaa 2160
aattcaaaat tttcgggttt attacaggga cagcagagat ccactttggc tgatacgcgt 2220
ggagttccgc gttacataac ttacggtaaa tggcccgcct ggctgaccgc ccaacgaccc 2280
ccgcccattg acgtcaataa tgacgtatgt tcccatagta acgccaatag ggactttcca 2340
ttgacgtcaa tgggtggagt atttacggta aactgcccac ttggcagtac atcaagtgta 2400
tcatatgcca agtacgcccc ctattgacgt caatgacggt aaatggcccg cctggcatta 2460
tgcccagtac atgaccttat gggactttcc tacttggcag tacatctacg tattagtcat 2520
cgctattacc atggtgatgc ggttttggca gtacatcaat gggcgtggat agcggtttga 2580
ctcacgggga tttccaagtc tccaccccat tgacgtcaat gggagtttgt tttggcacca 2640
aaatcaacgg gactttccaa aatgtcgtaa caactccgcc ccattgacgc aaatgggcgg 2700

-continued

```
taggcgtgta cggtgggagg tctatataag cagagctcgt ttagtgaacc gtcagatcgc   2760
ctggagacgc catccacgct gttttgacct ccatagaaga caccgcgatc ggatccgcca   2820
ccatgaagaa atgcaccatc ctggtggtgg ccagcctgct gctggtcgat agcctgctgc   2880
ccggctacgg ccagaataag agcgtgcagg cccagcggaa cctgaacgag ctgtgctaca   2940
acgaggaaaa cgacaacaag ctgtaccacg tgctgaacag caagaacggc aagatctaca   3000
accggaacat cgtgaacagg ctgctgggcg acgctctgaa cggcaagccc gaggaaaaga   3060
aggacgaccc ccccaaggac ggcaacaagg acgacctgcc caaagaagag aagaaagacg   3120
atctgcctaa agaggaaaaa aaagacgatc ctcctaagga ccccaagaag gatgaccctc   3180
ctaaagaggc ccagaacaag ctgaaccagc ccgtggtggc cgacgagaac gtggatcagg   3240
gacctggcgc ccctcagggc ccaggcgctc cacagggacc cggggcaccc caggggcctg   3300
gggccccaca gggaccaggg gctcctcagg gccctggcgc acctcagggg ccaggggccc   3360
ctcaggggcc tggcgctccc cagggacctg gcgcaccaca gggccctggg gctccccagg   3420
gcccaggcgc ccctcaggga ccaggcgcac cccagggacc cggcgctcct cagggacctg   3480
gggctccaca ggggccaggc gcaccacagg aacctcccca gcagcctcct cagcagccac   3540
cccagcagcc ccctcagcag cctcctcagc agccccccaca gcagcctcca cagcagccta   3600
gaccccagcc cgacggcaat aacaacaaca ataataacaa cggcaacaac aacgaggaca   3660
gctacgtgcc cagcgccgag cagatcctgg aattcgtgaa gcagatcagc agccagctga   3720
ccgaagagtg gagccagtgc agcgtgacat gcggctctgg cgtgagagtg cggaagcgga   3780
agaacgtgaa caagcagccc gagaacctga ccctggaaga tatcgacacc gagatctgca   3840
agatggacaa gtgcagcagc atcttcaaca tcgtgtccaa cagcctgtga tgactcgagc   3900
tcaagcttcg aattcccgat aatcaacctc tggattacaa aatttgtgaa agattgactg   3960
gtattcttaa ctatgttgct ccttttacgc tatgtggata cgctgcttta atgcctttgt   4020
atcatgctat tgcttcccgt atggctttca ttttctcctc cttgtataaa tcctggttgc   4080
tgtctcttta tgaggagttg tggcccgttg tcaggcaacg tggcgtggtg tgcactgtgt   4140
ttgctgacgc aacccccact ggttggggca ttgccaccac ctgtcagctc ctttccggga   4200
ctttcgcttt ccccctccct attgccacgg cggaactcat cgccgcctgc cttgcccgct   4260
gctggacagg ggctcggctg ttgggcactg acaattccgt ggtgttgtcg gggaagctga   4320
cgtcctttcc atggctgctc gcctgtgttg ccacctggat tctgcgcggg acgtccttct   4380
gctacgtccc ttcggccctc aatccagcgg accttccttc ccgcggcctg ctgccggctc   4440
tgcggcctct tccgcgtctt cgccttcgcc ctcagacgag tcggatctcc ctttgggccg   4500
cctccccgcg tcgacgcgtg aattcggtac ctttaagacc aatgacttac aaggcagctg   4560
tagatcttag ccactttttta aaagaaaagg ggggactgga agggctaatt cactcccaac   4620
gaagacaaga tcgtcgagag atgctgcata taagcagctg ctttttgctt gtactgggtc   4680
tctctggtta gaccagatct gagcctggga gctctctggc taactaggga acccactgct   4740
taagcctcaa taaagcttgc cttgagtgct tcaagtagtg tgtgcccgtc tgttgtgtga   4800
ctctggtaac tagagatccc tcagaccctt ttagtcagtg tggaaaatct ctagcagt     4858
```

```
<210> SEQ ID NO 48
<211> LENGTH: 1071
<212> TYPE: DNA
<213> ORGANISM: Artificial
<220> FEATURE:
<223> OTHER INFORMATION: Sequence of transgene for CSP-delta GPI CO
```

<400> SEQUENCE: 48
atgaagaaat gcaccatcct ggtggtggcc agcctgctgc tggtcgatag cctgctgccc 60
ggctacggcc agaataagag cgtgcaggcc cagcggaacc tgaacgagct gtgctacaac 120
gaggaaaacg acaacaagct gtaccacgtg ctgaacagca agaacggcaa gatctacaac 180
cggaacatcg tgaacaggct gctgggcgac gctctgaacg gcaagcccga ggaaaagaag 240
gacgaccccc ccaaggacgg caacaaggac gacctgccca aagaagagaa gaaagacgat 300
ctgcctaaag aggaaaaaaa agacgatcct cctaaggacc ccaagaagga tgaccctcct 360
aaagaggccc agaacaagct gaaccagccc gtggtggccg acgagaacgt ggatcaggga 420
cctggcgccc ctcagggccc aggcgctcca cagggacccg ggcaccccca ggggcctggg 480
gccccacagg gaccaggggc tcctcagggc cctggcgcac ctcaggggcc aggggcccct 540
caggggcctg gcgctcccca gggacctggc gcaccacagg gccctggggc tccccagggc 600
ccaggcgccc ctcagggacc aggcgcaccc cagggacccg gcgctcctca gggacctggg 660
gctccacagg ggccaggcgc accacaggaa cctccccagc agcctcctca gcagccaccc 720
cagcagcccc ctcagcagcc tcctcagcag cccccacagc agcctccaca gcagcctaga 780
ccccagcccg acggcaataa caacaacaat aataacaacg gcaacaacaa cgaggacagc 840
tacgtgccca gcgccgagca gatcctggaa ttcgtgaagc agatcagcag ccagctgacc 900
gaagagtgga gccagtgcag cgtgacatgc ggctctggcg tgagagtgcg gaagcggaag 960
aacgtgaaca agcagcccga gaacctgacc ctggaagata tcgacaccga gatctgcaag 1020
atggacaagt gcagcagcat cttcaacatc gtgtccaaca gcctgtgatg a 1071

<210> SEQ ID NO 49
<211> LENGTH: 442
<212> TYPE: PRT
<213> ORGANISM: Plasmodium falciparum
<220> FEATURE:
<221> NAME/KEY: MISC_FEATURE
<222> LOCATION: (1)..(442)
<223> OTHER INFORMATION: CSP protein GenBank: M15505.1

<400> SEQUENCE: 49

Met Met Arg Lys Leu Ala Ile Leu Ser Val Ser Ser Phe Leu Phe Val
1 5 10 15

Glu Ala Leu Phe Gln Glu Tyr Gln Cys Tyr Gly Ser Ser Ser Asn Thr
20 25 30

Arg Val Leu Asn Glu Leu Asn Tyr Asp Asn Ala Gly Thr Asn Leu Tyr
35 40 45

Asn Glu Leu Glu Met Asn Tyr Tyr Gly Lys Gln Glu Asn Trp Tyr Ser
50 55 60

Leu Lys Lys Asn Ser Arg Ser Leu Gly Glu Asn Asp Asp Gly Asp Asn
65 70 75 80

Asp Asn Gly Asn Asn Asn Asn Gly Asn Asn Asn Asn Gly Asp Asn Gly
85 90 95

Arg Glu Gly Lys Asp Glu Asp Lys Arg Asp Gly Asn Asn Glu Asp Asn
100 105 110

Glu Lys Leu Arg Lys Pro Lys His Lys Lys Leu Lys Gln Pro Gly Asp
115 120 125

Gly Asn Pro Asp Pro Asn Ala Asn Pro Asn Val Asp Pro Asn Ala Asn
130 135 140

Pro Asn Val Asp Pro Asn Ala Asn Pro Asn Ala Asn Pro Asn Ala Asn

-continued

```
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Asn Ala Asn Pro Asn Ala Asn
            180                 185                 190

Pro Asn Ala Asn Pro Asn Ala Asn Pro Asn Ala Asn Pro Asn Ala Asn
        195                 200                 205

Pro Asn Val Asp Pro Asn Ala Asn Pro Asn Ala Asn Pro Asn Ala Asn
    210                 215                 220

Pro Asn Ala Asn Pro Asn Ala Asn Pro Asn Ala Asn Pro Asn Ala Asn
225                 230                 235                 240

Pro Asn Ala Asn Pro Asn Ala Asn Pro Asn Ala Asn Pro Asn Ala Asn
                245                 250                 255

Pro Asn Ala Asn Pro Asn Ala Asn Pro Asn Ala Asn Pro Asn Ala Asn
            260                 265                 270

Pro Asn Ala Asn Pro Asn Ala Asn Pro Asn Ala Asn Pro Asn Ala Asn
        275                 280                 285

Pro Asn Ala Asn Pro Asn Ala Asn Pro Asn Ala Asn Pro Asn Ala Asn
    290                 295                 300

Pro Asn Ala Asn Pro Asn Ala Asn Pro Asn Ala Asn Pro Asn Lys Asn
305                 310                 315                 320

Asn Gln Gly Asn Gly Gln Gly His Asn Met Pro Asn Asp Pro Asn Arg
                325                 330                 335

Asn Val Asp Glu Asn Ala Asn Ala Asn Asn Ala Val Lys Asn Asn Asn
            340                 345                 350

Asn Glu Glu Pro Ser Asp Lys His Ile Glu Gln Tyr Leu Lys Lys Ile
        355                 360                 365

Gln Asn Ser Leu Ser Thr Glu Trp Ser Pro Cys Ser Val Thr Cys Gly
    370                 375                 380

Asn Gly Ile Gln Val Arg Ile Lys Pro Gly Ser Ala Asp Lys Pro Lys
385                 390                 395                 400

Asp Gln Leu Asp Tyr Glu Asn Asp Ile Glu Lys Lys Ile Cys Lys Met
                405                 410                 415

Glu Lys Cys Ser Ser Val Phe Asn Val Val Asn Ser Ser Ile Gly Leu
            420                 425                 430

Ile Met Val Leu Ser Phe Leu Phe Leu Asn
        435                 440
```

<210> SEQ ID NO 50
<211> LENGTH: 1669
<212> TYPE: DNA
<213> ORGANISM: Plasmodium falciparum
<220> FEATURE:
<221> NAME/KEY: misc_feature
<222> LOCATION: (1)..(1669)
<223> OTHER INFORMATION: CSP gene GenBank: M15505.1

<400> SEQUENCE: 50

```
gtagaaacca cgtaatatta taaattacaa ttcatgatga gaaaattagc tattttatct      60

gtttcttcct ttttatttgt tgaggcctta ttccaggaat accagtgcta tggaagttcg     120

tcaaacacaa gggttctaaa tgaattaaat tatgataatg caggcactaa tttatataat     180

gaattagaaa tgaattatta tgggaaacag gaaaattggt atagtcttaa aaaaaatagt     240

agatcacttg gagaaaatga tgatggagat aatgataatg gaaataataa taatggaaat     300

aataataatg gagataatgg tcgtgaaggt aaagatgaag ataaaagaga tggaaataac     360
```

-continued

```
gaagacaacg agaaattaag gaaaccaaaa cataaaaaat taaagcaacc aggggatggt    420

aatcctgatc caaatgccaa cccaaatgta gatccaaatg ccaacccaaa tgtagatcca    480

aatgcaaacc caaatgcaaa cccaaatgca aacccaaatg caaacccaaa tgcaaaccca    540

aatgcaaacc caaatgcaaa cccaaatgca aacccaaatg caaacccaaa tgcaaaccca    600

aatgcaaacc caaatgcaaa cccaaatgca aacccaaatg caaacccaaa tgcaaaccca    660

aacgtagatc ctaatgcaaa tccaaatgca aacccaaatg caaacccaaa cgcaaaccca    720

aatgcaaatc ctaatgcaaa tcctaatgca aatcctaatg ccaatccaaa tgcaaatcca    780

aatgcaaacc caaacgcaaa ccccaatgca aatcctaatg ccaatccaaa tgcaaatcca    840

aatgcaaacc caaacgcaaa ccccaatgca aatcctaatg ccaatccaaa tgcaaatcca    900

aatgcaaacc ccaatgcaaa tcctaatgcc aatccaaatg caaatccaaa tgcaaaccca    960

aatgcaaacc caaatgcaaa tcctaataaa aacaatcaag gtaatggaca aggtcacaat   1020

atgccaaatg acccaaaccg aaatgtagat gaaaatgcta atgccaacaa tgctgtaaaa   1080

aataataata acgaagaacc aagtgataag cacatagaac aatatttaaa gaaaatacaa   1140

aattctcttt caactgaatg gtccccatgt agtgtaactt gtggaaatgg tattcaagtt   1200

agaataaagc ctggctctgc tgataaacct aaagaccaat tagattatga aaatgatatt   1260

gaaaaaaaaa tttgtaaaat ggaaaaatgt tccagtgtgt ttaatgtcgt aaatagttca   1320

ataggattaa taatggtatt atccttcttg ttccttaatt agataaagaa cacatcttag   1380

tttgagttgt acaatattta taaaaatata tactactttt tttcttaatt ttcatttttc   1440

tttatatttt cctatttaat ttattttttt gtgaatattt aattatgttt gcgattaatt   1500

gtagaaatat atatgtatat actatattta tagaatgtgt tattctcaaa aacaacaaca   1560

aaaaaaaaaa aaaaaaaaaa aaaaaagaaa aaaggattaa aagtaaaata gttataaata   1620

ttttcaaaaa tatttataac acaaaaaata cttcgaagtt catttaaca               1669


<210> SEQ ID NO 51
<211> LENGTH: 388
<212> TYPE: PRT
<213> ORGANISM: Plasmodium reichenowi
<220> FEATURE:
<221> NAME/KEY: MISC_FEATURE
<222> LOCATION: (1)..(388)
<223> OTHER INFORMATION: CSP protein GenBank M60972.1

<400> SEQUENCE: 51

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Ala Asp Asn
65                  70                  75                  80

Gly Asp Ala Asp Asn Gly Asp Glu Gly Ile Asp Glu Asn Arg Arg His
                85                  90                  95

Arg Asn Lys Glu Gly Lys Glu Lys Leu Lys Lys Pro Lys His Asn Lys
            100                 105                 110

Leu Lys Gln Pro Gly Asn Asp Asn Val Asp Pro Asn Ala Asn Pro Asn
```

```
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Val Asp Pro Asn Ala Asn Pro Asn
145                 150                 155                 160

Val Asn Pro Asn Ala Asn Pro Asn Val Asp Pro Asn Ala Asn Pro Asn
                165                 170                 175

Val Asn Pro Asn Ala Asn Pro Asn Val Asn Pro Asn Ala Asn Pro Asn
            180                 185                 190

Val Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Arg Asn Asn Glu Ala Asn Gly Gln
            260                 265                 270

Gly His Asn Lys Pro Asn Asp Gln Asn Arg Asn Val Asn Glu Asn Ala
        275                 280                 285

Asn Ala Asn Asn Ala Gly Arg Asn Asn Asn Asn Glu Glu Pro Ser Asp
    290                 295                 300

Lys His Ile Glu Glu Phe Leu Lys Gln Ile Gln Asn Asn Leu Ser Thr
305                 310                 315                 320

Glu Trp Ser Pro Cys Ser Val Thr Cys Gly Asn Gly Ile Gln Val Arg
                325                 330                 335

Ile Lys Pro Gly Ser Ala Gly Lys Pro Lys Asp Gln Leu Asp Tyr Glu
            340                 345                 350

Asn Asp Leu Glu Lys Lys Ile Cys Lys Met Glu Lys Cys Ser Ser Val
        355                 360                 365

Phe Asn Val Val Asn Ser Ser Ile Gly Leu Ile Met Val Leu Ser Phe
    370                 375                 380

Leu Phe Leu Asn
385


<210> SEQ ID NO 52
<211> LENGTH: 1167
<212> TYPE: DNA
<213> ORGANISM: Plasmodium reichenowi
<220> FEATURE:
<221> NAME/KEY: misc_feature
<222> LOCATION: (1)..(1167)
<223> OTHER INFORMATION: CSP gene GenBank M60972.1

<400> SEQUENCE: 52

atgatgagaa aattagctat tttatctgtt tcttcctttt tatttgttga ggccttattc      60

caggaatatc agtgctatgg aagttcgtca aacacaaggg ttctaaatga attaaattat     120

gataatgcag gcactaattt atataatgaa ttagaaatga attattatgg gaaacaggaa     180

aattggtata gccttaaaaa aaatagtaga tcacttggag aaaatgatga tgcagataat     240

ggtgatgcag ataatggtga tgaaggtata gatgaaaata gaagacatag aaataaagaa     300

ggcaaagaga aattaaagaa accaaaacat aataaattaa agcaaccagg gaatgataat     360

gttgatccaa atgccaaccc aaatgtagat ccaaatgcca acccaaatgt agatcccaat     420
```

-continued

```
gcaaacccaa atgtagatcc caatgcaaac ccaaatgtag atcctaatgc aaacccaaat    480

gtaaatccca atgcaaaccc aaatgtagat cctaatgcaa acccaaatgt aaatcccaat    540

gcaaacccaa atgtaaatcc caatgcaaac ccaaatgtaa atcccaatgc aaacccaaat    600

gcaaatccta atgcaaatcc caatgcaaat cccaatgcaa acccaaatgc aaatcctaat    660

gcaaatccca atgcaaatcc caatgcaaac ccaaatgcaa atcctaatgc aaatcctaat    720

gcaaatccta atgcaaatcc taatgcaaat cctaatgcca atccaaacgc aaacccaaat    780

gcaaatccta atagaaacaa tgaagctaat ggacaaggtc acaataagcc aaatgaccaa    840

aaccgaaatg taaatgaaaa tgctaatgcc aacaatgctg gaagaaataa taataacgaa    900

gaaccaagtg ataagcacat agaagaattt ttaaagcaaa tacaaaataa tctttcaact    960

gaatggtccc catgtagtgt aacttgtgga aatggtattc aagttagaat aaagcctggc   1020

tctgctggta aacctaaaga ccaattagat tatgaaaatg accttgaaaa aaaaatttgt   1080

aaaatggaaa aatgttccag tgtgttcaat gtcgtaaata gttcaatagg attaataatg   1140

gtattatcct tcttgttcct taattag                                       1167
```

```
<210> SEQ ID NO 53
<211> LENGTH: 367
<212> TYPE: PRT
<213> ORGANISM: Plasmodium yoelii
<220> FEATURE:
<221> NAME/KEY: MISC_FEATURE
<222> LOCATION: (1)..(367)
<223> OTHER INFORMATION: CSP protein GenBank: J02695.1

<400> SEQUENCE: 53

Met Lys Lys Cys Thr Ile Leu Val Val Ala Ser Leu Leu Leu Val Asp
1               5                   10                  15

Ser Leu Leu Pro Gly Tyr Gly Gln Asn Lys Ser Val Gln Ala Gln Arg
            20                  25                  30

Asn Leu Asn Glu Leu Cys Tyr Asn Glu Glu Asn Asp Asn Lys Leu Tyr
        35                  40                  45

His Val Leu Asn Ser Lys Asn Gly Lys Ile Tyr Asn Arg Asn Ile Val
    50                  55                  60

Asn Arg Leu Leu Gly Asp Ala Leu Asn Gly Lys Pro Glu Glu Lys Lys
65                  70                  75                  80

Asp Asp Pro Pro Lys Asp Gly Asn Lys Asp Asp Leu Pro Lys Glu Glu
                85                  90                  95

Lys Lys Asp Asp Leu Pro Lys Glu Glu Lys Lys Asp Asp Pro Pro Lys
            100                 105                 110

Asp Pro Lys Lys Asp Asp Pro Pro Lys Glu Ala Gln Asn Lys Leu Asn
        115                 120                 125

Gln Pro Val Val Ala Asp Glu Asn Val Asp Gln Gly Pro Gly Ala Pro
    130                 135                 140

Gln Gly Pro Gly Ala Pro Gln Gly Pro Gly Ala Pro Gln Gly Pro Gly
145                 150                 155                 160

Ala Pro Gln Gly Pro Gly Ala Pro Gln Gly Pro Gly Ala Pro Gln Gly
                165                 170                 175

Pro Gly Ala Pro Gln Gly Pro Gly Ala Pro Gln Gly Pro Gly Ala Pro
            180                 185                 190

Gln Gly Pro Gly Ala Pro Gln Gly Pro Gly Ala Pro Gln Gly Pro Gly
        195                 200                 205

Ala Pro Gln Gly Pro Gly Ala Pro Gln Gly Pro Gly Ala Pro Gln Gly
    210                 215                 220
```

```
Pro Gly Ala Pro Gln Glu Pro Pro Gln Gln Pro Pro Gln Gln Pro Pro
225                 230                 235                 240

Gln Gln Pro Pro Gln Gln Pro Pro Gln Gln Pro Pro Gln Gln Pro Pro
                245                 250                 255

Gln Gln Pro Arg Pro Gln Pro Asp Gly Asn Asn Asn Asn Asn Asn Asn
            260                 265                 270

Asn Gly Asn Asn Asn Glu Asp Ser Tyr Val Pro Ser Ala Glu Gln Ile
        275                 280                 285

Leu Glu Phe Val Lys Gln Ile Ser Ser Gln Leu Thr Glu Glu Trp Ser
    290                 295                 300

Gln Cys Ser Val Thr Cys Gly Ser Gly Val Arg Val Arg Lys Arg Lys
305                 310                 315                 320

Asn Val Asn Lys Gln Pro Glu Asn Leu Thr Leu Glu Asp Ile Asp Thr
                325                 330                 335

Glu Ile Cys Lys Met Asp Lys Cys Ser Ser Ile Phe Asn Ile Val Ser
            340                 345                 350

Asn Ser Leu Gly Phe Val Ile Leu Leu Val Leu Val Phe Phe Asn
        355                 360                 365


<210> SEQ ID NO 54
<211> LENGTH: 1580
<212> TYPE: DNA
<213> ORGANISM: Plasmodium yoelii
<220> FEATURE:
<221> NAME/KEY: misc_feature
<222> LOCATION: (1)..(1580)
<223> OTHER INFORMATION: CSP gene GenBank J02695.1

<400> SEQUENCE: 54

aaaatgaaga agtgtaccat tttagttgta gcgtcacttt tattagttga ttctctactt     60

ccaggatatg gacaaaataa aagtgtccaa gcccaaagaa acttaaacga gctatgttac    120

aatgaagaaa atgataataa attgtatcac gtccttaact cgaagaatgg aaaaatatac    180

aatcgaaata tagtcaacag attacttggc gatgctctca acggaaaacc agaagaaaaa    240

aaagatgatc ccccaaaaga tggcaacaaa gatgatcttc caaaagaaga aaaaaaagat    300

gatcttccaa aagaagaaaa aaaagatgat cccccaaaag atcctaaaaa agatgatcca    360

ccaaaagagg ctcaaaataa attgaatcaa ccagtagtgg cagatgaaaa tgtagatcaa    420

gggccaggag caccacaagg gccaggagca ccacaaggac caggagcacc acagggtcca    480

ggagcaccac aaggaccagg agcaccacaa ggaccaggag caccacaagg tccaggagca    540

ccacagggtc caggagcacc acagggtcca ggagcaccac aaggaccagg agcaccacag    600

gggccaggag caccacaagg accaggagca ccacaaggac caggagcacc acaggggcca    660

ggagcaccac aagggccagg agcaccacaa gaaccacccc aacaaccacc ccaacaacca    720

ccacaacagc caccacaaca gccaccacaa cagccaccac aacagccacc acaacaacca    780

cgcccacagc cagatggtaa taacaacaat aacaataata atggtaataa taatgaagat    840

tcttatgtcc caagcgcgga acaaatacta gaatttgtta aacagataag tagtcaactc    900

acagaggaat ggtctcaatg tagtgtaacc tgtggttctg gtgtaagagt tagaaaacga    960

aaaaatgtaa acaagcaacc agaaaatttg accttagagg atattgatac tgaaatttgt   1020

aaaatggata aatgttcaag tatatttaat attgtaagca attcattagg atttgtaata   1080

ttattagtat tagtattctt taattaaata aacattacac attattataa atatttatat   1140

attatataaa tatttaatat acatataatg tgtgtagact ttattttttg tattgtgaac   1200
```

tttcctcatt tattacgatt atttttatat atatacatat ttaatatgta aattaaaaga 1260
aaaaagaaat aatagaaatc ttattatatt tatgatataa attaaaaaaa taaaatatat 1320
atacattaca aaatttactt tttttagttt attttttttcg tgtttattat atatgtaatt 1380
aacttgttat gacgatatcg aaactttatt tttgagaata tatttttatg aattagaata 1440
ttaataatta ttatggttat ttgtttggga atttatataa tttacaatat tatttaaggg 1500
caatctaaaa atattttatt gttatgatat ttgaaacatt ttatgtagct atccaaatta 1560
tttatttgtg taaaatattt 1580

<210> SEQ ID NO 55
<211> LENGTH: 341
<212> TYPE: PRT
<213> ORGANISM: Plasmodium coateneyi
<220> FEATURE:
<221> NAME/KEY: MISC_FEATURE
<222> LOCATION: (1)..(341)
<223> OTHER INFORMATION: CSP Protein GenBank AY135360.1

<400> SEQUENCE: 55

Met Lys Asn Phe Ile Leu Leu Ala Val Ser Ser Ile Leu Leu Val Asp
1 5 10 15

Leu Phe Pro Thr His Phe Gly His Asn Val Asp Leu Ser Arg Ala Ile
20 25 30

Asn Leu Asn Gly Val Ser Phe Asn Asn Val Asp Thr Ser Leu Leu Gly
35 40 45

Ala Ala Gln Val Arg Gln Ser Ala Ser Arg Gly Arg Gly Leu Gly Glu
50 55 60

Lys Pro Lys Lys Lys Ala Glu Lys Lys Glu Glu Glu Pro Lys Lys Pro
65 70 75 80

Asn Glu Asn Lys Leu Lys Gln Pro Val Asp Gly Ala Arg Asp Gly Pro
85 90 95

Ala Pro Ala Ala Asp Gly Ala Arg Asp Gly Pro Ala Pro Ala Ala Asp
100 105 110

Gly Ala Arg Asp Gly Pro Ala Pro Ala Ala Asp Gly Ala Arg Asp Gly
115 120 125

Pro Ala Pro Ala Ala Asp Gly Ala Arg Asp Gly Pro Ala Pro Ala Ala
130 135 140

Asp Gly Ala Arg Asp Gly Pro Ala Pro Ala Ala Asp Gly Ala Arg Asp
145 150 155 160

Gly Pro Ala Pro Ala Ala Asp Gly Ala Arg Asp Gly Pro Ala Pro Pro
165 170 175

Ala Asp Gly Ala Arg Asp Gly Pro Ala Pro Pro Ala Ala Asp Gly Ala
180 185 190

Arg Asp Gly Pro Ala Pro Pro Ala Ala Asp Gly Ala Arg Asp Gly Pro
195 200 205

Ala Pro Pro Ala Gly Gln Gly Gly Gly Asn Ala Ala Gly Gln Ala Gln
210 215 220

Gly Gly Gly Asn Ala Gly Asn Lys Lys Ala Gly Asp Ala Ala Gly Asn
225 230 235 240

Ala Gly Ala Ala Lys Gly Gln Gly Gln Asn Asn Glu Gly Ala Asn Val
245 250 255

Pro Asn Glu Lys Val Val Asn Asp Tyr Leu Gln Lys Ile Arg Ser Thr
260 265 270

Val Thr Thr Glu Trp Thr Pro Cys Ser Val Thr Cys Gly Asn Gly Val

```
        275                 280                 285

Arg Leu Arg Arg Lys Ala His Ala Glu Lys Lys Lys Pro Glu Asp Leu
    290                 295                 300

Thr Met Asp Asp Leu Asp Val Glu Val Cys Ala Met Asp Lys Cys Ala
305                 310                 315                 320

Gly Ile Phe Asn Phe Val Ser Asn Ser Leu Gly Leu Val Ile Leu Leu
                325                 330                 335

Val Leu Ala Phe Asn
            340


<210> SEQ ID NO 56
<211> LENGTH: 1049
<212> TYPE: DNA
<213> ORGANISM: Plasmodium coatneyi
<220> FEATURE:
<221> NAME/KEY: misc_feature
<222> LOCATION: (1)..(1049)
<223> OTHER INFORMATION: CSP gene AY135360.1

<400> SEQUENCE: 56

atgaagaact tcattctctt ggctgtttct tccatcctgt tggtggactt gttccccacg     60

cacttcggac ataatgtaga tctctccagg gccataaatt taaatggagt aagcttcaat    120

aatgtagaca ccagtttact tggcgcagca caggtaagac aaagtgctag ccgaggcaga    180

ggacttggtg agaaaccaaa aaaaaaggcg gaaaaaaaag aagaagaacc aaaaaagcca    240

aatgaaaata agctgaagca accagtagat ggagcacgag atgggccagc accagcagca    300

gatggagcaa gagatggacc agcaccagca gcagatggag cacgagatgg accagcacca    360

gcagcagatg gagcaagaga tggaccagca ccagcagcag atggagcaag agatggacca    420

gcaccagcag cagatggagc aagagatgga ccagcaccag cagcagatgg agcacgagat    480

ggaccagcac cagcagcaga tggagcaaga gatgggccag caccaccagc cgatggagca    540

agagatgggc cagcaccacc agcagcagat ggagcacgag atggaccagc accaccagca    600

gcagatggag cacgagatgg gccagcacca ccagcaggac aaggaggagg aaatgcagca    660

ggccaagcac aaggaggagg aaatgccgga aacaaaaaag caggagacgc agctggaaac    720

gcaggagcag caaaaggaca gggacaaaat aatgaaggtg cgaatgtccc aaatgagaaa    780

gttgtgaatg attacctaca gaaaattaga tctaccgtta ccaccgaatg gactccatgc    840

agtgtaacct gtggaaatgg tgtaagactt agaagaaaag ctcatgcaga aaagaaaaaa    900

ccagaggacc ttaccatgga tgaccttgac gtggaagttt gtgcaatgga taagtgcgct    960

ggcatattta actttgtgag taattcatta gggctagtca tattgttagt cctagcattc   1020

aattaagtag ctgacatcca ttattttcg                                     1049


<210> SEQ ID NO 57
<211> LENGTH: 371
<212> TYPE: PRT
<213> ORGANISM: Plasmodium knowlesi
<220> FEATURE:
<221> NAME/KEY: MISC_FEATURE
<222> LOCATION: (1)..(371)
<223> OTHER INFORMATION: CSP protein GenBank: DQ350294.2

<400> SEQUENCE: 57

Met Arg Asn Phe Ile Leu Leu Ala Val Ser Ser Ile Leu Leu Val Asp
1               5                   10                  15

Leu Leu Pro Thr His Phe Glu His Asn Val Asp Leu Ser Arg Ala Ile
            20                  25                  30
```

```
Asn Val Asn Gly Val Ser Phe Asn Asn Val Asp Thr Ser Ser Leu Gly
        35                  40                  45

Ala Ala Gln Val Arg Gln Ser Ala Ser Arg Gly Arg Gly Leu Gly Glu
    50                  55                  60

Lys Arg Lys Glu Gly Ala Asp Lys Glu Lys Lys Lys Glu Lys Glu Glu
65                  70                  75                  80

Glu Pro Lys Lys Pro Asn Glu Asn Lys Leu Lys Gln Pro Asn Pro Gly
                85                  90                  95

Gln Pro Gln Ala Gln Gly Asp Gly Ala Asn Ala Gly Gln Pro Gln Ala
            100                 105                 110

Gln Gly Asp Gly Ala Asn Ala Gly Gln Pro Gln Ala Gln Gly Asp Gly
        115                 120                 125

Ala Asn Ala Gly Gln Pro Gln Ala Gln Gly Asp Gly Ala Asn Ala Gly
    130                 135                 140

Gln Pro Gln Ala Gln Gly Asp Gly Ala Asn Ala Gly Gln Pro Gln Ala
145                 150                 155                 160

Gln Gly Asp Gly Ala Asn Ala Gly Gln Pro Gln Ala Gln Gly Asp Gly
                165                 170                 175

Ala Asn Ala Gly Gln Pro Gln Ala Gln Gly Asp Gly Ala Asn Ala Gly
            180                 185                 190

Gln Pro Gln Ala Gln Gly Asp Gly Ala Asn Ala Gly Gln Pro Gln Ala
        195                 200                 205

Gln Gly Asp Gly Ala Asn Ala Gly Gln Pro Gln Ala Gln Gly Asp Gly
    210                 215                 220

Ala Asn Ala Gly Gln Pro Gln Ala Gln Gly Asp Arg Ala Asn Ala Gly
225                 230                 235                 240

Gln Pro Gln Ala Gln Gly Asp Gly Ala Asn Val Pro Arg Gln Gly Arg
                245                 250                 255

Asn Gly Gly Gly Ala Pro Ala Gly Gly Asn Glu Gly Asn Lys Gln Ala
            260                 265                 270

Gly Lys Gly Gln Gly Gln Asn Asn Gln Gly Ala Asn Ala Pro Asn Glu
        275                 280                 285

Lys Val Val Asn Asp Tyr Leu His Lys Ile Arg Ser Ser Val Thr Thr
    290                 295                 300

Glu Trp Thr Pro Cys Ser Val Thr Cys Gly Asn Gly Val Arg Ile Arg
305                 310                 315                 320

Arg Lys Ala His Ala Gly Asn Lys Lys Ala Glu Asp Leu Thr Met Asp
                325                 330                 335

Asp Leu Glu Val Glu Ala Cys Val Met Asp Lys Cys Ala Gly Ile Phe
            340                 345                 350

Asn Val Val Ser Asn Ser Leu Gly Leu Val Ile Leu Leu Val Leu Ala
        355                 360                 365

Leu Phe Asn
    370
```

```
<210> SEQ ID NO 58
<211> LENGTH: 1113
<212> TYPE: DNA
<213> ORGANISM: Plasmodium knowlesi
<220> FEATURE:
<221> NAME/KEY: misc_feature
<222> LOCATION: (1)..(1113)
<223> OTHER INFORMATION: CSP gene GenBank: DQ350294.2

<400> SEQUENCE: 58
```

```
atgaggaact tcattctctt ggccgtctcc tccatcctgc tggtggactt gctccccaca     60

cacttcgaac ataatgtaga tctctccagg gccataaatg taaatggagt aagcttcaat    120

aatgtagaca ccagttcact tggcgcagca caggtaagac aaagtgctag ccgaggcaga    180

ggacttggtg agaagcgaaa agaaggagct gataaagaaa agaaaaaaga aaaagaagaa    240

gaaccaaaga agccaaatga aaataagctg aaacaaccga atccaggaca accacaagca    300

caaggagatg gagcaaatgc aggacaacca caagcacaag gagatggagc aaatgcagga    360

caaccacaag cacagggtga tggagcaaat gcaggacaac cacaagcaca aggagatgga    420

gcaaatgcag gacaaccaca agcacagggt gatggagcaa atgcaggaca accacaagca    480

caaggagatg gagcaaatgc aggacaacca caagcacagg gtgatggagc aaatgcagga    540

caaccacaag cacaaggaga tggagcaaat gcaggacaac cacaagcaca gggtgatgga    600

gcaaatgcag gacaaccaca agcacagggt gatggagcaa atgcaggaca accacaagca    660

cagggtgatg gagcaaatgc aggacaacca caagcacagg gtgatagggc gaatgcagga    720

caaccacaag cacaaggaga tggggcaaat gtaccacgac aaggaagaaa cgggggaggt    780

gcaccagcag gaggaaatga ggggaataaa caagcaggaa aaggacaggg acaaaacaat    840

cagggtgcga atgccccaaa tgaaaaagtt gtgaatgatt acctacacaa aattagatct    900

agcgttacca ccgagtggac tccatgcagt gtaacctgtg gaaatggtgt aagaattaga    960

agaaaagctc atgcaggtaa taaaaaggca gaggacctta ctatggatga ccttgaggtg   1020

gaagcttgtg taatggataa gtgcgctggc atatttaacg ttgtgagtaa ttcattaggg   1080

ttagtcatat tgttagtcct agcattattc aat                                1113
```

<210> SEQ ID NO 59
<211> LENGTH: 332
<212> TYPE: PRT
<213> ORGANISM: Plasmodium berghei
<220> FEATURE:
<221> NAME/KEY: MISC_FEATURE
<222> LOCATION: (1)..(332)
<223> OTHER INFORMATION: CSP protein GenBank M28887.1

<400> SEQUENCE: 59

```
Met Lys Lys Cys Thr Ile Leu Val Val Ala Ser Leu Leu Leu Val Asn
1               5                   10                  15

Ser Leu Leu Pro Gly Tyr Gly Gln Asn Lys Ile Ile Gln Ala Gln Arg
            20                  25                  30

Asn Leu Asn Glu Leu Cys Tyr Asn Glu Gly Asn Asp Asn Lys Leu Tyr
        35                  40                  45

His Val Leu Asn Ser Lys Asn Gly Lys Ile Tyr Asn Arg Asn Thr Val
    50                  55                  60

Asn Arg Leu Leu Ala Asp Ala Pro Glu Gly Lys Lys Asn Glu Lys Lys
65                  70                  75                  80

Asn Glu Lys Ile Glu Arg Asn Asn Lys Leu Lys Gln Pro Pro Pro Pro
                85                  90                  95

Pro Asn Pro Asn Asp Pro Pro Pro Pro Asn Pro Asn Asp Pro Pro Pro
            100                 105                 110

Pro Asn Pro Asn Asp Pro Pro Pro Pro Asn Pro Asn Asp Pro Ala Pro
        115                 120                 125

Pro Asn Ala Asn Asp Pro Ala Pro Pro Asn Ala Asn Asp Pro Ala Pro
    130                 135                 140

Pro Asn Ala Asn Asp Pro Ala Pro Pro Asn Ala Asn Asp Pro Ala Pro
145                 150                 155                 160
```

-continued

```
Pro Asn Ala Asn Asp Pro Ala Pro Pro Asn Ala Asn Asp Pro Ala Pro
                165                 170                 175

Pro Asn Ala Asn Asp Pro Pro Pro Pro Asn Pro Asn Asp Pro Ala Pro
            180                 185                 190

Pro Gln Gly Asn Asn Asn Pro Gln Pro Gln Pro Arg Pro Gln Pro Gln
        195                 200                 205

Pro Gln Pro Gln Pro Gln Pro Gln Pro Gln Pro Gln Pro Gln Pro Arg
    210                 215                 220

Pro Gln Pro Gln Pro Gln Pro Gly Gly Asn Asn Asn Asn Lys Asn Asn
225                 230                 235                 240

Asn Asn Asp Asp Ser Tyr Ile Pro Ser Ala Glu Lys Ile Leu Glu Phe
                245                 250                 255

Val Lys Gln Ile Arg Asp Ser Ile Thr Glu Glu Trp Ser Gln Cys Asn
            260                 265                 270

Val Thr Cys Gly Ser Gly Ile Arg Val Arg Lys Arg Lys Gly Ser Asn
        275                 280                 285

Lys Lys Ala Glu Asp Leu Thr Leu Glu Asp Ile Asp Thr Glu Ile Cys
    290                 295                 300

Lys Met Asp Lys Cys Ser Ser Ile Phe Asn Ile Val Ser Asn Ser Leu
305                 310                 315                 320

Gly Phe Val Ile Leu Leu Val Leu Val Phe Phe Asn
                325                 330
```

<210> SEQ ID NO 60
<211> LENGTH: 999
<212> TYPE: DNA
<213> ORGANISM: Plasmodium berghei
<220> FEATURE:
<221> NAME/KEY: misc_feature
<222> LOCATION: (1)..(999)
<223> OTHER INFORMATION: CSP gene GenBank: M28887.1

<400> SEQUENCE: 60

```
atgaagaagt gtaccatttt agttgtagcg tcacttttat tagttaattc tctacttcca      60

ggatatggac aaaataaaat catccaagcc caaaggaact taaacgagct atgttacaat     120

gaaggaaatg ataataaatt gtatcacgtg cttaactcta agaatggaaa aatatacaat     180

cgaaatacag tcaacagatt acttgccgat gctcccgaag gaaaaaaaaa tgagaaaaaa     240

aacgaaaaaa tagagcgtaa taataaattg aaacaaccac caccaccacc aaacccaaat     300

gacccaccac caccaaaccc aaatgaccca ccaccaccaa acccaaatga cccaccacca     360

ccaaacccaa atgacccagc accaccaaac gcaaatgacc cagcaccacc aaacgcaaat     420

gacccagcac caccaaacgc aaatgaccca gcaccaccaa acgcaaatga cccagcacca     480

ccaaacgcaa atgacccagc accaccaaac gcaaatgacc cagcaccacc aaacgcaaat     540

gacccaccac caccaaaccc aaatgaccca gcaccaccac aaggaaataa caatccacaa     600

ccacagccac ggccgcagcc acaaccacag ccacagccac aaccacagcc acagccacaa     660

ccacagccac gaccacagcc acaaccacag ccaggtggta ataacaataa caaaaataat     720

aataatgacg attcttatat cccaagcgcg gaaaaaatac tagaatttgt taaacagatc     780

agggatagta tcacagagga atggtctcaa tgtaacgtaa catgtggttc tggtataaga     840

gttagaaaac gaaaaggttc aaataagaaa gcagaagatt tgaccttaga agatattgat     900

actgaaattt gtaaaatgga taaatgttca agtatattta atattgtaag caattcatta     960

ggatttgtaa tattattagt attagtattc tttaattaa                            999
```

<210> SEQ ID NO 61
<211> LENGTH: 322
<212> TYPE: PRT
<213> ORGANISM: Plasmodium vivax
<220> FEATURE:
<221> NAME/KEY: MISC_FEATURE
<222> LOCATION: (1)..(322)
<223> OTHER INFORMATION: CSP protein GenBank: AY674050.1

<400> SEQUENCE: 61

```
Lys Ala Ile Asn Leu Asn Gly Val Asn Phe Asn Asn Val Asp Ala Ser
1               5                   10                  15

Ser Leu Gly Ala Ala His Val Gly Gln Ser Ala Ser Arg Gly Arg Gly
            20                  25                  30

Leu Gly Glu Asn Pro Asp Asp Glu Glu Gly Asp Ala Lys Lys Lys Lys
        35                  40                  45

Asp Gly Lys Lys Ala Glu Pro Lys Asn Pro Arg Glu Asn Lys Leu Lys
    50                  55                  60

Gln Pro Gly Asp Arg Ala Asp Gly Gln Pro Ala Gly Asp Arg Ala Asp
65                  70                  75                  80

Gly Gln Pro Ala Gly Asp Arg Ala Asp Gly Gln Pro Ala Gly Asp Arg
                85                  90                  95

Ala Ala Gly Gln Pro Ala Gly Asp Arg Ala Asp Gly Gln Pro Ala Gly
            100                 105                 110

Asp Arg Ala Ala Gly Gln Pro Ala Gly Asp Arg Ala Asp Gly Gln Pro
        115                 120                 125

Ala Gly Asp Arg Ala Ala Gly Gln Pro Ala Gly Asp Arg Ala Asp Gly
    130                 135                 140

Gln Pro Ala Gly Asp Arg Ala Ala Gly Gln Pro Ala Gly Asp Arg Ala
145                 150                 155                 160

Asp Gly Gln Pro Ala Gly Asp Arg Ala Ala Gly Gln Pro Ala Gly Asp
                165                 170                 175

Arg Ala Ala Gly Gln Pro Ala Gly Asp Arg Ala Asp Gly Gln Pro Ala
            180                 185                 190

Gly Asp Arg Ala Ala Gly Gln Pro Ala Gly Asp Arg Ala Ala Gly Gln
        195                 200                 205

Pro Ala Gly Asp Arg Ala Ala Gly Gln Pro Ala Gly Asn Gly Ala Gly
    210                 215                 220

Gly Gln Ala Ala Gly Gly Asn Ala Ala Asn Lys Lys Ala Glu Asp Ala
225                 230                 235                 240

Gly Gly Asn Ala Gly Gly Gln Gly Gln Asn Asn Glu Gly Ala Asn Ala
                245                 250                 255

Pro Asn Glu Lys Ser Val Lys Glu Tyr Leu Asp Lys Val Arg Ala Thr
            260                 265                 270

Val Gly Thr Glu Trp Thr Pro Cys Ser Val Thr Cys Gly Val Gly Val
        275                 280                 285

Arg Val Arg Arg Arg Val Asn Ala Ala Asn Lys Lys Pro Glu Asp Leu
    290                 295                 300

Thr Leu Asn Asp Leu Glu Thr Asp Val Cys Thr Met Asp Lys Cys Ala
305                 310                 315                 320

Gly Ile
```

<210> SEQ ID NO 62
<211> LENGTH: 968
<212> TYPE: DNA

<213> ORGANISM: Plasmodium vivax
<220> FEATURE:
<221> NAME/KEY: misc_feature
<222> LOCATION: (1)..(968)
<223> OTHER INFORMATION: CSP gene GenBank: AY674050.1

<400> SEQUENCE: 62
ccaaggccat aaatttaaat ggagtaaact tcaataatgt agacgccagt tcacttggcg 60
cggcacacgt aggacaaagt gctagccgag gcagaggact tggtgagaac ccagatgacg 120
aggaaggaga tgctaaaaaa aaaaaggatg gaaagaaagc agaaccaaaa aatccacgtg 180
aaaataagct gaaacaacca ggagacagag cagatggaca gccagcagga gacagagcag 240
atggacagcc agcaggagac agagcagatg gacagccagc aggtgataga gcagctggac 300
aaccagcagg tgatagagca gatggacagc cagcaggcga tagagcagct ggacagccag 360
caggcgatag agcagatgga cagccagcag gagatagagc agctggacag ccagcaggcg 420
atagagcaga tggacagcca gcaggagata gagcagctgg acagccagca ggcgatagag 480
cagatggaca gccagcagga gatagagcag ctggacaacc agcaggtgat agagcagctg 540
gacaaccagc aggagataga gcagatggac aaccagcagg agatagagca gctggacagc 600
cagcaggaga tagagcagct ggacagccag caggagatag agcagctgga cagccagcag 660
gaaatggtgc aggtggacag gcagcaggag gaaatgcggc aaacaagaag gcagaagacg 720
caggaggaaa cgcaggagga cagggacaaa ataatgaagg tgcgaatgcc ccaaatgaaa 780
agtctgtgaa agaataccta gataaagtta gagctaccgt tggcaccgaa tggactccat 840
gcagtgtaac ctgtggagtg ggtgtaagag tcagaagaag agttaatgca gctaacaaaa 900
aaccagagga tcttactttg aatgaccttg agactgatgt ttgtacaatg gataagtgtg 960
ctggcata 968

<210> SEQ ID NO 63
<211> LENGTH: 429
<212> TYPE: PRT
<213> ORGANISM: Plasmodium malariae
<220> FEATURE:
<221> NAME/KEY: MISC_FEATURE
<222> LOCATION: (1)..(429)
<223> OTHER INFORMATION: CSP protein GenBank: J03992.1

<400> SEQUENCE: 63

Met Lys Lys Leu Ser Val Leu Ala Ile Ser Ser Phe Leu Ile Val Asp
1               5                   10                  15

Phe Leu Phe Pro Gly Tyr His His Asn Ser Asn Ser Thr Lys Ser Arg
            20                  25                  30

Asn Leu Ser Glu Leu Cys Tyr Asn Asn Val Asp Thr Lys Leu Phe Asn
        35                  40                  45

Glu Leu Glu Val Arg Tyr Ser Thr Asn Gln Asp His Phe Tyr Asn Tyr
    50                  55                  60

Asn Lys Thr Ile Arg Leu Leu Asn Glu Asn Asn Asn Glu Lys Asp Gly
65                  70                  75                  80

Asn Val Thr Asn Glu Arg Lys Lys Lys Pro Thr Lys Ala Val Glu Asn
                85                  90                  95

Lys Leu Lys Gln Pro Pro Gly Asp Asp Asp Gly Ala Gly Asn Asp Ala
            100                 105                 110

Gly Asn Asp Ala Gly Asn Asp Ala Gly Asn Ala Ala Gly Asn Ala Ala
        115                 120                 125

Gly Asn Ala Ala Gly Asn Ala Ala Gly Asn Ala Ala Gly Asn Ala Ala

```
    130                 135                 140

Gly Asn Ala Ala Gly Asn Ala Ala Gly Asn Ala Ala Gly Asn Ala Ala
145                 150                 155                 160

Gly Asn Asp Ala Gly Asn Ala Ala Gly Asn Ala Ala Gly Asn Ala Ala
                165                 170                 175

Gly Asn Ala Ala Gly Asn Ala Ala Gly Asn Asp Ala Gly Asn Ala Ala
            180                 185                 190

Gly Asn Ala Ala Gly Asn Ala Ala Gly Asn Ala Ala Gly Asn Ala Ala
        195                 200                 205

Gly Asn Ala Ala Gly Asn Ala Ala Gly Asn Ala Ala Gly Asn Ala Ala
    210                 215                 220

Gly Asn Ala Ala Gly Asn Asp Ala Gly Asn Ala Ala Gly Asn Ala Ala
225                 230                 235                 240

Gly Asn Ala Ala Gly Asn Ala Ala Gly Asn Ala Ala Gly Asn Ala Ala
                245                 250                 255

Gly Asn Ala Ala Gly Asn Ala Ala Gly Asn Ala Ala Gly Asn Ala Ala
            260                 265                 270

Gly Asn Ala Ala Gly Asn Ala Ala Gly Asn Ala Ala Gly Asn Ala Ala
        275                 280                 285

Gly Asn Ala Ala Gly Asn Ala Ala Gly Asn Ala Ala Gly Asn Ala Ala
    290                 295                 300

Gly Asn Ala Ala Gly Asn Ala Ala Gly Asn Glu Lys Ala Lys Asn Lys
305                 310                 315                 320

Asp Asn Lys Val Asp Ala Asn Thr Asn Lys Lys Asp Asn Gln Glu Glu
                325                 330                 335

Asn Asn Asp Ser Ser Asn Gly Pro Ser Glu Glu His Ile Lys Asn Tyr
            340                 345                 350

Leu Glu Ser Ile Arg Asn Ser Ile Thr Glu Glu Trp Ser Pro Cys Ser
        355                 360                 365

Val Thr Cys Gly Ser Gly Ile Arg Ala Arg Arg Lys Val Gly Ala Lys
    370                 375                 380

Asn Lys Lys Pro Ala Glu Leu Val Leu Ser Asp Leu Glu Thr Glu Ile
385                 390                 395                 400

Cys Ser Leu Asp Lys Cys Ser Ser Ile Phe Asn Val Val Ser Asn Ser
                405                 410                 415

Leu Gly Ile Val Leu Val Leu Val Leu Ile Leu Phe His
            420                 425


<210> SEQ ID NO 64
<211> LENGTH: 1545
<212> TYPE: DNA
<213> ORGANISM: Plasmodium malariae

<400> SEQUENCE: 64

tttcacatac ataatttgct gaatattaaa aaaaaataaa taataagtaa ataataaaaa      60

cacaaaaaag tatatataaa tatagacttg ctccaacatg aagaagttat ctgtcttagc     120

aatatcctct tttttaattg ttgatttcct cttccctgga tatcatcaca actcaaattc     180

caccaagtca agaaatttaa gtgagttgtg ttacaataat gtggacacta aattatttaa     240

tgagttagaa gtcagatata gcacgaatca agatcatttc tataactata ataagacaat     300

cagattactt aatgaaaata acaatgaaaa agatggaaat gtgaccaatg aaagaaaaaa     360

aaaacccaca aaagctgttg aaaataaatt gaaacaaccc cccggagatg atgatggcgc     420

aggaaatgat gcaggaaatg atgcaggaaa tgatgcagga aatgcagcag gaaatgcagc     480
```

```
aggaaatgca gcaggaaatg cagcaggtaa cgcagcaggt aacgcagcag gaaatgcagc    540

aggaaatgca gcaggtaacg cagcaggaaa tgcagcagga aatgatgcag gaaatgcagc    600

aggtaacgca gcaggaaatg cagcaggaaa tgcagcagga aatgcagcag gaaatgatgc    660

aggaaatgca gcaggaaatg cagcaggaaa tgcagcaggt aacgcagcag gaaatgcagc    720

aggaaatgca gcaggtaacg cagcaggtaa cgcagcagga aatgcagcag gaaatgcagc    780

aggaaatgat gcaggaaatg cagcaggtaa cgcagcagga aatgcagcag gaaatgcagc    840

aggtaacgca gcaggtaacg cagcaggaaa tgcagcagga aatgcagcag gtaacgcagc    900

aggaaatgca gcaggaaatg cagcaggtaa cgcagcaggt aacgcagcag gaaatgcagc    960

aggaaatgca gcaggtaacg cagcaggaaa tgcagcagga aatgcagcag gtaacgcagc   1020

aggaaatgca gcaggaaatg aaaaagcgaa aaataaggat aataaagtgg atgcaaatac   1080

gaataaaaag gacaaccagg aagaaaataa tgattcgtct aatggtccat ctgaagaaca   1140

tataaagaat tatttagaaa gtattcgtaa tagtattacg gaggaatggt caccatgtag   1200

tgtaacttgt ggaagtggta taagggctag aagaaaggtt ggtgcaaaaa ataagaaacc   1260

tgcagaatta gttttaagtg accttgaaac tgaaatttgt tcactagata aatgctccag   1320

tatatttaat gtcgtaagta attcgttagg aatagtatta gttttagtct taatactctt   1380

tcactaaata aatagcatgt atctttcgaa atattatata catatatatt tatatatatt   1440

ttttctttct tttttctttt ttttgtgaat gattactaat gtttgcactt aattgtatat   1500

atattatata tattcaatat ataattctaa aaattaccag tattt                   1545
```

<210> SEQ ID NO 65
<211> LENGTH: 388
<212> TYPE: PRT
<213> ORGANISM: Plasmodium gallinaceum

<400> SEQUENCE: 65

```
Met Lys Lys Leu Ala Ile Leu Ser Ala Ser Ser Phe Leu Phe Ala Asp
1               5                   10                  15

Phe Leu Phe Gln Glu Tyr Gln His Asn Gly Asn Tyr Lys Asn Phe Arg
            20                  25                  30

Leu Leu Asn Glu Val Cys Tyr Asn Asn Met Asn Ile Gln Leu Tyr Asn
        35                  40                  45

Glu Leu Glu Met Glu Asn Tyr Met Ser Asn Thr Tyr Phe Tyr Asn Asn
    50                  55                  60

Lys Lys Thr Ile Arg Leu Leu Gly Glu Asn Asp Asn Glu Ala Asn Val
65                  70                  75                  80

Asn Arg Ala Asn Asn Asn Val Ala Asn Asp Asn Arg Ala Asn Gly Asn
                85                  90                  95

Arg Gly Asn Val Asn Arg Ala Asn Asp Arg Asn Ile Pro Tyr Phe Arg
            100                 105                 110

Glu Asn Val Val Asn Leu Asn Gln Pro Val Gly Gly Asn Gly Gly Val
        115                 120                 125

Gln Pro Ala Gly Gly Asn Gly Gly Val Gln Pro Ala Gly Gly Asn Gly
    130                 135                 140

Gly Val Gln Pro Ala Gly Gly Asn Gly Gly Val Gln Pro Ala Gly Gly
145                 150                 155                 160

Asn Gly Gly Val Gln Pro Ala Gly Gly Asn Gly Gly Val Gln Pro Ala
                165                 170                 175

Gly Gly Asn Gly Gly Val Gln Pro Ala Gly Gly Asn Gly Gly Ala Gln
```

```
            180                 185                 190

Pro Val Ala Ala Gly Gly Gly Ala Gln Pro Val Val Ala Asp Gly Gly
        195                 200                 205

Val Gln Pro Leu Arg Gln Glu Gly Asp Ala Glu Glu Asp Gly Gly Asn
    210                 215                 220

Gly Gly Ala Gln Pro Ala Gly Gly Asn Gly Gly Ala Gln Pro Ala Gly
225                 230                 235                 240

Gly Asn Gly Gly Ala Gln Pro Ala Gly Gly Asn Gly Gly Ala Gln Pro
                245                 250                 255

Ala Gly Gly Asn Gly Gly Ala Gln Pro Ala Gly Gly Asn Asp Ala Ala
            260                 265                 270

Lys Pro Asp Gly Gly Asn Asp Asp Asp Lys Pro Glu Gly Gly Asp Glu
        275                 280                 285

Lys Ser Glu Glu Glu Lys Glu Asp Glu Pro Ile Pro Asp Pro Thr Gln
    290                 295                 300

Glu Glu Ile Asp Lys Tyr Leu Lys Ser Ile Leu Gly Asn Val Thr Ser
305                 310                 315                 320

Glu Trp Thr Asn Cys Asn Val Thr Cys Gly Lys Gly Ile Gln Ala Lys
                325                 330                 335

Ile Lys Ser Thr Ser Ala Asn Lys Lys Arg Glu Glu Ile Thr Pro Asn
            340                 345                 350

Asp Val Glu Val Lys Ile Cys Glu Leu Glu Arg Cys Ser Phe Ser Ile
        355                 360                 365

Phe Asn Val Ile Ser Asn Ser Leu Gly Leu Ala Ile Ile Leu Thr Phe
    370                 375                 380

Leu Phe Phe Tyr
385


<210> SEQ ID NO 66
<211> LENGTH: 1260
<212> TYPE: DNA
<213> ORGANISM: Plasmodium gallinaceum
<220> FEATURE:
<221> NAME/KEY: misc_feature
<222> LOCATION: (1)..(1260)
<223> OTHER INFORMATION: CSP gene GenBank: U65959.1

<400> SEQUENCE: 66

tgatttcact aaaaatttta atatatataa tataatagtt taaaatagtg aagaatatat     60

ataggtgtac ttcaaaatga agaaattagc cattttatcg gcatcttcgt ttttatttgc    120

tgactttcta tttcaagagt atcaacacaa tggaaactac aaaaatttta gacttttaaa    180

tgaggtgtgt tataataata tgaatattca attatataat gaattggaaa tggaaaatta    240

catgagtaac acatatttct ataataataa aaaaaccatt agattacttg gagaaaatga    300

taatgaagca aatgttaata gagcaaataa taatgtagca aatgataata gagcaaatgg    360

taatagagga aatgttaata gagcaaatga tagaaatata ccatatttta gagaaaatgt    420

tgtgaatctt aatcaaccag ttggaggaaa tggtggtgtt caacctgctg gaggaaatgg    480

tggtgttcaa cctgctggag gaaatggtgg tgttcaacct gctggaggta atggtggtgt    540

tcaacctgct ggaggaaatg gtggtgttca acctgctgga ggaaatggtg gtgttcaacc    600

tgctggaggt aatggtggtg ttcaacctgc tggaggcaat ggtggtgctc aaccagttgc    660

agcaggtggt ggtgctcaac cagttgtagc agatggtggt gttcagcctc ttagacaaga    720

aggtgatgct gaagaggatg gaggaaatgg tggtgcccaa ccagctggag gaaatggtgg    780
```

```
tgctcaacca gctggaggaa atggtggtgc tcaaccagct ggaggaaatg gtggtgccca    840

acctgctgga ggaaatggtg gtgctcaacc tgctggagga aatgatgctg ctaaacctga    900

tggaggaaat gatgatgaca aacctgaagg aggagatgaa aaatctgaag aagaaaagga    960

ggatgaacca ataccagatc caactcaaga agaaatagat aaatatttaa aaagcatact   1020

tggtaatgtt acatctgaat ggactaattg caatgtaaca tgtgggaaag gtatacaagc   1080

taaaataaaa tctacatctg ctaataagaa aagagaagaa attactccaa atgatgttga   1140

agtaaaaatt tgcgaactag aaagatgttc ttttagcata tttaatgtta taagcaattc   1200

gttaggttta gctataattt taaccttttt attttttat taaataaata ttataaaatt   1260
```

```
<210> SEQ ID NO 67
<211> LENGTH: 388
<212> TYPE: PRT
<213> ORGANISM: Plasmodium reichenowi
<220> FEATURE:
<221> NAME/KEY: MISC_FEATURE
<222> LOCATION: (1)..(388)
<223> OTHER INFORMATION: CSP protein GenBank: U65959.1

<400> SEQUENCE: 67

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Ala Asp Asn
65                  70                  75                  80

Gly Asp Ala Asp Asn Gly Asp Glu Gly Ile Asp Glu Asn Arg Arg His
                85                  90                  95

Arg Asn Lys Glu Gly Lys Glu Lys Leu Lys Lys Pro Lys His Asn Lys
            100                 105                 110

Leu Lys Gln Pro Gly Asn Asp Asn Val Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Val Asp Pro Asn Ala Asn Pro Asn
145                 150                 155                 160

Val Asn Pro Asn Ala Asn Pro Asn Val Asp Pro Asn Ala Asn Pro Asn
                165                 170                 175

Val Asn Pro Asn Ala Asn Pro Asn Val Asn Pro Asn Ala Asn Pro Asn
            180                 185                 190

Val Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Arg Asn Asn Glu Ala Asn Gly Gln
            260                 265                 270
```

```
Gly His Asn Lys Pro Asn Asp Gln Asn Arg Asn Val Asn Glu Asn Ala
        275                 280                 285

Asn Ala Asn Asn Ala Gly Arg Asn Asn Asn Asn Glu Glu Pro Ser Asp
    290                 295                 300

Lys His Ile Glu Glu Phe Leu Lys Gln Ile Gln Asn Asn Leu Ser Thr
305                 310                 315                 320

Glu Trp Ser Pro Cys Ser Val Thr Cys Gly Asn Gly Ile Gln Val Arg
                325                 330                 335

Ile Lys Pro Gly Ser Ala Gly Lys Pro Lys Asp Gln Leu Asp Tyr Glu
            340                 345                 350

Asn Asp Leu Glu Lys Lys Ile Cys Lys Met Glu Lys Cys Ser Ser Val
        355                 360                 365

Phe Asn Val Val Asn Ser Ser Ile Gly Leu Ile Met Val Leu Ser Phe
    370                 375                 380

Leu Phe Leu Asn
385


<210> SEQ ID NO 68
<211> LENGTH: 1167
<212> TYPE: DNA
<213> ORGANISM: Plasmodium reichenowi

<400> SEQUENCE: 68

atgatgagaa aattagctat tttatctgtt tcttcctttt tatttgttga ggccttattc      60

caggaatatc agtgctatgg aagttcgtca aacacaaggg ttctaaatga attaaattat     120

gataatgcag gcactaattt atataatgaa ttagaaatga attattatgg gaaacaggaa     180

aattggtata gccttaaaaa aaatagtaga tcacttggag aaaatgatga tgcagataat     240

ggtgatgcag ataatggtga tgaaggtata gatgaaaata gaagacatag aaataaagaa     300

ggcaaagaga aattaaagaa accaaaacat aataaattaa agcaaccagg gaatgataat     360

gttgatccaa atgccaaccc aaatgtagat ccaaatgcca acccaaatgt agatcccaat     420

gcaaacccaa atgtagatcc caatgcaaac ccaaatgtag atcctaatgc aaacccaaat     480

gtaaatccca atgcaaaccc aaatgtagat cctaatgcaa acccaaatgt aaatcccaat     540

gcaaacccaa atgtaaatcc caatgcaaac ccaaatgtaa atcccaatgc aaacccaaat     600

gcaaatccta atgcaaatcc caatgcaaat cccaatgcaa acccaaatgc aaatcctaat     660

gcaaatccca atgcaaatcc caatgcaaac ccaaatgcaa atcctaatgc aaatcctaat     720

gcaaatccta atgcaaatcc taatgcaaat cctaatgcca atccaaacgc aaacccaaat     780

gcaaatccta atagaaacaa tgaagctaat ggacaaggtc acaataagcc aaatgaccaa     840

aaccgaaatg taaatgaaaa tgctaatgcc aacaatgctg gaagaaataa taataacgaa     900

gaaccaagtg ataagcacat agaagaattt ttaaagcaaa tacaaaataa tctttcaact     960

gaatggtccc catgtagtgt aacttgtgga aatggtattc aagttagaat aaagcctggc    1020

tctgctggta aacctaaaga ccaattagat tatgaaaatg accttgaaaa aaaaatttgt    1080

aaaatggaaa aatgttccag tgtgttcaat gtcgtaaata gttcaatagg attaataatg    1140

gtattatcct tcttgttcct taattag                                        1167


<210> SEQ ID NO 69
<211> LENGTH: 200
<212> TYPE: DNA
<213> ORGANISM: Artificial
<220> FEATURE:
<223> OTHER INFORMATION: DNA FLAP of CAEV
```

<400> SEQUENCE: 69
gttccagcca caatttgtcg ctgtagaatc agccatagca gcagccctag tcgccataaa 60
tataaaaaga aagggtgggc tggggacaag ccctatggat atttttatat ataataaaga 120
acagaaaaga ataaataata aatataataa aaattctcaa aaaattcaat tctgttatta 180
cagaataagg aaaagaggac 200

<210> SEQ ID NO 70
<211> LENGTH: 200
<212> TYPE: DNA
<213> ORGANISM: Artificial
<220> FEATURE:
<223> OTHER INFORMATION: DNA FLAP of EIAV

<400> SEQUENCE: 70
cttgtaacaa agggagggaa agtatgggag gacagacacc atgggaagta tttatcacta 60
atcaagcaca agtaatacat gagaaacttt tactacagca agcacaatcc tccaaaaaat 120
tttgttttta caaaatccct ggtgaacatg attggaaggg acctactagg gtgctgtgga 180
agggtgatgg tgcagtagta 200

<210> SEQ ID NO 71
<211> LENGTH: 200
<212> TYPE: DNA
<213> ORGANISM: Artificial
<220> FEATURE:
<223> OTHER INFORMATION: DNA FLAP of VISNA

<400> SEQUENCE: 71
ggaccctcat tactctaaat ataaaaagaa agggtgggct agggacaagc cctatggata 60
tatttatatt taataaggaa caacaaagaa tacagcaaca aagtaaatca aaacaagaaa 120
aaattcgatt ttgttattac agaacaagaa aaagagggca tccaggagag tggcaaggac 180
caacacaggt actttggggc 200

<210> SEQ ID NO 72
<211> LENGTH: 200
<212> TYPE: DNA
<213> ORGANISM: Artificial
<220> FEATURE:
<223> OTHER INFORMATION: DNA FLAP of VISNA

<400> SEQUENCE: 72
tactgatggc ttgcatactt cacaatttta aaagaaaggg aggaataggg ggacagactt 60
cagcagagag actaattaat ataataacaa cacaattaga aatacaacat ttacaaacca 120
aaattcaaaa aattttaaat tttagagtct actacagaga agggagagac cctgtgtgga 180
aaggaccggc acaattaatc 200

<210> SEQ ID NO 73
<211> LENGTH: 200
<212> TYPE: DNA
<213> ORGANISM: Artificial
<220> FEATURE:
<223> OTHER INFORMATION: DNA FLAP of HIV-2 ROD

<400> SEQUENCE: 73
tgcatgaatt ttaaaagaag ggggggaata ggggatatga ctccatcaga aagattaatc 60
aatatgatca ccacagaaca agagatacaa ttcctccaag ccaaaaattc aaaattaaaa 120
gattttcggg tctatttcag agaaggcaga gatcagttgt ggaaaggacc tggggaacta 180
ctgtggaaag gagaaggagc 200

<210> SEQ ID NO 74
<211> LENGTH: 200
<212> TYPE: DNA
<213> ORGANISM: Artificial
<220> FEATURE:
<223> OTHER INFORMATION: DNA FLAP of HIV-1 LAI

<400> SEQUENCE: 74
cagtattcat ccacaatttt aaaagaaaag gggggattgg ggggtacagt gcaggggaaa 60
gaatagtaga cataatagca acagacatac aaactaaaga attacaaaaa caaattacaa 120
aaattcaaaa ttttcgggtt tattacaggg acagcagaga tccactttgg aaaggaccag 180
caaagctcct ctggaaaggt 200

<210> SEQ ID NO 75
<211> LENGTH: 119
<212> TYPE: DNA
<213> ORGANISM: Artificial
<220> FEATURE:
<223> OTHER INFORMATION: DNA FLAP of HIV-1

<400> SEQUENCE: 75
ttttaaaaga aaagggggga ttggggggta cagtgcaggg gaaagaatag tagacataat 60
agcaacagac atacaaacta aagaattaca aaaacaaatt acaaaaattc aaaattttc 119

<210> SEQ ID NO 76
<211> LENGTH: 1578
<212> TYPE: DNA
<213> ORGANISM: Artificial
<220> FEATURE:
<223> OTHER INFORMATION: VSV-G Indiana optimized

<400> SEQUENCE: 76
ctcggatcct gatcagccac catgaaatgc ctgctctatc tggccttcct ctttatcggc 60
gtgaactgta agttcacgat cgtgtttccc cacaatcaga agggaaactg gaagaacgtc 120
ccgagcaact accactactg ccctagctca agcgacctga actggcacaa cgacctgatc 180
ggcaccgcta tccaggtgaa gatgccaaag agccacaagg ccatccaagc cgacggctgg 240
atgtgtcacg ccagcaaatg ggtgacgacg tgcgattttc gctggtatgg ccccaagtac 300
atcacccaat caatccgctc atttacaccc agcgtggagc aatgtaagga gagcatcgag 360
cagaccaagc aggggacctg gctcaacccc ggcttcccac cgcaaagctg cggatacgcc 420
accgtgaccg acgctgaggc cgtcatcgtg caggtgaccc cgcaccacgt gctggtggac 480
gagtacaccg gcgagtgggt ggattcacag tttatcaacg gaaagtgtag caattacatc 540
tgccccaccg tgcacaacag caccacctgg cactcagact ataaggtgaa gggcctctgc 600
gacagcaatc tgatctcaat ggacatcacc ttctttagcg aagacggcga actctcaagc 660
ctcgggaagg aaggcaccgg gttccgcagc aattactttg cttacgaaac cggcggcaag 720
gcctgcaaga tgcaatactg caagcactgg ggcgtgcgcc tgccaagcgg cgtgtggttt 780
gagatggctg ataaggacct gttcgccgct gcccgcttcc cggaatgccc cgaggggagc 840
agcatcagcg cccccagcca gacatcagtg gacgtgagcc tgatccagga tgtggaacgc 900
atcctggact acagcctgtg tcaggaaacg tggagcaaga tccgcgccgg actgcctatc 960
agccccgtgg atctcagcta cctggcccca aagaacccag gcaccggacc cgcctttaca 1020
atcatcaacg gcaccctgaa gtactttgaa acacgctaca tccgcgtcga catcgccgct 1080
cccatcctct cacgcatggt gggcatgatc tcagggacga ccacggagcg cgagctgtgg 1140
gatgactggg ccccgtatga agatgtggag atcggaccta acggcgtgct gcgcacatca 1200
agcgggtaca agttcccgct gtacatgatc ggccacggca tgctggacag cgacctgcac 1260
ctcagctcaa aggcccaggt ctttgagcac ccacacatcc aggacgctgc cagccagctc 1320
cccgacgacg aaagcctgtt ctttggagat acagggctca gcaagaaccc catcgagctg 1380
gtcgagggct ggttctcaag ctggaagagc agcatcgctt catttttttt catcatcggc 1440
ctcatcatcg ggctgtttct ggtgctgcgc gtcggcatcc acctgtgcat caagctgaag 1500
cacaccaaga agcgccagat ctataccgac atcgagatga atcgcctggg gaagtaagaa 1560
ttctgcagat atccagca 1578

<210> SEQ ID NO 77
<211> LENGTH: 511
<212> TYPE: PRT
<213> ORGANISM: Artificial
<220> FEATURE:
<223> OTHER INFORMATION: VSV-G Indiana

<400> SEQUENCE: 77

Met Lys Cys Leu Leu Tyr Leu Ala Phe Leu Phe Ile Gly Val Asn Cys
1 5 10 15

Lys Phe Thr Ile Val Phe Pro His Asn Gln Lys Gly Asn Trp Lys Asn
20 25 30

Val Pro Ser Asn Tyr His Tyr Cys Pro Ser Ser Ser Asp Leu Asn Trp
35 40 45

His Asn Asp Leu Ile Gly Thr Ala Ile Gln Val Lys Met Pro Lys Ser
50 55 60

His Lys Ala Ile Gln Ala Asp Gly Trp Met Cys His Ala Ser Lys Trp
65 70 75 80

Val Thr Thr Cys Asp Phe Arg Trp Tyr Gly Pro Lys Tyr Ile Thr Gln
85 90 95

Ser Ile Arg Ser Phe Thr Pro Ser Val Glu Gln Cys Lys Glu Ser Ile
100 105 110

Glu Gln Thr Lys Gln Gly Thr Trp Leu Asn Pro Gly Phe Pro Pro Gln
115 120 125

Ser Cys Gly Tyr Ala Thr Val Thr Asp Ala Glu Ala Val Ile Val Gln
130 135 140

Val Thr Pro His His Val Leu Val Asp Glu Tyr Thr Gly Glu Trp Val
145 150 155 160

Asp Ser Gln Phe Ile Asn Gly Lys Cys Ser Asn Tyr Ile Cys Pro Thr
165 170 175

Val His Asn Ser Thr Thr Trp His Ser Asp Tyr Lys Val Lys Gly Leu
180 185 190

Cys Asp Ser Asn Leu Ile Ser Met Asp Ile Thr Phe Phe Ser Glu Asp
195 200 205

Gly Glu Leu Ser Ser Leu Gly Lys Glu Gly Thr Gly Phe Arg Ser Asn
210 215 220

Tyr Phe Ala Tyr Glu Thr Gly Gly Lys Ala Cys Lys Met Gln Tyr Cys
225 230 235 240

Lys His Trp Gly Val Arg Leu Pro Ser Gly Val Trp Phe Glu Met Ala
245 250 255

-continued

```
Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510
```

<210> SEQ ID NO 78
<211> LENGTH: 1597
<212> TYPE: DNA
<213> ORGANISM: Artificial
<220> FEATURE:
<223> OTHER INFORMATION: VSV-G New Jersey optimized

<400> SEQUENCE: 78

```
taccgagctc ggatcctgat cagccaccat gctgtcatat ctgatctttg ccctggctgt     60

gagcccaatc ctcggaaaga tcgaaatcgt gttcccacaa cacaccacag gggactggaa    120

gcgcgtgccc cacgagtaca actactgccc gacctcagcc gacaagaata gccacggcac    180

gcagaccggc atccctgtgg agctgaccat gcccaagggg ctcacaacgc accaagtcga    240

aggcttcatg tgccacagcg ctctctggat gacaacctgc gattttcgct ggtatggccc    300

caagtacatc acgcacagca tccacaatga ggaaccaacc gactaccagt gcctcgaagc    360

catcaagtca tacaaggatg gggtgagctt caaccccggc ttcccgcccc aatcatgtgg    420

ctacggcacc gtgaccgacg ccgaggccca catcgtgacc gtgacacccc actcagtcaa    480

ggtggacgag tacacaggcg aatggatcga cccccacttc atcgggggcc gctgtaaggg    540

ccaaatctgc gagaccgtgc acaacagcac caagtggttt acgtcatcag acggcgaaag    600

cgtgtgcagc caactgttta cgctcgtggg cggcatcttc tttagcgaca gcgaggagat    660
```

```
caccagcatg ggcctcccgg agacaggaat ccgcagcaac tactttccgt acatcagcac    720

cgagggaatc tgtaagatgc ctttttgccg caagcaggga tataagctga agaatgacct    780

gtggttccag atcatggacc cggacctgga caagaccgtc cgcgatctgc cccacatcaa    840

ggactgtgat ctgtcatcaa gcatcatcac ccccggagaa cacgccacgg acatcagcct    900

catcagcgat gtggagcgca tcctcgacta cgctctctgc cagaacacat ggagcaagat    960

cgaaagcggc gaacccatca ccccagtgga cctgagctat ctcggcccaa agaaccccgg   1020

cgtggggccc gtgttcacca tcatcaacgg gagcctgcac tactttacaa gcaagtatct   1080

gcgcgtggag ctcgaaagcc cagtcatccc ccgcatggag gggaaggtgg ccgggacccg   1140

catcgtgcgc cagctgtggg accagtggtt cccttttggc gaggtggaaa tcggccccaa   1200

cggcgtgctg aagaccaagc aaggatataa gttcccgctg cacatcatcg ggacgggcga   1260

agtggacagc gatatcaaga tggagcgcgt ggtcaagcac tgggagcacc cacacatcga   1320

ggctgctcag acctttctca agaaggacga taccggcgaa gtcctgtatt acggggatac   1380

gggagtgagc aagaaccctg tggagctggt ggaaggctgg ttcagcggat ggcgctcaag   1440

cctgatgggc gtgctggccg tcatcatcgg atttgtgatc ctgatgttcc tcatcaagct   1500

gatcggcgtg ctgtcaagcc tgttccgccc taagcgccgc ccaatctaca agagcgacgt   1560

cgagatggcc cactttcgct aagaattctg cagatat                            1597


<210> SEQ ID NO 79
<211> LENGTH: 1563
<212> TYPE: DNA
<213> ORGANISM: Artificial
<220> FEATURE:
<223> OTHER INFORMATION: fusion VSV-G Ghandipura / Indiana
<220> FEATURE:
<221> NAME/KEY: CDS
<222> LOCATION: (1)..(1563)

<400> SEQUENCE: 79

atg acc agc agc gtg acc atc agc gtg gtg ctg ctg atc agc ttc atc       48
Met Thr Ser Ser Val Thr Ile Ser Val Val Leu Leu Ile Ser Phe Ile
1               5                   10                  15

acc ccc ctg tac agc tac ctg agc att gcc ttc ccc gag aac acc aag       96
Thr Pro Leu Tyr Ser Tyr Leu Ser Ile Ala Phe Pro Glu Asn Thr Lys
            20                  25                  30

ctg gac tgg aag ccc gtg acc aag aac acc cgg tac tgc ccc atg ggc      144
Leu Asp Trp Lys Pro Val Thr Lys Asn Thr Arg Tyr Cys Pro Met Gly
        35                  40                  45

ggc gag tgg ttt ctg gaa ccc ggc ctg cag gaa gag agc ttc ctg agc      192
Gly Glu Trp Phe Leu Glu Pro Gly Leu Gln Glu Glu Ser Phe Leu Ser
    50                  55                  60

agc acc ccc atc ggc gcc acc ccc agc aag agc gac ggc ttc ctg tgc      240
Ser Thr Pro Ile Gly Ala Thr Pro Ser Lys Ser Asp Gly Phe Leu Cys
65                  70                  75                  80

cac gcc gcc aag tgg gtg acc acc tgc gac ttc cgg tgg tac ggc ccc      288
His Ala Ala Lys Trp Val Thr Thr Cys Asp Phe Arg Trp Tyr Gly Pro
                85                  90                  95

aag tac atc acc cac agc atc cac aac atc aag ccc acc aga agc gac      336
Lys Tyr Ile Thr His Ser Ile His Asn Ile Lys Pro Thr Arg Ser Asp
            100                 105                 110

tgc gac aca gcc ctg gcc tct tac aag agc ggc acc ctg gtg tcc ctg      384
Cys Asp Thr Ala Leu Ala Ser Tyr Lys Ser Gly Thr Leu Val Ser Leu
        115                 120                 125

ggc ttc cct ccc gag agc tgc ggc tac gcc agc gtg acc gac agc gag      432
```

-continued

```
Gly Phe Pro Pro Glu Ser Cys Gly Tyr Ala Ser Val Thr Asp Ser Glu
    130                 135                 140

ttc ctg gtg att atg att acc ccc cac cac gtg ggc gtg gac gac tac      480
Phe Leu Val Ile Met Ile Thr Pro His His Val Gly Val Asp Asp Tyr
145                 150                 155                 160

cgg ggc cac tgg gtg gac cct ctg ttc gtg gga ggg gaa tgc gac cag      528
Arg Gly His Trp Val Asp Pro Leu Phe Val Gly Gly Glu Cys Asp Gln
                165                 170                 175

agc tac tgc gat acc atc cac aac tcc agc gtg tgg att ccc gcc gac      576
Ser Tyr Cys Asp Thr Ile His Asn Ser Ser Val Trp Ile Pro Ala Asp
            180                 185                 190

cag acc aag aag aac atc tgc ggc cag agc ttc acc cct ctg acc gtg      624
Gln Thr Lys Lys Asn Ile Cys Gly Gln Ser Phe Thr Pro Leu Thr Val
        195                 200                 205

acc gtg gcc tac gac aag acc aaa gag att gcc gcc gga ggg atc gtg      672
Thr Val Ala Tyr Asp Lys Thr Lys Glu Ile Ala Ala Gly Gly Ile Val
    210                 215                 220

ttc aag agc aag tac cac agc cac atg gaa ggc gcc agg acc tgc aga      720
Phe Lys Ser Lys Tyr His Ser His Met Glu Gly Ala Arg Thr Cys Arg
225                 230                 235                 240

ctg tcc tac tgc ggc cgg aac ggc atc aag ttc ccc aac ggc gag tgg      768
Leu Ser Tyr Cys Gly Arg Asn Gly Ile Lys Phe Pro Asn Gly Glu Trp
                245                 250                 255

gtg tcc ctg atg ctg aag ctg cgg agc aag cgg aac ctg tac ttc ccc      816
Val Ser Leu Met Leu Lys Leu Arg Ser Lys Arg Asn Leu Tyr Phe Pro
            260                 265                 270

tgc ctg aag atg tgc ccc acc ggc atc cgg ggc gag atc tac ccc agc      864
Cys Leu Lys Met Cys Pro Thr Gly Ile Arg Gly Glu Ile Tyr Pro Ser
        275                 280                 285

atc aga tgg gcc cag gtg ctg acc agc gag atc cag aga atc ctg gac      912
Ile Arg Trp Ala Gln Val Leu Thr Ser Glu Ile Gln Arg Ile Leu Asp
    290                 295                 300

tac agc ctg tgc cag aac acc tgg gac aag gtg gag cgg aaa gag ccc      960
Tyr Ser Leu Cys Gln Asn Thr Trp Asp Lys Val Glu Arg Lys Glu Pro
305                 310                 315                 320

ctg agc ccc ctg gac ctg agc tac ctg gcc agc aag tcc ccc ggc aag     1008
Leu Ser Pro Leu Asp Leu Ser Tyr Leu Ala Ser Lys Ser Pro Gly Lys
                325                 330                 335

ggc ctg gcc tac acc gtg atc aac ggc acc ctg agc ttc gcc cac acc     1056
Gly Leu Ala Tyr Thr Val Ile Asn Gly Thr Leu Ser Phe Ala His Thr
            340                 345                 350

aga tac gtg cgg atg tgg atc gac ggc ccc gtg ctg aaa gag ccc aag     1104
Arg Tyr Val Arg Met Trp Ile Asp Gly Pro Val Leu Lys Glu Pro Lys
        355                 360                 365

ggc aag aga gag agc ccc agc ggc atc agc agc gac atc tgg acc cag     1152
Gly Lys Arg Glu Ser Pro Ser Gly Ile Ser Ser Asp Ile Trp Thr Gln
    370                 375                 380

tgg ttc aag tac ggc gac atg gaa atc ggc ccc aac ggc ctg ctg aaa     1200
Trp Phe Lys Tyr Gly Asp Met Glu Ile Gly Pro Asn Gly Leu Leu Lys
385                 390                 395                 400

aca gcc ggc gga tac aag ttt cct tgg cac ctg atc ggc atg ggc atc     1248
Thr Ala Gly Gly Tyr Lys Phe Pro Trp His Leu Ile Gly Met Gly Ile
                405                 410                 415

gtg gac aac gag ctg cac gag ctg tcc gag gcc aac ccc ctg gat cac     1296
Val Asp Asn Glu Leu His Glu Leu Ser Glu Ala Asn Pro Leu Asp His
            420                 425                 430

ccc cag ctg ccc cac gcc cag agc att gcc gac gac agc gag gaa atc     1344
Pro Gln Leu Pro His Ala Gln Ser Ile Ala Asp Asp Ser Glu Glu Ile
        435                 440                 445
```

-continued

```
ttc ttc ggc gac acc ggc gtg agc aag aac ccc gtg gaa ctg gtg aca     1392
Phe Phe Gly Asp Thr Gly Val Ser Lys Asn Pro Val Glu Leu Val Thr
    450                 455                 460

ggc tgg ttc acc agc tgg aaa agc agc atc gct tca ttt ttt ttc atc     1440
Gly Trp Phe Thr Ser Trp Lys Ser Ser Ile Ala Ser Phe Phe Phe Ile
465                 470                 475                 480

atc ggc ctc atc atc ggg ctg ttt ctg gtg ctg cgc gtc ggc atc cac     1488
Ile Gly Leu Ile Ile Gly Leu Phe Leu Val Leu Arg Val Gly Ile His
                485                 490                 495

ctg tgc atc aag ctg aag cac acc aag aag cgc cag atc tat acc gac     1536
Leu Cys Ile Lys Leu Lys His Thr Lys Lys Arg Gln Ile Tyr Thr Asp
            500                 505                 510

atc gag atg aat cgc ctg ggg aag taa                                 1563
Ile Glu Met Asn Arg Leu Gly Lys
        515                 520


<210> SEQ ID NO 80
<211> LENGTH: 520
<212> TYPE: PRT
<213> ORGANISM: Artificial
<220> FEATURE:
<223> OTHER INFORMATION: Synthetic Construct

<400> SEQUENCE: 80

Met Thr Ser Ser Val Thr Ile Ser Val Val Leu Leu Ile Ser Phe Ile
1               5                   10                  15

Thr Pro Leu Tyr Ser Tyr Leu Ser Ile Ala Phe Pro Glu Asn Thr Lys
            20                  25                  30

Leu Asp Trp Lys Pro Val Thr Lys Asn Thr Arg Tyr Cys Pro Met Gly
        35                  40                  45

Gly Glu Trp Phe Leu Glu Pro Gly Leu Gln Glu Glu Ser Phe Leu Ser
    50                  55                  60

Ser Thr Pro Ile Gly Ala Thr Pro Ser Lys Ser Asp Gly Phe Leu Cys
65                  70                  75                  80

His Ala Ala Lys Trp Val Thr Thr Cys Asp Phe Arg Trp Tyr Gly Pro
                85                  90                  95

Lys Tyr Ile Thr His Ser Ile His Asn Ile Lys Pro Thr Arg Ser Asp
            100                 105                 110

Cys Asp Thr Ala Leu Ala Ser Tyr Lys Ser Gly Thr Leu Val Ser Leu
        115                 120                 125

Gly Phe Pro Pro Glu Ser Cys Gly Tyr Ala Ser Val Thr Asp Ser Glu
    130                 135                 140

Phe Leu Val Ile Met Ile Thr Pro His His Val Gly Val Asp Asp Tyr
145                 150                 155                 160

Arg Gly His Trp Val Asp Pro Leu Phe Val Gly Gly Glu Cys Asp Gln
                165                 170                 175

Ser Tyr Cys Asp Thr Ile His Asn Ser Ser Val Trp Ile Pro Ala Asp
            180                 185                 190

Gln Thr Lys Lys Asn Ile Cys Gly Gln Ser Phe Thr Pro Leu Thr Val
        195                 200                 205

Thr Val Ala Tyr Asp Lys Thr Lys Glu Ile Ala Ala Gly Gly Ile Val
    210                 215                 220

Phe Lys Ser Lys Tyr His Ser His Met Glu Gly Ala Arg Thr Cys Arg
225                 230                 235                 240

Leu Ser Tyr Cys Gly Arg Asn Gly Ile Lys Phe Pro Asn Gly Glu Trp
                245                 250                 255

Val Ser Leu Met Leu Lys Leu Arg Ser Lys Arg Asn Leu Tyr Phe Pro
```

```
            260                 265                 270

Cys Leu Lys Met Cys Pro Thr Gly Ile Arg Gly Glu Ile Tyr Pro Ser
        275                 280                 285

Ile Arg Trp Ala Gln Val Leu Thr Ser Glu Ile Gln Arg Ile Leu Asp
    290                 295                 300

Tyr Ser Leu Cys Gln Asn Thr Trp Asp Lys Val Glu Arg Lys Glu Pro
305                 310                 315                 320

Leu Ser Pro Leu Asp Leu Ser Tyr Leu Ala Ser Lys Ser Pro Gly Lys
                325                 330                 335

Gly Leu Ala Tyr Thr Val Ile Asn Gly Thr Leu Ser Phe Ala His Thr
            340                 345                 350

Arg Tyr Val Arg Met Trp Ile Asp Gly Pro Val Leu Lys Glu Pro Lys
        355                 360                 365

Gly Lys Arg Glu Ser Pro Ser Gly Ile Ser Ser Asp Ile Trp Thr Gln
    370                 375                 380

Trp Phe Lys Tyr Gly Asp Met Glu Ile Gly Pro Asn Gly Leu Leu Lys
385                 390                 395                 400

Thr Ala Gly Gly Tyr Lys Phe Pro Trp His Leu Ile Gly Met Gly Ile
                405                 410                 415

Val Asp Asn Glu Leu His Glu Leu Ser Glu Ala Asn Pro Leu Asp His
            420                 425                 430

Pro Gln Leu Pro His Ala Gln Ser Ile Ala Asp Asp Ser Glu Glu Ile
        435                 440                 445

Phe Phe Gly Asp Thr Gly Val Ser Lys Asn Pro Val Glu Leu Val Thr
    450                 455                 460

Gly Trp Phe Thr Ser Trp Lys Ser Ser Ile Ala Ser Phe Phe Phe Ile
465                 470                 475                 480

Ile Gly Leu Ile Ile Gly Leu Phe Leu Val Leu Arg Val Gly Ile His
                485                 490                 495

Leu Cys Ile Lys Leu Lys His Thr Lys Lys Arg Gln Ile Tyr Thr Asp
            500                 505                 510

Ile Glu Met Asn Arg Leu Gly Lys
        515                 520


<210> SEQ ID NO 81
<211> LENGTH: 1539
<212> TYPE: DNA
<213> ORGANISM: Artificial
<220> FEATURE:
<223> OTHER INFORMATION: fusion VSV-G Cocal / Indiana
<220> FEATURE:
<221> NAME/KEY: CDS
<222> LOCATION: (1)..(1539)

<400> SEQUENCE: 81

atg aac ttt ctg ctg ctg aca ttc atc gtg ctg cct ctg tgc agc cac       48
Met Asn Phe Leu Leu Leu Thr Phe Ile Val Leu Pro Leu Cys Ser His
1               5                   10                  15

gcc aag ttc agc atc gtg ttc ccc cag agc cag aag ggc aac tgg aag       96
Ala Lys Phe Ser Ile Val Phe Pro Gln Ser Gln Lys Gly Asn Trp Lys
            20                  25                  30

aac gtg ccc agc agc tac cac tac tgc ccc agc agc agc gac cag aac      144
Asn Val Pro Ser Ser Tyr His Tyr Cys Pro Ser Ser Ser Asp Gln Asn
        35                  40                  45

tgg cac aac gac ctg ctg ggc atc acc atg aag gtg aaa atg ccc aag      192
Trp His Asn Asp Leu Leu Gly Ile Thr Met Lys Val Lys Met Pro Lys
    50                  55                  60
```

```
acc cac aag gcc att cag gct gac ggc tgg atg tgc cac gcc gcc aag      240
Thr His Lys Ala Ile Gln Ala Asp Gly Trp Met Cys His Ala Ala Lys
65                  70                  75                  80

tgg atc acc acc tgc gac ttc cgg tgg tac ggc ccc aag tac atc acc      288
Trp Ile Thr Thr Cys Asp Phe Arg Trp Tyr Gly Pro Lys Tyr Ile Thr
                85                  90                  95

cac agc atc cac tcc atc cag ccc acc tcc gag cag tgc aaa gag agc      336
His Ser Ile His Ser Ile Gln Pro Thr Ser Glu Gln Cys Lys Glu Ser
            100                 105                 110

atc aag cag acc aag cag ggc acc tgg atg agc ccc ggc ttc cca ccc      384
Ile Lys Gln Thr Lys Gln Gly Thr Trp Met Ser Pro Gly Phe Pro Pro
        115                 120                 125

cag aac tgc ggc tac gcc acc gtg acc gac agc gtg gcc gtg gtg gtg      432
Gln Asn Cys Gly Tyr Ala Thr Val Thr Asp Ser Val Ala Val Val Val
    130                 135                 140

cag gcc acc ccc cac cac gtg ctg gtc gac gag tac acc ggc gag tgg      480
Gln Ala Thr Pro His His Val Leu Val Asp Glu Tyr Thr Gly Glu Trp
145                 150                 155                 160

atc gac agc cag ttc ccc aac ggc aag tgc gag aca gag gaa tgc gag      528
Ile Asp Ser Gln Phe Pro Asn Gly Lys Cys Glu Thr Glu Glu Cys Glu
                165                 170                 175

aca gtg cac aac agc acc gtg tgg tac agc gac tac aag gtg acc ggc      576
Thr Val His Asn Ser Thr Val Trp Tyr Ser Asp Tyr Lys Val Thr Gly
            180                 185                 190

ctg tgc gac gcc acc ctg gtg gac acc gag atc acc ttt ttc agc gag      624
Leu Cys Asp Ala Thr Leu Val Asp Thr Glu Ile Thr Phe Phe Ser Glu
        195                 200                 205

gac ggc aag aaa gag tcc atc ggc aag ccc aac acc ggc tac aga agc      672
Asp Gly Lys Lys Glu Ser Ile Gly Lys Pro Asn Thr Gly Tyr Arg Ser
    210                 215                 220

aac tac ttc gcc tac gag aag ggc gac aaa gtg tgc aag atg aac tac      720
Asn Tyr Phe Ala Tyr Glu Lys Gly Asp Lys Val Cys Lys Met Asn Tyr
225                 230                 235                 240

tgc aag cat gcc gga gtg agg ctg cct agc ggc gtg tgg ttc gag ttc      768
Cys Lys His Ala Gly Val Arg Leu Pro Ser Gly Val Trp Phe Glu Phe
                245                 250                 255

gtg gac cag gac gtg tac gcc gcc gcc aag ctg ccc gag tgc ccc gtg      816
Val Asp Gln Asp Val Tyr Ala Ala Ala Lys Leu Pro Glu Cys Pro Val
            260                 265                 270

ggc gcc acc atc agc gcc ccc acc cag acc agc gtg gac gtg agc ctg      864
Gly Ala Thr Ile Ser Ala Pro Thr Gln Thr Ser Val Asp Val Ser Leu
        275                 280                 285

atc ctg gac gtg gag aga atc ctg gac tac tct ctg tgt cag gaa acc      912
Ile Leu Asp Val Glu Arg Ile Leu Asp Tyr Ser Leu Cys Gln Glu Thr
    290                 295                 300

tgg tcc aag atc aga tcc aag cag ccc gtg agc cct gtg gac ctg agc      960
Trp Ser Lys Ile Arg Ser Lys Gln Pro Val Ser Pro Val Asp Leu Ser
305                 310                 315                 320

tac ctg gcc cct aag aac ccc ggc acc ggc cct gcc ttc acc atc atc     1008
Tyr Leu Ala Pro Lys Asn Pro Gly Thr Gly Pro Ala Phe Thr Ile Ile
                325                 330                 335

aac ggc acc ctg aag tac ttc gag aca cgg tac atc cgg atc gac atc     1056
Asn Gly Thr Leu Lys Tyr Phe Glu Thr Arg Tyr Ile Arg Ile Asp Ile
            340                 345                 350

gac aac ccc atc atc agc aag atg gtg ggc aag atc agc ggc agc cag     1104
Asp Asn Pro Ile Ile Ser Lys Met Val Gly Lys Ile Ser Gly Ser Gln
        355                 360                 365

acc gag cgg gag ctg tgg acc gag tgg ttc ccc tac gag ggc gtg gag     1152
Thr Glu Arg Glu Leu Trp Thr Glu Trp Phe Pro Tyr Glu Gly Val Glu
    370                 375                 380
```

```
atc ggc ccc aat ggc atc ctg aaa acc cct acc ggc tac aag ttc ccc      1200
Ile Gly Pro Asn Gly Ile Leu Lys Thr Pro Thr Gly Tyr Lys Phe Pro
385                 390                 395                 400

ctg ttc atg atc ggc cac ggc atg ctg gac agc gac ctg cac aag acc      1248
Leu Phe Met Ile Gly His Gly Met Leu Asp Ser Asp Leu His Lys Thr
                405                 410                 415

tcc cag gcc gag gtg ttc gag cac ccc cac ctg gcc gag gcc ccc aag      1296
Ser Gln Ala Glu Val Phe Glu His Pro His Leu Ala Glu Ala Pro Lys
            420                 425                 430

cag ctg ccc gaa gag gaa acc ctg ttc ttc ggc gac acc ggc atc tcc      1344
Gln Leu Pro Glu Glu Glu Thr Leu Phe Phe Gly Asp Thr Gly Ile Ser
        435                 440                 445

aag aac cct gtg gag ctg atc gag ggc tgg ttc agc agc tgg aag agc      1392
Lys Asn Pro Val Glu Leu Ile Glu Gly Trp Phe Ser Ser Trp Lys Ser
    450                 455                 460

agc atc gct tca ttt ttt ttc atc atc ggc ctc atc atc ggg ctg ttt      1440
Ser Ile Ala Ser Phe Phe Phe Ile Ile Gly Leu Ile Ile Gly Leu Phe
465                 470                 475                 480

ctg gtg ctg cgc gtc ggc atc cac ctg tgc atc aag ctg aag cac acc      1488
Leu Val Leu Arg Val Gly Ile His Leu Cys Ile Lys Leu Lys His Thr
                485                 490                 495

aag aag cgc cag atc tat acc gac atc gag atg aat cgc ctg ggg aag      1536
Lys Lys Arg Gln Ile Tyr Thr Asp Ile Glu Met Asn Arg Leu Gly Lys
            500                 505                 510

taa                                                                   1539


<210> SEQ ID NO 82
<211> LENGTH: 512
<212> TYPE: PRT
<213> ORGANISM: Artificial
<220> FEATURE:
<223> OTHER INFORMATION: Synthetic Construct

<400> SEQUENCE: 82

Met Asn Phe Leu Leu Leu Thr Phe Ile Val Leu Pro Leu Cys Ser His
1               5                   10                  15

Ala Lys Phe Ser Ile Val Phe Pro Gln Ser Gln Lys Gly Asn Trp Lys
            20                  25                  30

Asn Val Pro Ser Ser Tyr His Tyr Cys Pro Ser Ser Ser Asp Gln Asn
        35                  40                  45

Trp His Asn Asp Leu Leu Gly Ile Thr Met Lys Val Lys Met Pro Lys
    50                  55                  60

Thr His Lys Ala Ile Gln Ala Asp Gly Trp Met Cys His Ala Ala Lys
65                  70                  75                  80

Trp Ile Thr Thr Cys Asp Phe Arg Trp Tyr Gly Pro Lys Tyr Ile Thr
                85                  90                  95

His Ser Ile His Ser Ile Gln Pro Thr Ser Glu Gln Cys Lys Glu Ser
            100                 105                 110

Ile Lys Gln Thr Lys Gln Gly Thr Trp Met Ser Pro Gly Phe Pro Pro
        115                 120                 125

Gln Asn Cys Gly Tyr Ala Thr Val Thr Asp Ser Val Ala Val Val Val
    130                 135                 140

Gln Ala Thr Pro His His Val Leu Val Asp Glu Tyr Thr Gly Glu Trp
145                 150                 155                 160

Ile Asp Ser Gln Phe Pro Asn Gly Lys Cys Glu Thr Glu Glu Cys Glu
                165                 170                 175

Thr Val His Asn Ser Thr Val Trp Tyr Ser Asp Tyr Lys Val Thr Gly
```

-continued

```
            180                 185                 190

Leu Cys Asp Ala Thr Leu Val Asp Thr Glu Ile Thr Phe Phe Ser Glu
        195                 200                 205

Asp Gly Lys Lys Glu Ser Ile Gly Lys Pro Asn Thr Gly Tyr Arg Ser
    210                 215                 220

Asn Tyr Phe Ala Tyr Glu Lys Gly Asp Lys Val Cys Lys Met Asn Tyr
225                 230                 235                 240

Cys Lys His Ala Gly Val Arg Leu Pro Ser Gly Val Trp Phe Glu Phe
                245                 250                 255

Val Asp Gln Asp Val Tyr Ala Ala Ala Lys Leu Pro Glu Cys Pro Val
            260                 265                 270

Gly Ala Thr Ile Ser Ala Pro Thr Gln Thr Ser Val Asp Val Ser Leu
        275                 280                 285

Ile Leu Asp Val Glu Arg Ile Leu Asp Tyr Ser Leu Cys Gln Glu Thr
    290                 295                 300

Trp Ser Lys Ile Arg Ser Lys Gln Pro Val Ser Pro Val Asp Leu Ser
305                 310                 315                 320

Tyr Leu Ala Pro Lys Asn Pro Gly Thr Gly Pro Ala Phe Thr Ile Ile
                325                 330                 335

Asn Gly Thr Leu Lys Tyr Phe Glu Thr Arg Tyr Ile Arg Ile Asp Ile
            340                 345                 350

Asp Asn Pro Ile Ile Ser Lys Met Val Gly Lys Ile Ser Gly Ser Gln
        355                 360                 365

Thr Glu Arg Glu Leu Trp Thr Glu Trp Phe Pro Tyr Glu Gly Val Glu
    370                 375                 380

Ile Gly Pro Asn Gly Ile Leu Lys Thr Pro Thr Gly Tyr Lys Phe Pro
385                 390                 395                 400

Leu Phe Met Ile Gly His Gly Met Leu Asp Ser Asp Leu His Lys Thr
                405                 410                 415

Ser Gln Ala Glu Val Phe Glu His Pro His Leu Ala Glu Ala Pro Lys
            420                 425                 430

Gln Leu Pro Glu Glu Glu Thr Leu Phe Phe Gly Asp Thr Gly Ile Ser
        435                 440                 445

Lys Asn Pro Val Glu Leu Ile Glu Gly Trp Phe Ser Ser Trp Lys Ser
    450                 455                 460

Ser Ile Ala Ser Phe Phe Phe Ile Ile Gly Leu Ile Ile Gly Leu Phe
465                 470                 475                 480

Leu Val Leu Arg Val Gly Ile His Leu Cys Ile Lys Leu Lys His Thr
                485                 490                 495

Lys Lys Arg Gln Ile Tyr Thr Asp Ile Glu Met Asn Arg Leu Gly Lys
            500                 505                 510


<210> SEQ ID NO 83
<211> LENGTH: 1518
<212> TYPE: DNA
<213> ORGANISM: Artificial
<220> FEATURE:
<223> OTHER INFORMATION: Fusion VSV-G Piry / Indiana
<220> FEATURE:
<221> NAME/KEY: CDS
<222> LOCATION: (1)..(1518)

<400> SEQUENCE: 83

atg acc gat aca gtg ctg ggc aag ttc cag atc gtg ttc ccc gac cag       48
Met Thr Asp Thr Val Leu Gly Lys Phe Gln Ile Val Phe Pro Asp Gln
1               5                   10                  15
```

-continued

```
aac gag ctg gaa tgg acc ccc gtc gtg ggc gac agc cgg cat tgc cct        96
Asn Glu Leu Glu Trp Thr Pro Val Val Gly Asp Ser Arg His Cys Pro
            20                  25                  30

cag tcc agc gag atg cag ttc gac ggc agc aga agc cag acc atc ctg       144
Gln Ser Ser Glu Met Gln Phe Asp Gly Ser Arg Ser Gln Thr Ile Leu
        35                  40                  45

acc ggc aag gcc ccc gtg ggc atc aca ccc agc aag agc gac ggc ttc       192
Thr Gly Lys Ala Pro Val Gly Ile Thr Pro Ser Lys Ser Asp Gly Phe
    50                  55                  60

atc tgc cac gcc gcc aag tgg gtg acc acc tgc gac ttc cgg tgg tac       240
Ile Cys His Ala Ala Lys Trp Val Thr Thr Cys Asp Phe Arg Trp Tyr
65                  70                  75                  80

ggc ccc aag tac atc acc cac agc atc cac cac ctg cgg ccc acc acc       288
Gly Pro Lys Tyr Ile Thr His Ser Ile His His Leu Arg Pro Thr Thr
                85                  90                  95

tcc gac tgc gag aca gcc ctg cag cgg tac aag gac ggc agc ctg atc       336
Ser Asp Cys Glu Thr Ala Leu Gln Arg Tyr Lys Asp Gly Ser Leu Ile
            100                 105                 110

aac ctg ggc ttc cct ccc gag agc tgc ggc tac gcc acc gtg aca gac       384
Asn Leu Gly Phe Pro Pro Glu Ser Cys Gly Tyr Ala Thr Val Thr Asp
        115                 120                 125

agc gag gcc atg ctg gtg cag gtg acc ccc cac cac gtg ggc gtg gac       432
Ser Glu Ala Met Leu Val Gln Val Thr Pro His His Val Gly Val Asp
    130                 135                 140

gac tac cgg ggc cac tgg atc gac ccc ctg ttc cct ggc ggc gag tgc       480
Asp Tyr Arg Gly His Trp Ile Asp Pro Leu Phe Pro Gly Gly Glu Cys
145                 150                 155                 160

agc acc aat ttc tgc gat acc gtg cac aac agc agc gtg tgg att ccc       528
Ser Thr Asn Phe Cys Asp Thr Val His Asn Ser Ser Val Trp Ile Pro
                165                 170                 175

aag agc cag aaa acc gac atc tgc gcc cag agc ttc aag aac atc aag       576
Lys Ser Gln Lys Thr Asp Ile Cys Ala Gln Ser Phe Lys Asn Ile Lys
            180                 185                 190

atg acc gcc agc tac ccc agc gag gga gcc ctg gtg tcc gac cgg ttc       624
Met Thr Ala Ser Tyr Pro Ser Glu Gly Ala Leu Val Ser Asp Arg Phe
        195                 200                 205

gcc ttc cac agc gcc tac cac ccc aac atg ccc ggc agc acc gtg tgc       672
Ala Phe His Ser Ala Tyr His Pro Asn Met Pro Gly Ser Thr Val Cys
    210                 215                 220

atc atg gat ttc tgc gag cag aag ggc ctg cgg ttc acc aac ggc gag       720
Ile Met Asp Phe Cys Glu Gln Lys Gly Leu Arg Phe Thr Asn Gly Glu
225                 230                 235                 240

tgg atg ggc ctg aac gtg gag cag agc atc cgg gag aag aag atc agc       768
Trp Met Gly Leu Asn Val Glu Gln Ser Ile Arg Glu Lys Lys Ile Ser
                245                 250                 255

gcc atc ttc ccc aac tgc gtg gcc ggc acc gag atc cgg gcc acc ctg       816
Ala Ile Phe Pro Asn Cys Val Ala Gly Thr Glu Ile Arg Ala Thr Leu
            260                 265                 270

gaa tcc gag ggc gcc agg acc ctg acc tgg gag aca cag cgg atg ctg       864
Glu Ser Glu Gly Ala Arg Thr Leu Thr Trp Glu Thr Gln Arg Met Leu
        275                 280                 285

gac tac agc ctg tgc cag aac acc tgg gac aag gtg tcc cgg aaa gag       912
Asp Tyr Ser Leu Cys Gln Asn Thr Trp Asp Lys Val Ser Arg Lys Glu
    290                 295                 300

cct ctg tcc ccc ctg gac ctg agc tac ctg agc cct aga gcc cct ggc       960
Pro Leu Ser Pro Leu Asp Leu Ser Tyr Leu Ser Pro Arg Ala Pro Gly
305                 310                 315                 320

aag ggc atg gcc tac acc gtg atc aac ggc acc ctg cac agc gcc cac      1008
Lys Gly Met Ala Tyr Thr Val Ile Asn Gly Thr Leu His Ser Ala His
                325                 330                 335
```

```
gcc aag tat atc cgg acc tgg atc gac tac ggc gag atg aaa gag atc      1056
Ala Lys Tyr Ile Arg Thr Trp Ile Asp Tyr Gly Glu Met Lys Glu Ile
            340                 345                 350

aag ggc ggc agg ggc gag tac agc aag gcc cct gag ctg ctg tgg agc      1104
Lys Gly Gly Arg Gly Glu Tyr Ser Lys Ala Pro Glu Leu Leu Trp Ser
        355                 360                 365

cag tgg ttc gac ttc ggc ccc ttc aag atc ggc ccc aac ggc ctg ctg      1152
Gln Trp Phe Asp Phe Gly Pro Phe Lys Ile Gly Pro Asn Gly Leu Leu
    370                 375                 380

cac acc ggc aag acc ttc aag ttc cct ctg tat ctg atc gga gcc ggc      1200
His Thr Gly Lys Thr Phe Lys Phe Pro Leu Tyr Leu Ile Gly Ala Gly
385                 390                 395                 400

atc atc gac gag gac ctg cac gag ctg gac gaa gcc gcc cct atc gac      1248
Ile Ile Asp Glu Asp Leu His Glu Leu Asp Glu Ala Ala Pro Ile Asp
                405                 410                 415

cac ccc cag atg ccc gac gcc aag agc gtg ctg ccc gag gac gag gaa      1296
His Pro Gln Met Pro Asp Ala Lys Ser Val Leu Pro Glu Asp Glu Glu
            420                 425                 430

atc ttc ttc ggc gac acc ggc gtg agc aag aac ccc atc gag ctg atc      1344
Ile Phe Phe Gly Asp Thr Gly Val Ser Lys Asn Pro Ile Glu Leu Ile
        435                 440                 445

cag ggc tgg ttc agc aac tgg cgg agc agc atc gct tca ttt ttt ttc      1392
Gln Gly Trp Phe Ser Asn Trp Arg Ser Ser Ile Ala Ser Phe Phe Phe
    450                 455                 460

atc atc ggc ctc atc atc ggg ctg ttt ctg gtg ctg cgc gtc ggc atc      1440
Ile Ile Gly Leu Ile Ile Gly Leu Phe Leu Val Leu Arg Val Gly Ile
465                 470                 475                 480

cac ctg tgc atc aag ctg aag cac acc aag aag cgc cag atc tat acc      1488
His Leu Cys Ile Lys Leu Lys His Thr Lys Lys Arg Gln Ile Tyr Thr
                485                 490                 495

gac atc gag atg aat cgc ctg ggg aag taa                              1518
Asp Ile Glu Met Asn Arg Leu Gly Lys
            500                 505


<210> SEQ ID NO 84
<211> LENGTH: 505
<212> TYPE: PRT
<213> ORGANISM: Artificial
<220> FEATURE:
<223> OTHER INFORMATION: Synthetic Construct

<400> SEQUENCE: 84

Met Thr Asp Thr Val Leu Gly Lys Phe Gln Ile Val Phe Pro Asp Gln
1               5                   10                  15

Asn Glu Leu Glu Trp Thr Pro Val Val Gly Asp Ser Arg His Cys Pro
            20                  25                  30

Gln Ser Ser Glu Met Gln Phe Asp Gly Ser Arg Ser Gln Thr Ile Leu
        35                  40                  45

Thr Gly Lys Ala Pro Val Gly Ile Thr Pro Ser Lys Ser Asp Gly Phe
    50                  55                  60

Ile Cys His Ala Ala Lys Trp Val Thr Thr Cys Asp Phe Arg Trp Tyr
65                  70                  75                  80

Gly Pro Lys Tyr Ile Thr His Ser Ile His His Leu Arg Pro Thr Thr
                85                  90                  95

Ser Asp Cys Glu Thr Ala Leu Gln Arg Tyr Lys Asp Gly Ser Leu Ile
            100                 105                 110

Asn Leu Gly Phe Pro Pro Glu Ser Cys Gly Tyr Ala Thr Val Thr Asp
        115                 120                 125
```

```
Ser Glu Ala Met Leu Val Gln Val Thr Pro His His Val Gly Val Asp
    130                 135                 140

Asp Tyr Arg Gly His Trp Ile Asp Pro Leu Phe Pro Gly Gly Glu Cys
145                 150                 155                 160

Ser Thr Asn Phe Cys Asp Thr Val His Asn Ser Ser Val Trp Ile Pro
                165                 170                 175

Lys Ser Gln Lys Thr Asp Ile Cys Ala Gln Ser Phe Lys Asn Ile Lys
            180                 185                 190

Met Thr Ala Ser Tyr Pro Ser Glu Gly Ala Leu Val Ser Asp Arg Phe
        195                 200                 205

Ala Phe His Ser Ala Tyr His Pro Asn Met Pro Gly Ser Thr Val Cys
    210                 215                 220

Ile Met Asp Phe Cys Glu Gln Lys Gly Leu Arg Phe Thr Asn Gly Glu
225                 230                 235                 240

Trp Met Gly Leu Asn Val Glu Gln Ser Ile Arg Glu Lys Lys Ile Ser
                245                 250                 255

Ala Ile Phe Pro Asn Cys Val Ala Gly Thr Glu Ile Arg Ala Thr Leu
            260                 265                 270

Glu Ser Glu Gly Ala Arg Thr Leu Thr Trp Glu Thr Gln Arg Met Leu
        275                 280                 285

Asp Tyr Ser Leu Cys Gln Asn Thr Trp Asp Lys Val Ser Arg Lys Glu
    290                 295                 300

Pro Leu Ser Pro Leu Asp Leu Ser Tyr Leu Ser Pro Arg Ala Pro Gly
305                 310                 315                 320

Lys Gly Met Ala Tyr Thr Val Ile Asn Gly Thr Leu His Ser Ala His
                325                 330                 335

Ala Lys Tyr Ile Arg Thr Trp Ile Asp Tyr Gly Glu Met Lys Glu Ile
            340                 345                 350

Lys Gly Gly Arg Gly Glu Tyr Ser Lys Ala Pro Glu Leu Leu Trp Ser
        355                 360                 365

Gln Trp Phe Asp Phe Gly Pro Phe Lys Ile Gly Pro Asn Gly Leu Leu
    370                 375                 380

His Thr Gly Lys Thr Phe Lys Phe Pro Leu Tyr Leu Ile Gly Ala Gly
385                 390                 395                 400

Ile Ile Asp Glu Asp Leu His Glu Leu Asp Glu Ala Ala Pro Ile Asp
                405                 410                 415

His Pro Gln Met Pro Asp Ala Lys Ser Val Leu Pro Glu Asp Glu Glu
            420                 425                 430

Ile Phe Phe Gly Asp Thr Gly Val Ser Lys Asn Pro Ile Glu Leu Ile
        435                 440                 445

Gln Gly Trp Phe Ser Asn Trp Arg Ser Ser Ile Ala Ser Phe Phe Phe
    450                 455                 460

Ile Ile Gly Leu Ile Ile Gly Leu Phe Leu Val Leu Arg Val Gly Ile
465                 470                 475                 480

His Leu Cys Ile Lys Leu Lys His Thr Lys Lys Arg Gln Ile Tyr Thr
                485                 490                 495

Asp Ile Glu Met Asn Arg Leu Gly Lys
            500                 505
```

<210> SEQ ID NO 85
<211> LENGTH: 1560
<212> TYPE: DNA
<213> ORGANISM: Artificial
<220> FEATURE:
<223> OTHER INFORMATION: Fusion VSV-G Isfahan / Indiana

```
<220> FEATURE:
<221> NAME/KEY: CDS
<222> LOCATION: (1)..(1560)

<400> SEQUENCE: 85

atg aca tcc gtg ctg ttt atg gtg ggc gtg ctg ctc gga gct ttc gga       48
Met Thr Ser Val Leu Phe Met Val Gly Val Leu Leu Gly Ala Phe Gly
1               5                   10                  15

tct acc cac tgc agc atc cag atc gtg ttc ccc agc gag aca aag ctg       96
Ser Thr His Cys Ser Ile Gln Ile Val Phe Pro Ser Glu Thr Lys Leu
            20                  25                  30

gtg tgg aag ccc gtg ctg aag ggc acc cgg tac tgc ccc cag agc gcc      144
Val Trp Lys Pro Val Leu Lys Gly Thr Arg Tyr Cys Pro Gln Ser Ala
        35                  40                  45

gag ctg aac ctg gaa ccc gac ctg aaa acc atg gcc ttc gac agc aag      192
Glu Leu Asn Leu Glu Pro Asp Leu Lys Thr Met Ala Phe Asp Ser Lys
    50                  55                  60

gtg ccc atc ggc atc acc ccc agc aac agc gac ggc tac ctg tgc cac      240
Val Pro Ile Gly Ile Thr Pro Ser Asn Ser Asp Gly Tyr Leu Cys His
65                  70                  75                  80

gcc gcc aag tgg gtg acc acc tgc gac ttc cgg tgg tac ggc ccc aag      288
Ala Ala Lys Trp Val Thr Thr Cys Asp Phe Arg Trp Tyr Gly Pro Lys
                85                  90                  95

tac atc acc cac agc gtg cac agc ctg cgg ccc acc gtg agc gac tgc      336
Tyr Ile Thr His Ser Val His Ser Leu Arg Pro Thr Val Ser Asp Cys
            100                 105                 110

aag gcc gcc gtg gaa gct tac aac gct ggc acc ctg atg tac ccc ggc      384
Lys Ala Ala Val Glu Ala Tyr Asn Ala Gly Thr Leu Met Tyr Pro Gly
        115                 120                 125

ttc ccc ccc gag agc tgc ggc tac gcc agc atc acc gac agc gag ttc      432
Phe Pro Pro Glu Ser Cys Gly Tyr Ala Ser Ile Thr Asp Ser Glu Phe
    130                 135                 140

tac gtg atg ctg gtg acc ccc cac ccc gtg gga gtg gac gac tac cgg      480
Tyr Val Met Leu Val Thr Pro His Pro Val Gly Val Asp Asp Tyr Arg
145                 150                 155                 160

ggc cac tgg gtg gac cct ctg ttc ccc acc tcc gag tgc aac agc aac      528
Gly His Trp Val Asp Pro Leu Phe Pro Thr Ser Glu Cys Asn Ser Asn
                165                 170                 175

ttc tgc gag aca gtg cac aac gcc acc atg tgg att ccc aag gat ctg      576
Phe Cys Glu Thr Val His Asn Ala Thr Met Trp Ile Pro Lys Asp Leu
            180                 185                 190

aaa acc cac gac gtg tgc agc cag gac ttc cag acc atc aga gtg agc      624
Lys Thr His Asp Val Cys Ser Gln Asp Phe Gln Thr Ile Arg Val Ser
        195                 200                 205

gtg atg tac cct cag acc aag ccc acc aag gga gct gac ctg aca ctg      672
Val Met Tyr Pro Gln Thr Lys Pro Thr Lys Gly Ala Asp Leu Thr Leu
    210                 215                 220

aag agc aag ttc cac gcc cac atg aag ggc gac aga gtg tgc aag atg      720
Lys Ser Lys Phe His Ala His Met Lys Gly Asp Arg Val Cys Lys Met
225                 230                 235                 240

aag ttc tgc aac aag aac ggc ctg cgg ctg ggc aac ggc gag tgg atc      768
Lys Phe Cys Asn Lys Asn Gly Leu Arg Leu Gly Asn Gly Glu Trp Ile
                245                 250                 255

gaa gtg ggc gac gag gtg atg ctg gac aac agc aag ctg ctg tcc ctg      816
Glu Val Gly Asp Glu Val Met Leu Asp Asn Ser Lys Leu Leu Ser Leu
            260                 265                 270

ttc ccc gac tgc ctg gtg ggc agc gtg gtg aag agc acc ctg ctg tcc      864
Phe Pro Asp Cys Leu Val Gly Ser Val Val Lys Ser Thr Leu Leu Ser
        275                 280                 285

gag ggc gtg cag acc gcc ctg tgg gag aca gac cgg ctg ctg gac tac      912
```

```
Glu Gly Val Gln Thr Ala Leu Trp Glu Thr Asp Arg Leu Leu Asp Tyr
    290                 295                 300

agc ctg tgc cag aac acc tgg gag aag atc gac cgg aaa gag ccc ctg      960
Ser Leu Cys Gln Asn Thr Trp Glu Lys Ile Asp Arg Lys Glu Pro Leu
305                 310                 315                 320

agc gcc gtc gac ctg agc tac ctg gcc cct aga agc ccc ggc aag ggc     1008
Ser Ala Val Asp Leu Ser Tyr Leu Ala Pro Arg Ser Pro Gly Lys Gly
                325                 330                 335

atg gcc tac atc gtg gcc aac ggc agc ctg atg agc gcc cct gcc cgg     1056
Met Ala Tyr Ile Val Ala Asn Gly Ser Leu Met Ser Ala Pro Ala Arg
            340                 345                 350

tac atc aga gtg tgg atc gac agc ccc atc ctg aaa gag atc aag ggc     1104
Tyr Ile Arg Val Trp Ile Asp Ser Pro Ile Leu Lys Glu Ile Lys Gly
        355                 360                 365

aag aaa gag agc gcc agc ggc atc gac acc gtg ctg tgg gag cag tgg     1152
Lys Lys Glu Ser Ala Ser Gly Ile Asp Thr Val Leu Trp Glu Gln Trp
    370                 375                 380

ctg ccc ttc aac ggc atg gaa ctg ggc ccc aac ggc ctg atc aag acc     1200
Leu Pro Phe Asn Gly Met Glu Leu Gly Pro Asn Gly Leu Ile Lys Thr
385                 390                 395                 400

aag agc ggc tac aag ttc ccc ctg tac ctg ctg ggc atg ggc atc gtg     1248
Lys Ser Gly Tyr Lys Phe Pro Leu Tyr Leu Leu Gly Met Gly Ile Val
                405                 410                 415

gac cag gac ctg cag gaa ctg agc agc gtc aac ccc gtg gac cac ccc     1296
Asp Gln Asp Leu Gln Glu Leu Ser Ser Val Asn Pro Val Asp His Pro
            420                 425                 430

cac gtg cct atc gcc cag gcc ttc gtg agc gag ggc gag gaa gtg ttc     1344
His Val Pro Ile Ala Gln Ala Phe Val Ser Glu Gly Glu Glu Val Phe
        435                 440                 445

ttc ggc gac acc ggc gtg agc aag aac ccc atc gag ctg atc agc ggc     1392
Phe Gly Asp Thr Gly Val Ser Lys Asn Pro Ile Glu Leu Ile Ser Gly
    450                 455                 460

tgg ttc agc gac tgg aaa agc agc atc gct tca ttt ttt ttc atc atc     1440
Trp Phe Ser Asp Trp Lys Ser Ser Ile Ala Ser Phe Phe Phe Ile Ile
465                 470                 475                 480

ggc ctc atc atc ggg ctg ttt ctg gtg ctg cgc gtc ggc atc cac ctg     1488
Gly Leu Ile Ile Gly Leu Phe Leu Val Leu Arg Val Gly Ile His Leu
                485                 490                 495

tgc atc aag ctg aag cac acc aag aag cgc cag atc tat acc gac atc     1536
Cys Ile Lys Leu Lys His Thr Lys Lys Arg Gln Ile Tyr Thr Asp Ile
            500                 505                 510

gag atg aat cgc ctg ggg aag taa                                     1560
Glu Met Asn Arg Leu Gly Lys
        515


<210> SEQ ID NO 86
<211> LENGTH: 519
<212> TYPE: PRT
<213> ORGANISM: Artificial
<220> FEATURE:
<223> OTHER INFORMATION: Synthetic Construct

<400> SEQUENCE: 86

Met Thr Ser Val Leu Phe Met Val Gly Val Leu Leu Gly Ala Phe Gly
1               5                   10                  15

Ser Thr His Cys Ser Ile Gln Ile Val Phe Pro Ser Glu Thr Lys Leu
            20                  25                  30

Val Trp Lys Pro Val Leu Lys Gly Thr Arg Tyr Cys Pro Gln Ser Ala
        35                  40                  45

Glu Leu Asn Leu Glu Pro Asp Leu Lys Thr Met Ala Phe Asp Ser Lys
```

```
    50                  55                  60

Val Pro Ile Gly Ile Thr Pro Ser Asn Ser Asp Gly Tyr Leu Cys His
65                  70                  75                  80

Ala Ala Lys Trp Val Thr Thr Cys Asp Phe Arg Trp Tyr Gly Pro Lys
                85                  90                  95

Tyr Ile Thr His Ser Val His Ser Leu Arg Pro Thr Val Ser Asp Cys
            100                 105                 110

Lys Ala Ala Val Glu Ala Tyr Asn Ala Gly Thr Leu Met Tyr Pro Gly
        115                 120                 125

Phe Pro Pro Glu Ser Cys Gly Tyr Ala Ser Ile Thr Asp Ser Glu Phe
    130                 135                 140

Tyr Val Met Leu Val Thr Pro His Pro Val Gly Val Asp Asp Tyr Arg
145                 150                 155                 160

Gly His Trp Val Asp Pro Leu Phe Pro Thr Ser Glu Cys Asn Ser Asn
                165                 170                 175

Phe Cys Glu Thr Val His Asn Ala Thr Met Trp Ile Pro Lys Asp Leu
            180                 185                 190

Lys Thr His Asp Val Cys Ser Gln Asp Phe Gln Thr Ile Arg Val Ser
        195                 200                 205

Val Met Tyr Pro Gln Thr Lys Pro Thr Lys Gly Ala Asp Leu Thr Leu
    210                 215                 220

Lys Ser Lys Phe His Ala His Met Lys Gly Asp Arg Val Cys Lys Met
225                 230                 235                 240

Lys Phe Cys Asn Lys Asn Gly Leu Arg Leu Gly Asn Gly Glu Trp Ile
                245                 250                 255

Glu Val Gly Asp Glu Val Met Leu Asp Asn Ser Lys Leu Leu Ser Leu
            260                 265                 270

Phe Pro Asp Cys Leu Val Gly Ser Val Val Lys Ser Thr Leu Leu Ser
        275                 280                 285

Glu Gly Val Gln Thr Ala Leu Trp Glu Thr Asp Arg Leu Leu Asp Tyr
    290                 295                 300

Ser Leu Cys Gln Asn Thr Trp Glu Lys Ile Asp Arg Lys Glu Pro Leu
305                 310                 315                 320

Ser Ala Val Asp Leu Ser Tyr Leu Ala Pro Arg Ser Pro Gly Lys Gly
                325                 330                 335

Met Ala Tyr Ile Val Ala Asn Gly Ser Leu Met Ser Ala Pro Ala Arg
            340                 345                 350

Tyr Ile Arg Val Trp Ile Asp Ser Pro Ile Leu Lys Glu Ile Lys Gly
        355                 360                 365

Lys Lys Glu Ser Ala Ser Gly Ile Asp Thr Val Leu Trp Glu Gln Trp
    370                 375                 380

Leu Pro Phe Asn Gly Met Glu Leu Gly Pro Asn Gly Leu Ile Lys Thr
385                 390                 395                 400

Lys Ser Gly Tyr Lys Phe Pro Leu Tyr Leu Leu Gly Met Gly Ile Val
                405                 410                 415

Asp Gln Asp Leu Gln Glu Leu Ser Ser Val Asn Pro Val Asp His Pro
            420                 425                 430

His Val Pro Ile Ala Gln Ala Phe Val Ser Glu Gly Glu Glu Val Phe
        435                 440                 445

Phe Gly Asp Thr Gly Val Ser Lys Asn Pro Ile Glu Leu Ile Ser Gly
    450                 455                 460

Trp Phe Ser Asp Trp Lys Ser Ser Ile Ala Ser Phe Phe Phe Ile Ile
465                 470                 475                 480
```

```
Gly Leu Ile Ile Gly Leu Phe Leu Val Leu Arg Val Gly Ile His Leu
                485                 490                 495

Cys Ile Lys Leu Lys His Thr Lys Lys Arg Gln Ile Tyr Thr Asp Ile
            500                 505                 510

Glu Met Asn Arg Leu Gly Lys
        515


<210> SEQ ID NO 87
<211> LENGTH: 1536
<212> TYPE: DNA
<213> ORGANISM: Artificial
<220> FEATURE:
<223> OTHER INFORMATION: Fusion VSV-G New Jersey / Indiana
<220> FEATURE:
<221> NAME/KEY: CDS
<222> LOCATION: (1)..(1536)

<400> SEQUENCE: 87

atg agc atc atc agc tat atc gcc ttt ctg ctg ctg atc gac agc acc       48
Met Ser Ile Ile Ser Tyr Ile Ala Phe Leu Leu Leu Ile Asp Ser Thr
1               5                   10                  15

ctg ggc atc ccc atc ttc gtg ccc agc ggc cag aac atc agc tgg cag       96
Leu Gly Ile Pro Ile Phe Val Pro Ser Gly Gln Asn Ile Ser Trp Gln
            20                  25                  30

ccc gtg atc cag ccc ttc gac tac cag tgc ccc atc cac ggc aac ctg      144
Pro Val Ile Gln Pro Phe Asp Tyr Gln Cys Pro Ile His Gly Asn Leu
        35                  40                  45

ccc aac acc atg ggc ctg agc gcc acc aag ctg acc atc aag agc ccc      192
Pro Asn Thr Met Gly Leu Ser Ala Thr Lys Leu Thr Ile Lys Ser Pro
    50                  55                  60

agc gtg ttc agc acc gac aag gtg tcc ggc tgg atc tgc cac gcc gcc      240
Ser Val Phe Ser Thr Asp Lys Val Ser Gly Trp Ile Cys His Ala Ala
65                  70                  75                  80

gag tgg aaa acc acc tgc gac tac cgg tgg tac ggc ccc cag tac atc      288
Glu Trp Lys Thr Thr Cys Asp Tyr Arg Trp Tyr Gly Pro Gln Tyr Ile
                85                  90                  95

acc cac agc atc cac ccc atc agc ccc acc atc gac gag tgc aag cgg      336
Thr His Ser Ile His Pro Ile Ser Pro Thr Ile Asp Glu Cys Lys Arg
            100                 105                 110

atc atc agc cgg atc gcc agc ggc acc gac gag gac ctg ggc ttc cca      384
Ile Ile Ser Arg Ile Ala Ser Gly Thr Asp Glu Asp Leu Gly Phe Pro
        115                 120                 125

ccc cag agc tgc ggc tgg gcc agc gtg acc acc gtg agc aac acc aac      432
Pro Gln Ser Cys Gly Trp Ala Ser Val Thr Thr Val Ser Asn Thr Asn
    130                 135                 140

tac aag gtg gtg ccc cac agc gtg cac ctg gaa ccc tac ggc ggc cac      480
Tyr Lys Val Val Pro His Ser Val His Leu Glu Pro Tyr Gly Gly His
145                 150                 155                 160

tgg atc gac cac gac ttc aac ggc ggc gag tgc cgg gag aaa gtg tgc      528
Trp Ile Asp His Asp Phe Asn Gly Gly Glu Cys Arg Glu Lys Val Cys
                165                 170                 175

gag atg aag ggc aac cac agc atc tgg atc acc gac gag aca gtg cag      576
Glu Met Lys Gly Asn His Ser Ile Trp Ile Thr Asp Glu Thr Val Gln
            180                 185                 190

cac gag tgc gag aag cac atc gag gaa gtg gag ggc atc atg tac ggc      624
His Glu Cys Glu Lys His Ile Glu Glu Val Glu Gly Ile Met Tyr Gly
        195                 200                 205

aac gcc ccc agg ggc gac gcc atc tac atc aac aac ttc atc atc gac      672
Asn Ala Pro Arg Gly Asp Ala Ile Tyr Ile Asn Asn Phe Ile Ile Asp
    210                 215                 220
```

```
aag cac cac cgg gtg tac cgg ttc ggc ggc tcc tgc cgg atg aag ttc      720
Lys His His Arg Val Tyr Arg Phe Gly Gly Ser Cys Arg Met Lys Phe
225                 230                 235                 240

tgc aac aag gac ggc atc aag ttc acc aga ggc gac tgg gtg gag aaa      768
Cys Asn Lys Asp Gly Ile Lys Phe Thr Arg Gly Asp Trp Val Glu Lys
                245                 250                 255

acc gcc ggc acc ctg acc aac atc tac gag aac atc ccc gag tgc gcc      816
Thr Ala Gly Thr Leu Thr Asn Ile Tyr Glu Asn Ile Pro Glu Cys Ala
            260                 265                 270

gac ggc aca ctg gtg tcc ggc cac aga ccc ggc ctg gac ctg atc gac      864
Asp Gly Thr Leu Val Ser Gly His Arg Pro Gly Leu Asp Leu Ile Asp
        275                 280                 285

acc gtg ttc aac ctg gaa aac gtg gtg gag tac acc ctg tgc gag ggc      912
Thr Val Phe Asn Leu Glu Asn Val Val Glu Tyr Thr Leu Cys Glu Gly
    290                 295                 300

acc aag cgg aag atc aac aag cag gaa aag ctg acc agc gtc gac ctg      960
Thr Lys Arg Lys Ile Asn Lys Gln Glu Lys Leu Thr Ser Val Asp Leu
305                 310                 315                 320

agc tac ctg gcc ccc agg atc ggc ggc ttc ggc agc gtg ttc cgc gtg     1008
Ser Tyr Leu Ala Pro Arg Ile Gly Gly Phe Gly Ser Val Phe Arg Val
                325                 330                 335

cgg aat ggg acc ctg gaa aga gga agc aca aca tac att cgg atc gaa     1056
Arg Asn Gly Thr Leu Glu Arg Gly Ser Thr Thr Tyr Ile Arg Ile Glu
            340                 345                 350

gtg gaa ggc ccc gtg gtg gac agc ctg aac ggc atc gac ccc cgg acc     1104
Val Glu Gly Pro Val Val Asp Ser Leu Asn Gly Ile Asp Pro Arg Thr
        355                 360                 365

aac gcc agc cgg gtg ttc tgg gac gac tgg gag ctg gac ggc aac atc     1152
Asn Ala Ser Arg Val Phe Trp Asp Asp Trp Glu Leu Asp Gly Asn Ile
    370                 375                 380

tac cag ggc ttc aat ggc gtg tac aag ggc aag gat ggc aag atc cac     1200
Tyr Gln Gly Phe Asn Gly Val Tyr Lys Gly Lys Asp Gly Lys Ile His
385                 390                 395                 400

atc ccc ctg aac atg atc gag agc ggc atc atc gac gac gag ctg cag     1248
Ile Pro Leu Asn Met Ile Glu Ser Gly Ile Ile Asp Asp Glu Leu Gln
                405                 410                 415

cac gcc ttc cag gcc gac atc atc ccc cac ccc cac tac gac gac gac     1296
His Ala Phe Gln Ala Asp Ile Ile Pro His Pro His Tyr Asp Asp Asp
            420                 425                 430

gag atc cgg gag gac gac atc ttc ttc gac aac acc ggc gag aac ggc     1344
Glu Ile Arg Glu Asp Asp Ile Phe Phe Asp Asn Thr Gly Glu Asn Gly
        435                 440                 445

aac ccc gtg gac gcc gtg gtg gaa tgg gtg tcc gga tgg ggc agc agc     1392
Asn Pro Val Asp Ala Val Val Glu Trp Val Ser Gly Trp Gly Ser Ser
    450                 455                 460

atc gct tca ttt ttt ttc atc atc ggc ctc atc atc ggg ctg ttt ctg     1440
Ile Ala Ser Phe Phe Phe Ile Ile Gly Leu Ile Ile Gly Leu Phe Leu
465                 470                 475                 480

gtg ctg cgc gtc ggc atc cac ctg tgc atc aag ctg aag cac acc aag     1488
Val Leu Arg Val Gly Ile His Leu Cys Ile Lys Leu Lys His Thr Lys
                485                 490                 495

aag cgc cag atc tat acc gac atc gag atg aat cgc ctg ggg aag taa     1536
Lys Arg Gln Ile Tyr Thr Asp Ile Glu Met Asn Arg Leu Gly Lys
            500                 505                 510
```

<210> SEQ ID NO 88
<211> LENGTH: 511
<212> TYPE: PRT
<213> ORGANISM: Artificial
<220> FEATURE:
<223> OTHER INFORMATION: Synthetic Construct

<400> SEQUENCE: 88

```
Met Ser Ile Ile Ser Tyr Ile Ala Phe Leu Leu Leu Ile Asp Ser Thr
1               5                   10                  15

Leu Gly Ile Pro Ile Phe Val Pro Ser Gly Gln Asn Ile Ser Trp Gln
            20                  25                  30

Pro Val Ile Gln Pro Phe Asp Tyr Gln Cys Pro Ile His Gly Asn Leu
        35                  40                  45

Pro Asn Thr Met Gly Leu Ser Ala Thr Lys Leu Thr Ile Lys Ser Pro
    50                  55                  60

Ser Val Phe Ser Thr Asp Lys Val Ser Gly Trp Ile Cys His Ala Ala
65                  70                  75                  80

Glu Trp Lys Thr Thr Cys Asp Tyr Arg Trp Tyr Gly Pro Gln Tyr Ile
                85                  90                  95

Thr His Ser Ile His Pro Ile Ser Pro Thr Ile Asp Glu Cys Lys Arg
            100                 105                 110

Ile Ile Ser Arg Ile Ala Ser Gly Thr Asp Glu Asp Leu Gly Phe Pro
        115                 120                 125

Pro Gln Ser Cys Gly Trp Ala Ser Val Thr Thr Val Ser Asn Thr Asn
    130                 135                 140

Tyr Lys Val Val Pro His Ser Val His Leu Glu Pro Tyr Gly Gly His
145                 150                 155                 160

Trp Ile Asp His Asp Phe Asn Gly Gly Glu Cys Arg Glu Lys Val Cys
                165                 170                 175

Glu Met Lys Gly Asn His Ser Ile Trp Ile Thr Asp Glu Thr Val Gln
            180                 185                 190

His Glu Cys Glu Lys His Ile Glu Glu Val Glu Gly Ile Met Tyr Gly
        195                 200                 205

Asn Ala Pro Arg Gly Asp Ala Ile Tyr Ile Asn Asn Phe Ile Ile Asp
    210                 215                 220

Lys His His Arg Val Tyr Arg Phe Gly Gly Ser Cys Arg Met Lys Phe
225                 230                 235                 240

Cys Asn Lys Asp Gly Ile Lys Phe Thr Arg Gly Asp Trp Val Glu Lys
                245                 250                 255

Thr Ala Gly Thr Leu Thr Asn Ile Tyr Glu Asn Ile Pro Glu Cys Ala
            260                 265                 270

Asp Gly Thr Leu Val Ser Gly His Arg Pro Gly Leu Asp Leu Ile Asp
        275                 280                 285

Thr Val Phe Asn Leu Glu Asn Val Val Glu Tyr Thr Leu Cys Glu Gly
    290                 295                 300

Thr Lys Arg Lys Ile Asn Lys Gln Glu Lys Leu Thr Ser Val Asp Leu
305                 310                 315                 320

Ser Tyr Leu Ala Pro Arg Ile Gly Gly Phe Gly Ser Val Phe Arg Val
                325                 330                 335

Arg Asn Gly Thr Leu Glu Arg Gly Ser Thr Thr Tyr Ile Arg Ile Glu
            340                 345                 350

Val Glu Gly Pro Val Val Asp Ser Leu Asn Gly Ile Asp Pro Arg Thr
        355                 360                 365

Asn Ala Ser Arg Val Phe Trp Asp Asp Trp Glu Leu Asp Gly Asn Ile
    370                 375                 380

Tyr Gln Gly Phe Asn Gly Val Tyr Lys Gly Lys Asp Gly Lys Ile His
385                 390                 395                 400

Ile Pro Leu Asn Met Ile Glu Ser Gly Ile Ile Asp Asp Glu Leu Gln
```

```
            405                 410                 415

His Ala Phe Gln Ala Asp Ile Ile Pro His Pro His Tyr Asp Asp Asp
        420                 425                 430

Glu Ile Arg Glu Asp Asp Ile Phe Phe Asp Asn Thr Gly Glu Asn Gly
    435                 440                 445

Asn Pro Val Asp Ala Val Val Glu Trp Val Ser Gly Trp Gly Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
            485                 490                 495

Lys Arg Gln Ile Tyr Thr Asp Ile Glu Met Asn Arg Leu Gly Lys
        500                 505                 510


<210> SEQ ID NO 89
<211> LENGTH: 1557
<212> TYPE: DNA
<213> ORGANISM: Artificial
<220> FEATURE:
<223> OTHER INFORMATION: Fusion VSV-G New Jersey / Indiana
<220> FEATURE:
<221> NAME/KEY: CDS
<222> LOCATION: (1)..(1557)

<400> SEQUENCE: 89

atg ctg tca tat ctg atc ttt gcc ctg gct gtg agc cca atc ctc gga       48
Met Leu Ser Tyr Leu Ile Phe Ala Leu Ala Val Ser Pro Ile Leu Gly
1               5                   10                  15

aag atc gaa atc gtg ttc cca caa cac acc aca ggg gac tgg aag cgc       96
Lys Ile Glu Ile Val Phe Pro Gln His Thr Thr Gly Asp Trp Lys Arg
            20                  25                  30

gtg ccc cac gag tac aac tac tgc ccg acc tca gcc gac aag aat agc      144
Val Pro His Glu Tyr Asn Tyr Cys Pro Thr Ser Ala Asp Lys Asn Ser
        35                  40                  45

cac ggc acg cag acc ggc atc cct gtg gag ctg acc atg ccc aag ggg      192
His Gly Thr Gln Thr Gly Ile Pro Val Glu Leu Thr Met Pro Lys Gly
    50                  55                  60

ctc aca acg cac caa gtc gaa ggc ttc atg tgc cac agc gct ctc tgg      240
Leu Thr Thr His Gln Val Glu Gly Phe Met Cys His Ser Ala Leu Trp
65                  70                  75                  80

atg aca acc tgc gat ttt cgc tgg tat ggc ccc aag tac atc acg cac      288
Met Thr Thr Cys Asp Phe Arg Trp Tyr Gly Pro Lys Tyr Ile Thr His
                85                  90                  95

agc atc cac aat gag gaa cca acc gac tac cag tgc ctc gaa gcc atc      336
Ser Ile His Asn Glu Glu Pro Thr Asp Tyr Gln Cys Leu Glu Ala Ile
            100                 105                 110

aag tca tac aag gat ggg gtg agc ttc aac ccc ggc ttc ccg ccc caa      384
Lys Ser Tyr Lys Asp Gly Val Ser Phe Asn Pro Gly Phe Pro Pro Gln
        115                 120                 125

tca tgt ggc tac ggc acc gtg acc gac gcc gag gcc cac atc gtg acc      432
Ser Cys Gly Tyr Gly Thr Val Thr Asp Ala Glu Ala His Ile Val Thr
    130                 135                 140

gtg aca ccc cac tca gtc aag gtg gac gag tac aca ggc gaa tgg atc      480
Val Thr Pro His Ser Val Lys Val Asp Glu Tyr Thr Gly Glu Trp Ile
145                 150                 155                 160

gac ccc cac ttc atc ggg ggc cgc tgt aag ggc caa atc tgc gag acc      528
Asp Pro His Phe Ile Gly Gly Arg Cys Lys Gly Gln Ile Cys Glu Thr
                165                 170                 175

gtg cac aac agc acc aag tgg ttt acg tca tca gac ggc gaa agc gtg      576
Val His Asn Ser Thr Lys Trp Phe Thr Ser Ser Asp Gly Glu Ser Val
```

```
            180                 185                 190

tgc agc caa ctg ttt acg ctc gtg ggc ggc atc ttc ttt agc gac agc      624
Cys Ser Gln Leu Phe Thr Leu Val Gly Gly Ile Phe Phe Ser Asp Ser
        195                 200                 205

gag gag atc acc agc atg ggc ctc ccg gag aca gga atc cgc agc aac      672
Glu Glu Ile Thr Ser Met Gly Leu Pro Glu Thr Gly Ile Arg Ser Asn
    210                 215                 220

tac ttt ccg tac atc agc acc gag gga atc tgt aag atg cct ttt tgc      720
Tyr Phe Pro Tyr Ile Ser Thr Glu Gly Ile Cys Lys Met Pro Phe Cys
225                 230                 235                 240

cgc aag cag gga tat aag ctg aag aat gac ctg tgg ttc cag atc atg      768
Arg Lys Gln Gly Tyr Lys Leu Lys Asn Asp Leu Trp Phe Gln Ile Met
                245                 250                 255

gac ccg gac ctg gac aag acc gtc cgc gat ctg ccc cac atc aag gac      816
Asp Pro Asp Leu Asp Lys Thr Val Arg Asp Leu Pro His Ile Lys Asp
            260                 265                 270

tgt gat ctg tca tca agc atc atc acc ccc gga gaa cac gcc acg gac      864
Cys Asp Leu Ser Ser Ser Ile Ile Thr Pro Gly Glu His Ala Thr Asp
        275                 280                 285

atc agc ctc atc agc gat gtg gag cgc atc ctc gac tac gct ctc tgc      912
Ile Ser Leu Ile Ser Asp Val Glu Arg Ile Leu Asp Tyr Ala Leu Cys
    290                 295                 300

cag aac aca tgg agc aag atc gaa agc ggc gaa ccc atc acc cca gtg      960
Gln Asn Thr Trp Ser Lys Ile Glu Ser Gly Glu Pro Ile Thr Pro Val
305                 310                 315                 320

gac ctg agc tat ctc ggc cca aag aac ccc ggc gtg ggg ccc gtg ttc     1008
Asp Leu Ser Tyr Leu Gly Pro Lys Asn Pro Gly Val Gly Pro Val Phe
                325                 330                 335

acc atc atc aac ggg agc ctg cac tac ttt aca agc aag tat ctg cgc     1056
Thr Ile Ile Asn Gly Ser Leu His Tyr Phe Thr Ser Lys Tyr Leu Arg
            340                 345                 350

gtg gag ctc gaa agc cca gtc atc ccc cgc atg gag ggg aag gtg gcc     1104
Val Glu Leu Glu Ser Pro Val Ile Pro Arg Met Glu Gly Lys Val Ala
        355                 360                 365

ggg acc cgc atc gtg cgc cag ctg tgg gac cag tgg ttc cct ttt ggc     1152
Gly Thr Arg Ile Val Arg Gln Leu Trp Asp Gln Trp Phe Pro Phe Gly
    370                 375                 380

gag gtg gaa atc ggc ccc aac ggc gtg ctg aag acc aag caa gga tat     1200
Glu Val Glu Ile Gly Pro Asn Gly Val Leu Lys Thr Lys Gln Gly Tyr
385                 390                 395                 400

aag ttc ccg ctg cac atc atc ggg acg ggc gaa gtg gac agc gat atc     1248
Lys Phe Pro Leu His Ile Ile Gly Thr Gly Glu Val Asp Ser Asp Ile
                405                 410                 415

aag atg gag cgc gtg gtc aag cac tgg gag cac cca cac atc gag gct     1296
Lys Met Glu Arg Val Val Lys His Trp Glu His Pro His Ile Glu Ala
            420                 425                 430

gct cag acc ttt ctc aag aag gac gat acc ggc gaa gtc ctg tat tac     1344
Ala Gln Thr Phe Leu Lys Lys Asp Asp Thr Gly Glu Val Leu Tyr Tyr
        435                 440                 445

ggg gat acg gga gtg agc aag aac cct gtg gag ctg gtg gaa ggc tgg     1392
Gly Asp Thr Gly Val Ser Lys Asn Pro Val Glu Leu Val Glu Gly Trp
    450                 455                 460

ttc agc gga tgg cgc agc agc atc gct tca ttt ttt ttc atc atc ggc     1440
Phe Ser Gly Trp Arg Ser Ser Ile Ala Ser Phe Phe Phe Ile Ile Gly
465                 470                 475                 480

ctc atc atc ggg ctg ttt ctg gtg ctg cgc gtc ggc atc cac ctg tgc     1488
Leu Ile Ile Gly Leu Phe Leu Val Leu Arg Val Gly Ile His Leu Cys
                485                 490                 495

atc aag ctg aag cac acc aag aag cgc cag atc tat acc gac atc gag     1536
```

```
Ile Lys Leu Lys His Thr Lys Lys Arg Gln Ile Tyr Thr Asp Ile Glu
            500                 505                 510

atg aat cgc ctg ggg aag taa                                         1557
Met Asn Arg Leu Gly Lys
        515


<210> SEQ ID NO 90
<211> LENGTH: 518
<212> TYPE: PRT
<213> ORGANISM: Artificial
<220> FEATURE:
<223> OTHER INFORMATION: Synthetic Construct

<400> SEQUENCE: 90

Met Leu Ser Tyr Leu Ile Phe Ala Leu Ala Val Ser Pro Ile Leu Gly
1               5                   10                  15

Lys Ile Glu Ile Val Phe Pro Gln His Thr Thr Gly Asp Trp Lys Arg
            20                  25                  30

Val Pro His Glu Tyr Asn Tyr Cys Pro Thr Ser Ala Asp Lys Asn Ser
        35                  40                  45

His Gly Thr Gln Thr Gly Ile Pro Val Glu Leu Thr Met Pro Lys Gly
    50                  55                  60

Leu Thr Thr His Gln Val Glu Gly Phe Met Cys His Ser Ala Leu Trp
65                  70                  75                  80

Met Thr Thr Cys Asp Phe Arg Trp Tyr Gly Pro Lys Tyr Ile Thr His
                85                  90                  95

Ser Ile His Asn Glu Glu Pro Thr Asp Tyr Gln Cys Leu Glu Ala Ile
            100                 105                 110

Lys Ser Tyr Lys Asp Gly Val Ser Phe Asn Pro Gly Phe Pro Pro Gln
        115                 120                 125

Ser Cys Gly Tyr Gly Thr Val Thr Asp Ala Glu Ala His Ile Val Thr
    130                 135                 140

Val Thr Pro His Ser Val Lys Val Asp Glu Tyr Thr Gly Glu Trp Ile
145                 150                 155                 160

Asp Pro His Phe Ile Gly Gly Arg Cys Lys Gly Gln Ile Cys Glu Thr
                165                 170                 175

Val His Asn Ser Thr Lys Trp Phe Thr Ser Ser Asp Gly Glu Ser Val
            180                 185                 190

Cys Ser Gln Leu Phe Thr Leu Val Gly Gly Ile Phe Phe Ser Asp Ser
        195                 200                 205

Glu Glu Ile Thr Ser Met Gly Leu Pro Glu Thr Gly Ile Arg Ser Asn
    210                 215                 220

Tyr Phe Pro Tyr Ile Ser Thr Glu Gly Ile Cys Lys Met Pro Phe Cys
225                 230                 235                 240

Arg Lys Gln Gly Tyr Lys Leu Lys Asn Asp Leu Trp Phe Gln Ile Met
                245                 250                 255

Asp Pro Asp Leu Asp Lys Thr Val Arg Asp Leu Pro His Ile Lys Asp
            260                 265                 270

Cys Asp Leu Ser Ser Ser Ile Ile Thr Pro Gly Glu His Ala Thr Asp
        275                 280                 285

Ile Ser Leu Ile Ser Asp Val Glu Arg Ile Leu Asp Tyr Ala Leu Cys
    290                 295                 300

Gln Asn Thr Trp Ser Lys Ile Glu Ser Gly Glu Pro Ile Thr Pro Val
305                 310                 315                 320

Asp Leu Ser Tyr Leu Gly Pro Lys Asn Pro Gly Val Gly Pro Val Phe
                325                 330                 335
```

-continued

```
Thr Ile Ile Asn Gly Ser Leu His Tyr Phe Thr Ser Lys Tyr Leu Arg
            340                 345                 350

Val Glu Leu Glu Ser Pro Val Ile Pro Arg Met Glu Gly Lys Val Ala
        355                 360                 365

Gly Thr Arg Ile Val Arg Gln Leu Trp Asp Gln Trp Phe Pro Phe Gly
    370                 375                 380

Glu Val Glu Ile Gly Pro Asn Gly Val Leu Lys Thr Lys Gln Gly Tyr
385                 390                 395                 400

Lys Phe Pro Leu His Ile Ile Gly Thr Gly Glu Val Asp Ser Asp Ile
                405                 410                 415

Lys Met Glu Arg Val Val Lys His Trp Glu His Pro His Ile Glu Ala
            420                 425                 430

Ala Gln Thr Phe Leu Lys Lys Asp Asp Thr Gly Glu Val Leu Tyr Tyr
        435                 440                 445

Gly Asp Thr Gly Val Ser Lys Asn Pro Val Glu Leu Val Glu Gly Trp
    450                 455                 460

Phe Ser Gly Trp Arg Ser Ser Ile Ala Ser Phe Phe Phe Ile Ile Gly
465                 470                 475                 480

Leu Ile Ile Gly Leu Phe Leu Val Leu Arg Val Gly Ile His Leu Cys
                485                 490                 495

Ile Lys Leu Lys His Thr Lys Lys Arg Gln Ile Tyr Thr Asp Ile Glu
            500                 505                 510

Met Asn Arg Leu Gly Lys
        515
```

LENTIVIRAL VECTOR BASED IMMUNOLOGICAL COMPOUNDS AGAINST MALARIA

This application is the U.S. National Stage of International Application No. PCT/EP2011/056887, filed Apr. 29, 2011, which claims the benefit of European Application No. 10290238.4, filed May 3, 2010. Both of those applications are hereby incorporated herein by reference.

The invention relates to a lentiviral vector based immunological compounds against malaria.

In view of the impediments which have been observed in the design of vaccine strategies, many diseases that lead to high mortality and morbidity such as malaria still necessitate the development of new vaccine platforms capable of eliciting strong T-cell mediated immunity and advantageously potent humoral immune responses. Among parasitic infections affecting humans, malaria is a disease for which numerous attempts for such vaccines have been proposed.

However, concerning malaria, only vaccines containing radiation attenuated sporozoites consistently induce sterile immunity in rodents (Nussenzweig R. S. et al, Nature 216, 160-162 (1967)), monkeys (Gwadz; R. W. et al, Bull World Health Organ 57 Suppl 1, 165-173 (1979)) and humans (Clyde, D. F. et al, Am J. Med Sci 266, 169-177 (1973). Albeit very interesting, the irradiated sporozoite vaccine approach still needs to overcome numerous challenges, in particular related to safety, production, storage and distribution, before it can be considered promising for mass vaccination.

In a Review Article, Limbach K. J. & Richie T. L. (Parasit immunology, 2009, 31, 501-519) have considered different available vaccine platforms against malaria, which are based on the use of viral vectors as delivery means for the antigens eliciting an immune response. Such platforms include vaccines designed on the basis of poxvirus-vectored malaria antigens, or adenovirus-vectored malaria antigens, both types of vectors being inter alia proposed in approaches involving heterologous prime-boost regimens for administration. Apart from these poxvirus or adenovirus based technologies, the authors of the review disclose that novel vector systems may be promising in animal models considering accordingly yellow fever vectored strategies or alpha virus replicon vectored strategies. They also envisage various potentially interesting ways to overcome the persisting difficulties in designing vaccine vectors that may be efficient in providing long-lasting immunity in mammalian hosts and fulfil the requirements of safety for administration to human hosts. Such ways would include combination of heterologous delivery means for the antigens, use of adjuvants or immunomodulatory components.

In an attempt to overcome at least some of the drawbacks observed when assaying the proposed vaccine compositions of the prior art, the inventors have considered the approach of lentiviral vectors as a basis for a new vaccination platform with a view to develop prophylactic vaccines against malaria.

Malaria is a pathology which is transmitted to the host by *Anophele* mosquitoes and is endemic in many countries where it generates the death of many millions of people each year. Apart from mortality, malaria causes morbidity in a large proportion of the population in countries where it is endemic, thereby causing medical and economic major concerns for these countries.

Five species of *Plasmodium* parasites are known to infect human: *Plasmodium vivax, Plasmodium ovale, Plasmodium malariae, Plasmodium knowlesi* (17) and *Plasmodium falciparum*, the latter being the agent of malaria which causes almost all mortality cases. Infection in humans begins with inoculation of sporozoites forms of the parasite that originate from female mosquitoes. These forms of the parasite are rapidly transferred from the blood flow to the liver of the human host where they proceed with invasion of hepatocytes. Depending on the strain of *Plasmodium*, the duration of the intra-hepatic cycle of the parasite is from 5 to 15 days, the shorter (around 5.5 days) being for *P. falciparum*. The parasite amplifies in the liver as a result of asexual replication in the infected cells, giving rise to merozoite forms of the parasite. After the merozoites have been liberated from the hepatocytes, they progress toward a blood-stage infection which corresponds to the symptomatic phase of the infection in the human host. Accordingly, the merozoites rapidly penetrate into red blood cells (erythrocytes) through a specific membrane receptor. The merozoite invasion of the erythrocytes corresponds to the erythrocytic stage of the cycle which lasts for 48 to 72 hours depending on the strain of *Plasmodium*. During this stage, merozoites undergo multiple nuclear divisions, giving rise to the liberation of further merozoites, which are able to perform invasion of additional red blood cells and thus to repeat the cycle. In humans, the symptomatic disease is the result of the effects of invasion of erythrocytes, of their destruction and of the response of the hosts. During the infection, some of the parasital forms differenciate as gametocytes which are then ingested by mosquitoes where they undergo a sporogonic cycle, giving rise to sporozoites which then infect humans.

Due to the cycle of the infection encompassing distinct stages in the human body, and different forms of the parasite, various strategies have been proposed in order to deliver vaccine principles and various antigens of *Plasmodium* have been proposed as targets for the immune response, especially when addressing humoral antibody response.

Target candidates suitable for causing or improving the immune response may encompass various antigens with a view to design a vaccine and accordingly encompass "liver-stage antigens" (also designated as "pre-erythrocytic stage antigens") and/or "blood-stage antigens".

Within the frame of the present invention, the inventors have primarily considered that pre-erythrocytic stage antigens of malaria parasite may be advantageously used to elicit a protective immune response which would be uniformly effective at the level of a population, because they show less variability than antigens appearing at a later stage in the cycle of the parasite in humans. The inventors have also considered that for a long-term protection against malaria, means suitable to elicit cellular responses would be necessary, and would advantageously be supplemented by humoral responses.

The inventors have accordingly determined that a protective immune response would require the onset and development of efficient effector cells and memory cells and that said response should be strong enough to outperform the efficiency of the immune response which has been observed to natural infection.

The invention thus provides a novel lentiviral-based vector, as a new platform for the preparation or development of malaria vaccine which, in addition to the delivery means of the active principle for the immune composition, enables the determination of an appropriate immunization patterns suitable for eliciting a strong and long-lasting immune response when adapted to humans, as proved in a murine model commonly used for malaria.

The invention accordingly relates to lentiviral vector particles which are lentiviral vector particles, in particular replication-incompetent lentiviral vector particles, especially replication-incompetent HIV-based vector particles characterized in that (i) they are pseudotyped with a determined heterologous viral envelope protein or viral envelope proteins originating from a RNA virus and (ii) they comprise in their genome at least one recombinant polynucleotide encoding at least one polypeptide(s) carrying epitope(s) of a pre-erythrocytic stage antigen of a *Plasmodium* parasite capable of infecting a mammalian host, wherein said epitope(s) encompass(es) T-epitope(s).

In a particular embodiment of the invention, the encoded polypeptide of a pre-erythrocytic stage antigen of a *Plasmodium* parasite further comprises B-epitope(s).

According to the invention, the lentiviral vector particles are either designed to express proficient (i.e., integrative-competent) or deficient (i.e., integrative-incompetent) particles.

The expressions "malaria parasite" and "*Plasmodium* parasite>> are used interchangeably in the present application. They designate every and all forms of the parasite that are associated with the various stages of the cycle in the mammalian, especially human host, including in particular sporozoites, especially spororoites present in the blood flow after inoculation, or sporozoites developing in the hepatocytes, merozoites, including especially merozoites produced in the hepatocytes (forms of the pre-erythrocytic stage and including forms of the erythrocytic stage of the cycle such as merozoïtes contained in red-blood cells of the cycle). These forms of the parasite are characterized by various specific antigens that are well known and identified in the art, and can also be designated by reference to the stage of the infection.

The expressions "T-epitope" and "B-epitope" refer to antigenic determinants that are involved respectively in the adaptive immune response driven by T cells and in the immune response driven by B cells. In particular said T-epitopes and respectively B-epitopes elicit T cell, respectively B cell immune response when delivered to the host in suitable conditions.

The lentiviral vector particles (or lentiviral vectors or lentiviral-based vector particles) defined in the present invention are pseudotyped lentiviral vectors consisting of vector particles bearing envelope protein or envelope proteins which originate from a virus different from the particular lentivirus, especially HIV, in particular HIV-1, which provides the vector genome of the lentiviral vector particles. Accordingly, said envelope protein or envelope proteins, are "heterologous" viral envelope protein or viral envelope proteins with respect to the vector genome of the particles. In the following pages, reference will also be made to "envelope protein(s)" to encompass any type of envelope protein or envelope proteins suitable to perform the invention.

When reference is made to "lentiviral" vectors (lentiviral-based vectors) in the application, it encompasses, in a particular embodiment, HIV-based vectors and especially HIV-1-based vectors.

The lentiviral vectors according to the invention are replacement vectors, meaning that the sequences of the original lentivirus encoding the lentiviral proteins are essentially deleted in the genome of the vector or, when present, are modified, and especially mutated, especially truncated, to prevent expression of biologically active lentiviral proteins, in particular, in the case of HIV, to prevent the expression by said transfer vector, of functional ENV, GAG, and POL proteins and optionally of further structural and/or accessory and/or regulatory proteins of the lentivirus, especially of HIV.

The "vector genome" of the vector particles is a recombinant vector which also comprises the polynucleotide or transgene of interest encoding the polypeptide(s) of malaria parasite. The lentiviral-based sequence and polynucleotide/transgene of the vector genome are borne by a plasmid vector thus giving rise to the "transfer vector" also referred to as "sequence vector". Accordingly, these expressions are used interchangeably in the present application.

The vector genome as defined herein accordingly contains, apart from the so-called recombinant polynucleotide placed under control of proper regulatory sequences for its expression, the sequences of the original lentiviral genome which are non-coding regions of said genome, and are necessary to provide recognition signals for DNA or RNA synthesis and processing (mini-viral genome). These sequences are cis-acting sequences necessary for packaging, reverse transcription and transcription and furthermore for the particular purpose of the invention, they contain a functional sequence favouring nuclear import in cells and accordingly transgene transfer efficiency in said cells, which element is described as a DNA Flap element and contains or consists of the so-called central cPPT-CTS nucleotidic domain present in lentiviral genome sequences or in some retroelements such as those of yeasts.

The structure and composition of the vector genome used to prepare the lentiviral vectors of the invention are based on the principles described in the art and on examples of such lentiviral vectors primarily disclosed in (Zennou et al, 2000; Firat H. et al, 2002; VandenDriessche T. et al). Constructs of this type have been deposited at the CNCM (Institut Pasteur, France) as will be referred to herein. In this respect reference is also made to the disclosure, including to the deposited biological material, in patent applications WO 99/55892, WO 01/27300 and WO 01/27304.

According to a particular embodiment of the invention, a vector genome may be a replacement vector in which all the viral protein coding sequences between the 2 long terminal repeats (LTRs) have been replaced by the recombinant polynucleotide encoding the polypeptide of the malaria parasite, and wherein the DNA-Flap element has been re-inserted in association with the required cis-acting sequences described herein. Further features relating to the composition of the vector genome are disclosed in relation to the preparation of the particles.

A lentiviral vector particle of the invention may comprise in its genome more than one recombinant polynucleotide encoding at least one polypeptide carrying epitope(s) of a pre-erythrocytic stage antigen as disclosed herein. In particular, said vector genome comprises two polynucleotides which are consecutive or separated on the genome and which encode different polypeptides of either the same or distinct antigens of the pre-erythrocytic stage of a *Plasmodium* parasite or different polypeptides of distinct antigens of different forms of the malaria parasite, especially antigens of the pre-erythrocytic stage and antigens of the erythrocytic stage of the parasite.

In a particular embodiment, the vector genome contains two recombinant polynucleotides, each of them encoding a distinct polypeptide and each polypeptide originating from a different antigen of the same stage.

By the expression "polypeptide carrying epitope(s) of an antigen", it is intended according to the present invention a polypeptide which may be a native antigen of a *Plasmodium* parasite, a mutated version thereof and in particular a fragment of such a native antigen and especially a truncated version of such a native antigen. A polypeptide has an amino acid sequence which is sufficient to provide one or several epitope(s), and may accordingly have a length of at least about 4 amino acid residues and especially from about 4 to about 8 amino acid residues for conformational B epitopes or at least about 9 amino acid residues and in particular from about 9 to about 19 amino acid residues for sequential T epitopes.

In a particular embodiment of the invention, the recombinant polynucleotide of the lentiviral vector particles encodes a truncated version of an antigen of the malaria parasite, especially a fragment which results from the deletion of a functional domain of the full-length (i.e., native) antigen, when said domain is not useful or is detrimental to the elicitation of an immune response in a host.

In a particular embodiment of the invention, the lentiviral vector particles comprise in their genome, at least one recombinant polynucleotide which encodes a polypeptide(s) of an antigen from the circumsporozoite protein of a *Plasmodium* parasite, esp. of *Plasmodium falciparum* or *Plasmodium malariae, Plasmodium vivax, Plasmodium ovale* or *Plasmodium* knowlesi. It is especially a truncated version of the CSP and in particular a polypeptide devoid of the GPI anchoring motif of the CSP.

In an embodiment of the invention, the lentiviral vector particles comprise in their genome a recombinant polynucleotide which encodes a polypeptide(s) of an antigen selected from the group of the sporozoite surface protein 2 (TRAP/SSP2), liver-stage antigen (LSA in particular LSA3), Pf exported protein 1 (Pf Exp1)/Py hepatocyte erythrocyte protein (PyHEP17), and Pf antigen 2 (where Pf represents *Plasmodium falciparum* and Py represents *Plamsodium yoelii*), sporozoïte and liver stage antigen (SALSA), sporozoïte threonine and asparagines-rich (STARP) or other pre-erythrocytic antigen, possibly in addition to the polypeptide of an antigen of the CSP.

In a particular embodiment of the invention, the polypeptide of the antigen of the malaria parasite is a fragment of the CSP protein and it is co-expressed by the vector genome with a polypeptide of another antigen of the malaria parasite, either an antigen from the pre-erythrocytic stage or an antigen of the erythrocytic stage. Antigens of the erythrocytic stage which may be used to design the polynucleotide encoding the polypeptide according to the invention are merozoïte surface protein 1 (MSP2), in particular Merozoïte surface protein 1 (MSP-1), Merozoïte surface protein 2 (MSP-2) merozoïte surface protein 3 (MSP-3), Merozoïte surface protein 4 (MSP-4), Merozoïte surface protein 6 (MSP-6), Ring-infected erythrocyte surface antigen (RESA), Rhoptry associated protein 1 (RAP-1), Apical membrane antigen 1 (AMA-1), Erythrocyte binding antigen (EBA-175), Erythrocyte membrane-associated giant protein or Antigen 332 (Ag332), dnaK-type molecular chaperone, Glutamate-rich protein (GLURP), in particular MSP3-GLURP fusion protein (WO 2004/043488; ref 28), Erythrocyte membrane protein 1 (EMP-1), Serine repeat antigen (SERA), Clustered-asparagine-rich protein (CARP), Cirumsporozoite protein-related antigen precursor (CRA), Cytoadherence-linked asexual protein (CLAG), Acid basic repeat antigen (ABRA) or 101 kDa malaria antigen, Rhoptry antigen protein (RAP-2), Knob-associated histidine-rich protein (KHRP), Rhoptry antigen protein (RAP), Cysteine protease, Hypothetical protein PFE1325w, Protective antigen (MAg-1), Fructose-bisphosphate aldolase, Ribosomal phosphoprotein P0, P-type ATPase, Glucose-regulated protein (GRP78), Asparagine and aspartate-rich protein (AARP1), Interspersed repeat antigen or PFE0070w.}

Antigens of the sexual stage which may be used to design the polynucleotide encoding the polypeptide according to the invention are Sexual stage and sporozoite surface antigen, Antigen Pfg27/25, Antigen QF122, 11-1 polypeptide, Gametocyte-specific surface protein (Pfs230) Ookinete surface protein (P25), Chitinase, Multidrug resistance protein (MRP).

These antigens are disclosed by reference to *P. falciparum* and may have a counterpart in other *Plasmodium* species. They are reported in Vaughan K. et al (18).

Vaughan K et al disclose in particular epitopes of said antigens that may be used by the skilled person as a basis to prepare the recombinant polynucleotide(s) used in the vector of the invention.

The above-cited antigens of *Plasmodium* parasite have been disclosed in the prior art, including through their sequences which are available in data bases.

The circumsporozoite protein (CSP) is one of the preferred antigens for the preparation of the lentiviral vector particles of the invention. It constitutes the sporozoite coat protein, which has been recognized in the past as the target of protective antibodies. Apart from its ability to elicit anti-CS antibodies, this antigen further contains T-epitopes including especially CD8+ T-cells epitopes and CD4+ T-cells epitopes. Particular CSP antigens are disclosed through their amino acid sequences as SEQ ID No 20, 23, 26, 27, 28, 29, 30, 31, or as SEQ ID No 32 for a consensus of these sequences. The sequence of *P. vivax* is given in GenBank as AY674050.1.

In a particular embodiment of the invention, the lentiviral vector particles have in their genome a recombinant polynucleotide which encodes at least a polypeptide of the CSP-antigen of *Plasmodium yoelii* as illustrated in the examples or advantageously of *Plasmodium falciparum*, e.g., a polypeptide corresponding to a fragment of said CSP-antigen devoid of the GPI-anchoring motif in *Plasmodium yoelii* is CSP DGPI having sequence SEQ ID No 21. Said GPI motif corresponds to the last 12 amino acid residues in the C-terminal part in the native amino acid sequence of the CSP antigen of *Plasmodium Yoelii*. The counterpart of said fragment of the CSP protein in *P. Falciparum* is disclosed in the figures and sequences (SEQ ID No 23 for the native protein, SEQ ID No 24 for the sequence devoid of the GPI motif, SEQ ID No 25 for the sequence truncated in the N-terminal end) and used to provide evidence in a suitable murine model, of the capacity of the polypeptide to elicit a protective immune response and even a sterilizing protection against malaria.

In a particular embodiment of the invention, polynucleotide(s) of the lentiviral vector particles has(have) a mammalian codon optimized (CO) nucleotide sequence and optionally the lentiviral sequences of the genome of said particles has a mammalian codon optimized nucleotide sequence.

It has been observed that codon optimized nucleotide sequences, especially when optimized for expression in mammalian and in particular in human cells, enable the production of higher yield of particles in such mammalian or human cells. Production cells are illustrated in the examples. Accordingly, when lentiviral vector particles of the invention are administered to a mammalian, especially to a human host, higher amounts of particles are produced in said host which favour the elicitation of a strong immune response.

In a particular embodiment of the invention, the lentiviral vector particles disclosed herein further contain in their genome, a recombinant polynucleotide which encodes a polypeptide of an antigen of the blood stage of the cycle of the parasite as disclosed above and/or an antigen of the sexual stage.

The polypeptide is either the native antigen or a modified version thereof, especially a fragment which comprises or consists in T-cell epitope(s) or B-cell epitope(s) or both.

Examples of polypeptides expressed as a result of administering the lentiviral vector particles of the invention, are the polypeptides encoded by the vector plasmids (or sequence vectors) disclosed hereafter.

The invention also relates especially to these vector plasmids, deposited at the CNCM (Paris, France) on Apr. 20, 2010 and having the following features and accession number

| | |
|---|---|
| pTRIP-\|delta\|U3-CMV-$MSP1_{42}$-CO-WPRE | CNCM I-4303 |
| pTRIP-\|delta\|U3-CMV-Hep17-CO-WPRE | CNCM I-4304 |
| pTRIP-\|delta\|U3-CMV-Hep17\|delta\|SP-CO-WPRE | CNCM I-4305 |
| pTRIP-\|delta\|U3-CMV-CSP-CO-WPRE | CNCM I-4306 |
| pTRIP-\|delta\|U3-CMV-CSP\|delta\|SP-CO-WPRE | CNCM I-4307 |
| pTRIP-\|delta\|U3-CMV-CSP\|delta\|GPI-CO-WPRE | CNCM I-4308 |
| pTRIP-\|delta\|U3-CMV-CSP\|delta\|SP\|delta\|GPI-CO-WPRE | CNCM I-4309 |

These plasmids are described in the figures and sequences of the present application. The sequence of the transgene that they contain is from *P. yoelii*. Said transgene may be advantageously replaced by the appropriate sequence from *P. Falciparum*.

The invention also concerns variants of these plasmids, where the polynucleotide encoding the polynucleotide of a *Plasmodium* antigen is modified to encode a functional immunogenic variant thereof or is substituted by a corresponding polynucleotide codon optimized from another *Plasmodium* strain especially from *Plasmodium falciparum* is modified to substitute the CMV promoter by one of the herein cited promoters.

In the deposited plasmids the polynucleotide encoding the polypeptide of a *Palsmodium yoelii* antigen is codon optimized.

According to the invention, the lentiviral vector particles are pseudotyped with a heterologous viral envelope protein or viral polyprotein of envelope originating from a RNA virus which is not the lentivirus providing the lentiviral sequences of the genome of the lentiviral particles.

As examples of typing envelope proteins for the preparation of the lentiviral vector particles, the invention relates to viral transmembrane glycosylated (so-called G proteins) envelope protein(s) of a Vesicular Stomatitis Virus (VSV), which is(are) for example chosen in the group of VSV-G protein(s) of the Indiana strain, VSV-G protein(s) of the New Jersey strain, VSV-G protein(s) of the Cocal strain, VSV-G protein of the Isfahan strain, VSV-G protein(s) of Chandipura strain, VSV-G protein(s) of Pyri strain or VSV-G protein(s) of the SVCV strain.

The envelope glycoprotein of the vesicular stomatitis virus (VSV-G) is a transmembrane protein that functions as the surface coat of the wild type viral particles. It is also a suitable coat protein for engineered lentiviral vectors. Presently, nine virus species are definitively classified in the VSV gender, and nineteen rhabdoviruses are provisionally classified in this gender, all showing various degrees of cross-neutralisation. When sequenced, the protein G genes indicate sequence similarities. The VSV-G protein presents a N-terminal ectodomain, a transmembrane region and a C-terminal cytoplasmic tail. It is exported to the cell surface via the trans-Golgi network (endoplasmic reticulum and Golgi apparatus).

Vesicular stomatitis Indiana virus (VSIV) and Vesicular stomatitis New Jersey virus (VSNJV) are preferred strains to pseudotype the lentiviral vectors of the invention, or to design recombinant envelope protein(s) to pseudotype the lentiviral vectors. Their VSV-G proteins are disclosed in GenBank, where several strains are presented. For VSV-G New Jersey strain reference is especially made to the sequence having accession number V01214. For VSV-G of the Indiana strain, reference is made to the sequence having accession number AAA48370.1 in Genbank corresponding to strain JO2428.

Alternatively, among VSV, Chandipura virus (CHPV), Cocal virus (COCV), Perinet virus (PERV), Piry virus (PIRYV), SVCV or Isfahan virus may be good candidates to design pseudotyping envelope proteins, and especially to prepare particles used for a boosting step of the immunization, accordingly providing second envelope protein(s) or third envelope protein(s), or further envelope protein(s) when the vector particles of the invention are used in a prime-boost administration regimen. When used accordingly, Cocal virus envelope protein(s) would be preferred for a late or last administration in a prime-boost regimen. However, Chandipura virus (CHPV) and Piry virus (PIRYV) may provide envelope proteins having low fusogenicity as a result of their lower affinity for their receptor, when comparing the vector titers obtained with particles prepared with different envelopes. Therefore in a first approach these envelopes may be excluded from the choice of envelopes in order to prepare particles with an efficient transduction capacity.

The amino acid sequences and coding sequences of the VSV-G proteins referred to herein are disclosed in patent application WO 2009/019612. Particular examples of these amino acid sequences are also provided in the present application as SEQ ID No 77, 79, 82, 84, 86, 88, 90. Plasmids containing VSV-G encoding sequences are described in said application WO 2009/019612 which is incorporated by reference. The plasmids have been deposited at the CNCM (Paris, France). Nucleotide sequences encoding said envelope proteins are disclosed in the present application as SEQ ID No 76, 78, 81, 83, 85, 87, 89.

In a particular embodiment of the invention, said first and second and if any said third or further, viral envelope protein(s) are capable of uptake by antigen presenting cells and especially by dendritic cells including by liver dendritic cells by mean of fusion and/or of endocytosis. In a particular embodiment, the efficiency of the uptake may be used as a feature to choose the envelope of a VSV for pseudotyping. In this respect the relative titer of transduction (Titer DC/Titer of other transduced cells e.g. 293T cells) may be considered as a test and envelope having a relative good ability to fuse with DC would be preferred. Relative titers of transduction are illustrated in the examples.

Antigen Presenting Cells (APC) and especially Dentritic cells (DC) are proper target cells for pseudotyped lentiviral vectors which are used as immune compositions accordingly.

Polynucleotide encoding VSV envelope protein(s) (VSV-G) also targets splenocytes, in particular Antigen Presenting Cells (APC) or Dendritic Cells (DC), or liver cells including liver dendritic cells, hepatocytes or non parenchymal cells.

The envelope protein(s), also designated sometimes as surface protein in particular viruses, are said to "originate" from a different organism, and especially from different RNA virus strains, meaning that in said protein(s), essential features of the corresponding protein(s) expressed in a determined RNA virus are maintained. Said essential features, relate to the structure or to the function of the protein and are those which enable especially the obtained protein(s) to be expressed at the surface of the vector particles for pseudotyping said vectors. The envelope proteins are then capable of being recognized and internalized in the target cells of the hosts when present on the vector particles.

In a particular embodiment, protein(s) or glycoprotein(s), suitable for use in the design of pseudotyped lentiviral vectors of the kit of compounds are used as multimeric proteins, such as VSV-G protein which is trimeric.

The envelope protein(s) are expressed from a polynucleotide containing the coding sequence for said protein(s), which polynucleotide is inserted in a plasmid (designated envelope expression plasmid or pseudotyping env plasmid) used for the preparation of the lentiviral vector particles of the invention. The polynucleotide encoding the envelope protein(s) is under the control of regulatory sequences for the transcription and/or expression of the coding sequence (including optionally post-transcriptional regulatory elements (PRE) especially a polynucleotide such as the element of the Woodchuck hepatitis virus, i.e. the WPRE sequence obtainable from Invitrogen).

Accordingly, a nucleic acid construct is provided which comprises an internal promoter suitable for the use in mammalian cells, especially in human cells in vivo and the nucleic acid encoding the envelope protein under the control of said promoter. A plasmid containing this construct is used for transfection or for transduction of cells suitable for the preparation of particles. Promoters may in particular be selected for their properties as constitutive promoters, tissue-specific promoters, or inducible promoters. Examples of suitable promoters encompass the promoters of the following genes: EF1α, human PGK, PPI (preproinsulin), thiodextrin, HLA DR invariant chain (P33), HLA DR alpha chain, Ferritin L chain or Ferritin H chain, Chymosin beta 4, Chymosin beta 10, Cystatin Ribosomal Protein L41, CMVie or chimeric promoters such as GAG(CMV early enhancer/chicken β actin) disclosed in Jones S. et al (19).

These promoters may also be used in regulatory expression sequences involved in the expression of gag-pol derived proteins from the encapsidation plasmids.

Alternatively, when the envelope expression plasmid is intended for expression in stable packaging cell lines, especially for stable expression as continuously expressed viral particles, the internal promoter to express the envelope protein(s) is advantageously an inducible promoter such as one disclosed in Cockrell A. S. et al. (20). As examples of such promoters, reference is made to tetracycline and ecdysone inducible promoters. The packaging cell line may be the STAR packaging cell line (ref 20, 21) or a SODk packaging cell line, such as SODk0 derived cell lines, including SODk1 and SODk3 (ref 20, 22, 23, 24).

The nucleotide sequence used for the expression of the envelope protein(s) required for pseudotyping the lentiviral vector particles may alternatively be modified, thus providing a variant with respect to the nucleic acid encoding the native envelope protein(s) used as reference. The modification may be carried out to improve the codons usage (codon optimization) in the cells for the preparation of the vector particles and/or in the transduced cells of the host. It may be modified to express a protein different from the native protein(s), especially one which has an improved pseudotyping capacity, an improved capacity in the level of production, or an improved capacity with respect to prevention of sero-neutralization (also designated as cross-reactive proteins) with other envelope protein(s) used in the kit of compounds.

Such a modification of the polynucleotide encoding the envelope proteins(s) or modification of the envelope protein(s) (to generate variants of native envelopes) may affect and especially improve their level of production in a cell host or their ability to pseudotype the vector particles possibly by improving the density of envelope protein(s) associated with pseudovirions. Said modification may derive from a mutation in the amino acid sequence of said protein(s), for instance by addition, deletion or substitution of one or several nucleotides or nucleotidic fragments or may relate to post translational modifications and in particular to the glycosylation status of said envelope protein(s).

The envelope protein(s) used to pseudotype the lentiviral vectors of the invention are indeed especially glycoproteins.

It has already been shown that pseudotyping viral vectors with Vesicular Stomatitis Virus glycoprotein (VSV-G) enables the transduction of a large range of cell types from different species. This VSV-G glycoprotein, in addition to its broad tropism, has an interesting stability when used for vector pseudotyping. Therefore, VSV-G have been used as a standard for evaluating the efficiency of other pseudotypes (Cronin J. et al, 2005).

According to the invention, the lentiviral vector particles are the product recovered from co-transfection of mammalian cells, with:

a vector plasmid comprising (i) lentiviral, especially HIV-1, cis-active sequences necessary for packaging, reverse transcription, and transcription and further comprising a functional lentiviral, especially derived from HIV-1, DNA flap element and (ii) a polynucleotide encoding a polypeptide of an antigen of a malaria parasite as disclosed herein under the control of regulatory expression sequences, and optionally comprising sequences for integration;

an expression plasmid encoding a pseudotyping envelope derived from a RNA virus, said expression plasmid comprising a polynucleotide encoding an envelope protein or proteins for pseudotyping, wherein said envelope pseudotyping protein is advantageously from a VSV and is in particular a VSV-G or a variant thereof and, an encapsidation plasmid, which either comprises lentiviral, especially HIV-1, gag-pol packaging sequences suitable for the production of integration-competent vector particles or modified gag-pol packaging sequences suitable for the production of integration-deficient vector particles.

The invention thus also concerns lentiviral vector particles as described above, which are the product recovered from a stable cell line with a vector plasmid comprising (i) lentiviral, especially HIV-1, cis-active sequences necessary for packaging, reverse transcription, and transcription and further comprising a functional lentiviral, especially HIV-1, DNA flap element and optionally comprising cis-active sequences necessary for integration, said vector plasmid further comprising (ii) a polynucleotide of a truncated mammalian, especially human, codon-optimized sequence of the cs gene of a *Plasmodium* parasite, under the control of regulatory expression sequences, especially a promoter;

a VSV-G envelope expression plasmid comprising a polynucleotide encoding a VSV-G envelope protein or envelope proteins, wherein said polynucleotide is under the control of regulating expression sequences, in particular regulatory expression sequences comprising an inducible promoter, and;

an encapsidation plasmid, wherein the encapsidation plasmid either comprises lentiviral, especially HIV-1, gag-pol coding sequences suitable for the production of integration-competent vector particles or modified gag-pol coding sequences suitable for the production of integration-deficient vector particles, wherein said gag-pol sequences are from the same lentivirus sub-family as the DNA flap element, wherein said lentiviral gag-pol or modified gag-pol sequence is under the control of regulating expression sequences.

The stable cell lines expressing the vector particles of the invention are in particular obtained by transduction of the plasmids.

The polynucleotide encodes at least one polypeptide of a malaria antigen according to any embodiment disclosed in the present application. In particular, it encodes a polypeptide which is a truncated mammalian, especially human, codon-optimized sequence of the cs gene of a *Plasmodium* parasite, especially of *Plasmodium falciparum.*

In a particular embodiment, the polynucleotide encodes another polypeptide of a distinct antigen of the malaria parasite, or it encodes two or more polypeptides which originate and/or are derived from distinct antigens of said parasite as disclosed in the various embodiments. Accordingly, the vector plasmid may comprise several expression cassettes for the expression of the various polypeptides or may comprise bicistronic or multicistronic expression cassettes where the polynucleotides encoding the various polypeptides are separated by an IRES sequence of viral origin (Internal Ribosome Entry Site), or it may encode fusion protein(s).

The internal promoter contained the vector genome and controlling the expression of the polynucleotide encoding a polypeptide of an antigen of the malaria parasite (as a transgene or in an expression cassette) may be selected from the promoters of the following genes: EF1α, human PGK, PPI (preproinsulin), thiodextrin, HLA DR invariant chain (P33), HLA DR alpha chain, Ferritin L chain or Ferritin H chain, Chymosin beta 4, Chimosin beta 10, or Cystatin Ribosomal Protein L41 CMVie or chimeric promoters such as GAG (CMV early enhancer/chicken β actin) disclosed in Jones S. et al (19).

A promoter among the above cited internal promoters may also be selected for the expression of the envelope protein(s) and packaging (gag-pol derived) proteins.

Alternatively, vector particles can be produced from co-transfection of the plasmids disclosed herein, in stable packaging cell lines which thus become capable of continuously secreting vector particles. Promoters used in the regulatory expression sequences involved for the expression of the envelope protein(s) are advantageously inducible promoters.

The following particular embodiments may be carried out when preparing the lentiviral vector particles based on human lentivirus, and especially based on HIV virus.

According to the invention, the genome of the lentiviral vector particles is derived from a human lentivirus, especially from the HIV lentivirus. In particular, the pseudotyped lentiviral vector is an HIV-based vector, such as an HIV-1, or HIV-2 based vector, in particular is derived from HIV-1M, for example from the BRU or LAI isolates. Alternatively, the lentiviral vector providing the necessary sequences for the vector genome may be originating from lentiviruses such as EIAV, CAEV, VISNA, FIV, BIV, SIV, HIV-2, HIV-O which are capable of transfecting human cells.

As stated above, when considering it apart from the recombinant polynucleotide that it finally contains, the vector genome is a replacement vector in which the nucleic acid between the 2 long terminal repeats (LTRs) in the original lentivirus genome have been restricted to cis-acting sequences for DNA or RNA synthesis and processing, including for the efficient delivery of the transgene to the nuclear of cells in the host, or at least are deleted or mutated for essential nucleic acid segments that would enable the expression of lentiviral structure proteins including biological functional GAG polyprotein and possibly POL and ENV proteins.

In a particular embodiment, the vector genome is defective for the expression of biologically functional GAG, and advantageously for biologically functional POL and ENV proteins. Accordingly, the vector genome is devoid of the sequence encoding these proteins.

In a particular embodiment, the 5' LTR and 3' LTR sequences of the lentivirus are used in the vector genome, but the 3'-LTR at least is modified with respect to the 3'LTR of the original lentivirus at least in the U3 region which for example can be deleted or partially deleted for the enhancer. The 5'LTR may also be modified, especially in its promoter region where for example a Tat-independent promoter may be substituted for the U3 endogenous promoter.

In a particular embodiment the vector genome comprises one or several of the coding sequences for Vif-, Vpr, Vpu- and Nef-accessory genes (for HIV-1 lentiviral vectors). Alternatively, these sequences can be deleted independently or each other or can be non-functional.

The vector genome of the lentiviral vector particles comprises, as an inserted cis-acting fragment, at least one polynucleotide consisting in the DNA flap element or containing such DNA flap element. In a particular embodiment, the DNA flap is inserted upstream of the polynucleotide encoding the polypeptide of a malaria antigen, and is advantageously—although not necessarily—located in an approximate central position in the vector genome. A DNA flap suitable for the invention may be obtained from a retrovirus, especially from a lentivirus, in particular a human lentivirus especially a HIV-1 retrovirus, or from a retrovirus-like organism such as retrotransposon. It may be alternatively obtained from the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. The DNA flap may be either prepared synthetically (chemical synthesis) or by amplification of the DNA providing the DNA Flap from the appropriate source as defined above such as by Polymerase chain reaction (PCR). In a more preferred embodiment, the DNA flap is obtained from an HIV retrovirus, for example HIV-1 or HIV-2 virus including any isolate of these two types.

The DNA flap (defined in Zennou V. et al. ref 27, 2000, Cell vol 101, 173-185 or in WO 99/55892 and WO 01/27304), is a structure which is central in the genome of some lentiviruses especially in HIV, where it gives rise to a 3-stranded DNA structure normally synthesized during especially HIV reverse transcription and which acts as a cis-determinant of HIV genome nuclear import. The DNA flap enables a central strand displacement event controlled in cis by the central polypurine tract (cPPT) and the central termination sequence (CTS) during reverse transcription. When inserted in lentiviral-derived vectors, the polynucleotide enabling the DNA flap to be produced during reverse-transcription, stimulates gene transfer efficiency and complements the level of nuclear import to wild-type levels (Zennou et al., Cell, 2000).

Sequences of DNA flaps have been disclosed in the prior art, especially in the above cited patent applications. These sequences are also disclosed as SEQ ID NO 69 to SEQ ID NO 75. They are preferably inserted as a fragment, optionally with additional flanking sequences, in the vector genome, in a position which is preferably near the centre of said vector genome. Alternatively they may be inserted immediately upstream from the promoter controlling the expression of the polynucleotide(s) of the invention. Said fragments comprising the DNA flap, inserted in the vector genome may have a sequence of about 80 to about 200 bp, depending on its origin and preparation.

According to a particular embodiment, a DNA flap has a nucleotide sequence of about 90 to about 140 nucleotides.

In HIV-1, the DNA flap is a stable 99-nucleotide-long plus strand overlap. When used in the genome vector of the lentiviral vector of the invention, it may be inserted as a longer sequence, especially when it is prepared as a PCR fragment. A particular appropriate polynucleotide comprising the structure providing the DNA flap is a 178-base pair polymerase chain reaction (PCR) fragment encompassing the cPPT and CTS regions of the HIV-1 DNA (Zennou et al 2000).

This PCR fragment may especially be derived from infective DNA clone of HIV-1 LAI especially pLAI3 of HIV1, as a fragment corresponding to the sequence from nucleotide 4793 to 4971. If appropriate, restriction sites are added to one or both extremities of the obtained fragment, for cloning. For example, Nar I restriction sites may be added to the 5' extremities of primers used to perform the PCR reaction.

Therefore, the DNA flap used in the present invention, is deleted from the unnecessary 5' and 3' parts of the pol gene of the original lentiviral genome and is recombined with sequences of different origin.

It is specified that the DNA flap used in the genome vector and the polynucleotides of the encapsidation plasmid encoding the GAG and POL polyproteins should originate from the same lentivirus sub-family or from the same retrovirus-like organism.

Preferably, the other cis-activating sequences of the genome vector also originate from the same lentivirus or retrovirus-like organism, as the one providing the DNA flap.

The vector genome may further comprise one or several unique restriction site(s) for cloning the recombinant polynucleotide.

In a preferred embodiment, in said vector genome, the 3' LTR sequence of the lentiviral vector genome is devoid of at least the activator (enhancer) and possibly the promoter of the U3 region. In another particular embodiment, the 3' LTR region is devoid of the U3 region (delta U3). In this respect, reference is made to the description in WO 01/27300 and WO 01/27304.

In a particular embodiment, in the vector genome, the U3 region of the LTR 5' is replaced by a non lentiviral U3 or by a promoter suitable to drive tat-independent primary transcription. In such a case, the vector is independent of tat transactivator.

The vector genome also comprises the psi (ψ) packaging signal. The packaging signal is derived from the N-terminal fragment of the gag ORF. In a particular embodiment, its sequence could be modified by frameshift mutation(s) in order to prevent any interference of a possible transcription/translation of gag peptide, with that of the transgene.

The vector genome may optionally also comprise elements selected among a splice donor site (SD), a splice acceptor site (SA) and/or a Rev-responsive element (RRE).

According to a particular embodiment, the vector plasmid (or added genome vector) comprises the following cis-acting sequences for a transgenic expression cassette:

1. The LTR sequence (Long-Terminal Repeat), required for reverse transcription, the sequences required for transcription and including optionally sequences for viral DNA integration. The 3' LTR is deleted in the U3 region at least for the promoter to provide SIN vectors (Self-inactivating), without perturbing the functions necessary for gene transfer, for two major reasons: first, to avoid trans-activation of a host gene, once the DNA is integrated in the genome and secondly to allow self-inactivation of the viral cis-sequences after retrotranscription. Optionally, the tat-dependent U3 sequence from the 5'-LTR which drives transcription of the genome is replaced by a non endogenous promoter sequence. Thus, in target cells only sequences from the internal promoter will be transcribed (transgene).
2. The ψ region, necessary for viral RNA encapsidation.
3. The RRE sequence (REV Responsive Element) allowing export of viral messenger RNA from the nucleus to the cytosol after binding of the Rev protein.
4. The DNA flap element (cPPT/CTS, normally contained in Pol) to facilitate nuclear import.
5. Optionally post-transcriptional elements such as the WPRE cis-active sequence (Woodchuck hepatitis B virus Post-Responsive Element) also added to optimize stability of mRNA (Zufferey et al., 1999), the matrix or scaffold attachment regions (SAR and MAR sequences) such as those of the immunoglobulin-kappa gene (Park F. et al Mol Ther 2001; 4: 164-173).

The lentiviral vector of the invention is non replicative (replication-incompetent) i.e., the vector and lentiviral vector genome are regarded as suitable to alleviate concerns regarding replication competent lentiviruses and especially are not able to form new particles budding from the infected host cell after administration. This may be achieved in well known ways as the result of the absence in the lentiviral genome of the gag, pol or env genes, or their absence as "functional genes". The gag and pol genes are thus, only provided in trans. This can also be achieved by deleting other viral coding sequence(s) and/or cis-acting genetic elements needed for particles formation.

By "functional" it is meant a gene that is correctly transcribed, and/or correctly expressed. Thus, if present in the lentiviral vector genome of the invention in this embodiment contains sequences of the gag, pol, or env are individually either not transcribed or incompletely transcribed; the expression "incompletely transcribed" refers to the alteration in the transcripts gag, gag-pro or gag-pro-pol, one of these or several of these being not transcribed. Other sequences involved in lentiviral replication may also be mutated in the vector genome, in order to achieve this status. The absence of replication of the lentiviral vector should be distinguished from the replication of the lentiviral genome. Indeed, as described before, the lentiviral genome may contain an origin of replication ensuring the replication of the lentiviral vector genome without ensuring necessarily the replication of the vector particles.

In order to obtain lentiviral vectors according to the invention, the vector genome (as a vector plasmid) must be encapsidated in particles or pseudo-particles. Accordingly, lentiviral proteins, except the envelope proteins, have to be provided in trans to the vector genome in the producing system, especially in producing cells, together with the vector genome, having recourse to at least one encapsidation plasmid carrying the gag gene and either the pol lentiviral gene or an integrative-incompetent pol gene, and preferably lacking some or all of the coding sequences for Vif-, Vpr, Vpu- and Nef-accessory genes (for HIV-1 lentiviral vectors).

A further plasmid is used, which carries a polynucleotide encoding the envelope pseudotyping protein(s) selected for pseudotyping lentiviral vector particles.

In a preferred embodiment, the packaging plasmid encodes only the lentiviral proteins essential for viral particle synthesis. Accessory genes whose presence in the plasmid could raise safety concerns are accordingly removed. Accordingly, viral proteins brought in trans for packaging are respectively as illustrated for those originating from HIV-1:

1. GAG proteins for building of the matrix (MA, with apparent Molecular Weight p17), the capsid (CA, p24) and nucleocapsid (NC, p6).
2. POL encoded enzymes: integrase, protease and reverse transcriptase.
3. TAT and REV regulatory proteins, when TAT is necessary for the initiation of LTR-mediated transcription; TAT expression may be omitted if the U3 region of 5'LTR is substituted for a promoter driving tat-independent transcription. REV may be modified and accordingly used for example in a recombinant protein which would enable recognition of a domain replacing the RRE sequence in the vector genome, or used as a fragment enabling binding to the RRE sequence through its RBD (RNA Binding Domain).

In order to avoid any packaging of the mRNA generated from the genes contained in the packaging plasmid in the viral particles, the ψ region is removed from the packaging plasmid. A heterologous promoter is inserted in the plasmid to avoid recombination issues and a poly-A tail is added 3' from the sequences encoding the proteins. Appropriate promoters have been disclosed above.

The envelope plasmid encodes the envelope protein(s) for pseudotyping which are disclosed herein, under the control of an internal promoter, as disclosed herein.

Any or all the described plasmids for the preparation of the lentiviral vector particles of the invention may be codon optimized (CO) in the segment encoding proteins. Codon optimization according to the invention is preferably performed to improve translation of the coding sequences contained in the plasmids, in mammalian cells, especially human cells. According to the invention, codon optimization is especially suited to directly or indirectly improve the preparation of the vector particles or to improve their uptake by the cells of the host to whom they are administered, or to improve the efficiency of the transfer of the polynucleotide encoding the polypeptide of an antigen of the malaria parasite (transgene) in the genome of the transduced cells of the host. Methods for optimizing codons are well known in the art and codon optimization is especially performed using available programs to that effect. Codon optimization is illustrated for the coding sequences contained in the described pTRIP or pThV plasmids of the invention illustrated in the examples.

In a particular embodiment of the invention, the pseudotyped lentiviral vector is also, or alternatively, integrative-incompetent. In such a case, the vector genome and thus the recombinant polynucleotide which it contains do not integrate into the genome of the transduced cells or in the cells of the host to whom it has been administered.

The present invention relates to the use of a lentiviral vector wherein the expressed integrase protein is defective and which further comprises a polynucleotide especially encoding at least one polypeptide carrying epitope(s) of a pre-erythrocytic stage antigen of a *Plasmodium* parasite, in an immunogenic composition.

By “integration-incompetent”, it is meant that the integrase, preferably of lentiviral origin, is devoid of the capacity of integration of the lentiviral genome into the genome of the host cells i.e., an integrase protein mutated to specifically alter its integrase activity.

Integration-incompetent lentiviral vectors are obtained by modifying the pol gene encoding the Integrase, resulting in a mutated pol gene encoding an integrative deficient integrase, said modified pol gene being contained in the encapsidation plasmid. Such integration-incompetent lentiviral vectors have been described in patent application WO 2006/010834. Accordingly the integrase capacity of the protein is altered whereas the correct expression from the encapsidation plasmid of the GAG, PRO and POL proteins and/or the formation of the capsid and hence of the vector particles, as well as other steps of the viral cycle, preceding or subsequent to the integration step, such as the reverse transcription, the nuclear import, stay intact. An integrase is said defective when the integration that it should enable is altered in a way that an integration step takes place less than 1 over 1000, preferably less than 1 over 10000, when compared to a lentiviral vector containing a corresponding wild-type integrase.

In a particular embodiment of the invention, the defective integrase results from a mutation of class 1, preferably amino acid substitutions (one-amino acid substitution) or short deletions fulfilling the requirements of the expression of a defective integrase. The mutation is carried out within the pol gene. These vectors may carry a defective integrase with the mutation D64V in the catalytic domain of the enzyme, which specifically blocks the DNA cleaving and joining reactions of the integration step. The D64V mutation decreases integration of pseudotyped HIV-1 up to 1/10,000 of wild type, but keep their ability to transduce non dividing cells, allowing efficient transgene expression.

Other mutations in the pol gene which are suitable to affect the integrase capacity of the integrase of HIV-1 are the following: H12N, H12C, H16C, H16V, S81R, D41A, K42A, H51A, Q53C, D55V, D64E, D64V, E69A, K71A, E85A, E87A, D116N, D116I, D116A, N120G, N120I, N120E, E152G, E152A, D-35-E, K156E, K156A, E157A, K159E, K159A, K160A, R166A, D167A, E170A, H171A, K173A, K186Q, K186T, K188T, E198A, R199C, R199T, R199A, D202A, K211A, Q214L, Q216L, Q221 L, W235F, W235E, K236S, K236A, K246A, G247W, D253A, R262A, R263A and K264H.

In a particular embodiment, mutation in the pol gene is performed at either of the following positions D64, D116 or E152, or at several of these positions which are in the catalytic site of the protein. Any substitution at these positions is suitable, including those described above.

Another proposed substitution is the replacement of the amino acids residues RRK (positions 262 to 264) by the amino acids residues AAH.

In a particular embodiment of the invention, when the lentiviral vector is integration-incompetent, the lentiviral genome further comprises an origin of replication (ori), whose sequence is dependent on the nature of cells where the lentiviral genome has to be expressed. Said origin of replication may be from eukaryotic origin, preferably of mammalian origin, most preferably of human origin. It may alternatively be of viral origin, especially coming from DNA circular episomic viruses, such as SV40 or RPS. It is an advantageous embodiment of the invention to have an origin or replication inserted in the lentiviral genome of the lentiviral vector of the invention. Indeed, when the lentiviral genome does not integrate into the cell host genome (because of the defective integrase), the lentiviral genome is lost in cells that undergo frequent cell divisions; this is particularly the case in immune cells, such as B or T cells. The presence of an origin of replication ensures that at least one lentiviral genome is present in each cell, even after cell division, accordingly maximizing the efficiency of the immune response.

The lentiviral vector genome of said lentiviral vectors of the invention may especially be derived from HIV-1 plasmid pTRIPΔU3.CMV-GFP deposited at the CNCM (Paris, France) on Oct. 11, 1999 under number I-2330 (also described in WO01/27300). The sequence of pTRIPΔU3.CMV-eGFP is provided as SEQ ID No 35 and is described in FIG. 11.

When the vector genome is derived from these particular plasmids, a sequence of a recombinant polynucleotide as disclosed in the present application is inserted therein, in addition or in replacement of the GFP coding fragment. The GFP coding sequence may also be substituted by a different marker. The CMV promoter may also be substituted by another promoter, especially one of the promoters disclosed above, especially in relation to the expression of the transgene.

The WPRE sequence also contained in the particular deposited pTRIP vectors may optionally be deleted.

Vector particles may be produced after transfection of appropriate cells (such as mammalian cells or human cells, such as Human Embryonic Kidney cells illustrated by 293 T cells) by said plasmids, or by other processes. In the cells used for the expression of the lentiviral particles, all or some of the plasmids may be used to stably express their coding polynucleotides, or to transiently or semi-stably express their coding polynucleotides.

The concentration of particles produced can be determined by measuring the P24 (capsid protein for HIV-1) content of cell supernatants.

The lentiviral vector of the invention, once administered into the host, infects cells of the host, possibly specific cells, depending on the envelope proteins it was pseudotyped with. The infection leads to the release of the lentiviral vector genome into the cytoplasm of the host cell where the retrotranscription takes place. Once under a triplex form (via the DNA flap), the lentiviral vector genome is imported into the nucleus, where the polynucleotide(s) encoding polypeptide(s) of antigen(s) of the malaria parasite is (are) expressed via the cellular machinery. When non-dividing cells are transduced (such as DC), the expression may be stable. When dividing cells are transduced, such as B cells, the expression is temporary in absence of origin of replication in the lentiviral genome, because of nucleic acid dilution and cell division. The expression may be longer by providing an origin of replication ensuring a proper diffusion of the lentiviral vector genome into daughter cells after cell division. The stability and/or expression may also be increased by insertion of MAR (Matrix Associated Region) or SAR (Scaffold Associated Region) elements in the vector genome.

Indeed, these SAR or MAR regions are AT-rich sequences and enable to anchor the lentiviral genome to the matrix of the cell chromosome, thus regulating the transcription of the polynucleotide encoding at least one antigenic polypeptide, and particularly stimulating gene expression of the transgene and improving chromatin accessibility.

If the lentiviral genome is non integrative, it does not integrate into the host cell genome. Nevertheless, the at least one polypeptide encoded by the transgene is sufficiently expressed and longer enough to be processed, associated with MHC molecules and finally directed towards the cell surface. Depending on the nature of the polynucleotide(s) encoding polypeptide(s) of antigen(s) of malaria parasite, the at least one polypeptide epitope associated with the MHC molecule triggers a humoral or a cellular immune response.

Unless otherwise stated, or unless technically not relevant, the characteristics disclosed in the present application with respect to any of the various features, embodiments or examples of the structure or use of the lentiviral particles, especially regarding their envelope protein(s), or the recombinant polynucleotide, may be combined according to any possible combinations.

The invention further relates to a combination of compounds for separate administration to a mammalian host, which comprises at least:

(i) lentiviral vector particles of the invention which are pseudotyped with a first determined heterologous viral envelope pseudotyping protein or viral envelope pseudotyping proteins;

(ii) provided separately from lentiviral vector particles in (i), lentiviral vector particles of the invention which are pseudotyped with a second determined heterologous viral envelope pseudotyping protein or viral envelope pseudotyping proteins distinct from said first heterologous viral envelope pseudotyping protein(s);

wherein said first and second viral envelope pseudotyping protein(s) do not sero-neutralize with each other and are suitable for in vivo transduction of mammalian cells, especially of human cells.

The expression "combination of compounds" or alternatively "kit of compounds" means that the lentiviral vector particles constituting active ingredients of the kits or combinations, are provided as separate compounds in said kit or combination, and are intended for separate administration to a host, especially separate administration in time. Accordingly the invention enables to perform a prime-boost administration in a host in need thereof, where the first administration step elicits an immune, especially cellular, immune response and the later administration step(s) boost(s) the immune reaction including the cellular immune response. For each step of administration, it is preferred that the pseudotyping envelope protein(s) of the vector particles is different than the one used in the other step(s). Accordingly, the separate compounds of the kit or combination of the invention have distinct particles at least due to the difference in their pseudotyping envelope proteins.

The compounds of the kit thus are provided separately in time to the host in need thereof, especially to a mammalian host, in particular a human host.

Accordingly, said lentiviral vectors can be provided in separate packages or can be presented in a common package for a separate use thereof.

Therefore, the notice included in the packages and comprising the directions for use, may indicate that said lentiviral vector particles which are pseudotyped with distinct pseudotyping envelope protein or pseudotyping envelope proteins are for separate administration in time, especially for priming and subsequently boosting an immune reaction in a host.

In accordance with the invention, in the combination of compounds it is provided lentiviral vector particles which are pseudotyped with a first determined heterologous viral pseudotyping envelope protein, or viral pseudotyping envelope proteins, and lentiviral viral vector particles which are pseudotyped with a second determined heterologous viral pseudotyping envelope protein or viral pseudotyping envelope proteins. Accordingly, said first and second heterologous viral envelope protein(s) are different and in particular are originating from different virus strains. Thus, the lentiviral vector particles contained in the separate compounds of the of the kit of compounds of the invention are distinct from each other, at least due to the particular pseudotyping envelope protein(s) used for pseudotyping the vector particles.

In a particular embodiment of the invention, the combination of compounds comprises a third or a further type of lentiviral vector particles wherein the pseudotyping envelope protein(s) of the third lentiviral vector is different from said first and second pseudotyping envelope protein(s) and especially originates from a different virus strain.

When particles are successively administered which have different pseudotyping envelopes, the following order of administration with respect to said envelopes could be preferred: Indiana; New Jersey; Isfahan; SVCV/Cocal. Because Cocal pseudotyped lentiviral vectors seroneutralize several other envelopes, it is preferable, in the vaccination chronology, when Cocal envelopes are to be used in the preparation of particles, to administer particles pseudotyped with them as the last one in the administration regimen.

Apart from their pseudotyping envelope protein(s), the lentiviral vectors of the invention may be identical and especially may have identical vector genomes.

Alternatively, their vector genomes may be different, provided they carry the same recombinant determined polynucleotide (also designated as transgene), especially the same recombinant polynucleotide.

In another embodiment of the invention, the vector genomes of the lentiviral vectors are different by having at least one different recombinant polynucleotide, provided at least one of said different polynucleotides encodes polypeptide(s) having common antigenic determinant(s), or common epitope(s). Hence the different polynucleotides may be variants from each other that encode identical or variant polypeptides or may include sequences encoding different polypeptides.

A particular kit of compounds comprises lentiviral vectors wherein in at least one of the separate compounds, the vectors are pseudotyped with recombinant pseudotyping envelope protein(s) comprising combined domains or fragments originating from different envelope protein(s) of different viruses, especially of different genus of different species of VSV.

In a particular embodiment of the invention, at least one the first, second and if any third or further pseudotyping envelope protein(s) is (are) recombinant envelope protein(s) comprising the export determinant of the VSV-G of Indiana strain.

The export determinant of the VSV-G of the Indiana strain is a polypeptide encoded by the cytoplasmic fragment of the open reading frame of the envelope.

The export determinant of the VSV-G of the Indiana strain is a polypeptide comprising or having amino acid sequence YTDIE in the cytoplasmic tail (Nishimua N. et al. 2002).

Said recombinant envelope protein(s) may comprise the cytoplasmic tail of the VSV-G of an Indiana strain which is the intracellular portion of VSV-G delimited by a hydrophobic transmembrane domain.

A particular kit of compounds comprises lentiviral vectors wherein one or two or more of them is (are) pseudotyped with recombinant envelope protein(s) comprising the cytoplasmic domain of the indiana VSV and the ectodomain of a strain of a different VSV serotype. The transmembrane domain may also be the one of the Indiana VSV-G.

A particular kit of compounds comprises lentiviral vectors wherein one or both of them is (are) pseudotyped with recombinant envelope protein(s) comprising the transmembrane domain and the cytoplasmic domain of the indiana VSV and the ectodomain of the New-Jersey VSV.

Appropriate other modifications encompass mutations, especially point mutations, that improve pseudotyping. Such mutations for the VSV-G proteins may be carried out in the transmembrane domain by substituting or deleting one or several amino acid residues. Other examples of appropriate mutations are disclosed in Fredericksen B. L. et al (1995) or Nishimura N. et al (2003).

It is also especially possible to modify the glycosylation status of the VSV-G, in order to improve transduction efficiency of the lentiviral vector pseudotyped with these VSV-G proteins, when administered to a host.

VSV-G proteins from various strains of VSV are disclosed in the figures and their sequences can also be derived from databases, especially from GenBank. Especially the VSV-G proteins of Indiana and New-Jersey strains may be obtained by reference to the sequences disclosed as GenBank #AF170624 for New-Jersey VSV-G or GenBank #M11048 for Indiana strain.

Considering the glycoproteins of the New-Jersey and Indiana strains of VSV, it has been proposed that glycosylation at two asparagine residues (N180 and N336) favour the efficient pseudotyping of lentiviral vectors. This particular feature may be applied in the preparation of the lentiviral vectors of the invention.

The following constructs encoding VSV-G derived envelope proteins are particular examples of constructs for use in the preparation of the combination of lentiviral vector particles of the invention and are described in WO 2009/019612.

A VSV-G Indiana gene which is codon optimized as shown in SEQ ID No 76. A particular encapsidation plasmid is pThV-VSV.G (IND-CO) deposited at the CNCM (Paris, France) on Oct. 10, 2007, under number 1-3842 or in an alternative version of the plasmid construct, on Jul. 31, 2008, under number CNCM 1-4056 is suitable for use in preparing pseudotyped particles with an envelope from VSV-G Indiana New-Jersey. Other constructs may be derived from this particular plasmid, especially by substituting the promoter for a promoter among those listed in the present application.

A VSV-G New-Jersey gene codon optimized is disclosed in SEQ ID No 78. A particular encapsidation plasmid is pThV-VSV.G (NJ-CO) deposited at the CNCM (Paris, France) on Oct. 10, 2007, under number 1-3843 or in an alternative version of the plasmid construct, on Jul. 31, 2008, under number CNCM I-4058 is suitable for use in preparing pseudotyped particles with an envelope from VSV-G Indiana New-Jersey. Other constructs may be derived from this particular plasmid, especially by substituting the promoter for a promoter among those listed in the present application.

Other envelope genes suitable to carry out the invention having codon optimized sequences are illustrated in WO 2009/019612 and especially encompass VSV-G Chandipura gene and its expression product, VSV-G Cocal gene and its expression product, VSV-G Piry gene and its expression product, VSV-G Isfahan gene and its expression product, VSV-G Spring viremia carp virus gene and its expression product. A particular encapsidation plasmid, containing an envelope gene for VSV-G Cocal, is pThV-VSV.G (COCAL-CO) deposited at the CNCM (Paris, France) on Jul. 31, 2008, under number CNCM 1-4055. Another particular encapsidation plasmid, containing an envelope gene for VSV-G Isfahan, is pThV-VSV.G (ISFA-CO) deposited at the CNCM (Paris, France) on Jul. 31, 2008, under number CNCM 1-4057. Another particular encapsidation plasmid, containing an envelope gene for VSV-G Spring viremia carp virus, is pThV-VSV.G (SVCV-CO) deposited at the CNCM (Paris, France) on Jul. 31, 2008, under number CNCM 1-4059. These constructs are disclosed in patent application WO2009/019612.

Fusion envelope proteins, especially fusion proteins involving several different fragments of VSV-G proteins of different viruses and to the nucleic acid constructs encoding such proteins are used as alternative embodiments and are also disclosed in WO 2009/019612. A particular fusion envelope is the fusion between the ectodomain of the New-Jersey envelope protein and the transmembrane domain and cytoplasmic domain of the Indiana envelope protein as illustrated in the herein provided sequences.

Another fusion envelope protein suitable to perform the invention comprises the ectodomain of one VSV-G protein selected among VSV-G Chandipura, VSV-G Cocal, VSV-G Pyri, VSV-G Isfahan, or VSV-G SVCV and the tranmembrane and cytoplasmic domains of VSV-G Indiana. A nucleic acid molecule encoding said fusion protein is advantageously a codon optimized nucleic acid. Nucleic acid encoding the fusion protein are also described as SEQ ID No 77, 79, 81, 83 85, 87, 89.

In a particular embodiment of the invention, a combination of compounds is provided, wherein the lentiviral particles of the separate compounds encode (i) a polypeptide of the CSP antigen or (ii) a polypeptide of the CSP antigen devoid of the GPI-anchoring motif (CSP deltaGPI) or a CSP protein truncated in the N-terminal end (CSP NTer or also CSP delta SP).

In a particular embodiment, these compounds or some of them further encode at least one additional polypeptide of an antigen of the malaria parasite chosen in the groups disclosed herein, the distinct polypeptides of said antigens being either expressed from the same lentiviral particles or from distinct lentiviral particles.

In another particular embodiment of the invention, these compounds or some of them further encode at least one additional polypeptide of an antigen of the malaria parasite chosen in the groups disclosed herein.

The invention concerns especially lentiviral vector particles or a combination of compounds as herein defined for the prophylactic immunization against malaria parasite infection or against parasite-induced pathology in a mammalian host, especially in a human host.

Accordingly, the lentiviral vector particles, compositions comprising the same or the combination of compounds of the invention, when administered to a host in needs thereof, especially to a mammalian in particular to a human host, elicit an immune response, encompassing activation of naïve lymphocytes and generation of effector T-cell response and generation of immune memory antigen-specific T-cell response against antigen(s) of the malaria parasite. The immune response may either prevent the infection by the malaria parasite when such parasite is inoculated as sporozoite to the host or may prevent the onset or the development of a pathological state resulting from inoculation of malaria parasite in the form of sporozoite or prevent the onset or the development of the consequences of the generation of further forms of said parasite such a merozoite forms.

Accordingly, the lentiviral vector particles or the combination of compounds of the invention are suitable for prevention, control or inhibition of the onset of the pathology caused by inoculation of the parasite or by the induction of the exo-erythrocytic i.e., hepatic, stage of the cycle of the malaria parasite and in an advantageous embodiment are suitable to prevent, alleviate or inhibit the onset or development of the erythrocytic cycle of said parasite. Advantageously, it has been observed that the lentiviral vector particles of the invention used in a prime-boost regimen of administration enable the development of a protective immunity and especially enable a sterilizing protection against the malaria parasite-induced pathology. Such a sterilizing protection may result from controlling the consequences of the infection at the stage of liver infection, if not before, in cycle of the parasite.

In a particular embodiment of the invention, a composition of lentiviral vector particles is prepared wherein said lentiviral vector particles are formulated with a suitable administration vehicle for use for prophylactic immunization against malaria parasite infection or against parasite-induced pathology in a mammalian host, especially in a human host.

Physiologically acceptable vehicles may be chosen with respect to the administration route of the immunization composition. In a preferred embodiment administration may be carried out intramuscularly or, for children intranasally.

Accordingly, a combination of compounds can comprise separately provided compositions of lentiviral vector particles wherein each separate composition of the combination or kit of compounds comprises lentiviral vector particles, pseudotyped with a determined heterologous viral pseudotyping envelope protein or proteins, and wherein said pseudotyping envelope proteins do not cross-react with to sero-neutralize the pseudotyping envelope proteins of the lentiviral vector particles of another composition of the combination or kit of compounds.

Accordingly, such compositions or combination of compounds of said compositions are used for prophylactic immunisation against malaria parasite infection or against parasite-induced pathology in a mammalian host, especially in a human host, said use involving an immunisation pattern comprising administering an effective amount of the lentiviral particles to prime the cellular immune response of the host and later in time administering an effective amount of lentiviral particles to boost the cellular immune response of the host, and optionally repeating (once or several times) said administration step for boosting, wherein the lentiviral particles administered in each of the priming or boosting steps are pseudotyped with distinct pseudotyping envelope protein(s) which do not cross-neutralise with each other, and wherein said priming and boosting steps are separated in time by at least 6 weeks, in particular by at least 8 weeks.

In the examples which follow where mice models have been treated according to the prime-boost regimen with lentiviral vector particles of the invention, it has been shown by the inventors that mice immunized according to such a regimen and challenged 6 months after the last immunization step still exhibit a sterile protection for a significant proportion of the vaccinated mice (more than 40%) which illustrates that the lentiviral vector particles of the invention elicit a long-lasting sterile protection in a host, and would therefore constitute a suitable compound for immunization especially in a human host.

The invention relates, in a particular embodiment, to the lentiviral vector particles or combination of compounds as defined herein, for the prophylactic immunization against malaria parasite infection or against parasite-induced pathology in a mammalian host, especially in a human host, in a dosage regimen comprising separately provided doses of said lentiviral particles wherein the dose intended for priming and boosting the cellular immune response is a moderate dose and the dose intended for boosting the cellular immune response is higher than the dose for priming.

Accordingly, the dose intended for priming and boosting the cellular immune response which is used in the administration pattern, comprises from $10^7$ TU to $10^9$ TU of viral particles when integrative vectors are used, the dose intended for children being in the range of $10^7$ TU and for adults in the range of $10^9$ TU. The dose intended for priming and boosting comprises from $10^8$ to $10^{10}$ of lentiviral particles when integrative-incompetent vectors are used.

The lentiviral vector particles or the combination of compounds of the invention is especially used in a particular embodiment for the prophylactic immunization against malaria parasite infection or against parasite-induced pathology in mammalian, host, especially in a human host, in a dosage and administration regimen which is suitable to obtain at least one of the following effects in the host:

- eliciting sterile protection against malaria parasite infection, especially by *Plasmodium falciparum, Plasmodium malariae, Plasmodium vivax, Plasmodium knowlesi* or *Plasmodium ovale* in a human host;
- inhibiting extracellular forms of malaria parasite;
- preventing hepatocytes infection by malaria parasite or inhibition of liver stage amplification of infection;
- eliciting a specific T-cell immune response against malaria parasite antigen(s), especially a CD8+ T-cell response and/or a specific CD4+ T-cell response;
- eliciting a B-cell response against parasite antigen(s);

controlling parasitemia so as to reduce or alleviate the effects of infection by the malaria parasite;

eliciting a protective cellular immunity against the infection by the parasite or against the parasite-induced pathology;

eliciting memory T-cell immune response eliciting earlier and higher rebound of the CD4+ and CD8+ T-cell response during infection by the malaria parasite;

eliciting earlier and strong CT (CD8+T) response by stimulating intra hepatic memory lymphocytes upon *Plasmodium* infection.

preventing malaria parasite escape from immune response thereby allowing long-term control of the infection by the malaria parasite.

Among the above targeted effects, a cellular immune response (T-cell immune response), particularly a CD8-mediated cellular immune response or a CD4-mediated cellular immune response i.e., an immune response which is mediated by activated cells harbouring CD8 or CD4 receptors, preferably Cytotoxic T lymphocytes (CTL) and memory T cell response are advantageously targeted when defining the immunization regimen of the lentiviral particles of the invention.

The immune response can also involve a humoral response i.e., antibodies, elicited by said lentiviral vector particles, produced against said at least one polypeptide of the lentiviral vector. In a particular embodiment, said humoral response is a protective humoral response. The protective humoral response results mainly in maturated antibodies, having a high affinity for their antigen, such as IgG. In a particular aspect, the protective humoral response is T-cell dependent. In a particular embodiment, the protective humoral response induces the production of neutralizing antibodies.

In a particular embodiment of the invention, the lentiviral vector of the invention, even when used in a form which has defective integrase, is able to elicit an early immune response. The expression "early immune response" refers to a protective immune response (protection against the parasite or against the parasite-induced pathology) that is conferred within about one week after the administration of the composition.

In another particularly advantageous embodiment, the immune response conferred by the lentiviral particles of the invention is a long-lasting immune response i.e., said immune response encompasses memory cells response and in particular central memory cells response; in a particular embodiment it can be still detected at least several months, (as illustrated for mice in the examples a protection is still obtained after at least 6 months after the administration of the particles) which allows to consider that the protection may last in a human host over several years following the administration.

When the immune response includes a humoral response, the long-lasting response can be shown by the detection of specific antibodies, by any suitable methods such as ELISA, immunofluorescence (IFA), focus reduction neutralization tests (FRNT), immunoprecipitation, or Western blotting.

In a particular embodiment, said immune response, either humoral or cellular, early immune response and/or long-lasting immune response, is elicited with the non-integrative gene transfer vector, after a single administration of the composition of the invention.

The invention also concerns the use of the lentiviral vector particles or the use of a combination of compounds according to the definition given herein, for the manufacture of an immunogenic composition for prophylactic immunisation against malaria parasite infection or against parasite-induced pathology in a mammalian host, especially in a human host.

The invention also concerns a method of providing immunization in a mammalian host, especially in a human host, comprising the step of administering the lentiviral vectors of the invention to elicit the immune response, and optionally repeating the administration steps one or several times, to boost said response, in accordance with the present disclosure.

In a particular embodiment of the invention, the lentiviral vector particles or the combination of compounds may be used in association with an adjuvant compound suitable for administration to a mammalian, especially a human host, and/or with an immunostimulant compound, together with an appropriate delivery vehicle.

The compositions quoted above can be injected in a host via different routes: subcutaneous (s.c.), intradermal (i.d.), intramuscular (i.m.) or intravenous (i.v.) injection, oral administration and mucosal administration, especially intranasal administration or inhalation. The quantity to be administered (dosage) depends on the subject to be treated, including considering the condition of the patient, the state of the individual's immune system, the route of administration and the size of the host. Suitable dosages range expressed with respect to the content in equivalent p24 antigen of vector particles (for HIV-1 lentiviral vectors) and can be determined.

Other examples and features of the invention will be apparent when reading the examples and the figures which illustrate the preparation and application of the lentiviral vector particles with features that may be individually combined with the definitions given in the present description.

LEGEND OF THE FIGURES

FIG. 1. Nonintegrative lentiviral vector-based vaccination confers total inhibition of liver stage development. A. Study design. Naive mice were primed at week 0 with 100 ng of TRIP.NI CS particles pseudotyped with the VSV-G Indiana (VSV-G Ind) envelope and then boosted at week 8 with 1500 ng of TRIP.NI CS particles pseudotyped with the VSV-G New Jersey (VSV-G NJ) envelope. One group of vaccinated mice were challenged with 80.000 sporozoites (spz) of *Plasmodium yoelii* (17XNL-gfp$^+$ strain) and protective efficacy was measured by quantifying the liver parasite load 40 hours later. A second group of vaccinated mice were challenged with 500 spz of *Plasmodium yoelii* (17XNL-gfp$^+$ strain) and protective efficacy was evaluated by monitoring blood stage parasitemia every other day from day 3 post injection until day 14 by Giemsa-stained blood smears. In the two cases, the challenges were performed one month after the last immunization. B. Results of the parasite loads quantified using real-time RT-PCR for *P. yoelii* 18S rRNA in the livers of challenged mice. Data are presented as the number of copies of *plasmodium* 18S rRNA detected in individual control mice (n=5) and vaccinated mice (n=4). Mean+/−SD of duplicate is shown. C. Results of the monitoring of blood stage parasitemia. 0 indicates absence of parasites, + indicates presence of parasites.

FIG. 2. A. Study design. Mice primed with 100 ng of TRIP.NI CS particles pseudotyped with the VSV-G Indiana (VSV-G Ind) envelope and boosted 8 weeks later with 1500 ng of TRIP.NI CS particles pseudotyped with the VSV-G New Jersey (VSV-G NJ) envelope received a third immunization dose 5 months later with 1500 ng of TRIP.NI CS particles pseudotyped with the VSV-G Cocal. Vaccinated mice were challenged one month later with 500 spz of *Plasmodium yoelii* (17XNL strain) and protective efficacy was evaluated by monitoring blood stage parasitemia every other day from day 3 post injection until day 16 by Giemsa-stained blood smears. B. Percentage of mice completely protected against sporozoite challenge after a nonintegrative lentiviral vector-based regimen. C. Means of parasitemia of naive mice (CO-black curve), vaccinated mice completely protected (VAC-light grey curve) and vaccinated mice partially protected (VAC-grey curve) are depicted. D. Means of parasitemia from naive mice (CO— black), vaccinated mice partially protected (VAC-grey) and vaccinated mice completely protected (VAC-grey), 10 days after the challenge.

FIG. 3. Gross morphology of spleens and livers from mice vaccinated (VAC) or not (CO) at the final killing (3 weeks post-challenge) with 500 sporozoites of *Plasmodium yoelii.*

Figure 4:
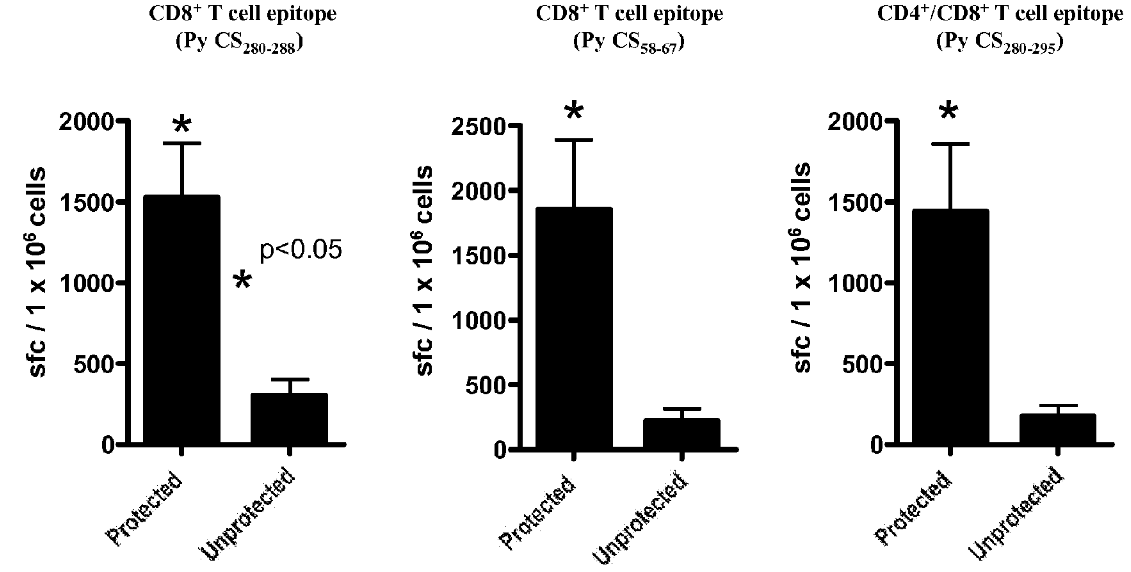

FIG. 4. CS protein-specific T cell responses from splenocytes of vaccinated mice 3 weeks after challenge. Ex vivo IFN□ ELISPOT was carried out using splenocytes from vaccinated mice harvested 3 weeks after the challenge with *Plasmodium yoelii*. Splenocytes were stimulated with synthetic peptides representing $CD8^+$ or $CD4^+$ defined epitopes. Data are expressed as mean+/−SD of spot forming cells (sfc) of duplicate wells. n=5 in the protected group and n=3 in the unprotected group. *: different from unprotected group $p<0.05$.

Figure 5:
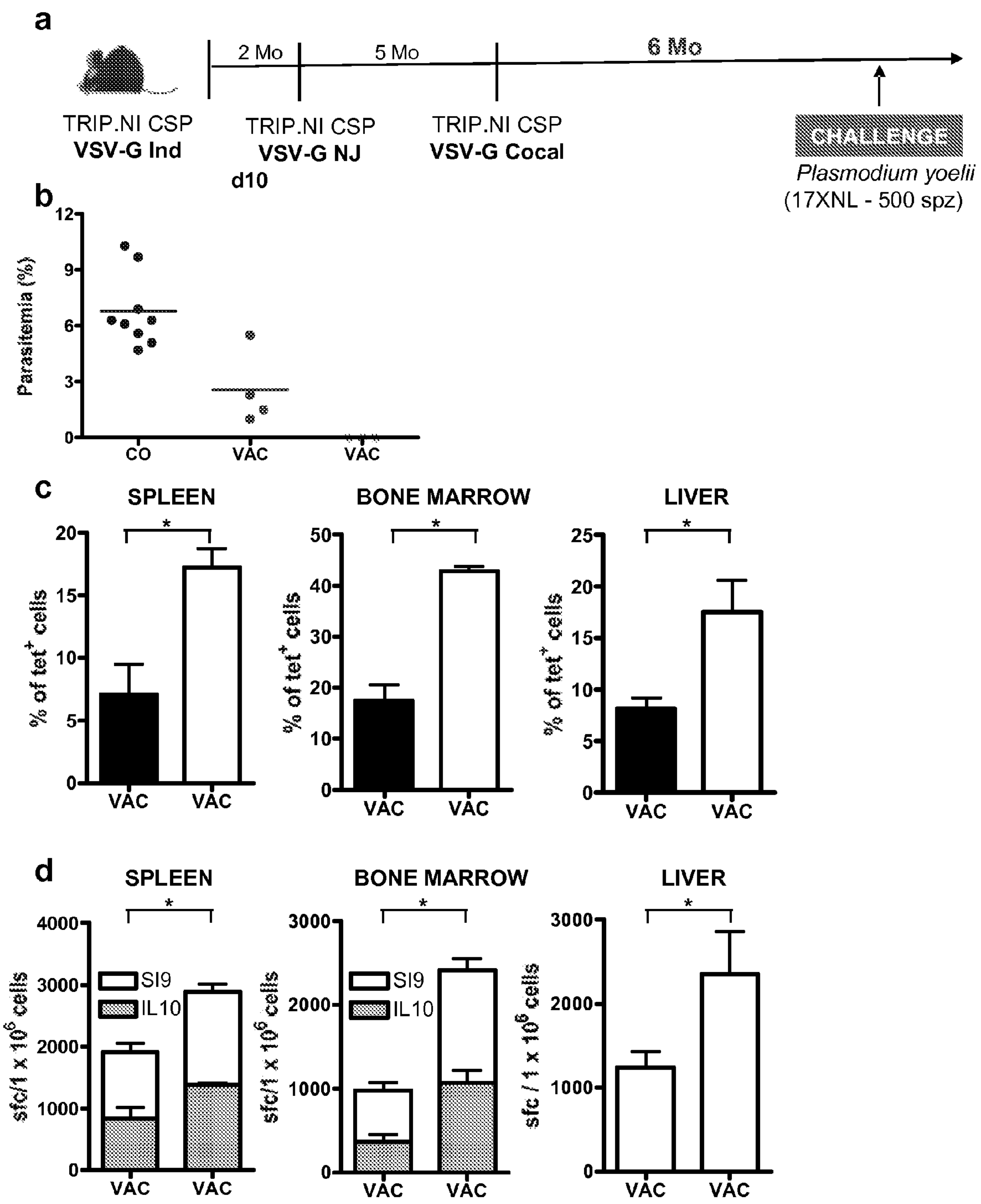

FIG. 5. Optimized non integrative lentiviral vectors confer long term sterile protection against malaria (a) Vaccine schedule. Mice were primed with 100 ng of TRIP.NI CSP particles pseudotyped with the VSV-G Indiana envelope and boosted 8 weeks later with 1500 ng of TRIP.NI CSP particles pseudotyped with the VSV-G New Jersey envelope. Five months later, they received a third injection of TRIP.NI CS particles (1500 ng) pseudotyped with the VSV-G Cocal envelope. Animals were challenged six months later with 500 sporozoites of *Plasmodium yoelii* (17XNL strain) and protective efficacy was evaluated by monitoring blood stage parasitemia every other day from day 3 post injection until day 16. (b) Means of parasitemia from naive mice (CO— black), vaccinated mice partially protected (VAC-light grey (middle)) and vaccinated mice completely protected (VAC-grey (right)), 10 days after the challenge. (c) Tetramer analysis of the % of CSP-specific $CD8^+$ T cells from the spleen, the bone marrow and the liver of mice at the final killing (3 weeks post-challenge). Black bars indicate vaccinated mice partially protected and white bars indicate vaccinated mice completely protected. (d) INF-g ELISPOT quantification of CSP-specific CD8+ T cells in the spleen, the bone marrow and the liver of mice. * $P<0.05$ (Student's t-test)

FIG. 6. Hep17-specific T cell responses induced by nonintegrative lentiviral vectors. Naive mice (n=5/group) were immunized or not (−) i.p. with a single injection of various doses (100 or 600 ng) of nonintegrative lentiviral vectors coding for Hep17. At 11 days post-immunization, Hep17-specific cellular immune responses against the CD8+ T cell epitopes (A) and the $CD4^+$ T cell epitopes (B) were assessed by IFN-γ ELISPOT. SFC, spot-forming cells.

FIG. 7. Hep17-specific T cell responses induced by integrative lentiviral vectors. Naive mice (n=5/group) were immunized (or not: -) i.m. with a single injection of integrative lentiviral vectors ($1\times10^7$ TU) coding for Hep17. At 11 days post-immunization, Hep17-specific cellular immune responses against the $CD8^+$ T cell epitopes (A) and the $CD4^+$ T cell epitopes (B) were assessed by IFN-γ ELISPOT. SFC, spot-forming cells.

Figure 8:
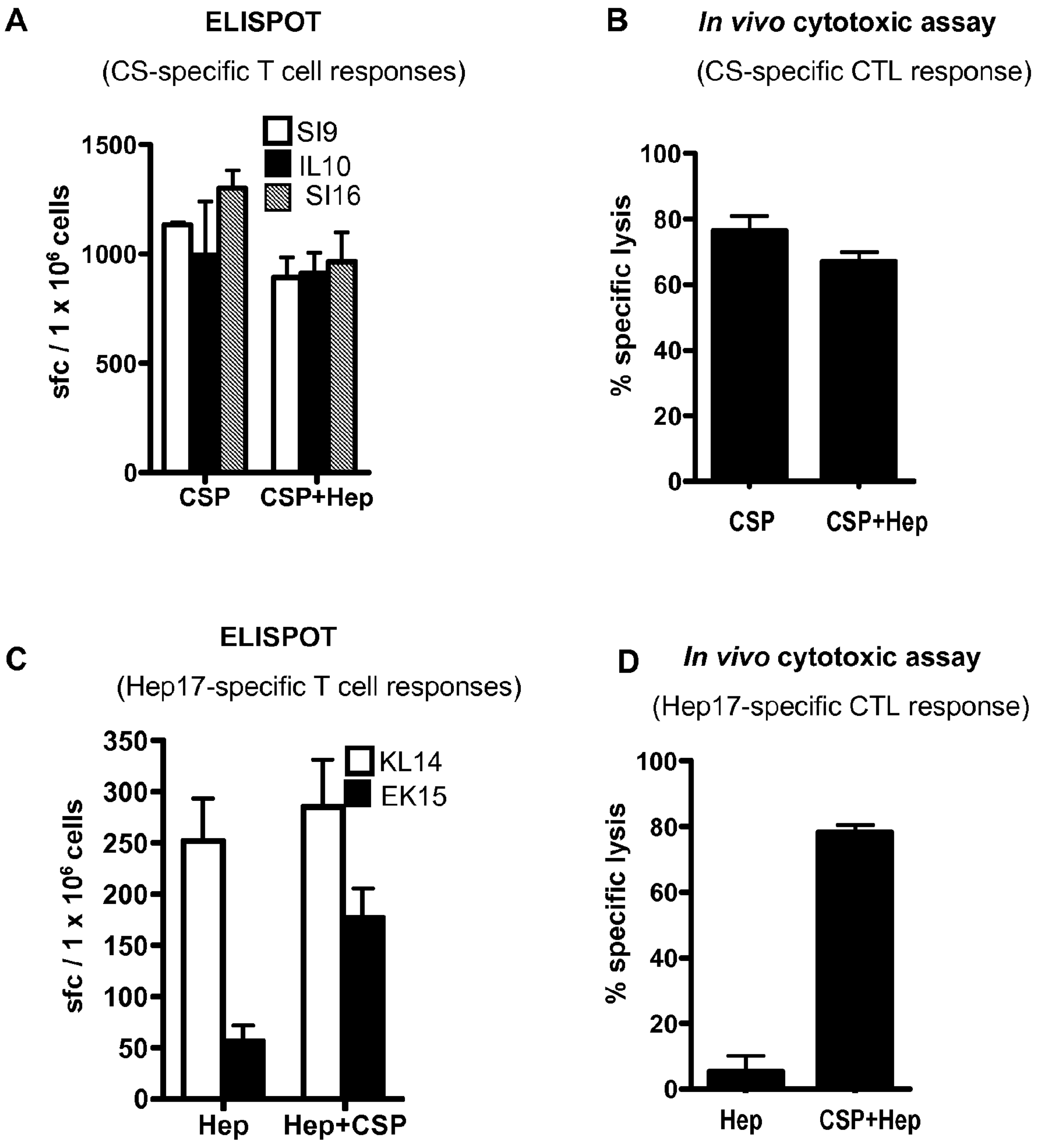

FIG. 8. CS— and Hep17 specific T cell responses elicited after coimmunizations with lentiviral particles. Naive mice (n=5/group) were immunized i.m. with a single injection of integrative lentiviral vectors ($1\times10^7$ TU) coding for CS (named CSP in figure A and B) or Hep17 (named Hep17 in figure C and D). For coimmunization experiments, naive mice were injected into one quadriceps with TRIP.I CS and into the opposite quadriceps with TRIP.I Hep17 particles (named CSP+Hep in figure A,B,C,D). At 11 days post-immunization, CS-specific cellular immune responses (A) and Hep17-specific cellular immune responses (C) were assessed by IFN-γ ELISPOT. SFC, spot-forming cells. For in vivo cytotoxic assays, immunized mice were injected at day 11 with target cells pulsed with CS peptides (C) or Hep17 peptides (D). Percentages of specific killing were determined 18 hours later, as described in Material and Methods section.

Figure 9:
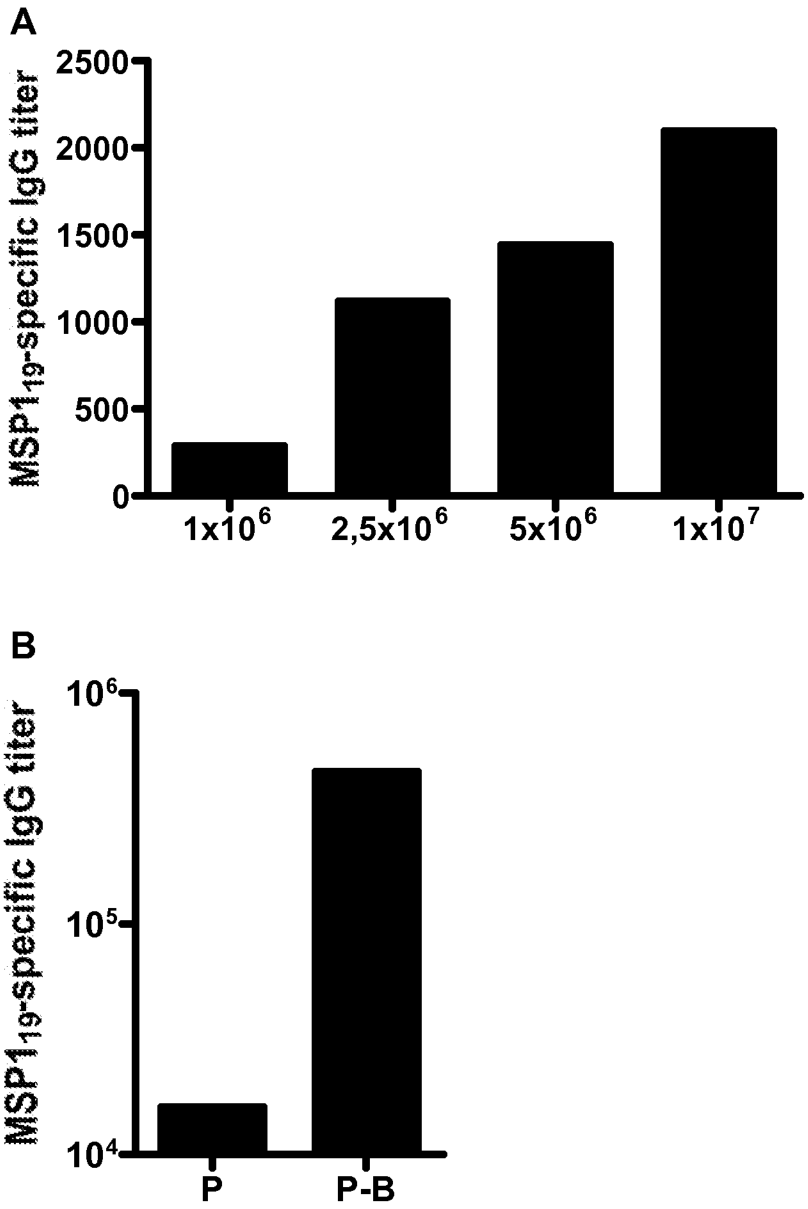

FIG. 9. A single dose of nonintegrative lentiviral vector coding for $MSP1_{42}$ elicits a strong and specific antibody response. A. Groups of adult mice (n=5) were immunized intraperitoneally with graded doses of TRIP.I $MSP1_{42}$. After 21 days, pooled sera (5 mice per group) were assessed for the presence of $MSP\text{-}1_{19}$-specific antibodies. B. Mice were primed with 100 ng of TRIP.I $MSP1_{42}$ particles pseudotyped with the VSV-G Indiana envelope. 3 months later, mice were boosted with 1000 ng of TRIP.NI $MSP1_{42}$ particles pseudotyped with the VSV-G cocal envelope. Results are the mean titers of $MSP\text{-}1_{19}$-specific antibodies detected in the sera of mice 3 weeks after the last immunization.

FIGS. 10(A) and 10(B). Alignments of *Plasmodium* CSP proteins and sequence of a consensus. The aligned *Plasmodium* CSP proteins are CSP *Plasmodium falciparum* (SEQ ID NO: 23), CSP *Plasmodium yoleii* (SEQ ID NO: 20), CSP *Plasmodium berghei* (SEQ ID NO: 26), CSP *Plasmodium malariae* (SEQ ID NO: 27), CSP *Plasmodium coatneyi* (SEQ ID NO: 28), CSP *Plasmodium knowlesi* (SEQ ID NO: 29), CSP *Plasmodium reichenowi* (SEQ ID NO: 30), and CSP *Plasmodium gallinaceum* (SEQ ID NO: 31). The consensus sequence is (SEQ ID NO: 32).

Figure 11:
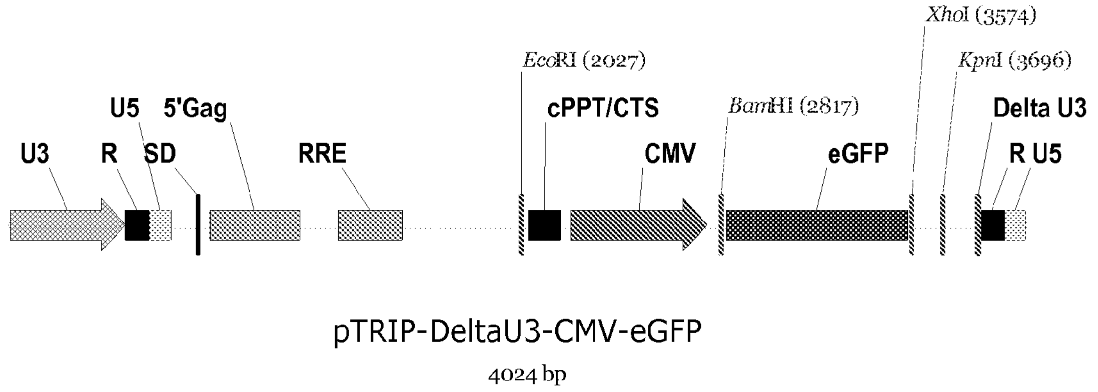

FIG. 11. Restriction map of plasmid pTRIP-DeltaU3-CMV-eGFP. SEQ ID No 33

Figure 12:
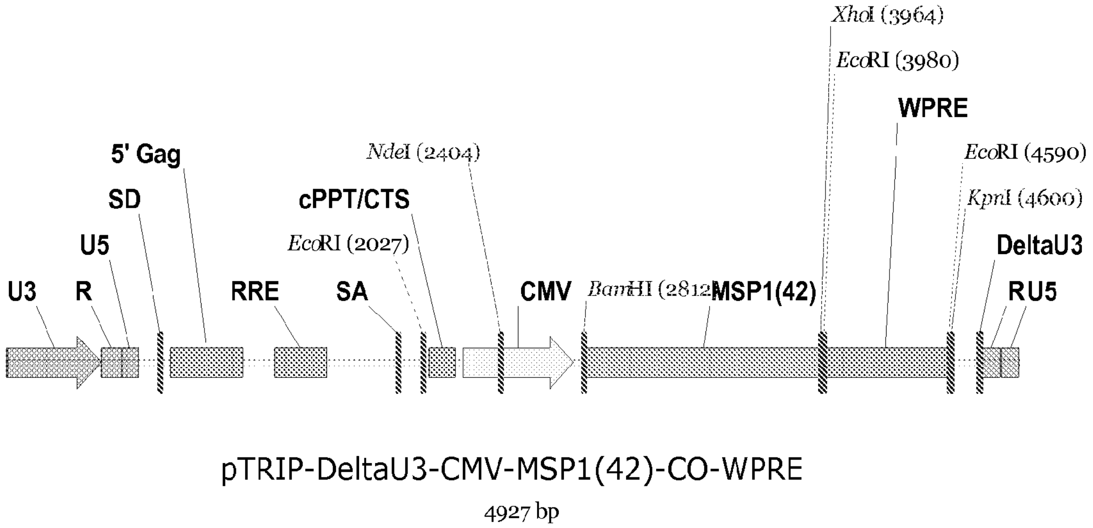

FIG. 12. Restriction map of plasmid pTRIP-ΔU3-CMV-$MSP1_{42}$ CO—WPRE (CNCM 1-4303 or SEQ ID No 34).

Figure 13:
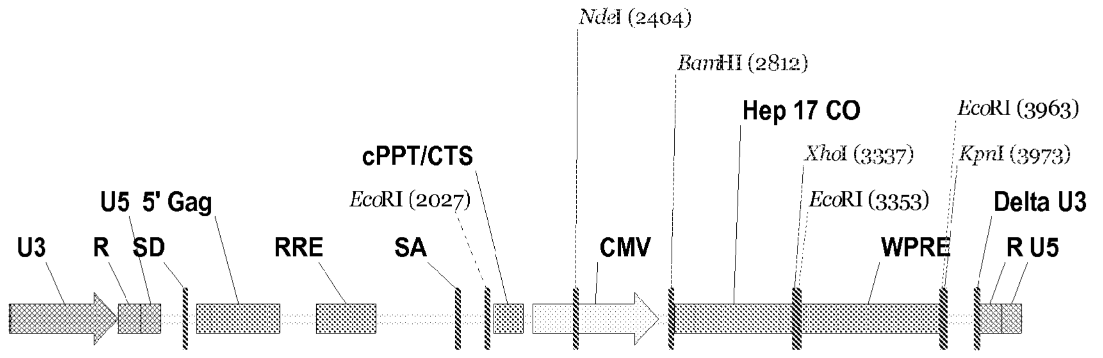

FIG. 13. Restriction map of plasmid pTRIP-ΔU3-CMV-Hep17 CO—WPRE (CNCM 1-4304 or SEQ ID No 37).

Figure 14:
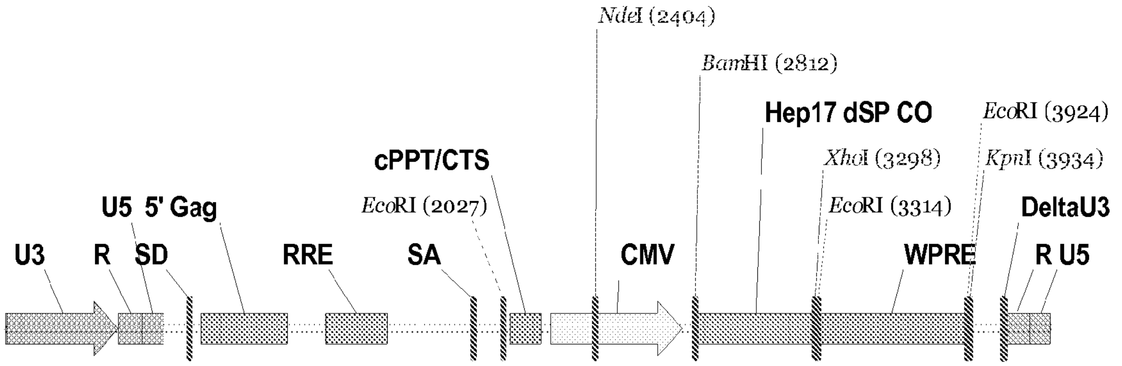

FIG. 14. Restriction map of plasmid pTRIP-ΔU3-CMV-Hep17 ΔSP CO—WPRE (CNCM 1-4305 or SEQ ID No 40).

Figure 15:
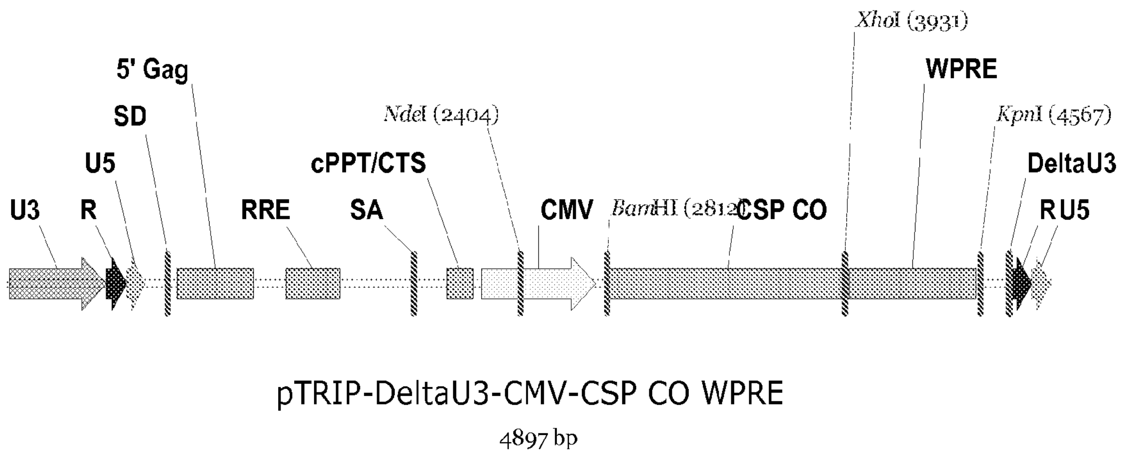

FIG. 15. Restriction map of plasmid pTRIP-ΔU3-CMV-CSP CO—WPRE (CNCM 1-4306 or SEQ ID No 43).

Figure 16:
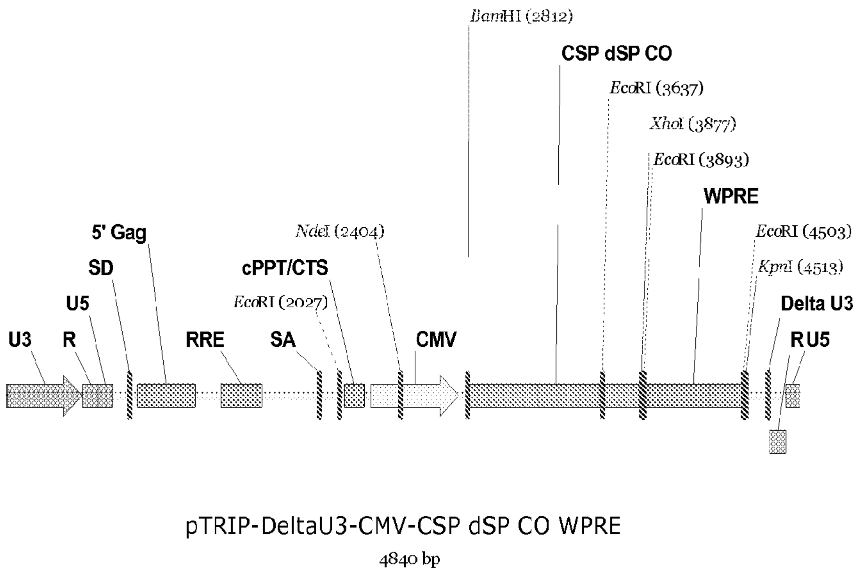

FIG. 16. Restriction map of plasmid pTRIP-ΔU3-CMV-CSP ΔSP CO—WPRE (CNCM 1-4307 or SEQ ID No 45).

Figure 17:
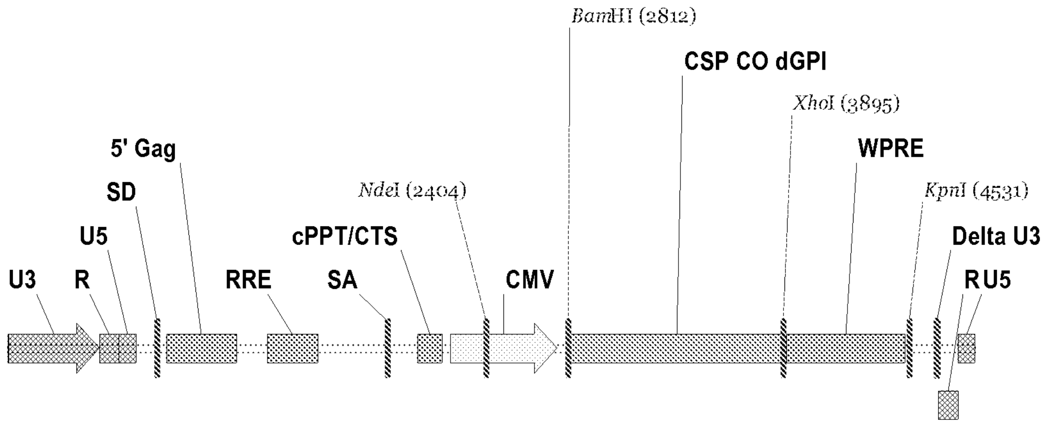

FIG. 17. Restriction map of plasmid pTRIP-ΔU3-CMV-CSP ΔGPI CO—WPRE (CNCM 1-4308 or SEQ ID No 47).

EXAMPLES

With a view to assess whether lentiviral vectors may represent an alternative strategy, a nonintegrative lentiviral vector coding for a truncated form of the circumsporozoite (CS) protein of *Plasmodium yoelii* (TRIP.NI CS) was designed and assayed in an animal mice model relevant for malaria. The CS protein is distributed uniformely over the surface of sporozoites and is also detected in infected liver cells[4, 5]. Thus, the induction of humoral immune responses against the CS protein reduces the hepatocyte infectivity, whereas the cellular immune responses against this antigen kill parasite-infected hepatocytes. This concept was recently supported by an elegant study that demonstrated that the CS protein was the main target of protective immunity in the irradiated sporozoite immunization model[6]. Moreover, among all the vaccine candidates tested so far in clinical trials, only the CS protein-based vaccine RTS, S has been shown to reduce significantly malaria incidence and cases of severe malaria in endemic countries[7, 8].

In order to elicit optimal immune responses against the CS protein, we combined three strategies: 1) to increase the level of antigen expression in transduced cells, we inserted in the vector backone a mamalian codon-optimized sequence of the CS protein under the control of the strong cytomegalovirus promoter and we added downstream the transgene the woodchuck post-transcriptional regulatory element sequence to increase mRNA stabilization and export to the cytoplasm; 2) we deleted the GPI anchoring sequence located at the 3' end of the cs gene since deletion of GPI-anchoring motif has been shown to improve the immunogenicity of the CS protein[9] 3) to increase the specific immune response, and in particular, to protect mice from infection by sporozoite challenge, mice received LV-based boosters. To circumvent the presence of neutralizing anti-envelope antibodies induced after the first immunization, lentiviral particles used for boost immunizations were pseudotyped with VSV-G envelopes from non-cross-reactive serotypes (VSV-G Indiana for the prime, VSV-G New Jersey and Cocal for the first and the second boost, respectively).

In a first series of experiment, mice were primed with a moderate dose of TRIP.NI CS and boosted 8 weeks later with a high dose of TRIP.NI CS (FIG. 1*a*). To evaluate protection induced by this prime-boost regimen, BALB/c mice were challenged with $80.10^3$ sporozoites of *Plasmodium yoelii* (17XNL gfp+ strain), the invasive form of the parasite present in the mosquitoe. The challenge was performed 4 weeks after the completion of immunization regimen. Forty hours after the challenge, the level of inhibition of liver stage development was determined by quantifying plasmodial 18S rRNA in the livers of mice. For this purpose, liver-extracted RNA was used for real-time PCR amplification of the plasmodial 18S rRNA sequences, using the EXPRESS One-Step SYBR® GreenER™ kit (invitrogen) and specific primers for the amplification of the 18S rRNA of *Plasmodium yoelii*. As shown in FIG. 1*b*, the inhibition of liver stage development of the parasite was complete for all immunized mice, i.e., no parasite 18S rRNA could be detected by quantitative RT-PCR. In parallel experiments, protection was also assessed by examining blood smears of immunized mice, which were challenged with 500 *Plasmodium yoelii* sporozoites, for the occurrence of erythrocytic stages. Peripheral blood smears were obtained daily from day 3 to 14 post-challenge, stained with Giemsa and examined by microscopy, to determine whether immunized mice became parasitemic, i.e., failed to develop protection. As shown in FIG. 1*c*, complete protection occurred in 60% of immunized mice.

In a second series of experiments, we added a third injection of TRIP.NI CS pseudotyped with a VSV-G Cocal envelope which does not cross-react with antibodies directed against the Indiana and New Jersey serotypes. One month after the last boost, immunized mice were challenged intravenously with 500 sporozoites, (FIG. 2*a*). Protective efficacy was evaluated by monitoring blood stage parasitemia every other day from day 3 post injection until day 21 by Giemsa-stained blood smears. After 5 days, all naive mice exhibited patent blood stage parasitemia. By contrast, 62.5% of immunized mice showed sterile immunity (as defined by the absence of parasitemia over the following 21 days) (FIG. 2*b*). Moreover, as compared with naive mice, immunized mice that developed parasitemia displayed a significant delay in the course of erythrocyte invasion (FIG. 2*c*). At day 10 post-challenge, immunized mice partially protected showed a two-fold reduction in the level of parasitemia compared to naive mice, demonstrating that in this case, the vaccine afforded also an immune control, albeit partial, of the parasite (FIG. 2*d*).

Hepatosplenomegaly is a prominent feature of malaria. We then performed a qualitative analysis of the organs from mice sacrificed 3 weeks post-challenge. Naive mice infected with the parasite displayed dramatic splenomegaly (FIG. 3). Moreover, spleens and livers showed dark pigmentation resulting from the accumulation of hemozoin produced by the parasite during digestion of red blood cell hemoglobin. By contrast, the capacity of 5 out of 8 vaccinated mice to mount a sterile immune response coincided with preservation of livers and spleens that displayed normal size and pigmentation.

In an attempt to understand why ⅓ of immunized mice did not shown sterile protection, we evaluated the CS protein-specific immune responses in vaccinated animals sacrificed at 3 weeks post-challenge. Challenged naive mice displayed no detectable CS protein-specific IFN-β producing T cells (data not shown). By contrast, in the vaccinated group, mice fully protected exhibited five to eight fold greater CSP-specific T cell responses as compared with mice vaccinated but partially protected, emphasizing the critical importance of the strength of T cell responses for immune control (FIG. 4).

Importantly, we also performed challenge experiments at 6 months after the last immunization. In this case, more than 40% of the vaccinated mice still failed to develop detectable parasitemia following challenge, illustrating the long-lasting sterile protection conferred by our vaccine strategy (FIG. 5).

Taken together, these data demonstrated that a prime-boost regimen based on non integrative lentiviral vectors can confer a high degree of protection against challenging infectious agents such as *plasmodium*.

Based on these results, we are currently developing a multi-stage vaccine approach. The rationale of this strategy is to improve the protective efficiency conferred by our vaccine approach by inducing a multi-immune response directed against antigens expressed in the liver stage and targeted by T-cell responses, as well as antigens expressed in the blood-stage and targeted by antibody responses. To this end, we have selected two pre-erythrocytic stage antigens (CS protein and Hepatocyte Erythrocyte Protein 17 kDa—HEP17) and one erythrocytic stage antigen (The 42-kDa fragment of the Merozoite Surface Protein 1—$MSP\text{-}1_{42}$). These antigens were selected because it has been shown that cytotoxic T cell responses specific of Hep17 are partially protective against sporozoite challenge and antibody responses specific of $MSP\text{-}1_{42}$ can also protect mice against a lethal challenge with blood-stage parasites[10], 11. Lentiviral vectors coding for Hep17 or $MSP\text{-}1_{42}$, were constructed as detailed in the Material and Methods part. To evaluate the immunogenicity of a single injection of lentiviral particles expressing Hep17, groups of mice (n=5/group) were immunized with 100 ng ($3.2\times10^7$ TU) or 600 ng ($1.9\times10^8$ TU) of TRIP.NI Hep17 and specific immune responses were assayed by Elispot. As shown in FIG. 6, relatively weak CD8 and CD4 responses could be detected in the spleens of immunized mice after stimulation with the 9-mer and 15-mer previously described[12].

We also tested the immunogenicity of TRIP.I Hep17 lentiviral particles. Groups of mice (n=5) were immunized im with $1\times10^7$ TRIP.I Hep17 particles. Hep-17-specific IFNg Elispot responses were evaluated 11 days later on splenocytes from immunized mice. As shown in FIG. 7, the most robust responses were detected against the CD4+ T cell epitopes (KL14 and EK15) and against one CD8+ T cell epitope (LA9). We also evaluated the T-cell responses obtained after co-immunization of TRIP.I Hep17 particles with TRIP.I CS particles. Mice received two injections: one injection of $1\times10^7$ TRIP.I Hep17 particles in the left quadriceps and one injection of $1\times10^7$ TRIP.I CS particles in the right quadriceps. In parallel, groups of mice were immunized with TRIP.I CS particles alone ($1\times10^7$ TU im) or TRIP.I Hep17 particles alone ($1\times10^7$ TU im). At day 11, one part of immunized mice were sacrificed for Elispot experiments. There was no huge difference between the frequency of CS-specific IFNg T cells in mice immunized with TRIP.CS particles alone or with TRIP.I CS and TRIP.I Hep17 particles (FIG. 8A). To evaluate cytotoxic T cell response in immunized mice, we performed an in vivo cytotoxic assay (as described in Material and Methods). At day 11, groups of mice immunized with TRIP.I CS particles alone or coimmunized with TRIP.I CS and Hep17 particles were challenged by iv injection with target cells pulsed with CS peptides. As expected, mice immunized with TRIP.I CS particles lyzed efficiently target cells and we did not detect significant difference between group of mice immunized with TRIP.I CS particles alone and group of mice that received both TRIP.I CS and TRIP.I Hep17 particles (FIG. 8B). Taken together, these results demonstrated that TRIP.I Hep17 particles co-administered with TRIP.I CS particles did not significantly interfere with the CS-specific T cell response elicited by TRIP.I CS particles. We also evaluated the frequency of Hep17-specific IFNg T cells in mice immunized with TRIP.I Hep17 alone or co-administrated with TRIP.I CS particles. Frequencies of specific T cells responding to stimulation to the five 9-mer peptides (CD8+ T cell epitopes) were the same in the two groups, as well as those measured after stimulation with the KL14 epitope (CD4+ T cell epitope). Strikingly, the responses detected against the CD4+ T cell epitope EK15 were twice higher in mice co-immunized than in mice immunized with TRIP.I Hep17 alone (FIG. 8C). As shown in FIG. 8D, the cytotoxic capacity of T cells against Hep17 peptides-pulsed targets were also greatly increased in mice co-immunized with TRIP.I Hep17 and TRIP.I CS particles. Collectively, these data demonstrate that CS-specific immune response enhances cytotoxic T cell responses specific for Hep17.

We next evaluated the ability of lentiviral vectors to initiate a B cell response against the blood stage malaria antigen merozoite surface protein-1 (MSP1). Mice (n=5) were immunized with various doses of integrative lentiviral vectors coding for the 42-kDa region of MSP1 from *Plasmodium yoelii* (TRIP.I $MSP1_{42}$) fused to at the N terminus to the secretory signal of the calreticuline. Three weeks after immunization, pooled sera collected from each group of immunized mice were tested for the presence of total anti-MSP1 antibodies directed against the protective C-terminal 19-kDa region ($MSP\text{-}1_{19}$)[13, 14] of the antigen. As shown in FIG. 9A, mice immunized with a dose as low as $1\times10^6$ TU displayed detectable levels of anti-$MSP\text{-}1_{19}$ antibodies and immunizations with $1\times10^7$ TU of this vector induced a strong secretion of anti-$MSP\text{-}1_{19}$ Ig with a mean titer reaching $2\times10^3$. To know whether anti-MSP1 response conferred by lentiviral vector immunization could be enhanced by a second immunization, mice immunized with 100 ng of TRIP.I $MSP1_{42}$ particles pseudotyped with VSV-G Indiana envelope were boosted 3 months later with 1000 ng of TRIP.NI $MSP1_{42}$ particles pseudotyped with the VSV-G Cocal envelope (FIG. 9B). 3 weeks after the last immunization, the levels of anti-$MSP\text{-}1_{19}$ antibodies in prime-boosted mice reached a mean value of $4\times10^5$ whereas the titer in the plasma of mice solely primed was $2\times10^4$. In conclusion, immunization with integrative lentiviral vectors can induce potent anti-$MSP\text{-}1_{19}$ Ig that have been shown to be protective against infection of red blood cells by parasites.

MATERIAL AND METHODS

Animals And Parasites.

Balb/c Ola Hsd (six-week-old female) were purchased from Harlan Laboratories (Gannat, France). All animal experiments were conducted in accordance with the guidelines of Animal Care at the Pasteur Institute. Infection experiments were performed with the *Plasmodium yoelii* (17XNL strain) wild-type or genetically modified to express the green fluorescent protein, allowing the detection of oocysts and sporozoites in living mosquitoes. *Plasmodium yoelii* was maintained by alternate cyclic passages in *Anopheles stephensi* and Balb/c mice. Mosquitoes were reared at the Center for Production and Infection of *Anopheles* (CEPIA) of the Pasteur Institute using standard procedures.

Plasmid Vectors Construction.

The mammalian codon optimized form of the gene coding for the full-length of the Py CS protein (amino acids 1-367; GenBank Accession No. M58295) was synthesized by Geneart. Since deletion of the GPI-anchoring motif has been shown to improve the immunogenicity of the CS protein, we constructed a codon optimized form of the cs gene deleted of the sequence encoding the last 11 amino acids. This sequence was obtained by PCR amplification of a fragment of the codon optimized cs gene using the following oligonucleotides (Sigma-Proligo): (forward) 5'GGTACC GGATCCGCCACCATGAAGAAATGCACC-3' (SEQ ID NO: 1) (underlined is the BamHI site); (reverse) 5'-AG CTCGAGTCATCACAGGCTGT TGGACACGATGTTGAAGATGC-3' (SEQ ID NO: 2) (underlined is the XhoI site). The resulting amplicon was cloned in a pCR 2.1-TOPO plasmid (Invitrogen) and sequenced (plasmid referred as pCR 2.1-TOPO CS). The pTRIP CS vector plasmid was generated by replacing the GFP sequence from pTRIP CMV-GFP-WPRE digested BamHI/XhoI by the truncated codon-optimized CS sequence obtained after a BamHI/xhoI digestion of the pCR 2.1-TOPO CS. For pTRIP Hep17, a mammalian codon-optimized sequence (Geneart) of the Py Hep17 gene (GenBank Accession No. U43539) including a kozak sequence and flanked of a BamH1 site in 5' and a XhoI site in 3' was cloned in pTRIP CMV-WPRE digested BamH1/XhoI. For MSP1 construct, a composite mammalian codon optimized sequence (Geneart) was designed to include: a sequence coding for the secretion signal of the calreticuline (MLLSVPLLLGLLGLAVA) (SEQ ID NO: 3) fused to the codon optimized sequence of the Py $MSP1_{42}$ (GenBank Accession No. J04668). The entire sequence digested BamH1/XhoI was cloned in pTRIP CMV-WPRE digested BamH1/XhoI.

Sequences of the pTRIP vectors are respectively designated as: SEQ ID NO 34, 37, 40, 43, 45 and 47.

Lentiviral Vector Production.

Vector particles were produced by transient calcium phosphate co-transfection of 293T cells with the vector plasmid pTRIP CS, a VSV-G envelope expression plasmid (pHCMV-G) and the pD64V encapsidation GAG POL plasmid for the production of integration-deficient vectors (the D64V substitution in the catalytic domain of the integrase blocks the DNA cleaving and joining reactions of the integration step) as previously described[15]. Quantification of the p24 antigen content of concentrated vector particles was performed with a commercial HIV-1 p24 enzyme-linked immunoabsorbent assay (ELISA) kit (Perkin Elmer Life Sciences). Vector titers of TRIP.I and TRIP.NI particles were determined by transducing HeLa cells treated with aphidicolin (SIGMA) and performing a quantitative PCR as previously described[15]. The titers of integrative and nonintegrative lentiviral vectors were similar according to p24 content and quantitative PCR measured in growth-arrested cells.

Mice Immunization and Challenge.

Six-week-old BALB/c mice were intraperitoneally (i.p.) immunized with 100 ng of TRIP.NI CS vector particles pseudotyped with the VSV-G Indiana envelope, diluted in 0.1 ml Dulbecco's phosphate-buffered saline. Eight weeks later, mice were boosted i.p. with 1500 ng of TRIP.NI CS vector particles pseudotyped with the VSV-G New Jersey envelope. Challenge of the immunized and the control mice consisted of the injection of 80,000 sporozoites intravenously 4 or more weeks after the last immunization. The outcome of the challenge was determined by measuring the parasite burden in the liver of mice by using a quantitative real-time RT-PCR method, as detailed later. We also determined, in control and immunized groups of mice, whether or not mice developed parasitemia after i.v. inoculation of 500 sporozoites, by microscopic examination of Giemsa-stained thin blood smears obtained daily, from the third day after challenge up to day 14. Briefly, a small drop of blood from challenged mice was placed on a microscope slide. The drop was smeared by using a second slide, air-dried, and fixed in 100% methanol for 30 seconds. Fixed slides were stained for 30 minutes in a fresh solution of 10% Giemsa (Reactfs RAL) diluted in water (Volvic), rinsed with water and dried in air. The slides were observed with ×100 oil immersion objective.

Quantification of *P. yoelii* by Real-Time RT-PCR.

Quantification of the parasite loads in the liver of the challenged mice was performed as previously described[16] with some modifications. 40 hours after challenge, livers were harvested and RNA was extracted with the RNeasy mini kit (Qiagen). 2 μg of RNA was used for the quantification of parasite specific 18S rRNA. The reaction of real-time RT-PCR was carried out with the EXPRESS One-Step SYBR® GreenER™ kit (invitrogen) and specific primers for the amplification of the 18S rRNA of *P. yoelii*. The sequences of the primers (Sigma-Proligo) are: 5'-GGGGATTGGTTTTGACGTTTTTGCG-3' (SEQ ID NO: 4) (forward primer) and 5'-AAGCATTAAATAAAGCGAATACATCCTTAT-3' (SEQ ID NO: 5) (reverse primer). Experiments were performed with a LightCycler™ apparatus (Roche diagnostics). The quantity of parasite RNA copies was assessed by extrapolation of threshold fluorescence values onto an internal standard curve prepared from serial dilutions of a plasmid construct (pCR 2.1-TOPO plasmid-Invitrogen) containing the 18S cDNA PCR-amplified fragment of the parasite.

Elispot Assay.

Nitrocellulose microplates (MAHA S4510, Millipore) were coated with capture antibody (Mouse IFNg Elispot pair, BD Pharmingen) and blocked with complete medium composed of RPMI 1640 Glutamax supplemented with 10% FCS, antibiotic, Hepes, non-essential amino-acids, b-mercaptoethanol and sodium pyruvate. Splenocytes from vector-immunized mice were added to the plates in triplicates at $0.125\times10^6$ cells/well. For quantification of CS-specific $CD8^+$ T cell responses, splenocytes were incubated with 2 μg/ml of the peptides (PolyPeptide Laboratories France) SYVPSAEQI (SEQ ID NO: 6) (Py $CS_{280-288}$) or IYNRNIVNRL (SEQ ID NO: 7) (Py $CS_{58-67}$). To evaluate the CS-specific $CD4^+$ T cell responses, splenocytes were incubated with 2 μg/ml of the peptides SYVPSAEQILEFVKQI (SEQ ID NO: 8) (Py $CS_{280-295}$). Twenty hours later, spots were revealed with the biotin-conjugated antibody (Mouse IFNg Elispot pair, BD Pharmingen) followed by streptavidin-AP (Roche) and BCIP/NB substrate solution (Promega). Spots were counted using a Bioreader 2000 (Biosys, Karben, Germany) and results were expressed as IFNγ spot-forming cells (sfc) per million splenocytes. The same protocol was applied for quantification of Hep17-specific T cell responses. Peptides used for stimulation in Elispot and in vivo cytotoxic assay are summarized in Table 1. The sequences presented in Table 1 are identified by the following sequence identification numbers: SYVPSAEQI (SEQ ID NO: 6). IYNRNIVNRL (SEQ ID NO: 7), SYVPSAEQILEFVKQI (SEQ ID NO: 8). KIYNRNIVNRLLGD (SEQ ID NO: 9), YNRNIVNRLLGDALNGKPEEK (SEQ ID NO: 10), LRKINVALA (SEQ ID NO: 11), EEIVKLTKN (SEQ ID NO: 12), KKSLRKINV (SEQ ID NO: 13), INVALATAL (SEQ ID NO: 14), LSVVSAILL (SEQ ID NO: 15), EEIVKLTKNKKSLRK (SEQ ID NO: 16), and KSLRKINVALATAL (SEQ ID NO: 17).

In vivo cytotoxic assay. For target cell preparation, splenocytes from naive mice were labelled with various concentrations (high, 5 μM; Low, 1 μM) of CFSE (carboxyfluorescein-diacetate succinimydyl ester, Vybrant CFDA-SE cell-tracer kit, Molecular Probes). Splenocytes labelled with high concentrations of CFSE were pulsed with combination of peptides at 5 μg/ml. The control population stained with low doses of CFSE was incubated in medium without peptides. Each mouse received $10^7$ CFSE-labelled cells of a mix containing an equal number of cells from each fraction, through the retroorbital vein. After 15-18 h, single-cell suspensions from spleen were analyzed by flow cytometry (Becton Dickinson, CellQuest software). The disappearance of peptide-pulsed cells was determined by comparing the ratio of pulsed (High CFSE fluorescence intensity) to unpulsed (Low CFSE fluorescence intensity) populations in immunized versus naive mice. The percentage of specific killing was established according to the following calculation: $(1-((CFSE_{low}\text{ naive}/CFSE_{high}\text{ naive})/(CFSE_{low}\text{ immunized}/CFSE_{high}\text{ immunized})))*100$.

TABLE 1

| Sequences of CS and Hep17 synthetic peptides. | | | |
|---|---|---|---|
| CSP | | | |
| CD8+ T cell epitopes | | | |
| SI9 | Rs 280-88 | **SYVPSAEQI** | Dominant |
| IL10 | Rs 58-67 | **IYNRNIVNRL** | Subdominant |
| CD4+ T helper cell epitopes with overlapping CD8+ T cell epitopes | | | |
| SI16 | Rs 280-95 | **SYVPSAEQILEFVKQI** | Dominant |
| KD14 | Rs 57-70 | **KIYNRNIVNRLLGD** | Dominant (nested dom. CD8+ T cell epitope) |
| YK21 | Rs 59-79 | **YNRNIVNRLLGDALNGKPEEK** | Subdominant (nested subdom. CD8+ T cell epitope) |

TABLE 1-continued

| Sequences of CS and Hep17 synthetic peptides. | | | |
|---|---|---|---|
| PyHEP17 | | | |
| CD8+ T cell epitopes (9-mer) | | | |
| L9A | Rs 73-81 | **LRKINVALA** | Subdominant |
| EN9 | Rs 61-69 | **EEIVKLTKN** | Subdominant |
| KV9 | Rs 70-78 | **KKSLRKINV** | Subdominant |
| IL9 | Rs 76-84 | **INVALATAL** | Subdominant |
| LL9 | Rs 84-92 | **LSVVSAILL** | Subdominant |
| CD4+ T cell epitope with nested CD8+ T cell epitopes (15-mer) | | | |
| EK15 | Rs 61-75 | **EEIVKLTKNKKSLRK** | Dominant |
| KL14 | Rs 71-84 | **KSLRKINVALATAL** | Dominant |

Ref
CSP:
G. Del Giudice et al., Immunol Lett 25 (1990), pp. 59-63
E. D. Franke, Infect Immun 68 (2000), pp. 3403-3411
L. Renia, Proc Natl Acad Sci USA 88 (1991), pp. 7963-7967.
W. R. Weiss, J Exp Med 171 (1990), pp. 763-773.
Py HEP17
Y. Charoenvit,, Infect Immun 67 (1999), pp. 5604-5614.
C. Dobaño, Mol Immunol 44 (11) (2007), pp. 3037-3048.

Recombinant $MSP1_{19}$ Protein.

*P. yoelii* YM $MSP1_{19}$ (aa 1649-1757) was amplified by PCR using the forward primer 5'-CGTGGATCCATGGACG-GCATGGATCTGCTG-3' (SEQ ID NO: 18) and the reverse primer 5'-GATGAATTCGGAGCTGCTGCTGCAGAA-CACG-3' (SEQ ID NO: 19) from pTRIP $MSP1_{42}$ and cloned into the glutathione S-transferase (GST)-fusion protein expression vector pGEX-2T (Amersham Biosciences, Bucks, UK). *Escherichia coli* BL21 star (Invitrogen) were transformed with pGEX-2T $MSP1_{19}$ and growth and induction were performed according to the manufacturer's instructions (pGEX vectors, GST gene fusion system, Amersham). After induction of the expression of the protein in BL21, cells were harvested and lysed using BugBuster reagent (Novagen). Recombinant protein was purified by GST bind resin chromatography using GST bind purification kit (Novagen) as per manufacturer's instructions.

Measurement of Serum Antibody Responses.

Sera were collected 3 weeks after the last immunization for the assessment of $MSP1_{19}$-specific antibodies by enzyme-linked immunosorbent assay (ELISA). Recombinant GST-$MSP1_{19}$ fusion protein or GST control were adsorbed overnight at 4° C. to 96 well Nunc-Immuno Maxisorp plates (Fischer Scientific, Wohlen, Germany) at 2 μg/ml in PBS. After three washes with 0.05% Tween 20 in PBS, wells were blocked by the addition of 100 μl of PBS containing 10% of foetal bovine serum (FBS) at room temperature for 1 hour. Plates were washed three times with 0.05% Tween 20 in PBS and 100 μl of tenfold serial dilutions of serum were added to the wells. After incubation for 2 hours at room temperature, the wells were washed and 100 μl of peroxydase goat anti-mouse immunoglobulin (H+L) (Jackson Immuno Research) diluted 1/4000 in PBS 10% FBS was added to each well. After incubation for 1 hour at room temperature, wells were washed and 100 μl of tetramethylbenzidine substrate reagent (BD Pharmingen) was added to each well. The plates were incubated at room temperature for 30 min, and 100 μl of 1N $H_2SO_4$ was added to stop the reaction. The plates were read for optical density at 450 nm. The endpoint titer was calculated as the reciprocal of the last dilution eliciting twice the optical density of sera from non immunized mice.

REFERENCES

1. Nussenzweig, R. S., et al Protective immunity produced by the injection of x-irradiated sporozoites of *plasmodium berghei*. Nature 216, 160-162 (1967).
2. Gwadz, R. W., et al Preliminary studies on vaccination of rhesus monkeys with irradiated sporozoites of *Plasmodium* knowlesi and characterization of surface antigens of these parasites. Bull World *Health Organ* 57 Suppl 1, 165-173 (1979).
3. Clyde, D. F., et al Immunization of man against sporozite-induced falciparum malaria. *Am J Med Sci* 266, 169-177 (1973).
4. Kappe, S. H., Buscaglia, C. A. & Nussenzweig, V. *Plasmodium* sporozoite molecular cell biology. *Annu Rev Cell Dev Biol* 20, 29-59 (2004).
5. Singh, A. P. et al. *Plasmodium* circumsporozoite protein promotes the development of the liver stages of the parasite. *Cell* 131, 492-504 (2007).
6. Kumar, K. A. et al. The circumsporozoite protein is an immunodominant protective antigen in irradiated sporozoites. *Nature* 444, 937-940 (2006).
7 Abdulla, S. et al. Safety and immunogenicity of RTS,S/AS02D malaria vaccine in infants. *N Engl J Med* 359, 2533-2544 (2008).
8. Bejon, P. et al. Efficacy of RTS,S/AS01E vaccine against malaria in children 5 to 17 months of age. *N Engl J Med* 359, 2521-2532 (2008).
9. Bruna-Romero, O., Rocha, C. D., Tsuji, M. & Gazzinelli, R. T. Enhanced protective immunity against malaria by vaccination with a recombinant adenovirus encoding the circumsporozoite protein of *Plasmodium* lacking the GPI-anchoring motif. *Vaccine* 22, 3575-3584 (2004).
10. Doolan, D. L. et al. Identification and characterization of the protective hepatocyte erythrocyte protein 17 kDa gene of *Plasmodium yoelii*, homolog of *Plasmodium falciparum* exported protein 1. *J Biol Chem* 271, 17861-17868 (1996).

11. Draper, S. J. et al. Effective induction of high-titer antibodies by viral vector vaccines. *Nat Med* 14, 819-821 (2008).
12. Dobano, C. & Doolan, D. L. Identification of minimal CD8+ and CD4+ T cell epitopes in the *Plasmodium yoelii* hepatocyte erythrocyte protein 17 kDa. *Mol Immunol* 44, 3037-3048 (2007).
13. Hirunpetcharat, C. et al. Complete protective immunity induced in mice by immunization with the 19-kilodalton carboxyl-terminal fragment of the merozoite surface protein-1 (MSP1[19]) of *Plasmodium yoelii* expressed in *Saccharomyces cerevisiae*: correlation of protection with antigen-specific antibody titer, but not with effector CD4+ T cells. *J Immunol* 159, 3400-3411 (1997).
14. Ahlborg, N., et al Protective immune responses to the 42-kilodalton (kDa) region of *Plasmodium yoelii* merozoite surface protein 1 are induced by the C-terminal 19-kDa region but not by the adjacent 33-kDa region. *Infect Immun* 70, 820-825 (2002).
15. Coutant, F., Frenkiel, M. P., Despres, P. & Charneau, P. Protective antiviral immunity conferred by a nonintegrative lentiviral vector-based vaccine. *PLoS ONE* 3, e3973 (2008).
16. Bruna-Romero, O. et al. Detection of malaria liver-stages in mice infected through the bite of a single *Anopheles* mosquito using a highly sensitive real-time PCR. *Int J Parasitol* 31, 1499-1502 (2001).
17. Daneshvar, C. et al. Laboratory Features of Human *Plasmodium* knowlesi Infection—Clinical Infectious Diseases (2009); 49: 852-860.
18. Vaughan K et al., Meta-analysis of immune epitope data for all *Plasmodia*: overview and applications for malarial immunobiology and vaccine-related issues, Parasite Immunology, 2009, 31, 78-97
19. Jones Stephanie et al, Lentiviral vector design for optimal T cell receptor gene expression in the transduction of peripheral blood lymphocytes and tumor-infiltrating lymphocyte, Human Gene Therapy, 20: 630-640 (June 2009).
20. Cockrell A. S. et al., Gene delivery by lentivirus vectors. Mol. Biotehnol. (2007) 36: 184-204.
21. Ikedia Y. et al. (2003). Continuous high titer HIV-1 vector production. Nature Biotechnology, 21: 569-572.
22. Cockrell A. S. et al. (2006). A trans-lentiviral packaging cell line for high-titer conditional self-inactivating HIV-1 vectors. Molecular Therapy, 14: 276-284.
23. Xu K. et al. (2001). Generation of a stable cell line producing high-titer self-inactivating lentiviral vectors.
24. Kafri. T. et al. (1999). A packaging cell line for lentivirus vectors. Journal of virolog 73: 576-584.
25. Zenou V. et al (2000) HIV genome nuclear import is mediated by a central DNA flap Cell. 101: 173-185.
26. Firat H. et al. The Journal of Gene Medicine (2002); 4: 38-45.
27. VandenDriesshe T. et al (2002), Lentiviral vectors containing the Human Immunodeficiency Virus type-1 central polypurine tract can efficiently transduce nondividing hepatocytes and antigen-presenting cells in vivo. Blood. 2002 Aug. 1; 100(3): 813-22.
28. Meral E. et al (2009) VACCINE, vol. 27, Issue 49, 16 Nov. 2009, pages 6862-6868.
29. Cronin J et al (2005)—Altering the Tropism of Lentiviral vectors through Pseudotyping-Curr Gene Ther. 2005, August; 5(4): 387-398.
30. Fredericksen B. L. et al. J. Virol. 1995-69: 1435-1443.
31. Nishimura N et al. PNAS 2002-99; 6755-6760

The invention claimed is:

1. A method of inducing a protective cellular immune response in a mammal against a pre-erythrocytic stage *Plasmodium* parasite antigen, comprising:

A) administering an effective amount of a first lentiviral particle to the mammal, wherein the first lentiviral particle (i) is pseudotyped with at least one determined heterologous viral envelope protein originating from a RNA virus and (ii) comprises in its genome at least one recombinant polynucleotide encoding a pre-erythrocytic stage antigen of a *Plasmodium* parasite capable of infecting a mammalian host, to thereby prime a protective cellular immune response of the mammal against the pre-erythrocytic stage *Plasmodium* parasite antigen; and B) after at least 6 weeks administering an effective amount of a second lentiviral particle to the mammal, wherein the second lentiviral particle (i) is pseudotyped with at least one determined heterologous viral envelope protein originating from a RNA virus and (ii) comprises in its genome at least one recombinant polynucleotide encoding a pre-erythrocytic stage antigen of a *Plasmodium* parasite capable of infecting a mammalian host, to thereby boost the protective cellular immune response of the host against the pre-erythrocytic stage *Plasmodium* parasite antigen;

wherein the first and second lentiviral particles are pseudotyped with distinct envelope protein(s) which do not sero-neutralize with each other.

2. A method of inducing a protective cellular immune response in a mammal against a pre-erythrocytic stage *Plasmodium* parasite antigen, comprising: administering to the mammal a first lentiviral particle; (i) pseudotyped with at least one determined heterologous viral envelope protein originating from a RNA virus and (ii) comprising in its genome at least one recombinant polynucleotide encoding a pre-erythrocytic stage *Plasmodium* parasite antigen;

wherein the lentiviral particle is administered in a dosage regimen comprising separately provided doses of said lentiviral particle for priming a protective cellular immune response and boosting the protective cellular immune response; and wherein the dose administered for boosting the protective cellular immune response against the at least one epitope is higher than the dose for priming the protective cellular immune response against the *Plasmodium* parasite antigen.

3. A method of inducing a protective cellular immune response in a mammal against a pre-erythrocytic stage *Plasmodium* parasite antigen, comprising administering to the mammal a first lentiviral particle (i) pseudotyped with at least one determined heterologous viral envelope protein originating from a RNA virus and (ii) comprising in its genome at least one recombinant polynucleotide encoding a pre-erythrocytic stage *Plasmodium* parasite antigen;

wherein the lentiviral particle is administered to the mammal in a dosage regimen comprising separately provided doses of said lentiviral particle for priming the protective cellular immune response and for boosting the protective cellular immune response;

wherein the dose administered for priming the protective cellular immune response and the dose administered for boosting the protective cellular immune response against the pre-erythrocytic stage *Plasmodium* parasite antigen comprise from $10^7$ to $10^9$ lentiviral particles when integrative-competent vector particles are used; and wherein the dose administered for priming the protective cellular immune response and the dose administered for boosting the protective cellular immune response against the pre-erythrocytic stage *Plasmodium* parasite antigen comprise from $10^8$ to $10^{10}$ lentiviral particles when integrative-incompetent vector particles are used.

4. The method of claim 1, further comprising administering an effective amount of a third lentiviral particle (i) pseudotyped with at least one determined heterologous viral envelope protein originating from a RNA virus and (ii) comprising in its genome at least one recombinant polynucleotide encoding at least one pre-erythrocytic stage *Plasmodium* parasite antigen, to thereby induce an antibody response in the host against the at least one *Plasmodium* parasite antigen.

5. The method of claim 2, further comprising administering an effective amount of a second lentiviral particle (i) pseudotyped with at least one determined heterologous viral envelope protein originating from a RNA virus and (ii) comprising in its genome at least one recombinant polynucleotide encoding at least one pre-erythrocytic stage *Plasmodium* parasite antigen, to thereby induce an antibody response in the host against the at least one *Plasmodium* parasite antigen.

6. The method of claim 3, further comprising administering an effective amount of a second lentiviral particle (i) pseudotyped with at least one determined heterologous viral envelope protein originating from a RNA virus and (ii) comprising in its genome at least one recombinant polynucleotide encoding at least one pre-erythrocytic stage *Plasmodium* parasite antigen, to thereby induce an antibody response in the host against the at least one *Plasmodium* parasite antigen.

7. The method of claim 1, wherein the pre-erythrocyte stage *Plasmodium* parasite antigens encoded by the first and second lentiviral particles are selected from a circumsporozoite protein antigen and a Hepatocyte Erythrocyte Protein 17 kDa (HEP17) antigen.

8. The method of claim 2, wherein the pre-erythrocyte stage *Plasmodium* parasite antigen encoded by the first lentiviral particle is selected from a circumsporozoite protein antigen and a HEP17 antigen.

9. The method of claim 3, wherein the pre-erythrocyte stage *Plasmodium* parasite antigen encoded by the first lentiviral particle is selected from a circumsporozoite protein antigen and a HEP17 antigen.

10. The method of claim 1, wherein the first and second lentiviral particles are pseudotyped with viral transmembrane glycosylated (G) envelope protein(s) of a Vesicular Stomatitis Virus (VSV).

11. The method of claim 2, wherein the first lentiviral particle is pseudotyped with viral transmembrane glycosylated (G) envelope protein(s) of a Vesicular Stomatitis Virus (VSV).

12. The method of claim 3, wherein the first lentiviral particle is pseudotyped with viral transmembrane glycosylated (G) envelope protein(s) of a Vesicular Stomatitis Virus (VSV).

13. The method of claim 4, wherein the third lentiviral particle is pseudotyped with viral transmembrane glycosylated (G) envelope protein(s) of a Vesicular Stomatitis Virus (VSV).

14. The method of claim 5, wherein the second lentiviral particle is pseudotyped with viral transmembrane glycosylated (G) envelope protein(s) of a Vesicular Stomatitis Virus (VSV).

15. The method of claim 6, wherein the second lentiviral particle is pseudotyped with viral transmembrane glycosylated (G) envelope protein(s) of a Vesicular Stomatitis Virus (VSV).

* * * * *